US012514920B1

(12) United States Patent
Song et al.

(10) Patent No.: US 12,514,920 B1
(45) Date of Patent: Jan. 6, 2026

(54) RESPIRATORY SYNCYTIAL VIRUS mRNA VACCINE, AND PREPARATION METHOD THEREFOR AND USE THEREOF

(71) Applicant: Hangzhou Tianlong Pharmaceutical Co., Ltd., Zhejiang (CN)

(72) Inventors: Gengshen Song, Zhejiang (CN); Kai Dong, Zhejiang (CN); Chen Pan, Zhejiang (CN); Wang Wang, Zhejiang (CN); Yuting Zhou, Zhejiang (CN); Xin Chai, Zhejiang (CN); Jing Li, Zhejiang (CN); Xiaowei Lang, Zhejiang (CN); Jinyu Zhang, Zhejiang (CN); Limin Liang, Zhejiang (CN); Huanyu Wang, Zhejiang (CN)

(73) Assignee: Hangzhou Tianlong Pharmaceutical Co., Ltd., Hangzhou (CN)

( * ) Notice: Subject to any disclaimer, the term of this patent is extended or adjusted under 35 U.S.C. 154(b) by 0 days.

(21) Appl. No.: 19/262,172

(22) Filed: Jul. 8, 2025

(30) Foreign Application Priority Data

Jul. 9, 2024 (CN) ......................... 202410911569.7

(51) Int. Cl.

| | |
|---|---|
| ***A61K 39/12*** | (2006.01) |
| ***A61K 39/155*** | (2006.01) |
| ***A61P 37/04*** | (2006.01) |
| *A61K 39/00* | (2006.01) |

(52) U.S. Cl.
CPC ............ *A61K 39/155* (2013.01); *A61P 37/04* (2018.01); *A61K 2039/53* (2013.01); *A61K 2039/55555* (2013.01)

(58) Field of Classification Search
None
See application file for complete search history.

(56) References Cited

U.S. PATENT DOCUMENTS

| | | | | |
|---|---|---|---|---|
| 2016/0046675 A1* | 2/2016 | Kwong | ................ | A61K 39/155 530/400 |
| 2023/0338506 A1 | 10/2023 | Shaw et al. | | |

FOREIGN PATENT DOCUMENTS

| | | | |
|---|---|---|---|
| CN | 102307591 | A | 1/2012 |
| CN | 112292395 | A | 1/2021 |
| CN | 118206622 | A | 6/2024 |
| CN | 118480560 | B | 11/2024 |
| WO | 2010077717 | A1 | 7/2010 |
| WO | 2014152027 | A1 | 9/2014 |
| WO | 2017070622 | A1 | 4/2017 |
| WO | 2019202035 | A1 | 10/2019 |
| WO | 2023166079 | A1 | 9/2023 |

OTHER PUBLICATIONS

M Gordon Joyce et al., Iterative structure-based improvement of a respiratory syncytial virus fusion glycoprotein vaccine, Nature Structural & Molecular Biology, vol. 23, 811-820 (2016).
J. S. McLellan et al., Structure-based design of a fusion glycoprotein vaccine for respiratory syncytial virus, Science, Nov. 1, 2013, 342(6158): 592-598.
J. O. Ngwuta et al., Prefusion F-specific antibodies determine the magnitude of RSV neutralizing activity in human sera, Sci Transl Med., Oct. 14, 2015, 7(309).
Sep. 26, 2024 First Office Action and Search Report issued in Chinese Patent Application No. 202410911569.7.
Oct. 28, 2024 Notice of Allowance issued in Chinese Patent Application No. 202410911569.7.
Jul. 8, 2025 First Office Action issued in New Zealand Patent Application No. 822682.

* cited by examiner

*Primary Examiner* — Shanon A. Foley
*Assistant Examiner* — Myron G Hill

(57) ABSTRACT

The present disclosure belongs to the technical field of mRNA vaccines, and particularly relates to a respiratory syncytial virus (RSV) vaccine, and a preparation method therefor and use thereof. The vaccine provided by the present disclosure comprises RNA encoding an RSV F protein or a variant thereof. The vaccine can prevent an RSV infection and complications thereof.

30 Claims, 18 Drawing Sheets

Specification includes a Sequence Listing.

SEQUENCE LISTING

```
Sequence total quantity: 225
SEQ ID NO: 1           moltype = AA  length = 574
FEATURE                Location/Qualifiers
source                 1..574
                       mol_type = protein
                       organism = Orthopneumovirus hominis
SEQUENCE: 1
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PPTNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEIN LCNVDIFNPK YDCKIMTSKT DVSSSVITSL GAIVSCYGKT  420
KCTASNKNRG IIKTFSNGCD YVSNKGMDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                            574

SEQ ID NO: 2           moltype = DNA  length = 1841
FEATURE                Location/Qualifiers
source                 1..1841
                       mol_type = other DNA
                       organism = synthetic construct
SEQUENCE: 2
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
gagcaccaac aaggccgtgg tgtctctgag caatggcgtg tccgtgctga ccatcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag gtgctggcct acgtggtgca gctgcctctg tatggcgtga tcgataccc c  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                    1841

SEQ ID NO: 3           moltype = DNA  length = 1539
FEATURE                Location/Qualifiers
source                 1..1539
                       mol_type = other DNA
                       organism = synthetic construct
SEQUENCE: 3
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtgcaa agtgctgcac  360
ctggaaggcg aagtgaacaa gatcaagagc gccctgctga gcaccaacaa ggccgtggtg  420
tctctgagca atggcgtgtc cgtgctgacc atcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg tgcattatca aagaagaggt gctggcctac  780
gtggtgcagc tgcctctgta tggcgtgatc gataccccct gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
```

-continued

```
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 4            moltype = AA  length = 510
FEATURE                 Location/Qualifiers
source                  1..510
                        mol_type = protein
                        organism = synthetic construct
SEQUENCE: 4
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGVAVCKVLH  120
LEGEVNKIKS ALLSTNKAVV SLSNGVSVLT IKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                  510

SEQ ID NO: 5            moltype = RNA  length = 1841
FEATURE                 Location/Qualifiers
source                  1..1841
                        mol_type = other RNA
                        organism = synthetic construct
SEQUENCE: 5
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
gagcaccaac aaggccgtgg tgtctctgag caatggcgtg tccgtgctga ccatcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag gtgctggcct acgtggtgca gctgcctctg tatggcgtga tcgataccc   900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 6            moltype = DNA  length = 1841
FEATURE                 Location/Qualifiers
source                  1..1841
                        mol_type = other DNA
                        organism = synthetic construct
SEQUENCE: 6
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
ccacagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
```

-continued

```
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag gtgctggcct acgtggtgca gctgcctctg tatggcgtga tcgataccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 7            moltype = DNA  length = 1539
FEATURE                 Location/Qualifiers
source                  1..1539
                        mol_type = other DNA
                        organism = synthetic construct
SEQUENCE: 7
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtacc acagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtgcaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg tgcattatca aagaagaggt gctggcctac  780
gtggtgcagc tgcctctgta tggcgtgatc gataccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 8            moltype = AA  length = 510
FEATURE                 Location/Qualifiers
source                  1..510
                        mol_type = protein
                        organism = synthetic construct
SEQUENCE: 8
MELLILKANA ITTILTAVTF CFASGQNITE EFYQSTCSAV SKGYLGALRT GWYHSVITIE  60
LSNIKENKCN GTDAKVKLIK QELDKYKNAV TDLQLLMQST PATGSGSAIC SGVAVCKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                   510

SEQ ID NO: 9            moltype = RNA  length = 1841
FEATURE                 Location/Qualifiers
source                  1..1841
                        mol_type = other RNA
                        organism = synthetic construct
SEQUENCE: 9
```

```
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
ccacagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag gtgctggcct acgtggtgca gctgcctctg tatggcgtga tcgataccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 10          moltype = DNA  length = 1841
FEATURE                Location/Qualifiers
source                 1..1841
                       mol_type = other DNA
                       organism = synthetic construct
SEQUENCE: 10
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag atcctggcct acgtggtgca gctgcctctg tatggcgtga tcgataccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 11          moltype = DNA  length = 1539
FEATURE                Location/Qualifiers
source                 1..1539
                       mol_type = other DNA
                       organism = synthetic construct
SEQUENCE: 11
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
```

-continued

```
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtgcaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg tgcattatca aagaagagat cctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 12          moltype = AA  length = 510
FEATURE                Location/Qualifiers
source                 1..510
                       mol_type = protein
                       organism = synthetic construct
SEQUENCE: 12
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGVAVCKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM CIIKEEILAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                  510

SEQ ID NO: 13          moltype = RNA  length = 1841
FEATURE                Location/Qualifiers
source                 1..1841
                       mol_type = other RNA
                       organism = synthetic construct
SEQUENCE: 13
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag atcctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 14          moltype = DNA  length = 1841
```

```
FEATURE              Location/Qualifiers
source               1..1841
                     mol_type = other DNA
                     organism = synthetic construct
SEQUENCE: 14
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
gagcaccaac aaggccgtgg tgtctctgag caatggcgtg tccgtgctga ccatcaaggt  540
gctggacctg aagaactaca tcgacaaaca gctgctgccc atcgtcaaca agcagtcctg  600
ccccatcagc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgcccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 15        moltype = DNA  length = 1539
FEATURE              Location/Qualifiers
source               1..1539
                     mol_type = other DNA
                     organism = synthetic construct
SEQUENCE: 15
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtgcaa agtgctgcac  360
ctggaaggcg aagtgaacaa gatcaagagc gccctgctga gcaccaacaa ggccgtggtg  420
tctctgagca atggcgtgtc cgtgctgacc atcaaggtgc tggacctgaa gaactacatc  480
gacaaacagc tgctgcccat cgtcaacaag cagtcctgcc ccatcagcaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg tgcattatca aagaagaggt gctggcctac  780
gtggtgcagc tgcctctgta tggcgtgatc gataccccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                       1539

SEQ ID NO: 16        moltype = AA  length = 510
FEATURE              Location/Qualifiers
source               1..510
                     mol_type = protein
                     organism = synthetic construct
SEQUENCE: 16
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGVAVCKVLH  120
LEGEVNKIKS ALLSTNKAVV SLSNGVSVLT IKVLDLKNYI DKQLLPIVNK QSCPISNIET  180
```

-continued

```
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                  510

SEQ ID NO: 17          moltype = RNA  length = 1841
FEATURE                Location/Qualifiers
source                 1..1841
                       mol_type = other RNA
                       organism = synthetic construct
SEQUENCE: 17
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
gagcaccaac aaggccgtgg tgtctctgag caatggcgtg tccgtgctga ccatcaaggt  540
gctggacctg aagaactaca tcgacaaaca gctgctgccc atcgtcaaca agcagtcctg  600
ccccatcagc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 18          moltype = DNA  length = 1841
FEATURE                Location/Qualifiers
source                 1..1841
                       mol_type = other DNA
                       organism = synthetic construct
SEQUENCE: 18
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
gagcaccaac aaggccgtgg tgtctctgag caatggcgtg tccgtgctga ccatcaaggt  540
gctggacctg aagaactaca tcgacaaaca gctgctgccc atcgtcaaca agcagtcctg  600
cagcatcagc cccatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
```

```
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 19          moltype = DNA  length = 1539
FEATURE                Location/Qualifiers
source                 1..1539
                       mol_type = other DNA
                       organism = synthetic construct
SEQUENCE: 19
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtgcaa agtgctgcac  360
ctggaaggcg aagtgaacaa gatcaagagc gccctgctga gcaccaacaa ggccgtggtg  420
tctctgagca atggcgtgtc cgtgctgacc atcaaggtgc tggacctgaa gaactacatc  480
gacaaacagc tgctgcccat cgtcaacaag cagtcctgca gcatcagccc catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg tgcattatca aagaagaggt gctggcctac  780
gtggtgcagc tgcctctgta tggcgtgatc gataccccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 20          moltype = AA  length = 510
FEATURE                Location/Qualifiers
source                 1..510
                       mol_type = protein
                       organism = synthetic construct
SEQUENCE: 20
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGVAVCKVLH  120
LEGEVNKIKS ALLSTNKAVV SLSNGVSVLT IKVLDLKNYI DKQLLPIVNK QSCSISPIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIVIIVILL SLIAVGLLLY                                    510

SEQ ID NO: 21          moltype = RNA  length = 1841
FEATURE                Location/Qualifiers
source                 1..1841
                       mol_type = other RNA
                       organism = synthetic construct
SEQUENCE: 21
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtgc aaagtgctgc acctggaagg cgaagtgaac aagatcaaga gcgccctgct  480
gagcaccaac aaggccgtgg tgtctctgag caatggcgtg tccgtgctga ccatcaaggt  540
gctggacctg aagaactaca tcgacaaaca gctgctgccc atcgtcaaca agcagtcctg  600
cagcatcagc cccatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
```

-continued

```
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 22          moltype = DNA  length = 1841
FEATURE                Location/Qualifiers
source                 1..1841
                       mol_type = other DNA
                       organism = synthetic construct
SEQUENCE: 22
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccatcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 23          moltype = DNA  length = 1539
FEATURE                Location/Qualifiers
source                 1..1539
                       mol_type = other DNA
                       organism = synthetic construct
SEQUENCE: 23
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca cctgcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgct tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgtgcacc atcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
```

-continued

```
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 24          moltype = AA  length = 510
FEATURE                Location/Qualifiers
source                 1..510
                       mol_type = protein
                       organism = synthetic construct
SEQUENCE: 24
MELLILKANA ITTILTAVTF CFASGQNITE EFYQSTCSAV SKGYLGALRT GWYTCVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVCT IKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                   510

SEQ ID NO: 25          moltype = RNA  length = 1841
FEATURE                Location/Qualifiers
source                 1..1841
                       mol_type = other RNA
                       organism = synthetic construct
SEQUENCE: 25
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccatcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggcgag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 26          moltype = DNA  length = 1841
FEATURE                Location/Qualifiers
source                 1..1841
                       mol_type = other DNA
                       organism = synthetic construct
SEQUENCE: 26
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcctgatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
```

```
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 27          moltype = DNA  length = 1539
FEATURE                Location/Qualifiers
source                 1..1539
                       mol_type = other DNA
                       organism = synthetic construct
SEQUENCE: 27
atggaactgc tgatcctgaa ggccaacgcc atcaccacca tcctgaccgc cgtgaccttc  60
tgttttgcca gcggccagaa catcaccgag gaattctact gcagcacctg tagcgccgtg  120
tccaagggat atctgggcgc ccttagaacc ggctggtaca ccagcgtgat cctgatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgct tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagtgcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 28          moltype = AA  length = 510
FEATURE                Location/Qualifiers
source                 1..510
                       mol_type = protein
                       organism = synthetic construct
SEQUENCE: 28
MELLILKANA ITTILTAVTF CFASGQNITE EFYCSTCSAV SKGYLGALRT GWYTSVILIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KCEPIINFYD PLVFPSSEFD ASISQVNEKI NQSLAFIRKS DELLHNVNAG  480
KSTTNIMITT IIIVIIVILL SLIAVGLLLY                                  510

SEQ ID NO: 29          moltype = RNA  length = 1841
FEATURE                Location/Qualifiers
source                 1..1841
                       mol_type = other RNA
                       organism = synthetic construct
SEQUENCE: 29
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcctgatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
```

```
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 30          moltype = DNA  length = 1841
FEATURE                Location/Qualifiers
source                 1..1841
                       mol_type = other DNA
                       organism = synthetic construct
SEQUENCE: 30
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcctgatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 31          moltype = DNA  length = 1539
FEATURE                Location/Qualifiers
source                 1..1539
                       mol_type = other DNA
                       organism = synthetic construct
SEQUENCE: 31
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca cctgcgtgat cctgatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgct tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgtgcacc ttcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
```

-continued

```
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccctt gctggaagct gcacacaagc 840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539
```

```
SEQ ID NO: 32           moltype = AA  length = 510
FEATURE                 Location/Qualifiers
source                  1..510
                        mol_type = protein
                        organism = synthetic construct
SEQUENCE: 32
MELLILKANA ITTILTAVTF CFASGQNITE EFYQSTCSAV SKGYLGALRT GWYTCVILIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVCT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                   510
```

```
SEQ ID NO: 33           moltype = RNA  length = 1841
FEATURE                 Location/Qualifiers
source                  1..1841
                        mol_type = other RNA
                        organism = synthetic construct
SEQUENCE: 33
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcctgatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tcccccccagc ccctcctccc 1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841
```

```
SEQ ID NO: 34           moltype = DNA  length = 1841
FEATURE                 Location/Qualifiers
source                  1..1841
                        mol_type = other DNA
                        organism = synthetic construct
SEQUENCE: 34
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
```

-continued

```
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga tcgtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc cccctcctcc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 35          moltype = DNA  length = 1539
FEATURE                Location/Qualifiers
source                 1..1539
                       mol_type = other DNA
                       organism = synthetic construct
SEQUENCE: 35
atggaactgc tgatcctgaa ggccaacgcc atcaccacca tcctgaccgc cgtgaccttc  60
tgttttgcca gcggccagaa catcaccgag gaattctact gcagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgct tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cgtcaacaag cagtcctgca gcatccccaa catcgagatc  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccct gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagtgcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 36          moltype = AA  length = 510
FEATURE                Location/Qualifiers
source                 1..510
                       mol_type = protein
                       organism = synthetic construct
SEQUENCE: 36
MELLILKANA ITTILTAVTF CFASGQNITE EFYCSTCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPIVNK QSCSIPNIEI  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KCEPIINFYD PLVFPSSEFD ASISQVNEKI NQSLAFIRKS DELLHNVNAG  480
KSTTNIMITT IIIVIIVILL SLIAVGLLLY                                    510
```

```
SEQ ID NO: 37          moltype = RNA  length = 1841
FEATURE                Location/Qualifiers
source                 1..1841
                       mol_type = other RNA
                       organism = synthetic construct
SEQUENCE: 37
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga tcgtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc   900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 38          moltype = DNA  length = 1841
FEATURE                Location/Qualifiers
source                 1..1841
                       mol_type = other DNA
                       organism = synthetic construct
SEQUENCE: 38
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccttcaaggt  540
gctggacctg aagaactaca tcgacaaaca gctgctgccc atcgtcaaca agcagtcctg  600
cagcatcccc aacatcgaga tcgtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc   900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 39          moltype = DNA  length = 1539
FEATURE                Location/Qualifiers
source                 1..1539
```

```
                        mol_type = other DNA
                        organism = synthetic construct
SEQUENCE: 39
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca cctgcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgct tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgtgcacc ttcaaggtgc tggacctgaa gaactacatc  480
gacaaacagc tgctgcccat cgtcaacaag cagtcctgca gcatccccaa catcgagatc  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 40           moltype = AA  length = 510
FEATURE                 Location/Qualifiers
source                  1..510
                        mol_type = protein
                        organism = synthetic construct
SEQUENCE: 40
MELLILKANA ITTILTAVTF CFASGQNITE EFYQSTCSAV SKGYLGALRT GWYTCVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVCT FKVLDLKNYI DKQLLPIVNK QSCSIPNIEI  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                  510

SEQ ID NO: 41           moltype = RNA  length = 1841
FEATURE                 Location/Qualifiers
source                  1..1841
                        mol_type = other RNA
                        organism = synthetic construct
SEQUENCE: 41
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccttcaaggt  540
gctggacctg aagaactaca tcgacaaaca gctgctgccc atcgtcaaca agcagtcctg  600
cagcatcccc aacatcgaga tcgtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
```

-continued

```
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 42          moltype = DNA  length = 1841
FEATURE                Location/Qualifiers
source                 1..1841
                       mol_type = other DNA
                       organism = synthetic construct
SEQUENCE: 42
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagcctg cggctctggc agcgcctgcg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 43          moltype = DNA  length = 1539
FEATURE                Location/Qualifiers
source                 1..1539
                       mol_type = other DNA
                       organism = synthetic construct
SEQUENCE: 43
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagcctgcg gctctggcag cgcctgcgct tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 44          moltype = AA  length = 510
FEATURE                Location/Qualifiers
source                 1..510
```

-continued

```
                        mol_type = protein
                        organism = synthetic construct
SEQUENCE: 44
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PACGSGSACA SGVAVSKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                 510

SEQ ID NO: 45           moltype = RNA  length = 1841
FEATURE                 Location/Qualifiers
source                  1..1841
                        mol_type = other RNA
                        organism = synthetic construct
SEQUENCE: 45
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagcctg cggctctggc agcgcctgcg cttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc c  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                    1841

SEQ ID NO: 46           moltype = DNA  length = 1841
FEATURE                 Location/Qualifiers
source                  1..1841
                        mol_type = other DNA
                        organism = synthetic construct
SEQUENCE: 46
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccatcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc c  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
```

-continued

```
gggcaacacc ctgtactgcg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 47          moltype = DNA  length = 1539
FEATURE                Location/Qualifiers
source                 1..1539
                       mol_type = other DNA
                       organism = synthetic construct
SEQUENCE: 47
atggaactgc tgatcctgaa ggccaacgcc atcaccacca tcctgaccgc cgtgaccttc  60
tgttttgcca gcggccagaa catcaccgag gaattctact gcagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc atcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccct gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagtgcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 48          moltype = AA  length = 510
FEATURE                Location/Qualifiers
source                 1..510
                       mol_type = protein
                       organism = synthetic construct
SEQUENCE: 48
MELLILKANA ITTILTAVTF CFASGQNITE EFYCSTCSAV SKGYLGALRT GWYTSVITIE  60
LSNIKENKCN GTDAKVKLIK QELDKYKNAV TDLQLLMQST PATGSGSAIC SGVAVSKVLH  120
LEGEVNKIKS ALLSTNKAVV SLSNGVSVLT IKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KCEPIINFYD PLVFPSSEFD ASISQVNEKI NQSLAFIRKS DELLHNVNAG  480
KSTTNIMITT IIIVIIVILL SLIAVGLLLY                                   510

SEQ ID NO: 49          moltype = RNA  length = 1841
FEATURE                Location/Qualifiers
source                 1..1841
                       mol_type = other RNA
                       organism = synthetic construct
SEQUENCE: 49
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccatcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
```

-continued

```
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 50          moltype = DNA  length = 1841
FEATURE                Location/Qualifiers
source                 1..1841
                       mol_type = other DNA
                       organism = synthetic construct
SEQUENCE: 50
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccatcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 51          moltype = DNA  length = 1539
FEATURE                Location/Qualifiers
source                 1..1539
                       mol_type = other DNA
                       organism = synthetic construct
SEQUENCE: 51
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca cctgcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgtgcacc atcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
```

-continued

```
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 52          moltype = AA  length = 510
FEATURE                Location/Qualifiers
source                 1..510
                       mol_type = protein
                       organism = synthetic construct
SEQUENCE: 52
MELLILKANA ITTILTAVTF CFASGQNITE EFYQSTCSAV SKGYLGALRT GWYTCVITIE  60
LSNIKENKCN GTDAKVKLIK QELDKYKNAV TDLQLLMQST PATGSGSAIC SGVAVSKVLH  120
LEGEVNKIKS ALLSTNKAVV SLSNGVSVCT IKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                   510

SEQ ID NO: 53          moltype = RNA  length = 1841
FEATURE                Location/Qualifiers
source                 1..1841
                       mol_type = other RNA
                       organism = synthetic construct
SEQUENCE: 53
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccatcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc   900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 54          moltype = DNA  length = 1841
FEATURE                Location/Qualifiers
source                 1..1841
                       mol_type = other DNA
                       organism = synthetic construct
SEQUENCE: 54
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcctgatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
```

```
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 55          moltype = DNA  length = 1539
FEATURE                Location/Qualifiers
source                 1..1539
                       mol_type = other DNA
                       organism = synthetic construct
SEQUENCE: 55
atggaactgc tgatcctgaa ggccaacgcc atcaccacca tcctgaccgc cgtgaccttc  60
tgttttgcca gcggccagaa catcaccgag gaattctact gcagcacctg tagcgccgtg  120
tccaagggat atctgggcgc ccttagaacc ggctggtaca ccagcgtgat cctgatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagtgcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 56          moltype = AA  length = 510
FEATURE                Location/Qualifiers
source                 1..510
                       mol_type = protein
                       organism = synthetic construct
SEQUENCE: 56
MELLILKANA ITTILTAVTF CFASGQNITE EFYCSTCSAV SKGYLGALRT GWYTSVILIE  60
LSNIKENKCN GTDAKVKLIK QELDKYKNAV TDLQLLMQST PATGSGSAIC SGVAVSKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KCEPIINFYD PLVFPSSEFD ASISQVNEKI NQSLAFIRKS DELLHNVNAG  480
KSTTNIMITT IIIVIIVILL SLIAVGLLLY                                510

SEQ ID NO: 57          moltype = RNA  length = 1841
FEATURE                Location/Qualifiers
source                 1..1841
                       mol_type = other RNA
                       organism = synthetic construct
SEQUENCE: 57
agcggctcgg ccattttgtc ccagtcagtc cggaggctgc ggctgcagaa gtaccgcctg  60
```

-continued

```
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcctgatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 58          moltype = DNA  length = 1841
FEATURE                Location/Qualifiers
source                 1..1841
                       mol_type = other DNA
                       organism = synthetic construct
SEQUENCE: 58
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcctgatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 59          moltype = DNA  length = 1539
FEATURE                Location/Qualifiers
source                 1..1539
                       mol_type = other DNA
                       organism = synthetic construct
SEQUENCE: 59
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca cctgcgtgat cctgatcgag  180
ctgagcaaca tcaaagaaaa caagtgcaac ggcaccgacg ccaaagtgaa gctgatcaag  240
```

-continued

```
caagagctgg acaagtacaa gaatgccgtg accgacctgc agctgctgat gcagtctaca  300
ccagccacag gctctggcag cgccatttgt tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgtgcacc ttcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 60          moltype = AA  length = 510
FEATURE                Location/Qualifiers
source                 1..510
                       mol_type = protein
                       organism = synthetic construct
SEQUENCE: 60
MELLILKANA ITTILTAVTF CFASGQNITE EFYQSTCSAV SKGYLGALRT GWYTCVILIE  60
LSNIKENKCN GTDAKVKLIK QELDKYKNAV TDLQLLMQST PATGSGSAIC SGVAVSKVLH  120
LEGEVNKIKS ALLSTNKAVV SLSNGVSVCT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                  510

SEQ ID NO: 61          moltype = RNA  length = 1841
FEATURE                Location/Qualifiers
source                 1..1841
                       mol_type = other RNA
                       organism = synthetic construct
SEQUENCE: 61
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcctgatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 62          moltype = DNA  length = 1841
FEATURE                Location/Qualifiers
```

-continued

```
source                  1..1841
                        mol_type = other DNA
                        organism = synthetic construct
SEQUENCE: 62
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga tcgtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc c  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 63           moltype = DNA  length = 1539
FEATURE                 Location/Qualifiers
source                  1..1539
                        mol_type = other DNA
                        organism = synthetic construct
SEQUENCE: 63
atggaactgc tgatcctgaa ggccaacgcc atcaccacca tcctgaccgc cgtgaccttc  60
tgttttgcca gcggccagaa catcaccgag gaattctact gcagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cgtcaacaag cagtcctgca gcatccccaa catcgagatc  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagtgcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 64           moltype = AA  length = 510
FEATURE                 Location/Qualifiers
source                  1..510
                        mol_type = protein
                        organism = synthetic construct
SEQUENCE: 64
MELLILKANA ITTILTAVTF CFASGQNITE EFYCSTCSAV SKGYLGALRT GWYTSVITIE  60
LSNIKENKCN GTDAKVKLIK QELDKYKNAV TDLQLLMQST PATGSGSAIC SGVAVSKVLH  120
LEGEVNKIKS ALLSTNKAVV SLSNGVSVLT FKVLDLKNYI DKQLLPIVNK QSCSIPNIEI  180
VIEFQQKNNR LLEITREFSV NAGVTTPVST YMLTNSELLS LINDMPITND QKKLMSNNVQ  240
```

```
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KCEPIINFYD PLVFPSSEFD ASISQVNEKI NQSLAFIRKS DELLHNVNAG  480
KSTTNIMITT IIIVIIVILL SLIAVGLLLY                                  510

SEQ ID NO: 65          moltype = RNA  length = 1841
FEATURE                Location/Qualifiers
source                 1..1841
                       mol_type = other RNA
                       organism = synthetic construct
SEQUENCE: 65
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga tcgtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagtgcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 66          moltype = DNA  length = 1841
FEATURE                Location/Qualifiers
source                 1..1841
                       mol_type = other DNA
                       organism = synthetic construct
SEQUENCE: 66
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccttcaaggt  540
gctggacctg aagaactaca tcgacaaaca gctgctgccc atcgtcaaca agcagtcctg  600
cagcatcccc aacatcgaga tcgtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
```

```
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 67          moltype = DNA  length = 1539
FEATURE                Location/Qualifiers
source                 1..1539
                       mol_type = other DNA
                       organism = synthetic construct
SEQUENCE: 67
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca cctgcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgtgcacc ttcaaggtgc tggacctgaa gaactacatc  480
gacaaacagc tgctgcccat cgtcaacaag cagtcctgca gcatccccaa catcgagatc  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 68          moltype = AA  length = 510
FEATURE                Location/Qualifiers
source                 1..510
                       mol_type = protein
                       organism = synthetic construct
SEQUENCE: 68
MELLILKANA ITTILTAVTF CFASGQNITE EFYQSTCSAV SKGYLGALRT GWYTCVITIE  60
LSNIKENKCN GTDAKVKLIK QELDKYKNAV TDLQLLMQST PATGSGSAIC SGVAVSKVLH  120
LEGEVNKIKS ALLSTNKAVV SLSNGVSVCT FKVLDLKNYI DKQLLPIVNK QSCSIPNIEI  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                   510

SEQ ID NO: 69          moltype = RNA  length = 1841
FEATURE                Location/Qualifiers
source                 1..1841
                       mol_type = other RNA
                       organism = synthetic construct
SEQUENCE: 69
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtgt  420
cgccgtgtct aaagtgctgc acctggaagg cgaagtgaac aagatcaaga gcgccctgct  480
gagcaccaac aaggccgtgg tgtctctgag caatggcgtg tccgtgtgca ccttcaaggt  540
gctggacctg aagaactaca tcgacaaaca gctgctgccc atcgtcaaca agcagtcctg  600
cagcatcccc aacatcgaga tcgtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
```

```
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 70          moltype = DNA  length = 1844
FEATURE                Location/Qualifiers
source                 1..1844
                       mol_type = other DNA
                       organism = synthetic construct
SEQUENCE: 70
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagcctg cggctctggc agcgcctgcg cttctggtgt  420
cgccgtgtct aaagtgctgc acctggaagg cgaagtgaac aagatcaaga gcgccctgct  480
gagcaccaac aaggccgtgg tgtctctgag cggctgcggc gtgtccgtgc tgaccttcaa  540
ggtgctggac ctgaagaact acatcgacaa acagctgctg cccatcgtca acaagcagtc  600
ctgcagcatc cccaacatcg agacagtgat cgagttccag cagaagaaca accggctgct  660
ggaaatcacc cgcgagttct ctgtgaatgc cggcgtgacc acacctgtgt ccacctacat  720
gctgaccaac agcgagctgc tgagcctgat caacgacatg cccatcacca acgaccagaa  780
aaagctgatg agcaacaacg tgcagatcgt gcggcagcag agctacagca tcatgagcat  840
tatcaaagaa gaggtgctgg cctacgtggt gcagctgcct ctgtatggcg tgatcgatac  900
cccttgctgg aagctgcaca caagccctct gtgcaccacc aacaccaaag agggcagcaa  960
catctgcctg accagaaccg acagaggctg gtactgcgat aatgccggca gcgtctcatt  1020
cttcccacaa gccgagacat gcaaggtgca gagcaaccgg gtgttctgcg acaccatgaa  1080
tagcagaacc ctgccttccg aagtgaatct gtgcaacgtg gacatcttca accctaagta  1140
cgactgcaag atcatgacca gcaagaccga cgtgtccagc agtgtgatca cctcactggg  1200
cgccatcgtg tcctgttacg gcaagaccaa gtgcaccgcc agcaacaagt gccggggcat  1260
catcaagacc ttcagcaacg gctgcgacta cgtgtccaac aaaggcgtgg acaccgtgtc  1320
tgtgggcaac accctgtact acgtgaacaa acaagagggc cagtctctgt acgtgaaggg  1380
cgagcccatc atcaacttct acgaccctct ggtgttcccc agcagcgagt tcgatgccag  1440
catcagccaa gtgaacgaga agatcaatca gagcctggcc ttcatcagaa agtccgatga  1500
gctgctgcac aacgtgaacg ccggcaagtc caccaccaat atcatgatca cgaccatcat  1560
catcgtgatt atcgtgatcc tgctgtccct gatcgccgtg ggcctgctgc tttattgata  1620
ataggctgga gcctcggtgg ccatgcttct tgccccttgg gcctcccccc agcccctcct  1680
ccccttcctg cacccgtacc cccgtggtct ttgaataaag tctgagtggg cggcaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaa                   1844

SEQ ID NO: 71          moltype = DNA  length = 1542
FEATURE                Location/Qualifiers
source                 1..1542
                       mol_type = other DNA
                       organism = synthetic construct
SEQUENCE: 71
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagcctgcg gctctggcag cgcctgcgct tctggtgtcg ccgtgtctaa agtgctgcac  360
ctggaaggcg aagtgaacaa gatcaagagc gccctgctga gcaccaacaa ggccgtggtg  420
tctctgagcg gctgcggcgt gtccgtgctg accttcaagg tgctggacct gaagaactac  480
atcgacaaac agctgctgcc catcgtcaac aagcagtcct gcagcatccc caacatcgag  540
acagtgatcg agttccagca gaagaacaac cggctgctgg aaatcacccg cgagttctct  600
gtgaatgccg gcgtgaccac acctgtgtcc acctacatgc tgaccaacag cgagctgctg  660
agcctgatca acgacatgcc catcaccaac gaccagaaaa agctgatgag caacaacgtg  720
cagatcgtgc ggcagcagag ctacagcatc atgagcatta tcaaagaaga ggtgctggcc  780
tacgtggtgc agctgcctct gtatggcgtg atcgataccc cttgctggaa gctgcacaca  840
agccctctgt gcaccaccaa caccaaagag ggcagcaaca tctgcctgac cagaaccgac  900
agaggctggt actgcgataa tgccggcagc gtctcattct tcccacaagc cgagacatgc  960
aaggtgcaga gcaaccgggt gttctgcgac accatgaata gcagaaccct gccttccgaa  1020
gtgaatctgt gcaacgtgga catcttcaac cctaagtacg actgcaagat catgaccagc  1080
aagaccgacg tgtccagcag tgtgatcacc tcactgggcg ccatcgtgtc ctgttacggc  1140
aagaccaagt gcaccgccag caacaagtgc cggggcatca tcaagacctt cagcaacggc  1200
tgcgactacg tgtccaacaa aggcgtggac accgtgtctg tgggcaacac cctgtactac  1260
gtgaacaaac aagagggcca gtctctgtac gtgaagggcg agcccatcat caacttctac  1320
gaccctctgg tgttccccag cagcgagttc gatgccagca tcagccaagt gaacgagaag  1380
atcaatcaga gcctggcctt catcagaaag tccgatgagc tgctgcacaa cgtgaacgcc  1440
```

-continued

```
ggcaagtcca ccaccaatat catgatcacg accatcatca tcgtgattat cgtgatcctg  1500
ctgtccctga tcgccgtggg cctgctgctt tattgataat ag                     1542

SEQ ID NO: 72          moltype = AA  length = 511
FEATURE                Location/Qualifiers
source                 1..511
                       mol_type = protein
                       organism = synthetic construct
SEQUENCE: 72
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PACGSGSACA SGVAVSKVLH  120
LEGEVNKIKS ALLSTNKAVV SLSGCGVSVL TFKVLDLKNY IDKQLLPIVN KQSCSIPNIE  180
TVIEFQQKNN RLLEITREFS VNAGVTTPVS TYMLTNSELL SLINDMPITN DQKKLMSNNV  240
QIVRQQSYSI MSIIKEEVLA YVVQLPLYGV IDTPCWKLHT SPLCTTNTKE GSNICLTRTD  300
RGWYCDNAGS VSFFPQAETC KVQSNRVFCD TMNSRTLPSE VNLCNVDIFN PKYDCKIMTS  360
KTDVSSSVIT SLGAIVSCYG KTKCTASNKC RGIIKTFSNG CDYVSNKGVD TVSVGNTLYY  420
VNKQEGQSLY VKGEPIINFY DPLVFPSSEF DASISQVNEK INQSLAFIRK SDELLHNVNA  480
GKSTTNIMIT TIIIVIIVIL LSLIAVGLLL Y                                 511

SEQ ID NO: 73          moltype = RNA  length = 1844
FEATURE                Location/Qualifiers
source                 1..1844
                       mol_type = other RNA
                       organism = synthetic construct
SEQUENCE: 73
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagcctg cggctctggc agcgcctgcg cttctggtgt  420
cgccgtgtct aaagtgctgc acctggaagg cgaagtgaac aagatcaaga gcgccctgct  480
gagcaccaac aaggccgtgg tgtctctgag cggctgcggc gtgtccgtgc tgaccttcaa  540
ggtgctggac ctgaagaact acatcgacaa acagctgctg cccatcgtca acaagcagtc  600
ctgcagcatc cccaacatcg agacagtgat cgagttccag cagaagaaca accggctgct  660
ggaaatcacc cgcgagttct ctgtgaatgc cggcgtgacc acacctgtgt ccacctacat  720
gctgaccaac agcgagctgc tgagcctgat caacgacatg cccatcacca acgaccagaa  780
aaagctgatg agcaacaacg tgcagatcgt gcggcagcag agctacagca tcatgagcat  840
tatcaaagaa gaggtgctgg cctacgtggt gcagctgcct ctgtatggcg tgatcgatac  900
cccttgctgg aagctgcaca caagccctct gtgcaccacc aacaccaaag agggcagcaa  960
catctgcctg accagaaccg acagaggctg gtactgcgat aatgccggca gcgtctcatt  1020
cttcccacaa gccgagacat gcaaggtgca gagcaaccgg gtgttctgcg acaccatgaa  1080
tagcagaacc ctgccttccg aagtgaatct gtgcaacgtg gacatcttca accctaagta  1140
cgactgcaag atcatgacca gcaagaccga cgtgtccagc agtgtgatca cctcactggg  1200
cgccatcgtg tcctgttacg gcaagaccaa gtgcaccgcc agcaacaagt gccggggcat  1260
catcaagacc ttcagcaacg gctgcgacta cgtgtccaac aaaggcgtgg acaccgtgtc  1320
tgtgggcaac accctgtact acgtgaacaa acaagagggc cagtctctgt acgtgaaggg  1380
cgagcccatc atcaacttct acgaccctct ggtgttcccc agcagcgagt tcgatgccag  1440
catcagccaa gtgaacgaga agatcaatca gagcctggcc ttcatcagaa agtccgatga  1500
gctgctgcac aacgtgaacg ccggcaagtc caccaccaat atcatgatca cgaccatcat  1560
catcgtgatt atcgtgatcc tgctgtccct gatcgccgtg ggcctgctgc tttattgata  1620
ataggctgga gcctcggtgg ccatgcttct tgccccttgg gcctcccccc agcccctcct  1680
ccccttcctg cacccgtacc cccgtggtct ttgaataaag tctgagtggg cggcaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaa                   1844

SEQ ID NO: 74          moltype = DNA  length = 1841
FEATURE                Location/Qualifiers
source                 1..1841
                       mol_type = other DNA
                       organism = synthetic construct
SEQUENCE: 74
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatctgcg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
```

```
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggctgc tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 75          moltype = DNA  length = 1539
FEATURE                Location/Qualifiers
source                 1..1539
                       mol_type = other DNA
                       organism = synthetic construct
SEQUENCE: 75
atggaactgc tgatcctgaa ggccaacgcc atcaccacca tcctgaccgc cgtgaccttc  60
tgttttgcca gcggccagaa catctgcgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccct gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggctgctc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 76          moltype = AA  length = 510
FEATURE                Location/Qualifiers
source                 1..510
                       mol_type = protein
                       organism = synthetic construct
SEQUENCE: 76
MELLILKANA ITTILTAVTF CFASGQNICE EFYQSTCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGCSLYV KGEPIINFYD PLVFPSDEFD ASISQVNEKI NQSLAFIRKS DELLHNVNAG  480
KSTTNIMITT IIVIIVILL SLIAVGLLLY                                   510

SEQ ID NO: 77          moltype = RNA  length = 1841
FEATURE                Location/Qualifiers
source                 1..1841
                       mol_type = other RNA
                       organism = synthetic construct
SEQUENCE: 77
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatctgcg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
```

-continued

```
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggctgc tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 78          moltype = DNA  length = 1841
FEATURE                Location/Qualifiers
source                 1..1841
                       mol_type = other DNA
                       organism = synthetic construct
SEQUENCE: 78
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg agtgcttcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tcttgctacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 79          moltype = DNA  length = 1539
FEATURE                Location/Qualifiers
source                 1..1539
                       mol_type = other DNA
                       organism = synthetic construct
SEQUENCE: 79
atggaactgc tgatcctgaa ggccaacgcc atcaccacca tcctgaccgc cgtgaccttc  60
tgttttgcca gcggccagaa catcaccgag tgcttctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
```

```
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccct gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc ttgctacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 80          moltype = AA  length = 510
FEATURE                Location/Qualifiers
source                 1..510
                       mol_type = protein
                       organism = synthetic construct
SEQUENCE: 80
MELLILKANA ITTILTAVTF CFASGQNITE CFYQSTCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSCYV KGEPIINFYD PLVFPSDEFD ASISQVNEKI NQSLAFIRKS DELLHNVNAG  480
KSTTNIMITT IIVIIVILL SLIAVGLLLY                                   510

SEQ ID NO: 81          moltype = RNA  length = 1841
FEATURE                Location/Qualifiers
source                 1..1841
                       mol_type = other RNA
                       organism = synthetic construct
SEQUENCE: 81
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg agtgcttcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tcttgctacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 82          moltype = DNA  length = 1841
FEATURE                Location/Qualifiers
source                 1..1841
                       mol_type = other DNA
                       organism = synthetic construct
SEQUENCE: 82
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaatgcta  180
```

```
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc   900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtgcg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 83          moltype = DNA  length = 1539
FEATURE                Location/Qualifiers
source                 1..1539
                       mol_type = other DNA
                       organism = synthetic construct
SEQUENCE: 83
atggaactgc tgatcctgaa ggccaacgcc atcaccacca tcctgaccgc cgtgaccttc  60
tgttttgcca gcggccagaa catcaccgag gaatgctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtgcgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 84          moltype = AA  length = 510
FEATURE                Location/Qualifiers
source                 1..510
                       mol_type = protein
                       organism = synthetic construct
SEQUENCE: 84
MELLILKANA ITTILTAVTF CFASGQNITE ECYQSTCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLCV KGEPIINFYD PLVFPSDEFD ASISQVNEKI NQSLAFIRKS DELLHNVNAG  480
KSTTNIMITT IIVIIVILL SLIAVGLLLY                                    510

SEQ ID NO: 85          moltype = RNA  length = 1841
```

-continued

```
FEATURE                Location/Qualifiers
source                 1..1841
                       mol_type = other RNA
                       organism = synthetic construct
SEQUENCE: 85
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaatgcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtgcg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 86          moltype = DNA  length = 1841
FEATURE                Location/Qualifiers
source                 1..1841
                       mol_type = other DNA
                       organism = synthetic construct
SEQUENCE: 86
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgtgcggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 87          moltype = DNA  length = 1539
FEATURE                Location/Qualifiers
source                 1..1539
                       mol_type = other DNA
```

-continued

```
                         organism = synthetic construct
SEQUENCE: 87
atggaactgc tgatcctgaa ggccaacgcc atcaccacca tcctgaccgc cgtgaccttc  60
tgttttgcca gcggccagaa catcaccgag gaattctact gcagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg tgcggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                          1539

SEQ ID NO: 88            moltype = AA  length = 510
FEATURE                  Location/Qualifiers
source                   1..510
                         mol_type = protein
                         organism = synthetic construct
SEQUENCE: 88
MELLILKANA ITTILTAVTF CFASGQNITE EFYCSTCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV CGEPIINFYD PLVFPSDEFD ASISQVNEKI NQSLAFIRKS DELLHNVNAG  480
KSTTNIMITT IIIVIIVILL SLIAVGLLLY                                    510

SEQ ID NO: 89            moltype = RNA  length = 1841
FEATURE                  Location/Qualifiers
source                   1..1841
                         mol_type = other RNA
                         organism = synthetic construct
SEQUENCE: 89
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ctgcagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgtgcggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
```

```
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 90          moltype = DNA  length = 1841
FEATURE                Location/Qualifiers
source                 1..1841
                       mol_type = other DNA
                       organism = synthetic construct
SEQUENCE: 90
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagctgc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tcccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 91          moltype = DNA  length = 1539
FEATURE                Location/Qualifiers
source                 1..1539
                       mol_type = other DNA
                       organism = synthetic construct
SEQUENCE: 91
atggaactgc tgatcctgaa ggccaacgcc atcaccacca tcctgaccgc cgtgaccttc  60
tgttttgcca gcggccagaa catcaccgag gaattctacc agagctgctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagtgcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 92          moltype = AA  length = 510
FEATURE                Location/Qualifiers
source                 1..510
                       mol_type = protein
```

```
                        organism = synthetic construct
SEQUENCE: 92
MELLILKANA ITTILTAVTF CFASGQNITE EFYQSCCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KCEPIINFYD PLVFPSDEFD ASISQVNEKI NQSLAFIRKS DELLHNVNAG  480
KSTTNIMITT IIIVIIVILL SLIAVGLLLY                                 510

SEQ ID NO: 93           moltype = RNA  length = 1841
FEATURE                 Location/Qualifiers
source                  1..1841
                        mol_type = other RNA
                        organism = synthetic construct
SEQUENCE: 93
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagctgc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tcccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                    1841

SEQ ID NO: 94           moltype = DNA  length = 1841
FEATURE                 Location/Qualifiers
source                  1..1841
                        mol_type = other DNA
                        organism = synthetic construct
SEQUENCE: 94
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggctgc aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaactgcca agagggccag tctctgtacg tgaagggcga  1380
```

-continued

```
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tcccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 95          moltype = DNA  length = 1539
FEATURE                Location/Qualifiers
source                 1..1539
                       mol_type = other DNA
                       organism = synthetic construct
SEQUENCE: 95
atggaactgc tgatcctgaa ggccaacgcc atcaccacca tcctgaccgc cgtgaccttc  60
tgttttgcca gcggctgcaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccct gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aactgccaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 96          moltype = AA  length = 510
FEATURE                Location/Qualifiers
source                 1..510
                       mol_type = protein
                       organism = synthetic construct
SEQUENCE: 96
MELLILKANA ITTILTAVTF CFASGCNITE EFYQSTCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NCQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 97          moltype = RNA  length = 1841
FEATURE                Location/Qualifiers
source                 1..1841
                       mol_type = other RNA
                       organism = synthetic construct
SEQUENCE: 97
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggctgc aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
```

```
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaactgcca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 98          moltype = DNA  length = 1841
FEATURE                Location/Qualifiers
source                 1..1841
                       mol_type = other DNA
                       organism = synthetic construct
SEQUENCE: 98
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag tgcatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc   900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaatg cgagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 99          moltype = DNA  length = 1539
FEATURE                Location/Qualifiers
source                 1..1539
                       mol_type = other DNA
                       organism = synthetic construct
SEQUENCE: 99
atggaactgc tgatcctgaa ggccaacgcc atcaccacca tcctgaccgc cgtgaccttc  60
tgttttgcca gcggccagtg catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccoctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
```

```
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaatgcg agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 100         moltype = AA  length = 510
FEATURE                Location/Qualifiers
source                 1..510
                       mol_type = protein
                       organism = synthetic construct
SEQUENCE: 100
MELLILKANA ITTILTAVTF CFASGQCITE EFYQSTCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKCEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 101         moltype = RNA  length = 1841
FEATURE                Location/Qualifiers
source                 1..1841
                       mol_type = other RNA
                       organism = synthetic construct
SEQUENCE: 101
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag tgcatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaatg cgagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 102         moltype = DNA  length = 1841
FEATURE                Location/Qualifiers
source                 1..1841
                       mol_type = other DNA
                       organism = synthetic construct
SEQUENCE: 102
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgcctgctct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
```

-continued

```
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc   900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 103          moltype = DNA  length = 1539
FEATURE                 Location/Qualifiers
source                  1..1539
                        mol_type = other DNA
                        organism = synthetic construct
SEQUENCE: 103
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca cctgcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg cctgctctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccctt  gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 104          moltype = AA  length = 510
FEATURE                 Location/Qualifiers
source                  1..510
                        mol_type = protein
                        organism = synthetic construct
SEQUENCE: 104
MELLILKANA ITTILTAVTF CFASGQNITE EFYQSTCSAV SKGYLGALRT GWYTCVITIE  60
LSNIKENKCN GTDAKVKLIK QELDKYKNAV TDLQLLMQST PATGSGSAIA SGVACSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                   510

SEQ ID NO: 105          moltype = RNA  length = 1841
FEATURE                 Location/Qualifiers
source                  1..1841
                        mol_type = other RNA
                        organism = synthetic construct
SEQUENCE: 105
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
```

-continued

```
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgcctgctct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 106          moltype = DNA  length = 1841
FEATURE                 Location/Qualifiers
source                  1..1841
                        mol_type = other DNA
                        organism = synthetic construct
SEQUENCE: 106
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggtg  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
ctgcgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 107          moltype = DNA  length = 1539
FEATURE                 Location/Qualifiers
source                  1..1539
                        mol_type = other DNA
                        organism = synthetic construct
SEQUENCE: 107
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtgca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
```

```
ccagccacag gctctggcag cgccattgcc tctggtgtct gcgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539
```

```
SEQ ID NO: 108         moltype = AA  length = 510
FEATURE                Location/Qualifiers
source                 1..510
                       mol_type = protein
                       organism = synthetic construct
SEQUENCE: 108
MELLILKANA ITTILTAVTF CFASGQNITE EFYQSTCSAV SKGYLGALRT GWCTSVITIE  60
LSNIKENKCN GTDAKVKLIK QELDKYKNAV TDLQLLMQST PATGSGSAIA SGVCVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510
```

```
SEQ ID NO: 109         moltype = RNA  length = 1841
FEATURE                Location/Qualifiers
source                 1..1841
                       mol_type = other RNA
                       organism = synthetic construct
SEQUENCE: 109
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggtg  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
ctgcgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841
```

```
SEQ ID NO: 110         moltype = DNA  length = 1841
FEATURE                Location/Qualifiers
source                 1..1841
```

```
                        mol_type = other DNA
                        organism = synthetic construct
SEQUENCE: 110
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tgcgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc c  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 111          moltype = DNA  length = 1539
FEATURE                 Location/Qualifiers
source                  1..1539
                        mol_type = other DNA
                        organism = synthetic construct
SEQUENCE: 111
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca cctgcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtg cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccct gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 112          moltype = AA  length = 510
FEATURE                 Location/Qualifiers
source                  1..510
                        mol_type = protein
                        organism = synthetic construct
SEQUENCE: 112
MELLILKANA ITTILTAVTF CFASGQNITE EFYQSTCSAV SKGYLGALRT GWYTCVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVCVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
```

-continued

```
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                   510

SEQ ID NO: 113          moltype = RNA  length = 1841
FEATURE                 Location/Qualifiers
source                  1..1841
                        mol_type = other RNA
                        organism = synthetic construct
SEQUENCE: 113
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
cacctgcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tgcgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 114          moltype = DNA  length = 1841
FEATURE                 Location/Qualifiers
source                  1..1841
                        mol_type = other DNA
                        organism = synthetic construct
SEQUENCE: 114
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
ctgcagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggttg  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
```

-continued

```
aaaaaaaaaa aaaaaaaaaa aaaaaaaaaa aaaaaaaaaa a                      1841

SEQ ID NO: 115          moltype = DNA  length = 1539
FEATURE                 Location/Qualifiers
source                  1..1539
                        mol_type = other DNA
                        organism = synthetic construct
SEQUENCE: 115
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtact gcagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggttgcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 116          moltype = AA  length = 510
FEATURE                 Location/Qualifiers
source                  1..510
                        mol_type = protein
                        organism = synthetic construct
SEQUENCE: 116
MELLILKANA ITTILTAVTF CFASGQNITE EFYQSTCSAV SKGYLGALRT GWYCSVITIE  60
LSNIKENKCN GTDAKVKLIK QELDKYKNAV TDLQLLMQST PATGSGSAIA SGCAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                   510

SEQ ID NO: 117          moltype = RNA  length = 1841
FEATURE                 Location/Qualifiers
source                  1..1841
                        mol_type = other RNA
                        organism = synthetic construct
SEQUENCE: 117
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
ctgcagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggttg  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
```

-continued

```
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 118          moltype = DNA  length = 1841
FEATURE                 Location/Qualifiers
source                  1..1841
                        mol_type = other DNA
                        organism = synthetic construct
SEQUENCE: 118
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
ctgcagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
ctgcgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 119          moltype = DNA  length = 1539
FEATURE                 Location/Qualifiers
source                  1..1539
                        mol_type = other DNA
                        organism = synthetic construct
SEQUENCE: 119
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtact gcagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtct gcgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
```

```
tccctgatcg ccgtgggcct gctgctttat tgataatag                        1539

SEQ ID NO: 120          moltype = AA  length = 510
FEATURE                 Location/Qualifiers
source                  1..510
                        mol_type = protein
                        organism = synthetic construct
SEQUENCE: 120
MELLILKANA ITTILTAVTF CFASGQNITE EFYQSTCSAV SKGYLGALRT GWYCSVITIE  60
LSNIKENKCN GTDAKVKLIK QELDKYKNAV TDLQLLMQST PATGSGSAIA SGVCVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 121          moltype = RNA  length = 1841
FEATURE                 Location/Qualifiers
source                  1..1841
                        mol_type = other RNA
                        organism = synthetic construct
SEQUENCE: 121
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
ctgcagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
ctgcgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 122          moltype = DNA  length = 1841
FEATURE                 Location/Qualifiers
source                  1..1841
                        mol_type = other DNA
                        organism = synthetic construct
SEQUENCE: 122
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtgcaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc  900
ttgctggaag ctgcacacat gccctctgtg caccaccaac accaaagagg gcagcaacat  960
ctgcctgacc agaaccgaca gaggctggta ctgcgataat gccggcagcg tctcattctt  1020
```

```
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 123          moltype = DNA  length = 1539
FEATURE                 Location/Qualifiers
source                  1..1539
                        mol_type = other DNA
                        organism = synthetic construct
SEQUENCE: 123
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tgcaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccct gctggaagct gcacacatgc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 124          moltype = AA  length = 510
FEATURE                 Location/Qualifiers
source                  1..510
                        mol_type = protein
                        organism = synthetic construct
SEQUENCE: 124
MELLILKANA ITTILTAVTF CFASGQNITE EFYQSTCSAV CKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTC PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 125          moltype = RNA  length = 1841
FEATURE                 Location/Qualifiers
source                  1..1841
                        mol_type = other RNA
                        organism = synthetic construct
SEQUENCE: 125
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtgcaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
```

```
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacat gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 126         moltype = DNA  length = 1841
FEATURE                Location/Qualifiers
source                 1..1841
                       mol_type = other DNA
                       organism = synthetic construct
SEQUENCE: 126
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atgcctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacat gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 127         moltype = DNA  length = 1539
FEATURE                Location/Qualifiers
source                 1..1539
                       mol_type = other DNA
                       organism = synthetic construct
SEQUENCE: 127
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat gcctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
```

```
atcgtgcggc agcagagcta cagcatcatg agcattatca aagaagaggt gctggcctac  780
gtggtgcagc tgcctctgta tggcgtgatc gataccccctt gctggaagct gcacacatgc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 128         moltype = AA  length = 510
FEATURE                Location/Qualifiers
source                 1..510
                       mol_type = protein
                       organism = synthetic construct
SEQUENCE: 128
MELLILKANA ITTILTAVTF CFASGQNITE EFYQSTCSAV SKGCLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTC PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIVIIVILL SLIAVGLLLY                                   510

SEQ ID NO: 129         moltype = RNA  length = 1841
FEATURE                Location/Qualifiers
source                 1..1841
                       mol_type = other RNA
                       organism = synthetic construct
SEQUENCE: 129
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atgcctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacat gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 130         moltype = DNA  length = 1841
FEATURE                Location/Qualifiers
source                 1..1841
                       mol_type = other DNA
                       organism = synthetic construct
SEQUENCE: 130
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
```

-continued

```
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtctt gcccagccac aggctctggc agcgccattg cctgcggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 131         moltype = DNA  length = 1539
FEATURE                Location/Qualifiers
source                 1..1539
                       mol_type = other DNA
                       organism = synthetic construct
SEQUENCE: 131
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtcttgc  300
ccagccacag gctctggcag cgccattgcc tgcggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 132         moltype = AA  length = 510
FEATURE                Location/Qualifiers
source                 1..510
                       mol_type = protein
                       organism = synthetic construct
SEQUENCE: 132
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQSC PATGSGSAIA CGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                   510

SEQ ID NO: 133         moltype = RNA  length = 1841
FEATURE                Location/Qualifiers
```

```
source                  1..1841
                        mol_type = other RNA
                        organism = synthetic construct
SEQUENCE: 133
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtctt gcccagccac aggctctggc agcgccattg cctgcggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 134          moltype = DNA  length = 1841
FEATURE                 Location/Qualifiers
source                  1..1841
                        mol_type = other DNA
                        organism = synthetic construct
SEQUENCE: 134
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtctt gcccagccac aggctctggc agcgccattt gctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 135          moltype = DNA  length = 1539
FEATURE                 Location/Qualifiers
source                  1..1539
                        mol_type = other DNA
                        organism = synthetic construct
```

```
SEQUENCE: 135
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtcttgc  300
ccagccacag gctctggcag cgccatttgc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 136         moltype = AA  length = 510
FEATURE                Location/Qualifiers
source                 1..510
                       mol_type = protein
                       organism = synthetic construct
SEQUENCE: 136
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQSC PATGSGSAIC SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIVIIVILL SLIAVGLLLY                                   510

SEQ ID NO: 137         moltype = RNA  length = 1841
FEATURE                Location/Qualifiers
source                 1..1841
                       mol_type = other RNA
                       organism = synthetic construct
SEQUENCE: 137
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtctt gcccagccac aggctctggc agcgccattt gctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tcccccagc ccctcctccc  1680
cttcctgcac ccgtaccccc gtggtctttg aataaagtct gagtgggcgg caaaaaaaaa  1740
```

```
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 138         moltype = DNA  length = 1841
FEATURE                Location/Qualifiers
source                 1..1841
                       mol_type = other DNA
                       organism = synthetic construct
SEQUENCE: 138
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtctt gcccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct actgcgtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 139         moltype = DNA  length = 1539
FEATURE                Location/Qualifiers
source                 1..1539
                       mol_type = other DNA
                       organism = synthetic construct
SEQUENCE: 139
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtcttgc  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
tgcgtgcagc tgcctctgta tggcgtgatc gataccccct gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 140         moltype = AA  length = 510
FEATURE                Location/Qualifiers
source                 1..510
                       mol_type = protein
                       organism = synthetic construct
```

```
SEQUENCE: 140
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQSC PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY CVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                 510

SEQ ID NO: 141          moltype = RNA  length = 1841
FEATURE                 Location/Qualifiers
source                  1..1841
                        mol_type = other RNA
                        organism = synthetic construct
SEQUENCE: 141
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtctt gcccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct actgcgtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 142          moltype = DNA  length = 1871
FEATURE                 Location/Qualifiers
source                  1..1871
                        mol_type = other DNA
                        organism = synthetic construct
SEQUENCE: 142
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttctgcg gctttctgct  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct actgcgtgca  900
gctgcctctg tatggcgtga tcgatacccc ttgctggaag ctgcacacaa gccctctgtg  960
caccaccaac accaaagagg gcagcaacat ctgcctgacc agatgcgaca gaggctggta  1020
ctgcgataat gccggcagcg tctcattctt cccacaagcc gagacatgca aggtgcagag  1080
caaccgggtg ttctgcgaca ccatgaatag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
```

-continued

```
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 143          moltype = DNA  length = 1569
FEATURE                 Location/Qualifiers
source                  1..1569
                        mol_type = other DNA
                        organism = synthetic construct
SEQUENCE: 143
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggctc tttctgcggc tttctgctcg gagtgggcag cgccattgcc  360
tctggtgtcg ccgtgtctaa agtgctgcac ctggaaggcg aagtgaacaa gatcaagagc  420
gccctgctga gcaccaacaa ggccgtggtg tctctgagca atggcgtgtc cgtgctgacc  480
ttcaaggtgc tggacctgaa gaactacatc gacaaacagc tgctgcccat cctgaacaag  540
cagtcctgca gcatccccaa catcgagaca gtgatcgagt tccagcagaa gaacaaccgg  600
ctgctggaaa tcacccgcga gttctctgtg aatgccggcg tgaccacacc tgtgtccacc  660
tacatgctga ccaacagcga gctgctgagc ctgatcaacg acatgcccat caccaacgac  720
cagaaaaagc tgatgagcaa caacgtgcag atcgtgcggc agcagagcta cagcatcatg  780
agcattatca aagaagaggt gctggcctac gtggtgcagc tgcctctgta tggcgtgatc  840
gataccccctt gctggaagct gcacacaagc cctctgtgca ccaccaacac caaagagggc  900
agcaacatct gcctgaccag atgcgacaga ggctggtact gcgataatgc cggcagcgtc  960
tcattcttcc cacaagccga gacatgcaag gtgcagagca accgggtgtt ctgcgacacc  1020
atgaatagca gaaccctgcc ttccgaagtg aatctgtgca acgtggacat cttcaaccct  1080
aagtacgact gcaagatcat gaccagcaag accgacgtgt ccagcagtgt gatcacctca  1140
ctgggcgcca tcgtgtcctg ttacggcaag accaagtgca ccgccagcaa caagaaccgg  1200
ggcatcatca agaccttcag caacggctgc gactacgtgt ccaacaaagg cgtggacacc  1260
gtgtctgtgg gcaacaccct gtactacgtg aacaaacaag agggccagtc tctgtacgtg  1320
aagggcgagc ccatcatcaa cttctacgac cctctggtgt tccccagcga cgagttcgat  1380
gccagcatca gccaagtgaa cgagaagatc aatcagagcc tggccttcat cagaaagtcc  1440
gatgagctgc tgcacaacgt gaacgccggc aagtccacca ccaatatcat gatcacgacc  1500
atcatcatcg tgattatcgt gatcctgctg tccctgatcg ccgtgggcct gctgctttat  1560
tgataatag                                                          1569

SEQ ID NO: 144          moltype = AA  length = 520
FEATURE                 Location/Qualifiers
source                  1..520
                        mol_type = protein
                        organism = synthetic construct
SEQUENCE: 144
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSFCG FLLGVGSAIA  120
SGVAVSKVLH LEGEVNKIKS ALLSTNKAVV SLSNGVSVLT FKVLDLKNYI DKQLLPILNK  180
QSCSIPNIET VIEFQQKNNR LLEITREFSV NAGVTTPVST YMLTNSELLS LINDMPITND  240
QKKLMSNNVQ IVRQQSYSIM SIIKEEVLAY VVQLPLYGVI DTPCWKLHTS PLCTTNTKEG  300
SNICLTRCDR GWYCDNAGSV SFFPQAETCK VQSNRVFCDT MNSRTLPSEV NLCNVDIFNP  360
KYDCKIMTSK TDVSSSVITS LGAIVSCYGK TKCTASNKNR GIIKTFSNGC DYVSNKGVDT  420
VSVGNTLYYV NKQEGQSLYV KGEPIINFYD PLVFPSDEFD ASISQVNEKI NQSLAFIRKS  480
DELLHNVNAG KSTTNIMITT IIVIIVILL SLIAVGLLLY                         520

SEQ ID NO: 145          moltype = RNA  length = 1871
FEATURE                 Location/Qualifiers
source                  1..1871
                        mol_type = other RNA
                        organism = synthetic construct
SEQUENCE: 145
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttctgcg gctttctgct  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
```

-continued

```
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agatgcgaca gaggctggta  1020
ctgcgataat gccggcagcg tctcattctt cccacaagcc gagacatgca aggtgcagag  1080
caaccgggtg ttctgcgaca ccatgaatag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 146          moltype = DNA  length = 1871
FEATURE                 Location/Qualifiers
source                  1..1871
                        mol_type = other DNA
                        organism = synthetic construct
SEQUENCE: 146
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttcctgt gctttctgct  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agaaccgaca gaggctggta  1020
ctgcgataat gccggcagcg tctcattctt cccatgcgcc gagacatgca aggtgcagag  1080
caaccgggtg ttctgcgaca ccatgaatag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 147          moltype = DNA  length = 1569
FEATURE                 Location/Qualifiers
source                  1..1569
                        mol_type = other DNA
                        organism = synthetic construct
SEQUENCE: 147
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggctc tttcctgtgc tttctgctcg gagtgggcag cgccattgcc  360
tctggtgtcg ccgtgtctaa agtgctgcac ctggaaggcg aagtgaacaa gatcaagagc  420
gccctgctga gcaccaacaa ggccgtggtg tctctgagca atggcgtgtc cgtgctgacc  480
ttcaaggtgc tggacctgaa gaactacatc gacaaacagc tgctgcccat cctgaacaag  540
cagtcctgca gcatccccaa catcgagaca gtgatcgagt tccagcagaa gaacaaccgg  600
ctgctggaaa tcacccgcga gttctctgtg aatgccggcg tgaccacacc tgtgtccacc  660
tacatgctga ccaacagcga gctgctgagc ctgatcaacg acatgcccat caccaacgac  720
cagaaaaagc tgatgagcaa caacgtgcag atcgtgcggc agcagagcta cagcatcatg  780
agcattatca aagaagaggt gctggcctac gtggtgcagc tgcctctgta tggcgtgatc  840
gataccccct gctggaagct gcacacaagc cctctgtgca ccaccaacac caaagagggc  900
```

```
agcaacatct gcctgaccag aaccgacaga ggctggtact gcgataatgc cggcagcgtc  960
tcattcttcc catgcgccga gacatgcaag gtgcagagca accgggtgtt ctgcgacacc  1020
atgaatagca gaaccctgcc ttccgaagtg aatctgtgca acgtggacat cttcaaccct  1080
aagtacgact gcaagatcat gaccagcaag accgacgtgt ccagcagtgt gatcacctca  1140
ctgggcgcca tcgtgtcctg ttacggcaag accaagtgca ccgccagcaa caagaaccgg  1200
ggcatcatca agaccttcag caacggctgc gactacgtgt ccaacaaagg cgtggacacc  1260
gtgtctgtgg gcaacaccct gtactacgtg aacaaacaag agggccagtc tctgtacgtg  1320
aagggcgagc ccatcatcaa cttctacgac cctctggtgt tccccagcga cgagttcgat  1380
gccagcatca gccaagtgaa cgagaagatc aatcagagcc tggccttcat cagaaagtcc  1440
gatgagctgc tgcacaacgt gaacgccggc aagtccacca ccaatatcat gatcacgacc  1500
atcatcatcg tgattatcgt gatcctgctg tccctgatcg ccgtgggcct gctgctttat  1560
tgataatag                                                          1569

SEQ ID NO: 148         moltype = AA  length = 520
FEATURE                Location/Qualifiers
source                 1..520
                       mol_type = protein
                       organism = synthetic construct
SEQUENCE: 148
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSFLC FLLGVGSAIA  120
SGVAVSKVLH LEGEVNKIKS ALLSTNKAVV SLSNGVSVLT FKVLDLKNYI DKQLLPILNK  180
QSCSIPNIET VIEFQQKNNR LLEITREFSV NAGVTTPVST YMLTNSELLS LINDMPITND  240
QKKLMSNNVQ IVRQQSYSIM SIIKEEVLAY VVQLPLYGVI DTPCWKLHTS PLCTTNTKEG  300
SNICLTRTDR GWYCDNAGSV SFFPCAETCK VQSNRVFCDT MNSRTLPSEV NLCNVDIFNP  360
KYDCKIMTSK TDVSSSVITS LGAIVSCYGK TKCTASNKNR GIIKTFSNGC DYVSNKGVDT  420
VSVGNTLYYV NKQEGQSLYV KGEPIINFYD PLVFPSDEFD ASISQVNEKI NQSLAFIRKS  480
DELLHNVNAG KSTTNIMITT IIIVIIVILL SLIAVGLLLY                        520

SEQ ID NO: 149         moltype = RNA  length = 1871
FEATURE                Location/Qualifiers
source                 1..1871
                       mol_type = other RNA
                       organism = synthetic construct
SEQUENCE: 149
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttcctgt gctttctgct  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agaaccgaca gaggctggta  1020
ctgcgataat gccggcagcg tctcattctt cccatgcgcc gagacatgca aggtgcagag  1080
caaccgggtg ttctgcgaca ccatgaatag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 150         moltype = DNA  length = 1871
FEATURE                Location/Qualifiers
source                 1..1871
                       mol_type = other DNA
                       organism = synthetic construct
SEQUENCE: 150
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
```

-continued

```
cgccaaagtg aagctgatca agcaagagct ggacaagtac aagaatgccg tgaccgacct  360
gcagctgctg atgcagtcta caccagccac aggctctggc tctttcctgg gctttctgtg  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agaaccgaca gaggctggta  1020
ctgcgataat gccggcagcg tctcattctt ccccacaagcc gagacatgca aggtgcagag  1080
caaccgggtg ttctgcgaca ccatgtgcag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 151         moltype = DNA  length = 1569
FEATURE                Location/Qualifiers
source                 1..1569
                       mol_type = other DNA
                       organism = synthetic construct
SEQUENCE: 151
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggctc tttcctgggc tttctgtgcg gagtgggcag cgccattgcc  360
tctggtgtcg ccgtgtctaa agtgctgcac ctggaaggcg aagtgaacaa gatcaagagc  420
gccctgctga gcaccaacaa ggccgtggtg tctctgagca atggcgtgtc cgtgctgacc  480
ttcaaggtgc tggacctgaa gaactacatc gacaaacagc tgctgcccat cctgaacaag  540
cagtcctgca gcatccccaa catcgagaca gtgatcgagt tccagcagaa gaacaaccgg  600
ctgctggaaa tcacccgcga gttctctgtg aatgccggcg tgaccacacc tgtgtccacc  660
tacatgctga ccaacagcga gctgctgagc ctgatcaacg acatgcccat caccaacgac  720
cagaaaaagc tgatgagcaa caacgtgcag atcgtgcggc agcagagcta cagcatcatg  780
agcattatca aagaagaggt gctggcctac gtggtgcagc tgcctctgta tggcgtgatc  840
gatacccctt gctggaagct gcacacaagc cctctgtgca ccaccaacac caaagagggc  900
agcaacatct gcctgaccag aaccgacaga ggctggtact gcgataatgc cggcagcgtc  960
tcattcttcc cacaagccga gacatgcaag gtgcagagca accgggtgtt ctgcgacacc  1020
atgtgcagca gaaccctgcc ttccgaagtg aatctgtgca acgtggacat cttcaaccct  1080
aagtacgact gcaagatcat gaccagcaag accgacgtgt ccagcagtgt gatcacctca  1140
ctgggcgcca tcgtgtcctg ttacggcaag accaagtgca ccgccagcaa caagaaccgg  1200
ggcatcatca agaccttcag caacggctgc gactacgtgt ccaacaaagg cgtggacacc  1260
gtgtctgtgg gcaacaccct gtactacgtg aacaaacaag agggccagtc tctgtacgtg  1320
aagggcgagc ccatcatcaa cttctacgac cctctggtgt tccccagcga cgagttcgat  1380
gccagcatca gccaagtgaa cgagaagatc aatcagagcc tggccttcat cagaaagtcc  1440
gatgagctgc tgcacaacgt gaacgccggc aagtccacca ccaatatcat gatcacgacc  1500
atcatcatcg tgattatcgt gatcctgctg tccctgatcg ccgtgggcct gctgctttat  1560
tgataatag                                                          1569

SEQ ID NO: 152         moltype = AA  length = 520
FEATURE                Location/Qualifiers
source                 1..520
                       mol_type = protein
                       organism = synthetic construct
SEQUENCE: 152
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSFLG FLCGVGSAIA  120
SGVAVSKVLH LEGEVNKIKS ALLSTNKAVV SLSNGVSVLT FKVLDLKNYI DKQLLPILNK  180
QSCSIPNIET VIEFQQKNNR LLEITREFSV NAGVTTPVST YMLTNSELLS LINDMPITND  240
QKKLMSNNVQ IVRQQSYSIM SIIKEEVLAY VVQLPLYGVI DTPCWKLHTS PLCTTNTKEG  300
SNICLTRTDR GWYCDNAGSV SFFPQAETCK VQSNRVFCDT MCSRTLPSEV NLCNVDIFNP  360
KYDCKIMTSK TDVSSSVITS LGAIVSCYGK TKCTASNKNR GIIKTFSNGC DYVSNKGVDT  420
VSVGNTLYYV NKQEGQSLYV KGEPIINFYD PLVFPSDEFD ASISQVNEKI NQSLAFIRKS  480
DELLHNVNAG KSTTNIMITT IIIVIIVILL SLIAVGLLLY                        520

SEQ ID NO: 153         moltype = RNA  length = 1871
```

```
FEATURE                Location/Qualifiers
source                 1..1871
                       mol_type = other RNA
                       organism = synthetic construct
SEQUENCE: 153
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttcctgg gctttctgtg  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agaaccgaca gaggctggta  1020
ctgcgataat gccggcagcg tctcattctt cccacaagcc gagacatgca aggtgcagag  1080
caaccgggtg ttctgcgaca ccatgtgcag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 154         moltype = DNA  length = 1871
FEATURE                Location/Qualifiers
source                 1..1871
                       mol_type = other DNA
                       organism = synthetic construct
SEQUENCE: 154
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttcctgg gctttctgct  420
cggagtgtgc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agaaccgaca gaggctggta  1020
ctgcgataat gccggcagcg tctcattctt cccacaagcc gagacatgca aggtgcagag  1080
caaccgggtg ttctgcgaca cctgcaatag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 155         moltype = DNA  length = 1569
FEATURE                Location/Qualifiers
```

```
source                  1..1569
                        mol_type = other DNA
                        organism = synthetic construct
SEQUENCE: 155
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggctc tttcctgggc tttctgctcg gagtgtgcag cgccattgcc  360
tctggtgtcg ccgtgtctaa agtgctgcac ctggaaggcg aagtgaacaa gatcaagagc  420
gccctgctga gcaccaacaa ggccgtggtg tctctgagca atggcgtgtc cgtgctgacc  480
ttcaaggtgc tggacctgaa gaactacatc gacaaacagc tgctgcccat cctgaacaag  540
cagtcctgca gcatccccaa catcgagaca gtgatcgagt tccagcagaa gaacaaccgg  600
ctgctggaaa tcacccgcga gttctctgtg aatgccggcg tgaccacacc tgtgtccacc  660
tacatgctga ccaacagcga gctgctgagc ctgatcaacg acatgcccat caccaacgac  720
cagaaaaagc tgatgagcaa caacgtgcag atcgtgcggc agcagagcta cagcatcatg  780
agcattatca aagaagaggt gctggcctac gtggtgcagc tgcctctgta tggcgtgatc  840
gataccccctt gctggaagct gcacacaagc cctctgtgca ccaccaacac caaagagggc  900
agcaacatct gcctgaccag aaccgacaga ggctggtact gcgataatgc cggcagcgtc  960
tcattcttcc cacaagccga gacatgcaag gtgcagagca accgggtgtt ctgcgacacc  1020
tgcaatagca gaaccctgcc ttccgaagtg aatctgtgca acgtggacat cttcaaccct  1080
aagtacgact gcaagatcat gaccagcaag accgacgtgt ccagcagtgt gatcacctca  1140
ctgggcgcca tcgtgtcctg ttacggcaag accaagtgca ccgccagcaa caagaaccgg  1200
ggcatcatca agaccttcag caacggctgc gactacgtgt ccaacaaagg cgtggacacc  1260
gtgtctgtgg gcaacaccct gtactacgtg aacaaacaag agggccagtc tctgtacgtg  1320
aagggcgagc ccatcatcaa cttctacgac cctctggtgt tccccagcga cgagttcgat  1380
gccagcatca gccaagtgaa cgagaagatc aatcagagcc tggccttcat cagaaagtcc  1440
gatgagctgc tgcacaacgt gaacgccggc aagtccacca ccaatatcat gatcacgacc  1500
atcatcatcg tgattatcgt gatcctgctg tccctgatcg ccgtgggcct gctgctttat  1560
tgataatag                                                         1569

SEQ ID NO: 156          moltype = AA  length = 520
FEATURE                 Location/Qualifiers
source                  1..520
                        mol_type = protein
                        organism = synthetic construct
SEQUENCE: 156
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSFLG FLLGVCSAIA  120
SGVAVSKVLH LEGEVNKIKS ALLSTNKAVV SLSNGVSVLT FKVLDLKNYI DKQLLPILNK  180
QSCSIPNIET VIEFQQKNNR LLEITREFSV NAGVTTPVST YMLTNSELLS LINDMPITND  240
QKKLMSNNVQ IVRQQSYSIM SIIKEEVLAY VVQLPLYGVI DTPCWKLHTS PLCTTNTKEG  300
SNICLTRTDR GWYCDNAGSV SFFPQAETCK VQSNRVFCDT CNSRTLPSEV NLCNVDIFNP  360
KYDCKIMTSK TDVSSSVITS LGAIVSCYGK TKCTASNKNR GIIKTFSNGC DYVSNKGVDT  420
VSVGNTLYYV NKQEGQSLYV KGEPIINFYD PLVFPSDEFD ASISQVNEKI NQSLAFIRKS  480
DELLHNVNAG KSTTNIMITT IIIVIIVILL SLIAVGLLLY                       520

SEQ ID NO: 157          moltype = RNA  length = 1871
FEATURE                 Location/Qualifiers
source                  1..1871
                        mol_type = other RNA
                        organism = synthetic construct
SEQUENCE: 157
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttcctgg gctttctgct  420
cggagtgtgc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agaaccgaca gaggctggta  1020
ctgcgataat gccggcagcg tctcattctt cccacaagcc gagacatgca aggtgcagag  1080
caaccgggtg ttctgcgaca cctgcaatag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
```

```
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 158          moltype = DNA  length = 1871
FEATURE                 Location/Qualifiers
source                  1..1871
                        mol_type = other DNA
                        organism = synthetic construct
SEQUENCE: 158
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttcctgg gcttttgcct  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agaaccgaca gaggctggta  1020
ctgcgataat gccggcagcg tctcattctt cccacaagcc gagacatgca aggtgcagag  1080
caaccgggtg ttctgcgaca ccatgtgcag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 159          moltype = DNA  length = 1569
FEATURE                 Location/Qualifiers
source                  1..1569
                        mol_type = other DNA
                        organism = synthetic construct
SEQUENCE: 159
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggctc tttcctgggc ttttgcctcg gagtgggcag cgccattgcc  360
tctggtgtcg ccgtgtctaa agtgctgcac ctggaaggcg aagtgaacaa gatcaagagc  420
gccctgctga gcaccaacaa ggccgtggtg tctctgagca atggcgtgtc cgtgctgacc  480
ttcaaggtgc tggacctgaa gaactacatc gacaaacagc tgctgcccat cctgaacaag  540
cagtcctgca gcatccccaa catcgagaca gtgatcgagt tccagcagaa gaacaaccgg  600
ctgctggaaa tcacccgcga gttctctgtg aatgccggcg tgaccacacc tgtgtccacc  660
tacatgctga ccaacagcga gctgctgagc ctgatcaacg acatgcccat caccaacgac  720
cagaaaaagc tgatgagcaa caacgtgcag atcgtgcggc agcagagcta cagcatcatg  780
agcattatca aagaagaggt gctggcctac gtggtgcagc tgcctctgta tggcgtgatc  840
gatacccctt gctggaagct gcacacaagc cctctgtgca ccaccaacac caaagagggc  900
agcaacatct gcctgaccag aaccgacaga ggctggtact gcgataatgc cggcagcgtc  960
tcattcttcc cacaagccga gacatgcaag gtgcagagca accgggtgtt ctgcgacacc  1020
atgtgcagca gaaccctgcc ttccgaagtg aatctgtgca acgtggacat cttcaaccct  1080
aagtacgact gcaagatcat gaccagcaag accgacgtgt ccagcagtgt gatcacctca  1140
ctgggcgcca tcgtgtcctg ttacggcaag accaagtgca ccgccagcaa caagaaccgg  1200
ggcatcatca agaccttcag caacggctgc gactacgtgt ccaacaaagg cgtggacacc  1260
gtgtctgtgg gcaacaccct gtactacgtg aacaaacaag agggccagtc tctgtacgtg  1320
aagggcgagc ccatcatcaa cttctacgac cctctggtgt tccccagcga cgagttcgat  1380
gccagcatca gccaagtgaa cgagaagatc aatcagagcc tggccttcat cagaaagtcc  1440
gatgagctgc tgcacaacgt gaacgccggc aagtccacca ccaatatcat gatcacgacc  1500
atcatcatcg tgattatcgt gatcctgctg tccctgatcg ccgtgggcct gctgctttat  1560
```

-continued

```
tgataatag                                                          1569

SEQ ID NO: 160          moltype = AA  length = 520
FEATURE                 Location/Qualifiers
source                  1..520
                        mol_type = protein
                        organism = synthetic construct
SEQUENCE: 160
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSFLG FCLGVGSAIA  120
SGVAVSKVLH LEGEVNKIKS ALLSTNKAVV SLSNGVSVLT FKVLDLKNYI DKQLLPILNK  180
QSCSIPNIET VIEFQQKNNR LLEITREFSV NAGVTTPVST YMLTNSELLS LINDMPITND  240
QKKLMSNNVQ IVRQQSYSIM SIIKEEVLAY VVQLPLYGVI DTPCWKLHTS PLCTTNTKEG  300
SNICLTRTDR GWYCDNAGSV SFFPQAETCK VQSNRVFCDT MCSRTLPSEV NLCNVDIFNP  360
KYDCKIMTSK TDVSSSVITS LGAIVSCYGK TKCTASNKNR GIIKTFSNGC DYVSNKGVDT  420
VSVGNTLYYV NKQEGQSLYV KGEPIINFYD PLVFPSDEFD ASISQVNEKI NQSLAFIRKS  480
DELLHNVNAG KSTTNIMITT IIIVIIVILL SLIAVGLLLY                        520

SEQ ID NO: 161          moltype = RNA  length = 1871
FEATURE                 Location/Qualifiers
source                  1..1871
                        mol_type = other RNA
                        organism = synthetic construct
SEQUENCE: 161
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttcctgg gcttttgcct  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agaaccgaca gaggctggta  1020
ctgcgataat gccggcagcg tctcattctt cccacaagcc gagacatgca aggtgcagag  1080
caaccgggtg ttctgcgaca ccatgtgcag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 162          moltype = DNA  length = 1871
FEATURE                 Location/Qualifiers
source                  1..1871
                        mol_type = other DNA
                        organism = synthetic construct
SEQUENCE: 162
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tctttcctgg gctgcctgct  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
```

-continued

```
caccaccaac accaaagagg gcagcaacat ctgcctgacc agaaccgaca gaggctggta  1020
ctgcgataat gccggcagcg tctcattctt cccacaagcc gagacatgca aggtgcagag  1080
caaccgggtg ttctgcgact gcatgaatag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871

SEQ ID NO: 163          moltype = DNA  length = 1569
FEATURE                 Location/Qualifiers
source                  1..1569
                        mol_type = other DNA
                        organism = synthetic construct
SEQUENCE: 163
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggctc tttcctgggc tgcctgctcg gagtgggcag cgccattgcc  360
tctggtgtcg ccgtgtctaa agtgctgcac ctggaaggcg aagtgaacaa gatcaagagc  420
gccctgctga gcaccaacaa ggccgtggtg tctctgagca atggcgtgtc cgtgctgacc  480
ttcaaggtgc tggacctgaa gaactacatc gacaaacagc tgctgcccat cctgaacaag  540
cagtcctgca gcatccccaa catcgagaca gtgatcgagt tccagcagaa gaacaaccgg  600
ctgctggaaa tcacccgcga gttctctgtg aatgccggcg tgaccacacc tgtgtccacc  660
tacatgctga ccaacagcga gctgctgagc ctgatcaacg acatgcccat caccaacgac  720
cagaaaaagc tgatgagcaa caacgtgcag atcgtgcggc agcagagcta cagcatcatg  780
agcattatca aagaagaggt gctggcctac gtggtgcagc tgcctctgta tggcgtgatc  840
gataccccctt gctggaagct gcacacaagc cctctgtgca ccaccaacac caaagagggc  900
agcaacatct gcctgaccag aaccgacaga ggctggtact gcgataatgc cggcagcgtc  960
tcattcttcc cacaagccga gacatgcaag gtgcagagca accgggtgtt ctgcgactgc  1020
atgaatagca gaaccctgcc ttccgaagtg aatctgtgca acgtggacat cttcaaccct  1080
aagtacgact gcaagatcat gaccagcaag accgacgtgt ccagcagtgt gatcacctca  1140
ctgggcgcca tcgtgtcctg ttacggcaag accaagtgca ccgccagcaa caagaaccgg  1200
ggcatcatca agaccttcag caacggctgc gactacgtgt ccaacaaagg cgtggacacc  1260
gtgtctgtgg gcaacaccct gtactacgtg aacaaacaag agggccagtc tctgtacgtg  1320
aagggcgagc ccatcatcaa cttctacgac cctctggtgt tccccagcga cgagttcgat  1380
gccagcatca gccaagtgaa cgagaagatc aatcagagcc tggccttcat cagaaagtcc  1440
gatgagctgc tgcacaacgt gaacgccggc aagtccacca ccaatatcat gatcacgacc  1500
atcatcatcg tgattatcgt gatcctgctg tccctgatcg ccgtgggcct gctgctttat  1560
tgataatag                                                         1569

SEQ ID NO: 164          moltype = AA  length = 520
FEATURE                 Location/Qualifiers
source                  1..520
                        mol_type = protein
                        organism = synthetic construct
SEQUENCE: 164
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSFLG CLLGVGSAIA  120
SGVAVSKVLH LEGEVNKIKS ALLSTNKAVV SLSNGVSVLT FKVLDLKNYI DKQLLPILNK  180
QSCSIPNIET VIEFQQKNNR LLEITREFSV NAGVTTPVST YMLTNSELLS LINDMPITND  240
QKKLMSNNVQ IVRQQSYSIM SIIKEEVLAY VVQLPLYGVI DTPCWKLHTS PLCTTNTKEG  300
SNICLTRTDR GWYCDNAGSV SFFPQAETCK VQSNRVFCDC MNSRTLPSEV NLCNVDIFNP  360
KYDCKIMTSK TDVSSSVITS LGAIVSCYGK TKCTASNKNR GIIKTFSNGC DYVSNKGVDT  420
VSVGNTLYYV NKQEGQSLYV KGEPIINFYD PLVFPSDEFD ASISQVNEKI NQSLAFIRKS  480
DELLHNVNAG KSTTNIMITT IIIVIIVILL SLIAVGLLLY                        520

SEQ ID NO: 165          moltype = RNA  length = 1871
FEATURE                 Location/Qualifiers
source                  1..1871
                        mol_type = other RNA
                        organism = synthetic construct
SEQUENCE: 165
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
```

-continued

```
gcagctgctg atgcagtcta caccagccac aggctctggc tctttcctgg gctgcctgct  420
cggagtgggc agcgccattg cctctggtgt cgccgtgtct aaagtgctgc acctggaagg  480
cgaagtgaac aagatcaaga gcgccctgct gagcaccaac aaggccgtgg tgtctctgag  540
caatggcgtg tccgtgctga ccttcaaggt gctggacctg aagaactaca tcgacaaaca  600
gctgctgccc atcctgaaca agcagtcctg cagcatcccc aacatcgaga cagtgatcga  660
gttccagcag aagaacaacc ggctgctgga aatcacccgc gagttctctg tgaatgccgg  720
cgtgaccaca cctgtgtcca cctacatgct gaccaacagc gagctgctga gcctgatcaa  780
cgacatgccc atcaccaacg accagaaaaa gctgatgagc aacaacgtgc agatcgtgcg  840
gcagcagagc tacagcatca tgagcattat caaagaagag gtgctggcct acgtggtgca  900
gctgcctctg tatggcgtga tcgatacccc ttgctggaag ctgcacacaa gccctctgtg  960
caccaccaac accaaagagg gcagcaacat ctgcctgacc agaaccgaca gaggctggta  1020
ctgcgataat gccggcagcg tctcattctt cccacaagcc gagacatgca aggtgcagag  1080
caaccgggtg ttctgcgact gcatgaatag cagaaccctg ccttccgaag tgaatctgtg  1140
caacgtggac atcttcaacc ctaagtacga ctgcaagatc atgaccagca agaccgacgt  1200
gtccagcagt gtgatcacct cactgggcgc catcgtgtcc tgttacggca agaccaagtg  1260
caccgccagc aacaagaacc ggggcatcat caagaccttc agcaacggct gcgactacgt  1320
gtccaacaaa ggcgtggaca ccgtgtctgt gggcaacacc ctgtactacg tgaacaaaca  1380
agagggccag tctctgtacg tgaagggcga gcccatcatc aacttctacg accctctggt  1440
gttccccagc gacgagttcg atgccagcat cagccaagtg aacgagaaga tcaatcagag  1500
cctggccttc atcagaaagt ccgatgagct gctgcacaac gtgaacgccg gcaagtccac  1560
caccaatatc atgatcacga ccatcatcat cgtgattatc gtgatcctgc tgtccctgat  1620
cgccgtgggc ctgctgcttt attgataata ggctggagcc tcggtggcca tgcttcttgc  1680
cccttgggcc tccccccagc ccctcctccc cttcctgcac ccgtaccccc gtggtctttg  1740
aataaagtct gagtgggcgg caaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa a                                                       1871
```

```
SEQ ID NO: 166         moltype = DNA  length = 1841
FEATURE                Location/Qualifiers
source                 1..1841
                       mol_type = other DNA
                       organism = synthetic construct
SEQUENCE: 166
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tgcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgccttgc tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841
```

```
SEQ ID NO: 167         moltype = DNA  length = 1539
FEATURE                Location/Qualifiers
source                 1..1539
                       mol_type = other DNA
                       organism = synthetic construct
SEQUENCE: 167
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggctg cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
```

-continued

```
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgccttgcta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 168          moltype = AA  length = 510
FEATURE                 Location/Qualifiers
source                  1..510
                        mol_type = protein
                        organism = synthetic construct
SEQUENCE: 168
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGCAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPCYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 169          moltype = RNA  length = 1841
FEATURE                 Location/Qualifiers
source                  1..1841
                        mol_type = other RNA
                        organism = synthetic construct
SEQUENCE: 169
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc tgcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgccttgc tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 170          moltype = DNA  length = 1841
FEATURE                 Location/Qualifiers
source                  1..1841
                        mol_type = other DNA
                        organism = synthetic construct
SEQUENCE: 170
```

-continued

```
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tgcggcgtga tcgataccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 171         moltype = DNA  length = 1539
FEATURE                Location/Qualifiers
source                 1..1539
                       mol_type = other DNA
                       organism = synthetic construct
SEQUENCE: 171
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgtg cggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 172         moltype = AA  length = 510
FEATURE                Location/Qualifiers
source                 1..510
                       mol_type = protein
                       organism = synthetic construct
SEQUENCE: 172
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLCGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
```

-continued

```
KSTTNIMITT IIIVIIVILL SLIAVGLLLY                          510

SEQ ID NO: 173          moltype = RNA  length = 1841
FEATURE                 Location/Qualifiers
source                  1..1841
                        mol_type = other RNA
                        organism = synthetic construct
SEQUENCE: 173
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tgcggcgtga tcgataccccc 900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 174          moltype = DNA  length = 1841
FEATURE                 Location/Qualifiers
source                  1..1841
                        mol_type = other DNA
                        organism = synthetic construct
SEQUENCE: 174
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgcctgcg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagctgca tgagcattat  840
caaagaagag gtgctggcct acgtggtgca gctgcctctg tatggcgtga tcgataccccc 900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 175          moltype = DNA  length = 1539
```

```
FEATURE                Location/Qualifiers
source                 1..1539
                       mol_type = other DNA
                       organism = synthetic construct
SEQUENCE: 175
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgcctgcgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagctgcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 176         moltype = AA  length = 510
FEATURE                Location/Qualifiers
source                 1..510
                       mol_type = protein
                       organism = synthetic construct
SEQUENCE: 176
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSACA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSCM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 177         moltype = RNA  length = 1841
FEATURE                Location/Qualifiers
source                 1..1841
                       mol_type = other RNA
                       organism = synthetic construct
SEQUENCE: 177
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgcctgcg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagctgca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
```

```
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 178         moltype = DNA  length = 1841
FEATURE                Location/Qualifiers
source                 1..1841
                       mol_type = other DNA
                       organism = synthetic construct
SEQUENCE: 178
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agctgcattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcatttg  840
caaagaagag gtgctggcct acgtggtgca gctgcctctg tatggcgtga tcgataccCC  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 179         moltype = DNA  length = 1539
FEATURE                Location/Qualifiers
source                 1..1539
                       mol_type = other DNA
                       organism = synthetic construct
SEQUENCE: 179
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag ctgcattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcatttgca aagaagaggt gctggcctac  780
gtggtgcagc tgcctctgta tggcgtgatc gataccCCtt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 180         moltype = AA  length = 510
```

```
FEATURE                Location/Qualifiers
source                 1..510
                       mol_type = protein
                       organism = synthetic construct
SEQUENCE: 180
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSCIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SICKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                 510

SEQ ID NO: 181         moltype = RNA  length = 1841
FEATURE                Location/Qualifiers
source                 1..1841
                       mol_type = other RNA
                       organism = synthetic construct
SEQUENCE: 181
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agctgcattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcatttg  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                    1841

SEQ ID NO: 182         moltype = DNA  length = 1841
FEATURE                Location/Qualifiers
source                 1..1841
                       mol_type = other DNA
                       organism = synthetic construct
SEQUENCE: 182
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agctgcattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tactgcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
```

-continued

```
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 183          moltype = DNA  length = 1539
FEATURE                 Location/Qualifiers
source                  1..1539
                        mol_type = other DNA
                        organism = synthetic construct
SEQUENCE: 183
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag ctgcattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta ctgcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 184          moltype = AA  length = 510
FEATURE                 Location/Qualifiers
source                  1..510
                        mol_type = protein
                        organism = synthetic construct
SEQUENCE: 184
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSCIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYCIM SIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIVIIVILL SLIAVGLLLY                                  510

SEQ ID NO: 185          moltype = RNA  length = 1841
FEATURE                 Location/Qualifiers
source                  1..1841
                        mol_type = other RNA
                        organism = synthetic construct
SEQUENCE: 185
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agctgcattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
```

```
gaccaacagc gagctgctga gcctgatcaa cgacatgccc atcaccaacg accagaaaaa  780
gctgatgagc aacaacgtgc agatcgtgcg gcagcagagc tactgcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 186         moltype = DNA  length = 1841
FEATURE                Location/Qualifiers
source                 1..1841
                       mol_type = other DNA
                       organism = synthetic construct
SEQUENCE: 186
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agctgcattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagctgcat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 187         moltype = DNA  length = 1539
FEATURE                Location/Qualifiers
source                 1..1539
                       mol_type = other DNA
                       organism = synthetic construct
SEQUENCE: 187
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag ctgcattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agctgcatca aagaagaggt gctggcctac  780
gtggtgcagc tgcctctgta tggcgtgatc gatacccctt gctggaagct gcacacaagc  840
cctctgtgca ccaccaacac caaagagggc agcaacatct gcctgaccag aaccgacaga  900
```

-continued

```
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539
```

```
SEQ ID NO: 188         moltype = AA  length = 510
FEATURE                Location/Qualifiers
source                 1..510
                       mol_type = protein
                       organism = synthetic construct
SEQUENCE: 188
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSCIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SCIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                   510
```

```
SEQ ID NO: 189         moltype = RNA  length = 1841
FEATURE                Location/Qualifiers
source                 1..1841
                       mol_type = other RNA
                       organism = synthetic construct
SEQUENCE: 189
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agctgcattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagctgcat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841
```

```
SEQ ID NO: 190         moltype = DNA  length = 1841
FEATURE                Location/Qualifiers
source                 1..1841
                       mol_type = other DNA
                       organism = synthetic construct
SEQUENCE: 190
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
```

```
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gctgcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 191          moltype = DNA  length = 1539
FEATURE                 Location/Qualifiers
source                  1..1539
                        mol_type = other DNA
                        organism = synthetic construct
SEQUENCE: 191
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gatacccctt gctggaagct gcacacaagc  840
cctctgtgca ccaccaacac caaagagggc tgcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagtgcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 192          moltype = AA  length = 510
FEATURE                 Location/Qualifiers
source                  1..510
                        mol_type = protein
                        organism = synthetic construct
SEQUENCE: 192
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG CNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KCEPIINFYD PLVFPSDEFD ASISQVNEKI NQSLAFIRKS DELLHNVNAG  480
KSTTNIMITT IIIVIIVILL SLIAVGLLLY                                   510

SEQ ID NO: 193          moltype = RNA  length = 1841
FEATURE                 Location/Qualifiers
source                  1..1841
                        mol_type = other RNA
                        organism = synthetic construct
```

```
SEQUENCE: 193
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc  900
ttgctggaag ctgcacacaa gccctctgtg caccaccaac accaaagagg gctgcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 194          moltype = DNA  length = 1841
FEATURE                 Location/Qualifiers
source                  1..1841
                        mol_type = other DNA
                        organism = synthetic construct
SEQUENCE: 194
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccc  900
ttgctggaag ctgcacacaa gccctctgtg caccacctgc accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 195          moltype = DNA  length = 1539
FEATURE                 Location/Qualifiers
source                  1..1539
                        mol_type = other DNA
                        organism = synthetic construct
SEQUENCE: 195
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
```

-continued

```
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccccctt gctggaagct gcacacaagc  840
cctctgtgca ccacctgcac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagtgcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 196          moltype = AA  length = 510
FEATURE                 Location/Qualifiers
source                  1..510
                        mol_type = protein
                        organism = synthetic construct
SEQUENCE: 196
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIA SGVAVSKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTCTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KCEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 197          moltype = RNA  length = 1841
FEATURE                 Location/Qualifiers
source                  1..1841
                        mol_type = other RNA
                        organism = synthetic construct
SEQUENCE: 197
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccacctgc accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagtgcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841
```

```
SEQ ID NO: 198          moltype = DNA  length = 1841
FEATURE                 Location/Qualifiers
source                  1..1841
                        mol_type = other DNA
                        organism = synthetic construct
SEQUENCE: 198
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgact gcggctggta ctgcgataat gccggcagcg tctcattctt  1020
cccacaagcc gagacatgca aggtgcagag caaccgggtg ttctgcgaca ccatgaatag  1080
cagaaccctg ccttgcgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 199          moltype = DNA  length = 1539
FEATURE                 Location/Qualifiers
source                  1..1539
                        mol_type = other DNA
                        organism = synthetic construct
SEQUENCE: 199
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccattgcc tctggtgtcg ccgtgtctaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cctgaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg agcattatca aagaagaggt gctggcctac  780
gtggtgcagc tgcctctgta tggcgtgatc gataccoctt gctggaagct gcacacaagc  840
cctctgtgca ccaccaacac caaagagggc agcaacatct gcctgaccag aaccgactgc  900
ggctggtact gcgataatgc cggcagcgtc tcattcttcc cacaagccga gacatgcaag  960
gtgcagagca accgggtgtt ctgcgacacc atgaatagca gaaccctgcc ttgcgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactacgtg  1260
aacaaacaag agggccagtc tctgtacgtg aagggcgagc ccatcatcaa cttctacgac  1320
cctctggtgt tccccagcga cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 200          moltype = AA  length = 510
FEATURE                 Location/Qualifiers
source                  1..510
                        mol_type = protein
                        organism = synthetic construct
SEQUENCE: 200
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIA SGVAVSKVLH  120
```

-continued

```
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM SIIKEEVLAY VVQLPLYGVI DTPCWKLHTS PLCTTNTKEG SNICLTRTDC  300
GWYCDNAGSV SFFPQAETCK VQSNRVFCDT MNSRTLPCEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 201         moltype = RNA  length = 1841
FEATURE                Location/Qualifiers
source                 1..1841
                       mol_type = other RNA
                       organism = synthetic construct
SEQUENCE: 201
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattg cctctggtgt  420
cgccgtgtct aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcctgaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgagcattat  840
caaagaagag gtgctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgact gcggctggta ctgcgataat gccggcagcg tctcattctt  1020
cccacaagcc gagacatgca aggtgcagag caaccgggtg ttctgcgaca ccatgaatag  1080
cagaaccctg ccttgcgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactacg tgaacaaaca agagggccag tctctgtacg tgaagggcga  1380
gcccatcatc aacttctacg accctctggt gttccccagc gacgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 202         moltype = DNA  length = 1841
FEATURE                Location/Qualifiers
source                 1..1841
                       mol_type = other DNA
                       organism = synthetic construct
SEQUENCE: 202
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtat  420
cgccgtgtgc aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag atcctggcct acgtggtgca gctgcctctg tatggcgtga tcgataccccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
```

```
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 203         moltype = DNA  length = 1539
FEATURE                Location/Qualifiers
source                 1..1539
                       mol_type = other DNA
                       organism = synthetic construct
SEQUENCE: 203
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtgcaac ggcaccgacg ccaaagtgaa gctgatcaag  240
caagagctgg acaagtacaa gaatgccgtg accgacctgc agctgctgat gcagtctaca  300
ccagccacag gctctggcag cgccatttgt tctggtatcg ccgtgtgcaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg tgcattatca aagaagagat cctggcctac  780
gtggtgcagc tgcctctgta tggcgtgatc gataccccctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                         1539

SEQ ID NO: 204         moltype = AA  length = 510
FEATURE                Location/Qualifiers
source                 1..510
                       mol_type = protein
                       organism = synthetic construct
SEQUENCE: 204
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGIAVCKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM CIIKEEILAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIVIIVILL SLIAVGLLLY                                    510

SEQ ID NO: 205         moltype = RNA  length = 1841
FEATURE                Location/Qualifiers
source                 1..1841
                       mol_type = other RNA
                       organism = synthetic construct
SEQUENCE: 205
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtgca acggcaccga  300
cgccaaagtg aagctgatca agcaagagct ggacaagtac aagaatgccg tgaccgacct  360
gcagctgctg atgcagtcta caccagccac aggctctggc agcgccattt gttctggtat  420
cgccgtgtgc aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag atcctggcct acgtggtgca gctgcctctg tatggcgtga tcgatacccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
```

```
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 206         moltype = DNA  length = 1841
FEATURE                Location/Qualifiers
source                 1..1841
                       mol_type = other DNA
                       organism = synthetic construct
SEQUENCE: 206
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtaca acggcaccga  300
ggtgaaagtg aagctgatca agcaagagct ggacaagtac aagagcgccg tgaccgacct  360
gcagctgctg atgcagtcta caccagccac aggctctggc agcgccattt gttctggtat  420
cgccgtgtgc aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag atcctggcct acgtggtgca gctgcctctg tatggcgtga tcgataccoc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                      1841

SEQ ID NO: 207         moltype = DNA  length = 1539
FEATURE                Location/Qualifiers
source                 1..1539
                       mol_type = other DNA
                       organism = synthetic construct
SEQUENCE: 207
atggaactgc tgatcctgaa ggccaacgcc atcaccacca tcctgaccgc cgtgaccttc  60
tgttttgcca gcggccagaa catcaccgag gaattctacc agagcacctg tagcgccgtg  120
tccaagggat atctgggcgc ccttagaacc ggctggtaca ccagcgtgat caccatcgag  180
ctgagcaaca tcaaagaaaa caagtacaac ggcaccgagg tgaaagtgaa gctgatcaag  240
caagagctgg acaagtacaa gagcgccgtg accgacctgc agctgctgat gcagtctaca  300
ccagccacag gctctggcag cgccatttgt tctggtatcg ccgtgtgcaa agtgctgcac  360
ctggaaggcg aagtgaacaa gatcaagagc gccctgctga gcaccaacaa ggccgtggtg  420
tctctgagca atggcgtgtc cgtgctgacc ttcaaggtgc tggacctgaa gaactacatc  480
gacaaacagc tgctgcccat cgtcaacaag cagtcctgca gcatccccaa catcgagaca  540
gtgatcgagt tccagcagaa gaacaaccgg ctgctggaaa tcacccgcga gttctctgtg  600
aatgccggcg tgaccacacc tgtgtccacc tacatgctga ccaacagcga gctgctgagc  660
ctgatcaacg acatgcccat caccaacgac cagaaaaagc tgatgagcaa caacgtgcag  720
atcgtgcggc agcagagcta cagcatcatg tgcattatca aagaagagat cctggcctac  780
gtggtgcagc tgcctctgta tggcgtgatc gataccoctt gctggaagct gcacacaagc  840
cctctgtgca ccaccaacac caaagagggc agcaacatct gcctgaccag aaccgacaga  900
ggctggtact gcgataatgc cggcagcgtc tcattcttcc cacaagccga gacatgcaag  960
gtgcagagca accgggtgtt ctgcgacacc atgaatagca gaaccctgcc ttccgaagtg  1020
aatctgtgca acgtggacat cttcaaccct aagtacgact gcaagatcat gaccagcaag  1080
accgacgtgt ccagcagtgt gatcacctca ctgggcgcca tcgtgtcctg ttacggcaag  1140
accaagtgca ccgccagcaa caagaaccgg ggcatcatca agaccttcag caacggctgc  1200
gactacgtgt ccaacaaagg cgtggacacc gtgtctgtgg gcaacaccct gtactgcgtg  1260
aacaaacaag agggccagtc tctgtacgtg aagggcgagc ccatcatcaa cttctacgac  1320
```

```
cctctggtgt tccccagcag cgagttcgat gccagcatca gccaagtgaa cgagaagatc  1380
aatcagagcc tggccttcat cagaaagtcc gatgagctgc tgcacaacgt gaacgccggc  1440
aagtccacca ccaatatcat gatcacgacc atcatcatcg tgattatcgt gatcctgctg  1500
tccctgatcg ccgtgggcct gctgctttat tgataatag                        1539

SEQ ID NO: 208         moltype = AA  length = 510
FEATURE                Location/Qualifiers
source                 1..510
                       mol_type = protein
                       organism = synthetic construct
SEQUENCE: 208
MELLILKANA ITTILTAVTF CFASGQNITE EFYQSTCSAV SKGYLGALRT GWYTSVITIE  60
LSNIKENKYN GTEVKVKLIK QELDKYKSAV TDLQLLMQST PATGSGSAIC SGIAVCKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM CIIKEEILAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                   510

SEQ ID NO: 209         moltype = RNA  length = 1841
FEATURE                Location/Qualifiers
source                 1..1841
                       mol_type = other RNA
                       organism = synthetic construct
SEQUENCE: 209
agcggctcgg ccattttgtc ccagtcagtc cggaggctgc ggctgcagaa gtaccgcctg  60
cggagtaact gcaaaggcca ccatggaact gctgatcctg aaggccaacg ccatcaccac  120
catcctgacc gccgtgacct tctgttttgc cagcggccag aacatcaccg aggaattcta  180
ccagagcacc tgtagcgccg tgtccaaggg atatctgggc gcccttagaa ccggctggta  240
caccagcgtg atcaccatcg agctgagcaa catcaaagaa aacaagtaca acggcaccga  300
ggtgaaagtg aagctgatca agcaagagct ggacaagtac aagagcgccg tgaccgacct  360
gcagctgctg atgcagtcta caccagccac aggctctggc agcgccattt gttctggtat  420
cgccgtgtgc aaagtgctgc acctggaagg cgaagtgaac aagatcaaga gcgccctgct  480
gagcaccaac aaggccgtgg tgtctctgag caatggcgtg tccgtgctga ccttcaaggt  540
gctggacctg aagaactaca tcgacaaaca gctgctgccc atcgtcaaca agcagtcctg  600
cagcatcccc aacatcgaga cagtgatcga gttccagcag aagaacaacc ggctgctgga  660
aatcacccgc gagttctctg tgaatgccgg cgtgaccaca cctgtgtcca cctacatgct  720
gaccaacagc gagctgctga gcctgatcaa cgacatgccc atcaccaacg accagaaaaa  780
gctgatgagc aacaacgtgc agatcgtgcg gcagcagagc tacagcatca tgtgcattat  840
caaagaagag atcctggcct acgtggtgca gctgcctctg tatggcgtga tcgataccc  900
ttgctggaag ctgcacacaa gccctctgtg caccaccaac accaaagagg gcagcaacat  960
ctgcctgacc agaaccgaca gaggctggta ctgcgataat gccggcagcg tctcattctt  1020
cccacaagcc gagacatgca aggtgcagag caaccgggtg ttctgcgaca ccatgaatag  1080
cagaaccctg ccttccgaag tgaatctgtg caacgtggac atcttcaacc ctaagtacga  1140
ctgcaagatc atgaccagca agaccgacgt gtccagcagt gtgatcacct cactgggcgc  1200
catcgtgtcc tgttacggca agaccaagtg caccgccagc aacaagaacc ggggcatcat  1260
caagaccttc agcaacggct gcgactacgt gtccaacaaa ggcgtggaca ccgtgtctgt  1320
gggcaacacc ctgtactgcg tgaacaaaca agagggccag tctctgtacg tgaagggcga  1380
gcccatcatc aacttctacg accctctggt gttccccagc agcgagttcg atgccagcat  1440
cagccaagtg aacgagaaga tcaatcagag cctggccttc atcagaaagt ccgatgagct  1500
gctgcacaac gtgaacgccg gcaagtccac caccaatatc atgatcacga ccatcatcat  1560
cgtgattatc gtgatcctgc tgtccctgat cgccgtgggc ctgctgcttt attgataata  1620
ggctggagcc tcggtggcca tgcttcttgc cccttgggcc tccccccagc ccctcctccc  1680
cttcctgcac ccgtaccccc gtggtctttg aataaagtct gagtgggcgg caaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa a                     1841

SEQ ID NO: 210         moltype = AA  length = 574
FEATURE                Location/Qualifiers
source                 1..574
                       mol_type = protein
                       organism = Orthopneumovirus hominis
SEQUENCE: 210
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 211         moltype = AA  length = 510
FEATURE                Location/Qualifiers
source                 1..510
```

```
                        mol_type = protein
                        organism = synthetic construct
SEQUENCE: 211
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGVAVCKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 212          moltype = AA  length = 510
FEATURE                 Location/Qualifiers
source                  1..510
                        mol_type = protein
                        organism = synthetic construct
SEQUENCE: 212
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGIAVCKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 213          moltype = AA  length = 510
FEATURE                 Location/Qualifiers
source                  1..510
                        mol_type = protein
                        organism = synthetic construct
SEQUENCE: 213
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGIAVCKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM CIIKEEILAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY                                  510

SEQ ID NO: 214          moltype = AA  length = 510
FEATURE                 Location/Qualifiers
source                  1..510
                        mol_type = protein
                        organism = synthetic construct
SEQUENCE: 214
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PATGSGSAIC SGIAVCKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM CIIKEEILAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                  510

SEQ ID NO: 215          moltype = AA  length = 510
FEATURE                 Location/Qualifiers
source                  1..510
                        mol_type = protein
                        organism = synthetic construct
SEQUENCE: 215
MELLILKANA ITTILTAVTF CFASGQNITE EFYQSTCSAV SKGYLGALRT GWYTSVITIE  60
LSNIKENKCN GTDAKVKLIK QELDKYKNAV TDLQLLMQST PACGSGSACA SGIAVSKVLH  120
LEGEVNKIKS ALLSTNKAVV SLSNGVSVLT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEILAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                  510

SEQ ID NO: 216          moltype = AA  length = 510
FEATURE                 Location/Qualifiers
```

```
source                  1..510
                        mol_type = protein
                        organism = synthetic construct
SEQUENCE: 216
MELLILKANA ITTILTAVTF CFASGQNITE EFYQSTCSAV SKGYLGALRT GWYTCVITIE  60
LSNIKENKCN GTDAKVKLIK QELDKYKNAV TDLQLLMQST PATGSGSAIA SGIAVSKVLH  120
LEGEVNKIKS ALLSTNKAVV SLSNGVSVCT FKVLDLKNYI DKQLLPIVNK QSCSIPNIET  180
VIEFQQKNNR LLEITREFSV NAGVTTPVST YMLTNSELLS LINDMPITND QKKLMSNNVQ  240
IVRQQSYSIM SIIKEEILAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGQSLYV KGEPIINFYD PLVFPSSEFD ASISQVNEKI NQSLAFIRKS DELLHNVNAG  480
KSTTNIMITT IIIVIIVILL SLIAVGLLLY                                 510

SEQ ID NO: 217          moltype = RNA  length = 82
FEATURE                 Location/Qualifiers
source                  1..82
                        mol_type = other RNA
                        organism = synthetic construct
SEQUENCE: 217
agcggctcgg ccattttgtc ccagtcagtc cggaggctgc ggctgcagaa gtaccgcctg  60
cggagtaact gcaaaggcca cc                                           82

SEQ ID NO: 218          moltype = RNA  length = 69
FEATURE                 Location/Qualifiers
source                  1..69
                        mol_type = other RNA
                        organism = synthetic construct
SEQUENCE: 218
agactcctcc ccatcctctc cctctgtccc tctgtccctc tgaccctgca ctgtcccagc  60
accgccacc                                                          69

SEQ ID NO: 219          moltype = RNA  length = 57
FEATURE                 Location/Qualifiers
source                  1..57
                        mol_type = other RNA
                        organism = synthetic construct
SEQUENCE: 219
gggaaataag agagaaaaga agagtaagaa gaaatataag accccggcgc cgccacc     57

SEQ ID NO: 220          moltype = RNA  length = 54
FEATURE                 Location/Qualifiers
source                  1..54
                        mol_type = other RNA
                        organism = synthetic construct
SEQUENCE: 220
gagaataaac tagtattctt ctggtcccca cagactcaga gagaacccgc cacc        54

SEQ ID NO: 221          moltype = RNA  length = 47
FEATURE                 Location/Qualifiers
source                  1..47
                        mol_type = other RNA
                        organism = synthetic construct
SEQUENCE: 221
gggaaataag agagaaaaga agagtaagaa gaaatataag agccacc                47

SEQ ID NO: 222          moltype = RNA  length = 110
FEATURE                 Location/Qualifiers
source                  1..110
                        mol_type = other RNA
                        organism = synthetic construct
SEQUENCE: 222
gctggagcct cggtggccat gcttcttgcc ccttgggcct ccccccagcc cctcctcccc  60
ttcctgcacc cgtacccccg tggtctttga ataaagtctg agtgggcggc             110

SEQ ID NO: 223          moltype = RNA  length = 110
FEATURE                 Location/Qualifiers
source                  1..110
                        mol_type = other RNA
                        organism = synthetic construct
SEQUENCE: 223
gctggagcct cggtggccta gcttcttgcc ccttgggcct ccccccagcc cctcctcccc  60
ttcctgcacc cgtacccccg tggtctttga ataaagtctg agtgggcggc             110

SEQ ID NO: 224          moltype = RNA  length = 295
FEATURE                 Location/Qualifiers
source                  1..295
                        mol_type = other RNA
                        organism = synthetic construct
```

-continued

```
SEQUENCE: 224
ctcgagctgg tactgcatgc acgcaatgct agctgcccct ttcccgtcct gggtaccccg  60
agtctccccc gacctcgggt cccaggtatg ctcccacctc cacctgcccc actcaccacc  120
tctgctagtt ccagacacct cccaagcacg cagcaatgca gctcaaaacg cttagcctag  180
ccacaccccc acgggaaaca gcagtgatta acctttagca ataaacgaaa gtttaactaa  240
gctatactaa ccccagggtt ggtcaatttc gtgccagcca caccctggag ctagc       295

SEQ ID NO: 225          moltype = RNA  length = 110
FEATURE                 Location/Qualifiers
source                  1..110
                        mol_type = other RNA
                        organism = synthetic construct
SEQUENCE: 225
tgataatagg ctggagcctc ggtggccatg cttcttgccc cttgggcctc cccccagccc  60
ctcctcccct tcctgcaccc gtacccccgt ggtctttgaa taaagtctga            110
```

RESPIRATORY SYNCYTIAL VIRUS mRNA VACCINE, AND PREPARATION METHOD THEREFOR AND USE THEREOF

CROSS-REFERENCE TO RELATED APPLICATION

The present application claims priority from Chinese Patent Application No. 202410911569.7 filed on Jul. 9, 2024, the contents of which are incorporated herein by reference in their entirety.

REFERENCE TO SEQUENCE LISTING

This application includes a Sequence Listing filed electronically as an XML file named "[P24435904US].SEQ.xml", created on Feb. 18, 2025, with a size of 499,066 bytes. The Sequence Listing is incorporated herein by reference.

TECHNICAL FIELD

The present disclosure belongs to the technical field of nucleic acid vaccines, and particularly relates to a respiratory syncytial virus mRNA vaccine, and a preparation method therefor and use thereof.

BACKGROUND

Respiratory syncytial virus (RSV) is a negative-sense RNA virus of the genus Pneumovirus in the family Paramyxoviridae. In 1956, scientists isolated the RSV virus from chimpanzee respiratory specimens, which was called respiratory syncytial virus because it caused adjacent cells to fuse during cell culture and the cells to transform into a syncytium-like structure.

The RSV virus is an important pathogen causing lower respiratory tract infections in infants, the elderly, and patients with immune function deficiencies. RSV is airborne, enters the trachea and lungs by inhalation through the mouth and nose, and invades epithelial cells to cause airway trauma, such that the respiratory mucus is secreted from the surface of the airway to block the lumen, causing dyspnea. Common symptoms of an RSV infection include runny nose, fever, cough, and asthma, which can cause respiratory distress and even airway obstruction in serious cases, leading to respiratory failure and even death.

RSV is a common respiratory virus. It generally causes cold-like symptoms. The RSV infection mainly occurs in autumn, winter, and spring, and is one of the leading causes of severe respiratory diseases in infants under 5 years of age and the elderly over 65 years of age. For the vast majority of young people, RSV usually causes mild cold-like symptoms, but for infants, young children, and the elderly, the RSV infection is a potentially fatal disease.

The RSV infection has become a worldwide public health problem. RSV is the most common viral pathogen causing acute lower respiratory tract infections (ALRTIs) in children under 5 years of age worldwide, and is the leading cause of hospitalization for viral respiratory tract infections in infants and young children. Data show that the RSV infection accounts for 28% of all ALRTIs, with RSV hospital deaths in children accounting for 13% to 22% of deaths due to ALRTI.

The RSV infection is characterized by a widespread global epidemic, and the epidemic is affected by factors such as geographic location, temperature, and humidity. For example, the epidemic season of RSV starts from mid-October to mid-May of the following year in northern China, and occurs frequently in winter and spring in southern China, which is closely related to temperature. RSV has only one serotype, which is divided into subtypes A and B. These two subtypes are alternately epidemic in the northern part of the country.

Vaccines are the most economical and effective means of preventing RSV infection. WHO has listed the development of RSV vaccines as one of the urgent problems to be solved. However, since the development of RSV vaccines began in the 1960s, no effective vaccine certified by regulatory agencies has been approved for marketing. Recently, major breakthroughs in RSV vaccines have been made one after another. On May 3, 2023, a respiratory syncytial virus (RSV) vaccine developed by GSK, Arexvy, received marketing approval from the FDA, making it the world's first RSV vaccine to be approved for marketing. The vaccine is mainly used for patients over 60 years of age to prevent lower respiratory tract (bronchus and lungs) diseases caused by the RSV infection. This was followed on Jun. 1, 2023 by the US FDA's marketing approval of an RSV protein vaccine from Pfizer, Abrysvo™, for the prevention of acute respiratory tract diseases and lower respiratory tract diseases caused by RSV in adults over 60 years of age.

At present, the technical routes of RSV vaccines under development include attenuated live vaccines, subunit vaccines, recombinant vector vaccines, mRNA vaccines, etc. Traditional vaccines are usually based on inactivated or attenuated live virus vaccines, or subunit proteins derived from pathogens. Although these vaccines produce an effective immune response, they have a number of associated safety issues. For example, rather than having a protective effect on vaccinees, the early-developed inactivated RSV vaccines develop an enhanced respiratory disease (ERD), that is, not only do they fail to prevent the vaccinees from being infected with the RSV virus, but also lead to an aggravation of the condition of the vaccinees after they are infected with the RSV virus. In a clinical trial of an inactivated RSV vaccine, 16 out of the 20 infants in the trial group were severely ill and required hospitalization, with a hospitalization rate up to 80%, and two of them died.

mRNA vaccines function by introducing mRNA encoding a viral antigen into the body, and producing an antigen by expression in the body, which in turn stimulates the body to produce an immune response, and they have relatively high safety because mRNA exists only in the cytoplasm, is not integrated into a host genome, and can be naturally degraded in the body. mRNA vaccines themselves can be used as adjuvants to induce the body to produce natural immune effects. Moreover, mRNA vaccines can induce strong humoral immunity and cellular immunity, and generally have a stronger immune effect than traditional inactivated vaccines and subunit protein vaccines. mRNA vaccines do not need to be combined with other vaccine adjuvants, so that adverse reactions caused by other substances can be reduced. Compared with traditional vaccines, mRNA vaccines have a relatively simple production process flow and a short research and development period, and have the technical advantage of rapid response to the research and development of vaccines for new sudden infectious diseases. mRNA vaccines have been successfully made in the development of new coronavirus vaccines, and the safety and efficacy of mRNA vaccine technology have been demonstrated through large-scale population vaccination.

Neutralizing antibodies caused by the RSV infection are mainly directed against the F protein. RSV F protein is a type I fusion glycoprotein, which is relatively conserved among RSV types, and is an ideal target protein for vaccine antigens. The F protein transitions between two conformations: a metastable pre-fusion conformation (pre-F) and a stable post-fusion conformation (post-F). Although the antigenic epitopes targeted by the neutralizing antibodies are present in both conformations of the F protein, the characteristics of the natural immune response in humans to the RSV infection suggest that epitopes for most of the RSV neutralizing antibodies are located in the pre-fusion conformation of the F protein. Because of the instability of the pre-fusion conformation of the F protein, F protein subunit vaccines based on inactivated RSV vaccines or extracted directly from RSV have failed.

Based on the above problems, in order to further reduce the risk of respiratory syncytial virus in immunocompromised populations (including children and the elderly), there is an urgent need to provide a novel mRNA vaccine for preventing RSV, which has good stability and can significantly improve the humoral immunity effect after vaccination.

SUMMARY

The present disclosure provides an mRNA vaccine encoding an RSV F protein, particularly a pre-fusion conformation pre-F of the F protein. The protein comprises 3 naturally occurring mutations of P102A, I379V, and M447V (SEQ ID NO: 210) based on a sequence of a wild-type protein of subtype RSV A2 set forth in SEQ ID NO: 1 (GenBank ID: 138251). The mutated sequence with these three amino acid residues is conserved in other RSV A virus strains, and based on this, candidate mutant antigen sequences are designed taking differences in the F protein sequences of the current mainstream virus strains into account.

RSV viruses include subtypes A and B, whose F proteins are approximately 90% identical in the amino acid sequence. For a sequence of an F0 precursor polypeptide of subtype A, for example, virus strain A2 (GenBank GI: 138251; Swiss Prot P03420), and a sequence of an F0 precursor polypeptide of subtype B, for example, virus strain 18537 (GenBank GI: 138250; Swiss Prot P13843), both are sequences of 574 amino acids, and signal peptide sequences of both have also been reported as amino acids 1 to 25 (GenBank and UniProt). In the two sequences, due to high homology of F protein sequences of both RSV virus type A and type B, the RSV pre-F mRNA and the vaccine prepared therefrom designed by the present disclosure are effective for preventing infections of RSV virus type A and type B.

As described herein, the three-dimensional structure of pre-F is used as a guide to engineer and construct a stabilized form of a pre-fusion F protein ("pre-F" antigen) and is used in animal models to produce an RSV neutralizing immune response that is significantly enhanced compared with that achieved by an immunogen of Abrysvo™ based on the RSV F protein and provides protection against RSV challenge in the animal models. The pre-F antigen can be used as a potential vaccine for RSV and as a diagnostic molecule.

In some embodiments, the recombinant RSV F protein comprises one or more amino acid substitutions that stabilize the protein in a pre-fusion conformation. For example, the substitutions stabilize a membrane distal portion of the F protein (comprising the N-terminal region of an F1 polypeptide) in a pre-fusion conformation. Which makes one or more antibodies specifically bind to pre-fusion conformation of RSV F protein or an antigenic site present in the pre-fusion conformation rather than in the post-fusion conformation of the RSV F protein, such as antigenic site D.

In some other embodiments, the recombinant RSV F protein may comprise one or more modifications (e.g., truncations and amino acid substitutions) to the C-terminus of the F1 polypeptide that, together with modifications stabilizing the membrane distal region of the F polypeptide, can increase the stabilization of the recombinant F protein in the pre-fusion conformation.

The present application relates to the following embodiments:

1. An immunogenic composition, comprising a ribonucleic acid (RNA) of a respiratory syncytial virus (RSV), wherein the RNA encodes a wild-type RSV F protein or a variant thereof;
 wherein a sequence of the wild-type RSV F protein is SEQ ID NO: 1.
2. The composition according to embodiment 1, wherein the variant of the RSV F protein comprises one or more mutant forms selected from the following: a sequence truncation, a sequence deletion, and a site mutation.
3. The composition according to embodiment 2, wherein the sequence truncation comprises a lack of a cytoplasmic domain, for example, the sequence truncation is to truncate amino acids at positions 550 to 574 of the C-terminus of the RSV F protein, and for example, the truncation is to retain amino acids at positions 1 to 549 of the RSV F protein relative to the wild-type F protein.
4. The composition according to embodiment 2 or 3, wherein the sequence deletion is selected from one or more of the following: a deletion of amino acids at positions 104 to 136 and a deletion of amino acids at positions 104 to 144; optionally, the amino acids for the sequence deletion are replaced by a GSGS oligopeptide or a GS oligopeptide.
5. The composition according to any one of embodiments 2 to 4, wherein the site mutation comprises one or more selected from the following: P102A, I379V, and M447V, for example, the site mutation comprises P102A and I379V; P102A and M447V; I379V and M447V; P102A, I379V, and M447V.
6. The composition according to embodiment 5, wherein the site mutation further comprises one or more selected from the following: S46G, S215P, L373R, S213P, and N216P, for example, site mutations selected from: S46G, S215P, and L373R.
7. The composition according to embodiment 5 or 6, wherein the site mutation further comprises one or more selected from the following:
 (i) Q26C, N27C, T29C, E31C, F32C, Q34C, T36C, S41C, Y44C, Y53C, T54C, S55C, T100C, T103C, L138C, G139C, F140C, L141C, L142C, G145C, S146C, A147C, 1148C, A149C, S150C, V152C, A153C, V154C, S155C, N183GC, S186C, L188C, S287C, 1288C, S290C, 1291C, 1292C, V300C, L305C, Y306C, S319C, N325C, S330C, T337C, R339C, Q354C, T369C, M370C, N371C, S377C, N428C, Y458C, K461C, Q462C, K465C, L467C, Y468C, K470C, G471C;
 (ii) T54H, T58L, S190I, S190F, V207L, T219I, V296I;
 (iii) E92D, K465Q, D486S; and
 (iv) V152I, C69Y, D73E, A74V, N88S.
8. The composition according to embodiment 5 or 6, wherein the site mutation further comprises one or more combinations selected from the following:

(i) E31C, Q34C, T54C, S55C, T100C, I148C, A149C, V152C, V154C, S155C, L188C, I288C, S290C, R339C, S377C, Y458C, L467C, G471C;
(ii) S190F, V296I, V207L, T219I, S190I;
(iii) E92D, K465Q, D486S; and
(iv) V152I, C69Y, D73E, A74V, N88S.

9. The composition according to embodiment 5 or 6, wherein the site mutation further comprises one or more combinations selected from the following:
(i) T54C, S55C, T100C, I148C, A149C, V152C, V154C, S155C, L188C, I288C, S290C, R339C, S377C, Y458C;
(ii) S190F, V296I, V207L, T219I, S190I;
(iii) E92D, K465Q, D486S; and
(iv) V152I, C69Y, D73E, A74V, N88S.

10. The composition according to embodiment 5 or 6, wherein the site mutation further comprises one or more combinations selected from the following:
(i) T54C, I148C, A149C, V152C, S155C, I288C, S290C, Y458C;
(ii) S190F, V296I, V207L;
(iii) E92D, K465Q, D486S; and
(iv) V152I, C69Y, D73E, A74V, N88S.

11. The composition according to any one of embodiments 1 to 10, wherein the variant of the RSV F protein comprises mutations P102A, I379V, and M447V, the variant of the RSV F protein is a truncated protein in which amino acids at positions 550 to 574 of SEQ ID NO: 1 are truncated, and amino acids at positions 104 to 144 are substituted by a GS linker, and the variant of the RSV F protein further comprises a combination of site mutations selected from any one of the following groups:

| Protein variant | Site mutation | | | | |
|---|---|---|---|---|---|
| No. | Group 1 | Group 2 | Group 3 | Group 4 | Group 5 |
| YK-RSV-061 | A149C, S155C, S290C, Y458C | S190F, V296I | E92D, K465Q, D486S | S46G, S215P, L373R | V152I |
| YK-RSV-003 | A149C, S155C, S290C, Y458C | S190F, V296I | E92D, K465Q, D486S | S46G, S215P, L373R | / |
| YK-RSV-062 | A149C, S155C, S290C, Y458C | S190F, V296I | E92D, K465Q, D486S | S46G, S215P, L373R | C69Y, D73E, A74V, N88S, V152I |
| YK-RSV-054 | I148C, I288C | S190F, V207L | E92D, K465Q | S46G, S215P, L373R | / |
| YK-RSV-039 | T54C, V152C | S190F, V207L | E92D, K465Q | S46G, S215P, L373R | / |
| YK-RSV-044 | T100C, A149C | S190F, V207L | E92D, K465Q | S46G, S215P, L373R | / |
| YK-RSV-012 | S55C, L188C | S190F, T219I | E92D, K465Q, D486S | S46G, S215P, L373R | / |
| YK-RSV-015 | S55C, A149C, L188C, Y458C | S190I | E92D, K465Q, D486S | S46G, S215P, L373R | / |
| YK-RSV-001 | A149C, S155C, S290C, Y458C | S190I | E92D, D486S, K465Q | S46G, S215P, L373R | / |
| YK-RSV-036 | S55C, V154C | S190F, V207L | E92D, K465Q | S46G, S215P, L373R | / |
| YK-RSV-060 | R339C, S377C | S190F, V207L | E92D, K465Q | S46G, S215P, L373R | / |
| YK-RSV-011 | Q34C, G471C | S190F, T219I | E92D, K465Q, D486S | S46G, S215P, L373R | / |
| YK-RSV-030 | E31C, L467C | S190F, V207L | E92D, K465Q | S46G, S215P, L373R | / |

12. The composition according to any one of embodiments 6 to 10, wherein the variant of the RSV F protein comprises mutations P102A, 1379V, and M447V, the variant of the RSV F protein is a truncated protein in which amino acids at positions 550 to 574 of SEQ ID NO: 1 are truncated, and amino acids at positions 104 to 144 are substituted by a GS linker, and the variant of the RSV F protein further comprises a combination of site mutations selected from any one of the following groups:

| Protein variant | Site mutation | | | | |
|---|---|---|---|---|---|
| No. | Group 1 | Group 2 | Group 3 | Group 4 | Group 5 |
| YK-RSV-061 | A149C, S155C, S290C, Y458C | S190F, V296I | E92D, K465Q, D486S | S46G, S215P, L373R | V152I |
| YK-RSV-003 | A149C, S155C, S290C, Y458C | S190F, V296I | E92D, K465Q, D486S | S46G, S215P, L373R | / |
| YK-RSV-062 | A149C, S155C, S290C, Y458C | S190F, V296I | E92D, K465Q, D486S | S46G, S215P, L373R | C69Y, D73E, A74V, N88S, V152I |
| YK-RSV-054 | I148C, I288C | S190F, V207L | E92D, K465Q | S46G, S215P, L373R | / |
| YK-RSV-039 | T54C, V152C | S190F, V207L | E92D, K465Q | S46G, S215P, L373R | / |
| YK-RSV-044 | T100C, A149C | S190F, V207L | E92D, K465Q | S46G, S215P, L373R | / |
| YK-RSV-012 | S55C, L188C | S190F, T219I | E92D, K465Q, D486S | S46G, S215P, L373R | / |
| YK-RSV-015 | S55C, A149C, L188C, Y458C | S190I | E92D, K465Q, D486S | S46G, S215P, L373R | / |
| YK-RSV-001 | A149C, S155C, S290C, Y458C | S190I | E92D, D486S, K465Q | S46G, S215P, L373R | / |
| YK-RSV-036 | S55C, V154C | S190F, V207L | E92D, K465Q | S46G, S215P, L373R | / |
| YK-RSV-060 | R339C, S377C | S190F, V207L | E92D, K465Q | S46G, S215P, L373R | / |

13. The composition according to any one of embodiments 1 to 10, wherein the variant of the RSV F protein comprises mutations P102A, I379V, and M447V, the variant of the RSV F protein is a truncated protein in which amino acids at positions 550 to 574 of SEQ ID NO: 1 are truncated, and amino acids at positions 104 to 144 are substituted by a GS linker, and the variant of the RSV F protein further comprises a combination of mutations selected from any one of the following groups:

| Protein variant | Site mutation | | | | |
|---|---|---|---|---|---|
| No. | Group 1 | Group 2 | Group 3 | Group 4 | Group 5 |
| YK-RSV-061 | A149C, S155C, S290C, Y458C | S190F, V296I | E92D, K465Q, D486S | S46G, S215P, L373R | V152I |
| YK-RSV-003 | A149C, S155C, S290C, Y458C | S190F, V296I | E92D, K465Q, D486S | S46G, S215P, L373R | / |
| YK-RSV-062 | A149C, S155C, S290C, Y458C | S190F, V296I | E92D, K465Q, D486S | S46G, S215P, L373R | C69Y, D73E, A74V, N88S, V152I |
| YK-RSV-054 | I148C, I288C | S190F, V207L | E92D, K465Q | S46G, S215P, L373R | / |
| YK-RSV-039 | T54C, V152C | S190F, V207L | E92D, K465Q | S46G, S215P, L373R | / |

14. The composition according to any one of embodiments 1 to 13, wherein the variant of the RSV F protein comprises an amino acid sequence having at least 80%, at least 85%, at least 90%, at least 95% or at least 98% or 100% identity to a sequence of SEQ ID NO: 204 (YK-RSV-061), SEQ ID NO: 12 (YK-RSV-003), SEQ ID NO: 208 (YK-RSV-062), SEQ ID NO: 176 (YK-RSV-054), SEQ ID NO: 116 (YK-RSV-039), SEQ ID NO: 136 (YK-RSV-044), SEQ ID NO: 40 (YK-RSV-012), SEQ ID NO: 52 (YK-RSV-015), SEQ ID NO: 4 (YK-RSV-001), SEQ ID NO: 104 (YK-RSV-036), SEQ ID NO: 200 (YK-RSV-060), SEQ ID NO: 36 (YK-RSV-011), or SEQ ID NO: 80 (YK-RSV-030).

15. The composition according to embodiment 14, wherein the variant of the RSV F protein comprises an amino acid sequence having at least 80%, at least 85%, at least 90%, at least 95% or at least 98% or 100% identity to a sequence of SEQ ID NO: 204 (YK-RSV-061), SEQ ID NO: 12 (YK-RSV-003), SEQ ID NO: 208 (YK-RSV-062), SEQ ID NO: 176 (YK-RSV-054), SEQ ID NO: 116 (YK-RSV-039), SEQ ID NO: 136 (YK-RSV-044), SEQ ID NO: 40 (YK-RSV-012), SEQ ID NO: 52 (YK-RSV-015), SEQ ID NO: 4 (YK-RSV-001), SEQ ID NO: 104 (YK-RSV-036), or SEQ ID NO: 200 (YK-RSV-060).

16. The composition according to embodiment 15, wherein the variant of the RSV F protein comprises an amino acid sequence having at least 80%, at least 85%, at least 90%, at least 95% or at least 98% or 100% identity to a sequence of SEQ ID NO: 204 (YK-RSV-061), SEQ ID NO: 12 (YK-RSV-003), SEQ ID NO: 208 (YK-RSV-062), SEQ ID NO: 176 (YK-RSV-054), or SEQ ID NO: 116 (YK-RSV-039).

17. The composition according to any one of embodiments 1 to 16, wherein an open reading frame (ORF) encoding the RSV F protein or the variant thereof comprises a nucleotide sequence having at least 80%, at least 85%, at least 90%, at least 95% or at least 98% or 100% identity to SEQ ID NO: 203, SEQ ID NO: 11, SEQ ID NO: 207, SEQ ID NO: 175, SEQ ID NO: 115, SEQ ID NO: 135, SEQ ID NO: 39, SEQ ID NO: 51, SEQ ID NO: 3, SEQ ID NO: 103, SEQ ID NO: 199, SEQ ID NO: 35, or SEQ ID NO: 79.

18. The composition according to embodiment 17, wherein the ORF comprises a nucleotide sequence having at least 80%, at least 85%, at least 90%, at least 95% or at least 98% or 100% identity to SEQ ID NO: 203, SEQ ID NO: 11, SEQ ID NO: 207, SEQ ID NO: 175, SEQ ID NO: 115, SEQ ID NO: 135, SEQ ID NO: 39, SEQ ID NO: 51, SEQ ID NO: 3, SEQ ID NO: 103, or SEQ ID NO: 199.

19. The composition according to embodiment 18, wherein the ORF comprises a nucleotide sequence having at least 80%, at least 85%, at least 90%, at least 95% or at least 98% or 100% identity to SEQ ID NO: 203, SEQ ID NO: 11, SEQ ID NO: 207, SEQ ID NO: 175, or SEQ ID NO: 115.

20. The composition according to any one of embodiments 1 to 19, wherein the RNA of the RSV further comprises a 5' untranslated region (UTR).

21. The composition according to embodiment 20, wherein a sequence of the 5' UTR is: SEQ ID NO: 217, SEQ ID NO: 218, SEQ ID NO: 219, SEQ ID NO: 220, or SEQ ID NO: 221.

22. The composition according to embodiment 21, wherein the sequence of the 5' UTR is SEQ ID NO: 217.

23. The composition according to any one of embodiments 1 to 22, wherein the RNA of the RSV further comprises a 3' untranslated region (UTR).

24. The composition according to embodiment 23, wherein a sequence of the 3' UTR is: SEQ ID NO: 222, SEQ ID NO: 223, SEQ ID NO: 224, or SEQ ID NO: 225.

25. The composition according to embodiment 24, wherein the sequence of the 3' UTR is SEQ ID NO: 222.

26. The composition according to any one of embodiments 1 to 25, wherein the RNA of the RSV further comprises a poly(A) tail.

27. The composition according to embodiment 26, wherein the poly(A) tail has a length of 50 to 150 nucleotides.

28. The composition according to any one of embodiments 1 to 27, wherein the RNA of the RSV further comprises a 5' cap structure.

29. The composition according to embodiment 28, wherein the 5' cap structure is: 7mG(5')ppp(5')NlmpNp.

30. The composition according to any one of embodiments 1 to 29, wherein a sequence of an open reading frame (ORF) encoding the RSV F protein or the variant thereof in the RSV RNA is codon-optimized.

31. The composition according to embodiment 30, wherein the sequence of the ORF comprises at least one base modification.

32. The composition according to embodiment 31, wherein the base modification comprises any one or more selected from the following: pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyluridine.

33. The composition according to embodiment 32, wherein the base modification comprises replacement of uracil by pseudouridine and/or N1-methylpseudouridine.

34. The composition according to embodiment 31, wherein the base modification is 1 to 100% base modification, for example, 100% base modification.

35. The composition according to any one of embodiments 1 to 34, wherein a sequence of the RNA of the RSV has at least 80%, at least 85%, at least 90%, at least 95% or at least 98% or 100% identity to SEQ ID NO: 205, SEQ ID NO: 13, SEQ ID NO: 209, SEQ ID NO: 177, SEQ ID NO: 117, SEQ ID NO: 137, SEQ ID NO: 41, SEQ ID NO: 53, SEQ ID NO: 5, SEQ ID NO: 105, SEQ ID NO: 201, SEQ ID NO: 37, or SEQ ID NO: 81.

36. The composition according to embodiment 35, wherein the sequence of the RNA of the RSV has at least 80%, at least 85%, at least 90%, at least 95% or at least 98% or 100% identity to SEQ ID NO: 205, SEQ ID NO: 13, SEQ ID NO: 209, SEQ ID NO: 177, SEQ ID NO: 117, SEQ ID NO: 137, SEQ ID NO: 41, SEQ ID NO: 53, SEQ ID NO: 5, SEQ ID NO: 105, or SEQ ID NO: 201.

37. The composition according to embodiment 36, wherein the sequence of the RNA of the RSV has at least 80%, at least 85%, at least 90%, at least 95% or at least 98% or 100% identity to SEQ ID NO: 205, SEQ ID NO: 13, SEQ ID NO: 209, SEQ ID NO: 177, or SEQ ID NO: 117.

38. The composition according to any one of embodiments 1 to 37, wherein the RNA of the RSV is mRNA.

39. The composition according to any one of embodiments 1 to 38, wherein a sequence encoding the RSV F protein or the variant thereof has at least 80%, at least 85%, at least 90%, at least 95% or at least 98% or 100% identity to SEQ ID NO: 202, SEQ ID NO: 10, SEQ ID NO: 206, SEQ ID NO: 174, SEQ ID NO: 114, SEQ ID NO: 134, SEQ ID NO: 38, SEQ ID NO: 50, SEQ ID NO: 2, SEQ ID NO: 102, SEQ ID NO: 198, SEQ ID NO: 34, or SEQ ID NO: 78.

40. The composition according to embodiment 39, wherein the sequence encoding the RSV F protein or the variant thereof has at least 80%, at least 85%, at least 90%, at least 95% or at least 98% or 100% identity to SEQ ID NO: 202, SEQ ID NO: 10, SEQ ID NO: 206, SEQ ID NO: 174, SEQ ID NO: 114, SEQ ID NO: 134, SEQ ID NO: 38, SEQ ID NO: 50, SEQ ID NO: 2, SEQ ID NO: 102, or SEQ ID NO: 198.

41. The composition according to embodiment 40, wherein the sequence encoding the RSV F protein or the variant thereof has at least 80%, at least 85%, at least 90%, at least 95% or at least 98% or 100% identity to SEQ ID NO: 202, SEQ ID NO: 10, SEQ ID NO: 206, SEQ ID NO: 174, or SEQ ID NO: 114.

42. A method for preparing the composition according to any one of embodiments 1 to 41, comprising:

providing a template from which the RNA of the RSV can be produced by transcription;

performing transcription using the template under conditions suitable for the transcription for the RNA.

43. The method according to embodiment 42, further comprising a purification step selected from the following: lithium chloride precipitation, affinity chromatography, buffer exchanged by ultrafiltration, cellulose chromatography.

44. The composition according to any one of embodiments 1 to 41, wherein the composition is a vaccine and further comprises a pharmaceutically acceptable excipient.

45. The composition according to embodiment 44, wherein the pharmaceutically acceptable excipient comprises a lipid mixture, and the lipid mixture is, for example, a lipid nanoparticle (LNP).

46. The composition according to embodiment 44 or 45, wherein the vaccine is an mRNA vaccine.

47. The composition according to embodiment 45, wherein the lipid nanoparticle comprises, for example, a cationic lipid, a neutral lipid, a structural lipid, and a polymer-conjugated lipid.

48. The composition according to embodiment 47, wherein the cationic lipid is a compound with a structure of formula I, or a N-oxide, a solvate, a pharmaceutically acceptable salt or a stereoisomer thereof, wherein $G_1$ is $C_{1-6}$ alkylene; $G_2$ is $C_{2-8}$ alkylene; $G_3$ is $C_{1-3}$ alkylene; $L_1$ is $C_{6-15}$ linear alkyl; $L_2$ is $C_{12-25}$ branched alkyl;

for example, YK-009 with a structure of formula I-I:

formula I

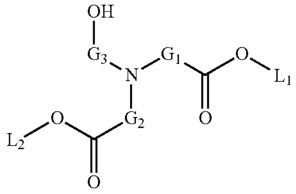

formula I-I

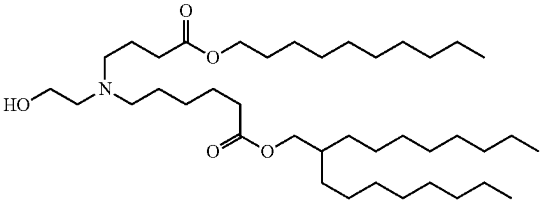

YK-009 .

49. The composition according to embodiment 47, wherein the cationic lipid is a compound with a structure of formula II, or a N-oxide, a solvate, a pharmaceutically acceptable salt or a stereoisomer thereof, wherein $G_1$ is $C_{2-8}$ alkylene; $G_2$ is $C_{2-8}$ alkylene; $L_1$ is —C(O)O— or —OC(O)—; $L_2$ is —C(O)O— or —OC(O)—; $R_1$ is $C_{6-25}$ linear or branched alkyl; $R_2$ is $C_{6-25}$ linear or branched alkyl; $G_3$ is $HO(CH_2)_2$— or $HO(CH_2)_3$—; $G_4$ is $HO(CH_2)_2$— or $HO(CH_2)_3$—; L is $(CH_2)_2$— or —$(CH_2)_3$— or —$(CH_2)_4$—;

for example, YK-401 with a structure of formula II-I or YK-402 with a structure of formula II-II:

formula II

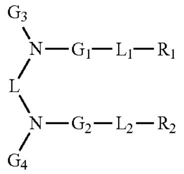

formula II-I

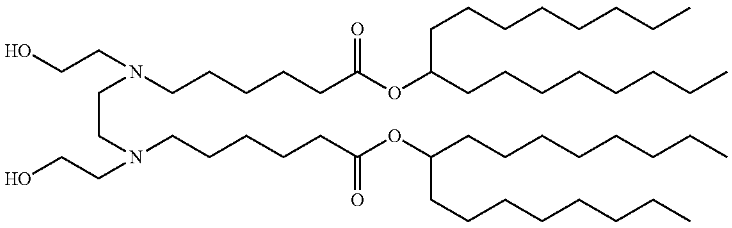

YK-401

-continued formula II-II

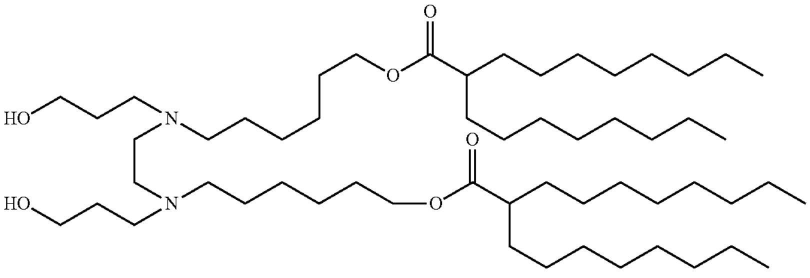

YK-402 .

50. The composition according to embodiment 47, wherein the cationic lipid is a compound with structure of formula III, or a N-oxide, a solvate, a pharmaceutically acceptable salt or a stereoisomer thereof, wherein $G_1$ is $C_{1-6}$ alkylene; $G_2$ is $C_{2-8}$ alkylene; $R_1$ is $C_{6-20}$ linear or branched alkyl; $R_2$ is $C_{12-25}$ branched alkyl; $G_3$ is: $HO(CH_2)_2N(CH_3)(CH_2)_2$—, $HO(CH_2)_2N(CH_2CH_3)(CH_2)_2$—, $(HO(CH_2)_2)_2N(CH_2)_2$—, $CH_3O(CH_2)_2N(CH_3)(CH_2)_2$—, $(CH_3)_2N(CH_2)_3SC(O)O(CH_2)_2$—, $(CH_3)_2N(CH_2)_3SC(O)$—, $CH_3NH(CH_2)_2N(CH_3)(CH_2)_2$—, or $CH_3CH_2NH(CH_2)_2$—;

for example, YK-201 with a structure of formula III-I or YK-202 with a structure of formula III-II:

51. The composition according to embodiment 47, wherein the cationic lipid is a compound with a structure of formula IV, or a N-oxide, a solvate, a pharmaceutically acceptable salt or a stereoisomer thereof, wherein $G_1$ is $C_{1-8}$ alkylene; $G_2$ is $C_{2-8}$ alkylene; $R_1$ is $C_{6-25}$ linear or branched alkyl; $R_2$ is $C_{12-25}$ linear or branched alkyl; $G_3$ is $HO(CH_2)_2N(R_3)CH_2CH(OH)CH_2$—, wherein $R_3$ is —$CH_3$ or —$CH_2CH_3$ or —$CH_2CH_2OH$;

for example, YK-305 with a structure of formula IV-J or YK-310 with a structure of formula IV-II:

formula III

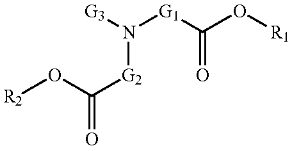

formula III-I

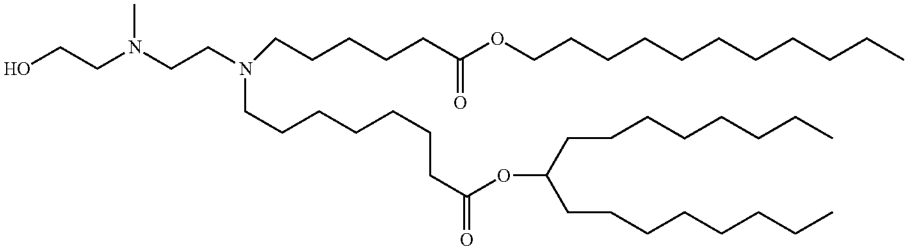

YK-201 formula III-II

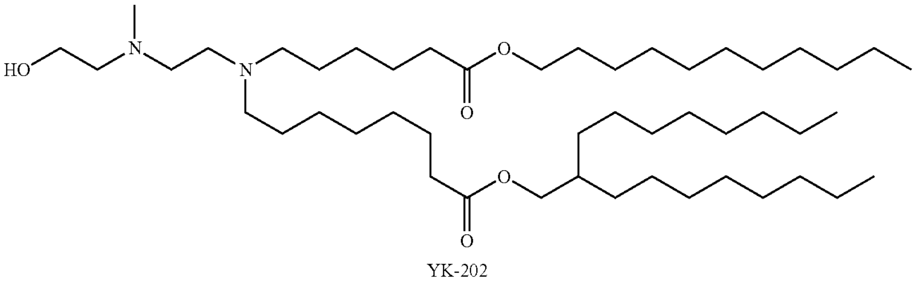

YK-202 .

formula IV

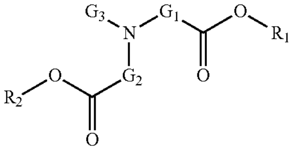

formula IV-I

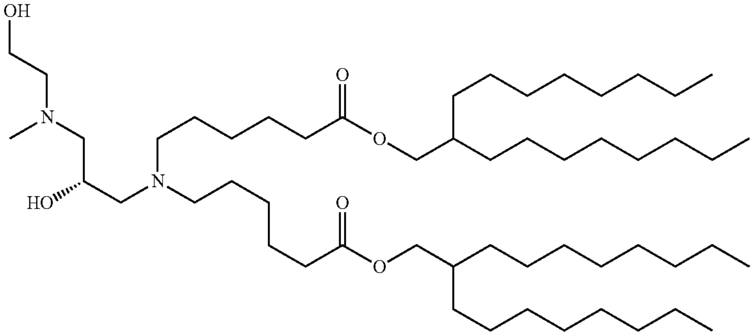

YK-305 formula IV-II

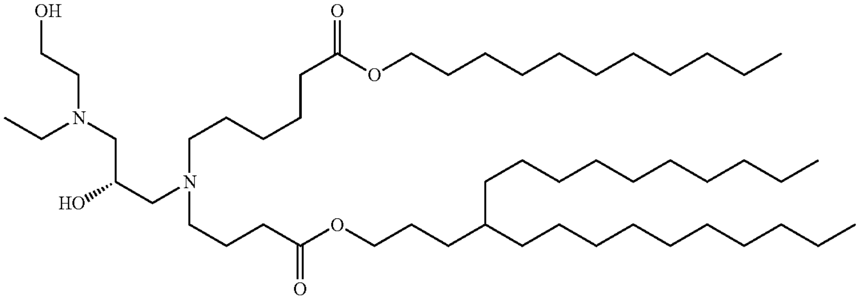

YK-310

.

52. The composition according to embodiment 47, wherein the cationic lipid is a compound with a structure of formula V, or a N-oxide, a solvate, a pharmaceutically acceptable salt or a stereoisomer thereof, wherein $G_1$ and $G_2$ are each independently unsubstituted $C_6$-$C_{10}$ alkylene; $G_3$ is unsubstituted $C_1$-$C_{12}$ alkylene; $R_1$ and $R_2$ are each independently $C_6$-$C_{24}$ alkyl or $C_6$-$C_{24}$ alkenyl; $R_3$ is $OR_5$, N, —C(═O)$OR_4$, —OC(═O)$R_4$, or —$NR_5$C(═O)$R_4$; $R_4$ is $C_1$-$C_{12}$ hydrocarbyl; and $R_5$ is H or $C_1$-$C_6$ alkyl;

for example, ALC0315 with a structure of formula V-I:

formula V

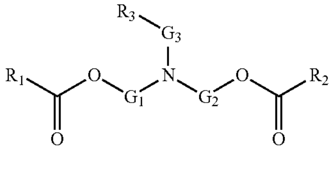

-continued formula V-I

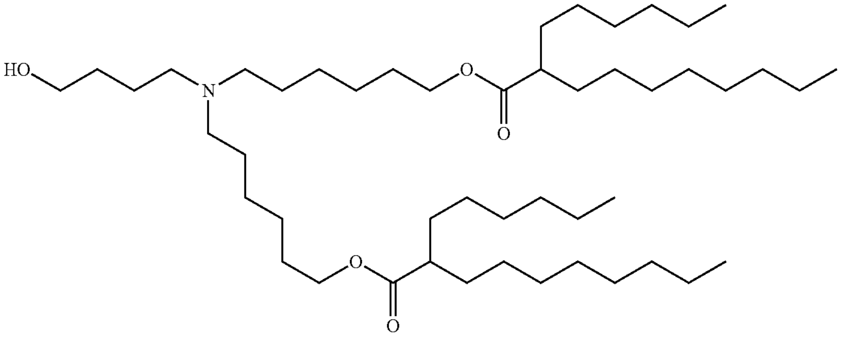

53. The composition according to embodiment 47, wherein the cationic lipid is a compound with a structure of formula VI, or a N-oxide, a solvate, a pharmaceutically acceptable salt or a stereoisomer thereof, formula VI

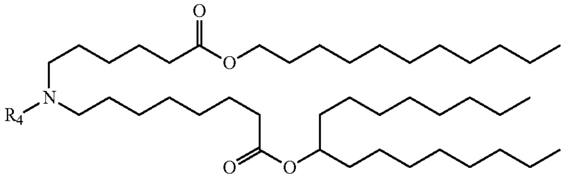

wherein $R_4$ is selected from —$(CH_2)_n$Q and —$(CH_2)_n$CHQR; Q is selected from the group consisting of: —OR, —OH, —$O(CH_2)_nN(R)_2$, —OC(O)R, —$CX_3$, —CN, —N(R)C(O)R, —N(H)C(O)R, —$N(R)S(O)_2R$, —$N(H)S(O)_2R$, —$N(R)C(O)N(R)_2$, —$N(H)C(O)N(R)_2$, —N(H)C(O)N(H)(R), —$N(R)C(S)N(R)_2$, —$N(H)C(S)N(R)_2$, —N(H)C(S)N(H)(R), —$N(R)S(O)_2R_8$, and a heterocyclic ring; n is 1, 2, or 3; wherein R is hydrogen, $C_{1-3}$ alkyl, $C_{2-3}$ alkenyl, or $(CH_2)_qOR^*$, wherein q is 1, 2, or 3, R* is $C_{1-12}$ alkyl or $C_{2-12}$ alkenyl; X is fluoro, chloro, bromo, or iodo; $R_8$ is $C_{3-6}$ cycloalkyl or a heterocyclic ring;

for example, SM102 with a structure of formula VI-I formula VI-I

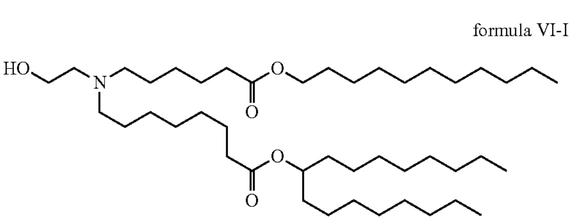 [SMILES: CCCCCCCCCCCOC(=O)CCCCCN(CCO)CCCCCCCC(=O)OC(CCCCCCCC)CCCCCCCC]

54. The composition according to embodiment 47, wherein the cationic lipid is a compound with a structure of formula VII, or a N-oxide, a solvate, a pharmaceutically acceptable salt, or a stereoisomer thereof:

formula VII

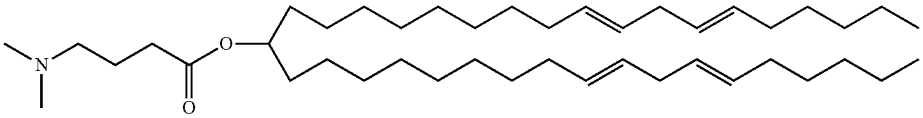

55. The composition according to the preceding embodiment 47 wherein the cationic lipid comprises the following compounds: YK-009 YK-401, YK-305 ALC0315 SM102, DLIN-MC3

YK-009

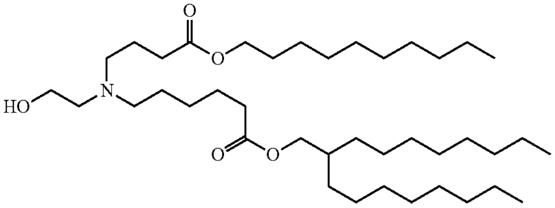

YK-401

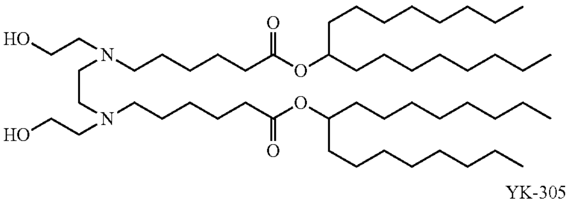

YK-305

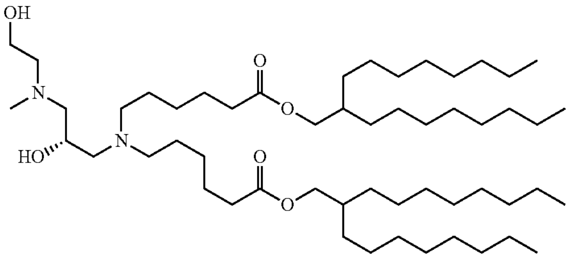

ALC0315

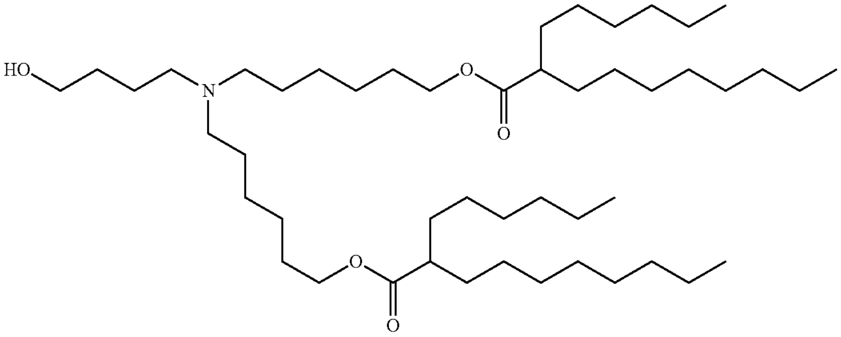

SM102

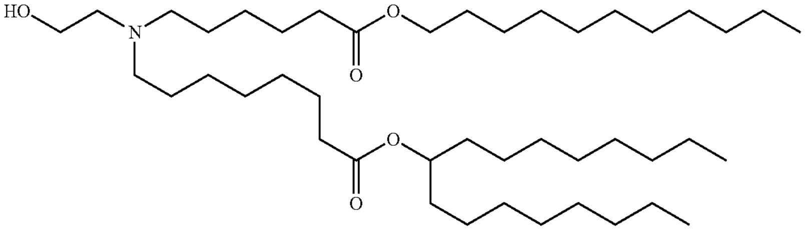

DLIN-MC3

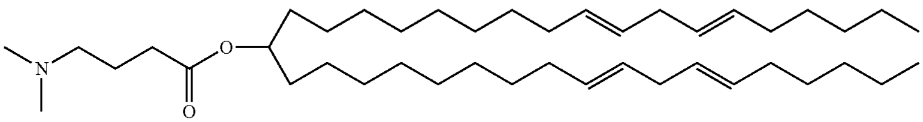

56. The composition according to any one of embodiments 47 to 55, wherein the cationic lipid and the neutral lipid are at a molar ratio of (1-10):1.
57. The composition according to any one of embodiments 47 to 55, wherein the cationic lipid and the structural lipid are at a molar ratio of (1-5):1.
58. The composition according to any one of embodiments 47 to 55, wherein the cationic lipid, the neutral lipid, the structural lipid, and the polymer-conjugated lipid are at a molar ratio of (25-75):(5-25):(15-65):(0.5-10).
59. The composition according to embodiment 58, wherein the cationic lipid, the neutral lipid, the structural lipid, and the polymer-conjugated lipid are at a molar ratio of (35-49):(7.5-15):(35-55):(1-5), for example, 49:10:39.5:1.5 or 45:10:43.5:1.5.
60. The composition according to any one of embodiments 47 to 59, wherein the neutral lipid is selected from one or more of phosphatidylcholine, phosphatidylethanolamine, sphingomyelin, ceramide, sterol, and derivatives thereof.
61. The composition according to any one of embodiments 47 to 60, wherein the neutral lipid is selected from one or more of the following: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphorylcholine (DUPC), 1-palmitoyl-2-oleoyl-sn-glycero-3-phosphocholine (POPC), 1,2-di-O-octadecadienyl-sn-glycero-3-phosphocholine (18:0 Diether PC), 1-oleoyl-2-cholesterol-hemisuccinyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonyl-sn-glycero-3-phosphorylcholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (4ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphatidylethanolamine (DMPE), 1-stearyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, and lysophosphatidylethanolamine (LPE).
62. The composition according to any one of embodiments 47 to 61, wherein the neutral lipid is DOPE and/or DSPC.
63. The composition according to any one of embodiments 47 to 62, wherein the structural lipid is selected from one or more of the following: cholesterol, non-sterol, sitosterol, ergosterol, campesterol, stigmasterol, brassicasterol, tomatidine, ursolic acid, α-tocopherol and corticosteroid.
64. The composition according to embodiment 63, wherein the structural lipid is cholesterol.

65. The composition according to any one of embodiments 47 to 64, wherein the polymer-conjugated lipid is selected from one or more of the following: PEG-modified phosphatidylethanolamine, PEG-modified phosphatidic acid, PEG-modified ceramide, PEG-modified dialkylamine, PEG-modified diacylglycerol, PEG-modified dialkylglycerol.
66. The composition according to the preceding embodiment 65, wherein the polymer-conjugated lipid is selected from one or more of the following: distearoyl phosphatidylethanolamine polyethylene glycol 2000 (DSPE-PEG2000), dimyristoylglycerol-3-methoxy polyethylene glycol 2000 (DMG-PEG2000), and methoxypoly(ethylene glycol) ditetradecylacetamide (ALC-0159).
67. The composition according to any one of embodiments 44 to 66, wherein an effective dose of the RSV RNA is 25 to 200 g; preferably, 50 to 100 g.
68. The composition according to any one of embodiments 44 to 67, wherein the vaccine is in a form of an injection.
69. A method for preparing the composition according to any one of embodiments 44 to 68, comprising: mixing the RNA of the RSV with the pharmaceutically acceptable excipient, for example, to encapsulate at least a portion of the RNA within a lipid nanoparticle.
70. A use of the composition according to any one of embodiments 1 to 41 and 44 to 68 in the preparation of a vaccine for inducing a protective immune response to RSV in a subject, particularly a humoral immune response, for example, including the production of neutralizing antibodies, for example, over 40 years of age or under 10 years of age, for example, over 50 years of age, over 55 years of age, over 60 years of age, over 65 years of age, over 70 years of age, over 75 years of age, or over 80 years of age, or under 8 years of age, under 7 years of age, under 6 years of age, under 5 years of age, under 4 years of age, under 3 years of age, or under 2 years of age.
71. A use of the composition according to any one of embodiments 1 to 41 and 44 to 68 in the preparation of a vaccine for preventing an RSV infection.

The beneficial effect of the present disclosure lies in at least one of the following:

The present application obtains at least 11 ribonucleic acids encoding a variant of an RSV F protein based on a wild-type RSV F protein through a particular variant form (including a sequence truncation, a site mutation, and/or a sequence deletion), and thus provides a novel mRNA vaccine for preventing RSV, which has high stability and can significantly improve the humoral immunity effect after inoculation. The effect includes at least one of the following:

- increasing a binding rate of a pre-fusion epitope Φ on an RSV F mutant to a corresponding antibody;
- improving the stability of a pre-fusion conformation of an RSV F mutant after treatment under different temperature, osmotic pressure, and pH conditions;
- improving the binding quantity and binding capacity of an antibody to a specific antigenic epitope (epitope Φ, epitope Quaternary, and/or epitope V) for a pre-fusion conformation of an RSV F mutant;
- increasing the titer of a neutralizing antibody produced after the immunization with an RSV F protein;
- significantly reducing inflammatory responses and viral load in the body (including the lungs and turbinate);
- being able to be simultaneously applied to a plurality of RSV subtypes.

Specifically, the results and technical effects of the present disclosure are as follows:

(1) Through a Western Blot test, the results show that the following 50 RSV F mutants all have significant protein expression: YK-RSV-001, YK-RSV-002, YK-RSV-003, YK-RSV-004, YK-RSV-005, YK-RSV-008, YK-RSV-009, YK-RSV-010, YK-RSV-011, YK-RSV-012, YK-RSV-013, YK-RSV-014, YK-RSV-015, YK-RSV-016, YK-RSV-017, YK-RSV-018, YK-RSV-019, YK-RSV-022, YK-RSV-029, YK-RSV-030, YK-RSV-031, YK-RSV-032, YK-RSV-033, YK-RSV-034, YK-RSV-035, YK-RSV-036, YK-RSV-037, YK-RSV-038, YK-RSV-039, YK-RSV-040, YK-RSV-041, YK-RSV-042, YK-RSV-043, YK-RSV-044, YK-RSV-045, YK-RSV-046, YK-RSV-048, YK-RSV-050, YK-RSV-051, YK-RSV-052, YK-RSV-053, YK-RSV-054, YK-RSV-055, YK-RSV-056, YK-RSV-057, YK-RSV-058, YK-RSV-059, YK-RSV-060, YK-RSV-061, and YK-RSV-062.

(2) By detecting the binding rates of epitopes on RSV F mutants to corresponding antibodies, the following 42 RSV F mutants (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060, YK-RSV-005, YK-RSV-010, YK-RSV-017, YK-RSV-030, YK-RSV-038, YK-RSV-043, YK-RSV-055, YK-RSV-056, YK-RSV-057, YK-RSV-048, YK-RSV-052, YK-RSV-013, YK-RSV-002, YK-RSV-009, YK-RSV-050, YK-RSV-032, YK-RSV-019, YK-RSV-040, YK-RSV-046, YK-RSV-008, YK-RSV-059, YK-RSV-034, YK-RSV-004, YK-RSV-058, YK-RSV-016, YK-RSV-029, YK-RSV-035, YK-RSV-037, YK-RSV-011, YK-RSV-045, YK-RSV-051) are selected to have binding rates of an epitope Φ and an epitope II thereon to the corresponding antibodies of about 80% or more, all with good binding rates.

(3) By performing a stability test after stress treatment under different temperature, osmolarity, and pH conditions, the following 20 mutants (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060, YK-RSV-009, YK-RSV-010, YK-RSV-011, YK-RSV-030, YK-RSV-043, YK-RSV-048, YK-RSV-050, YK-RSV-055, YK-RSV-057) are all selected to have a stress resistance parameter of above 0.44, up to 0.68, after storage at 4° C. for one week; a stress resistance parameter of above 0.64 after incubation at 50° C. for 60 min; a stress resistance parameter of above 0.61 after treatment under a high osmotic pressure condition for 60 min; a stress resistance parameter of above 0.70 after treatment under a low osmotic pressure condition for 60 min; a stress resistance parameter of above 0.56 after treatment under conditions of pH=3.5 and pH=10 for 60 min. The stress resistance parameters after treatment under the above different conditions are all superior to or comparable to those of the controls.

(4) By detecting binding levels of different epitopes to corresponding antibodies by ELISA, the following 15 mutants (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060, YK-RSV-011, YK-RSV-030, YK-RSV-048, YK-RSV-050) are selected to have an epitope (1), an epitope Quaternary, and an epitope V thereon that are all able to well bind to the corresponding antibodies, and have a relatively large number of binding epitopes and relatively strong binding capacity.

For example, the binding levels of the epitope Φ on YK-RSV-061, YK-RSV-003, and YK-RSV-062 to the RSV pre-F antibody (3C12) are 1.83 to 2.00 times that on the control PC—RSV-064; the binding levels of the epitope Quaternary to the RSV pre-F antibody (7H11) are 2.01-2.12 times that on the control PC—RSV-064.

The binding level of the epitope Φ on YK-RSV-054 to the RSV pre-F antibody (3C12) is 2.52 times that on the control PC—RSV-064; the binding level of the epitope Quaternary to the RSV pre-F antibody (7H11) is 1.82 times that on the control PC—RSV-064; the binding level of the epitope V to the RSV F antibody (7E11) is 3.30 times that on the control PC—RSV-064; the binding level of the epitope II to the RSV F antibody (11A9) is 1.79 times that on the control PC—RSV-064; the binding level of the epitope III to the RSV F antibody (4B9) is 2.27 times that on the control PC—RSV-064.

(5) The affinity of the target protein for different antibodies is analyzed by a BLI method. The detection results show that: the epitope Φ and the epitope Quaternary on 13 mutants (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060, YK-RSV-011, YK-RSV-030) bind with the strongest affinity to the corresponding antibodies.

The affinity constant $K_D$ values for the binding of the epitope D on the mutants to the RSV pre-F antibody (3C12) are 3.26E-12 M to 7.79E-11 M, which are significantly lower than the $K_D$ value ($K_D$ of about E-10 M, with a difference of about 1 to 2 orders of magnitude) of the controls, indicating that the affinity of the antigens for the antibody is stronger.

The affinity constant $K_D$ values for the binding of the epitope Quaternary on the mutants to the RSV pre-F antibody (7H11) are 3.05E-12 M to 6.13E-10 M, and except that the $K_D$ values for YK-RSV-044, YK-RSV-060, and YK-RSV-030 are comparable to those of the controls, the $K_D$ values for the other mutants are significantly lower than those of the controls (with a difference of 1 to 2 orders of magnitude), indicating that the affinity of the antigens for the antibody is stronger.

(6)

Mouse: Binding Antibody

The IgG titers specific for the pre-fusion F and post-fusion F proteins in the serum of mice on day 35 after the immunization are detected by an ELISA method. The detection results show that 11 test samples (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060) are selected to have pre-F IgG antibody titers of 2.52 to 5.31 times that of the Abrysvo™ positive control, and have post-F IgG antibody titers of 1.13 to 5.21 times that of the Abrysvo™ positive control.

In all of the test samples being detected, the pre-F/post-F ratios are all higher than 1, indicating that the IgG titers produced by the pre-fusion F proteins are higher than those of IgG produced by the post-fusion F proteins.

Mouse: Neutralizing Antibody

1) RSV type A virus: the neutralizing antibody titers in the serum of mice on day 35 after the immunization are detected by a plaque reduction neutralization-based microneutralization test method, and 11 test samples (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060) are selected to have neutralizing antibody titer $IC_{50}$ values of 3.72 to 12.67 times that of the Abrysvo™ positive control, and have $IC_{90}$ values of 2.34 to 14.41 times that of the Abrysvo™ positive control, which are all superior to those of the positive control.

2) RSV type B virus: 11 test samples (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060) have neutralizing antibody titer $IC_{50}$ values of 2.85 to 10.63 times that of the Abrysvo™ positive control, and have $IC_{90}$ values of 2.88 to 14.23 times that of the Abrysvo™ positive control, with neutralizing antibody titers all significantly higher than that of the positive control.

(7)

Cotton Rat: Binding Antibody

The IgG titers specific for the pre-fusion F and post-fusion F proteins in the serum of cotton rats on days 42 and 48 after the immunization are detected by an ELISA method. For 11 test samples (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060):

The pre-F IgG antibody titers on day 42 are 3.05 to 13.10 times that of the Abrysvo™ positive control, and the post-F IgG antibody titers are 2.36 to 6.38 times that of the Abrysvo™ positive control, all of which are significantly higher than that of the positive control. The pre-F/post-F ratios of all the test samples range from 1.39 to 3.95, indicating that the IgG antibody titers produced by the pre-fusion F proteins are significantly higher than those produced by the post-fusion F proteins.

The pre-F IgG antibody titers on day 48 are 4.44 to 12.35 times that of the Abrysvo™ positive control, and the post-F IgG antibody titers are 1.51 to 6.83 times that of the Abrysvo™ positive control, all of which are significantly higher than those of the positive control. The pre-F/post-F ratios of all the test samples range from 1.78 to 4.29, indicating that the IgG antibody titers produced by the pre-fusion F proteins are still significantly higher than those produced by the post-fusion F proteins on day 48 after the immunization.

Cotton Rat: Neutralizing Antibody

The neutralizing antibody titers produced by the RSV A2 virus in the serum of cotton rats are detected. The detection results show that, for 11 test samples (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060):

1) On day 42 after the immunization, for the RSV A2 virus, the neutralizing antibody titer $IC_{50}$ values are 2.10 to 14.30 times that of the Abrysvo™ positive control, and $IC_{90}$ values are 2.26 to 22.33 times that of the Abrysvo™ positive control, all of which are significantly higher than those of the positive control.

The neutralizing antibody titer $IC_{50}$ values produced by the RSV B virus are 2.16 to 14.63 times that of the Abrysvo™ positive control, and $IC_{90}$ values are 2.49 to 17.26 times that of the Abrysvo™ positive control, all of which are significantly higher than those of the positive control.

2) On day 48 after the immunization, the neutralizing antibody $IC_{50}$ values produced by the RSV A2 virus are 1.70 to 7.57 times that of the Abrysvo™ positive control, and $IC_{90}$ values are 1.46 to 11.56 times that of the Abrysvo™ positive control, all of which are higher than those of the positive control.

(8) The results for pathological sections of the lungs of cotton rats show that, for 11 test samples (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060): The peribronchiolar infiltration scores are 0.33 to 0.83, indicating mild inflammatory infiltration. All the test samples have interstitium infiltration scores superior to that of the positive control Abrysvo™, and the scores are 0.67 to 1.17, indicating mild inflammatory infiltration. All the test samples have low overall inflammatory response scores, and the total pathological scores are 1.00 to 2.00, all of which are lower than that of the control LNP. The scores of two indicators of perivascular infiltration and alveolar infiltration of the control and the test samples are all 0, indicating that there are no visible lesions in the tissue.

(9) The results for viral loads in the lungs and turbinates of cotton rats show that: the viral loads after immunization in the lungs of 11 test samples (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060) are 1.61-2.08, which are lower than that of the positive control Abrysvo™; the viral loads in the turbinates are 0.62 to 1.51, which are only 0.19 to 0.45 times that of the positive control Abrysvo™, with significantly reduced viral loads, indicating that the test samples have a better antiviral effect.

DETAILED DESCRIPTION

Figure 1:
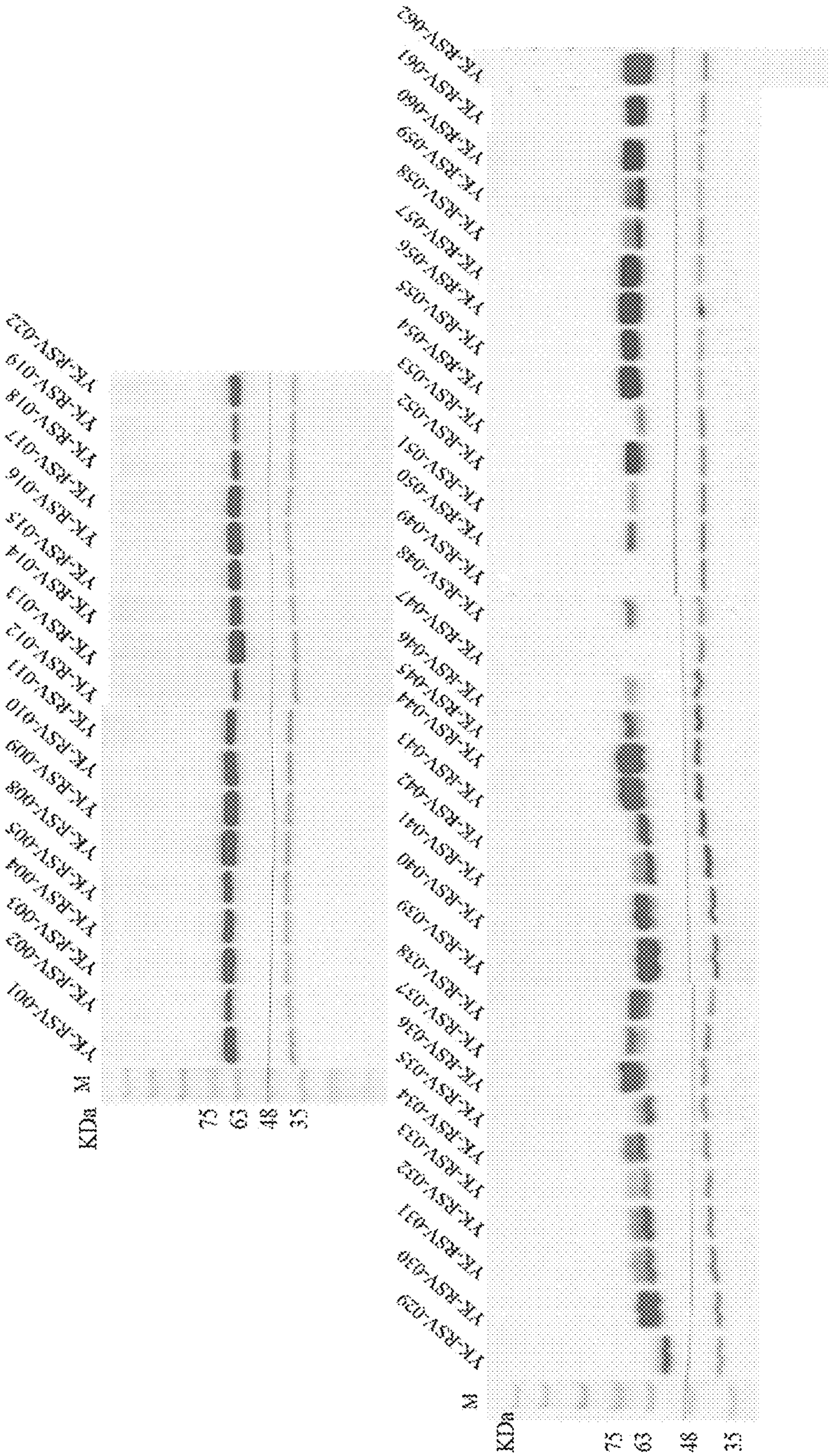
FIG. 1: antigen expression of YK-RSV-001-YK-RSV-062.
Figure 2A:
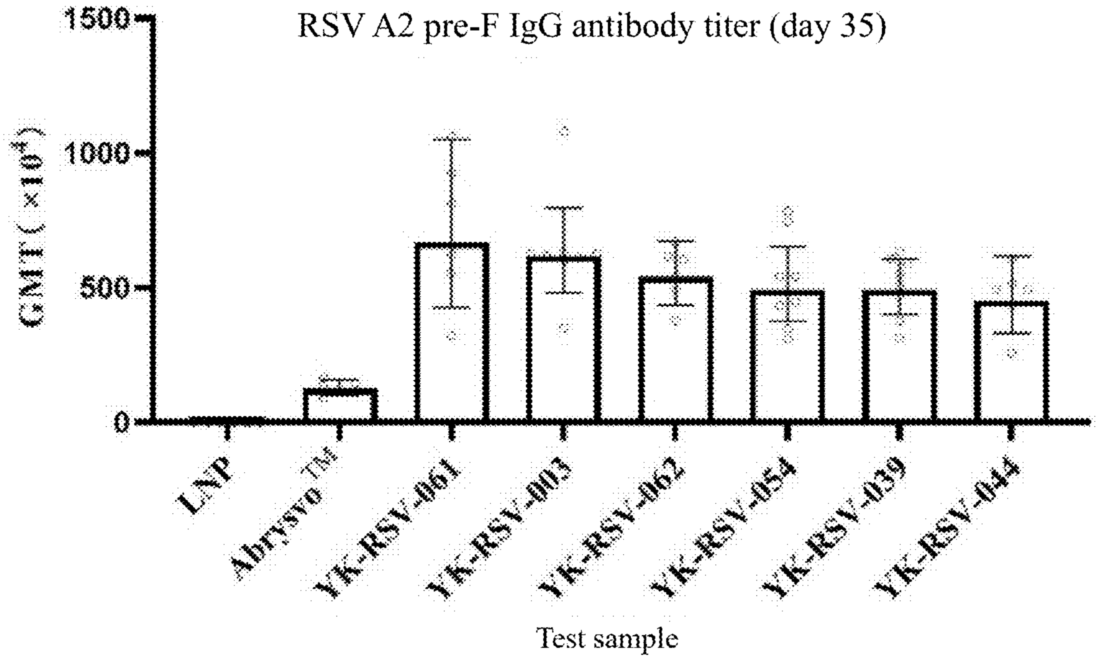
FIGS. 2A and 2B show RSV A2 pre-F binding antibody titers in the serum of mice on day 35, respectively.
Figure 2B:
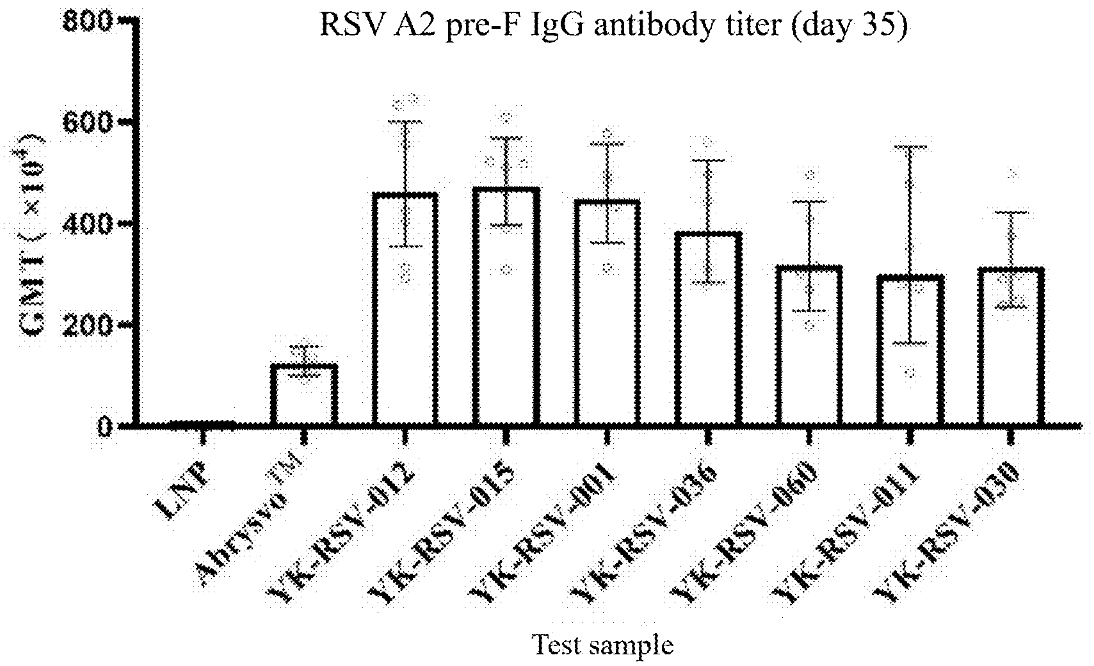
Figure 3A:
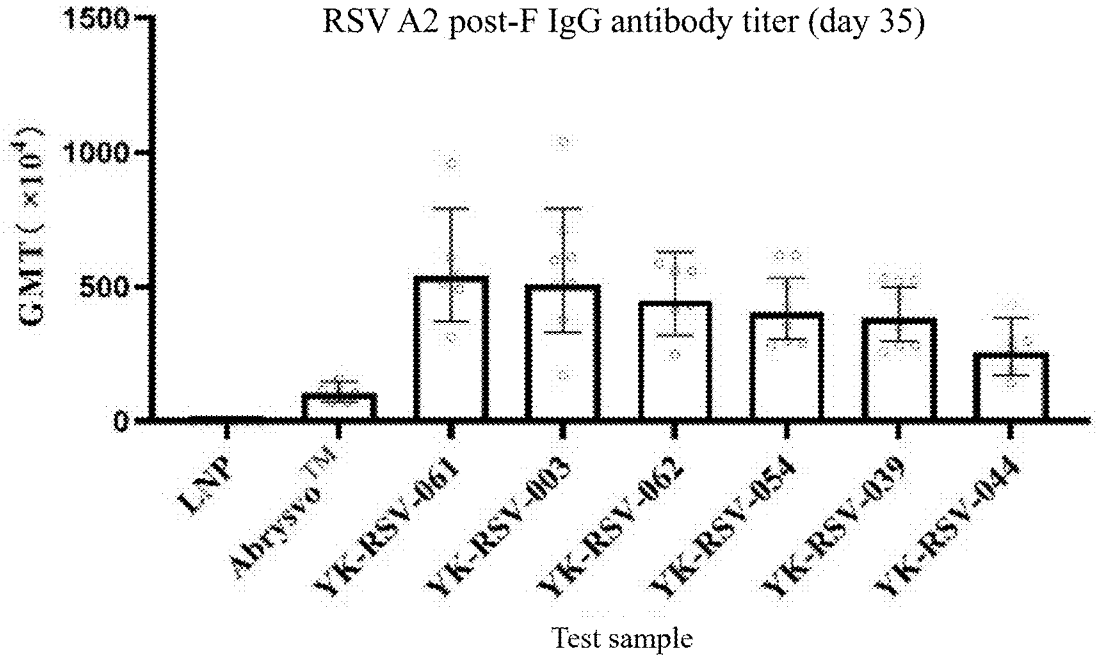
FIGS. 3A and 3B show RSV A2 post-F binding antibody titers in the serum of mice on day 35, respectively.
Figure 3B:
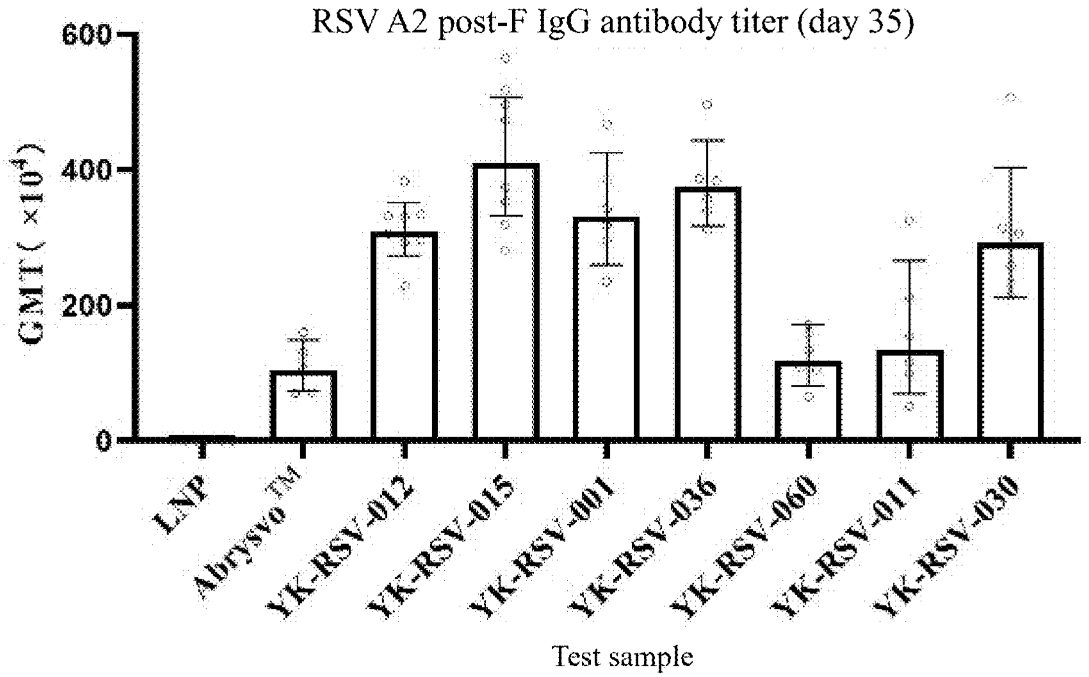
Figure 4A:
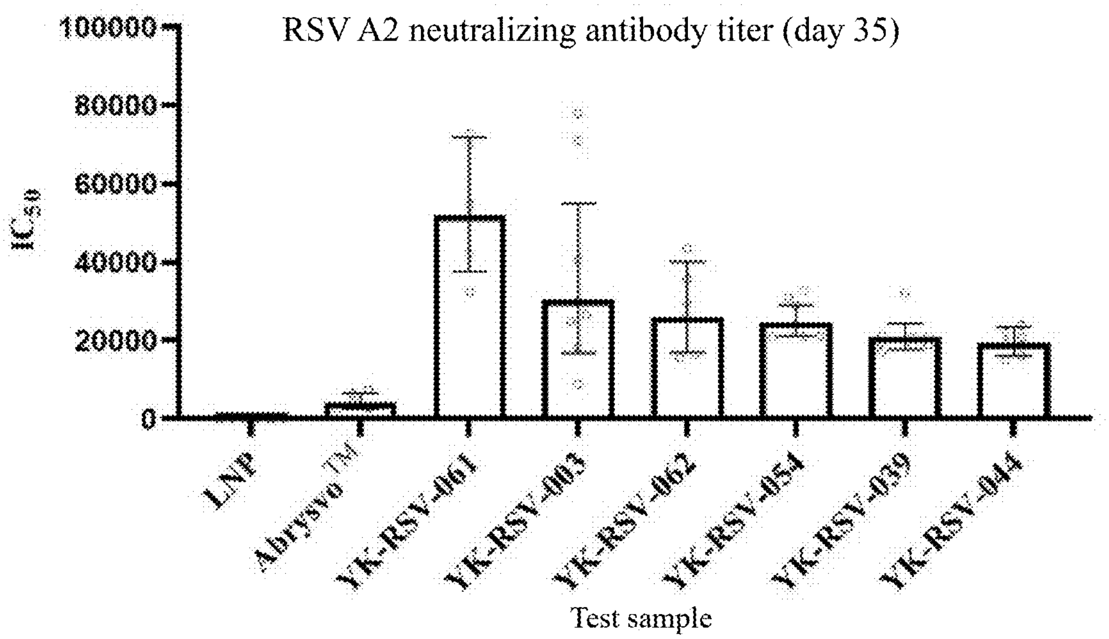
FIGS. 4A and 4B show RSV A2 neutralizing antibody titer $IC_{50}$ in the serum of mice on day 35, respectively.
Figure 4B:
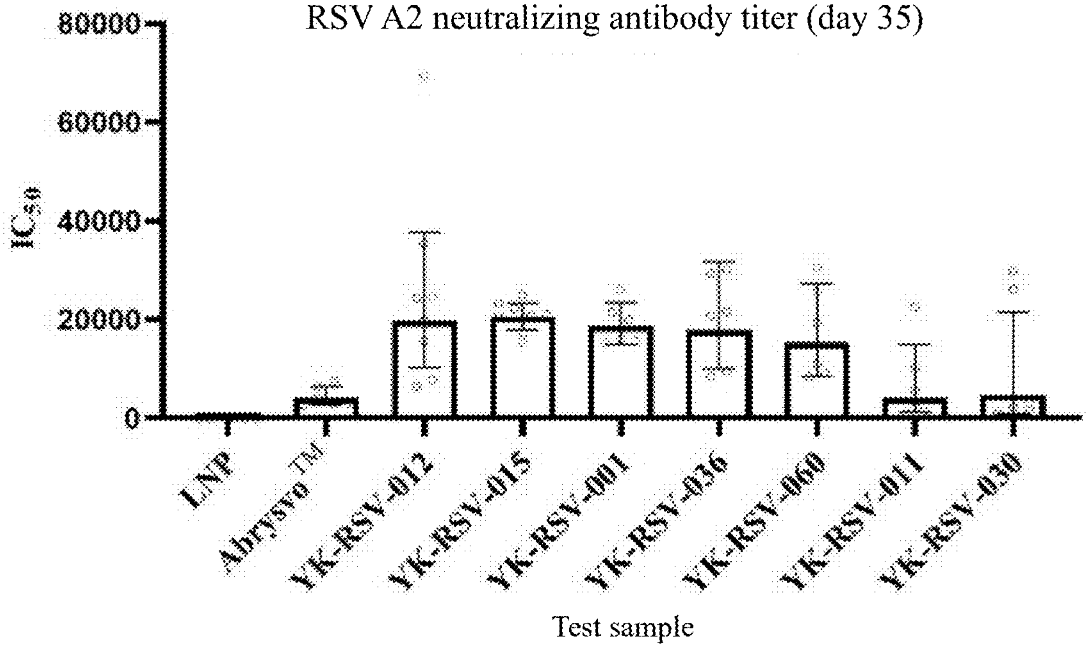
Figure 5A:
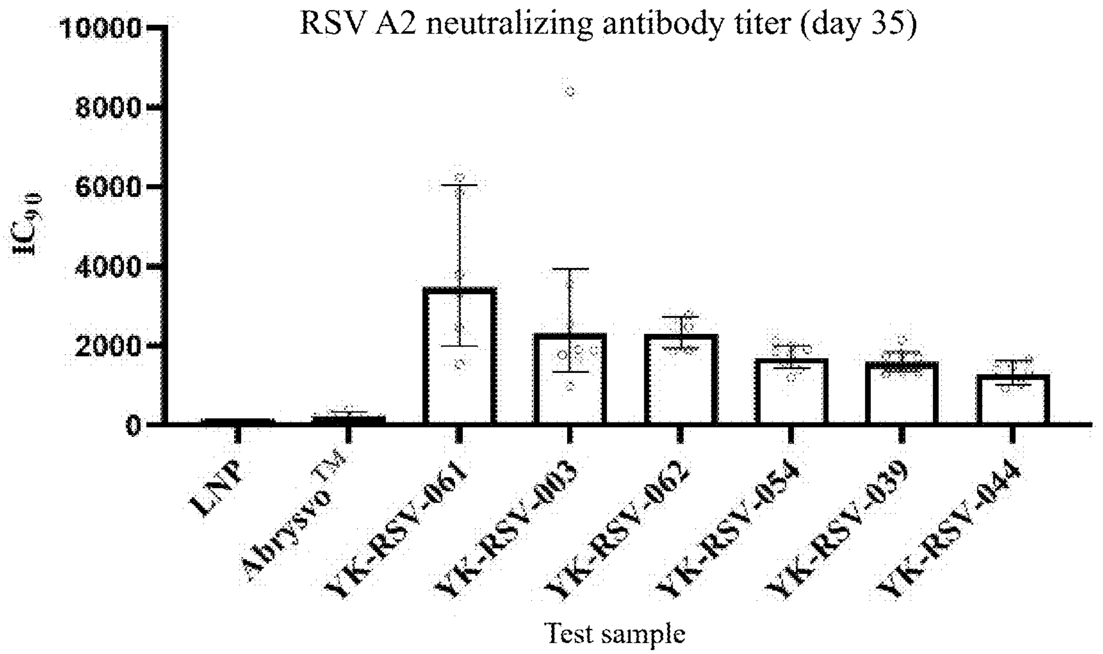
FIGS. 5A and 5B show RSV A2 neutralizing antibody titer $IC_{90}$ in the serum of mice on day 35, respectively.
Figure 5B:
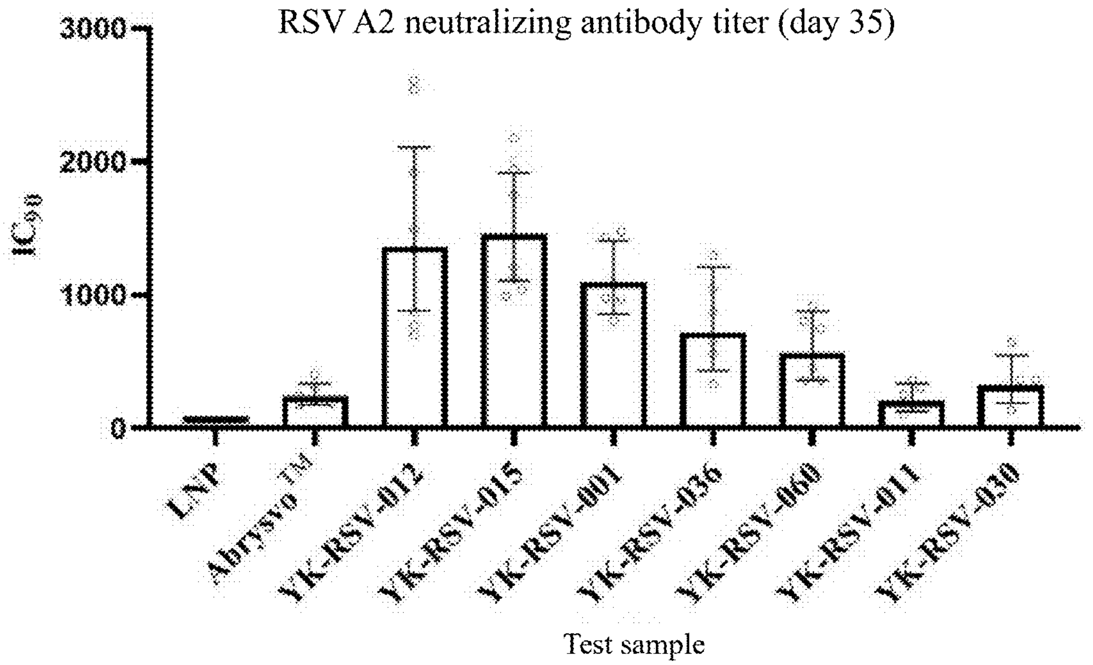
Figure 6A:
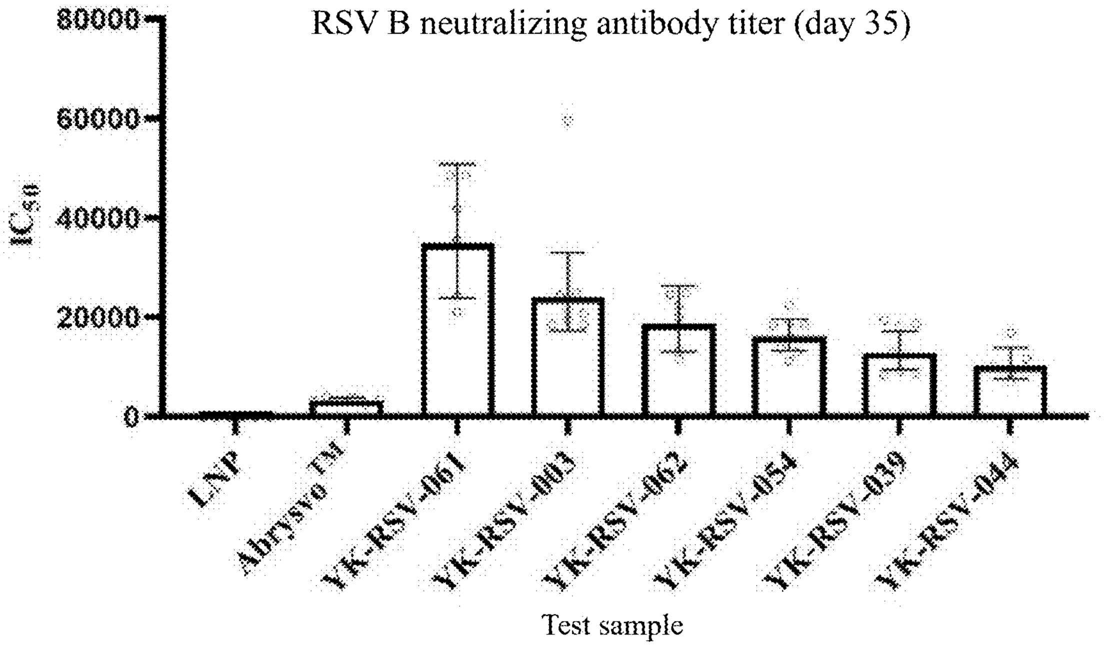
FIGS. 6A and 6B show RSV B neutralizing antibody titer $IC_{50}$ in the serum of mice on day 35, respectively.
Figure 6B:
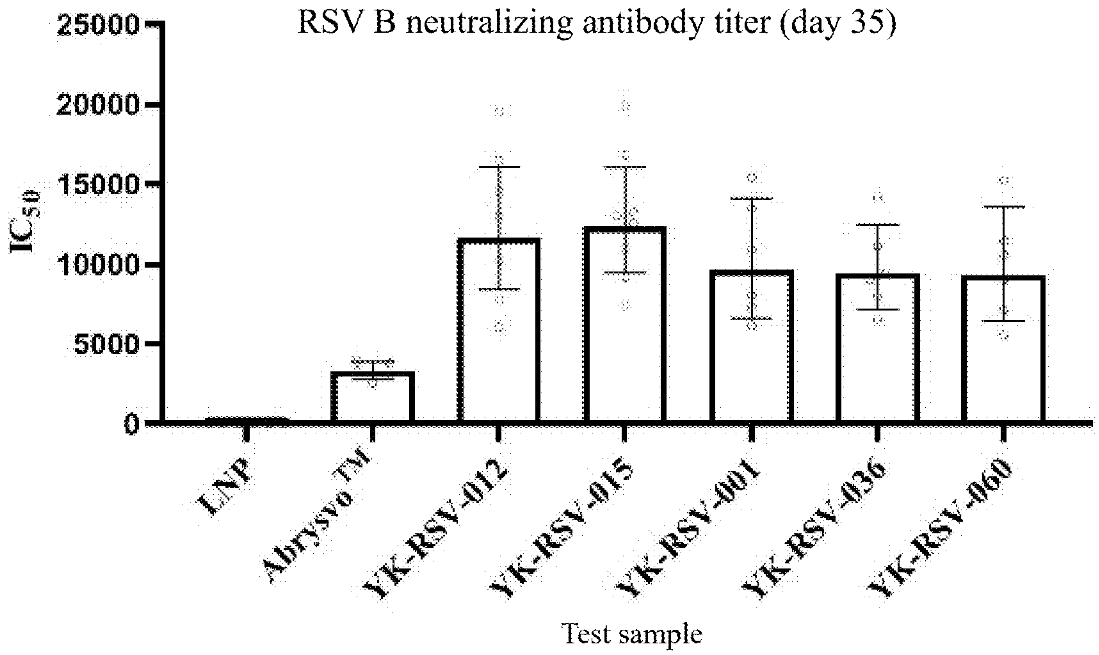
Figure 7A:
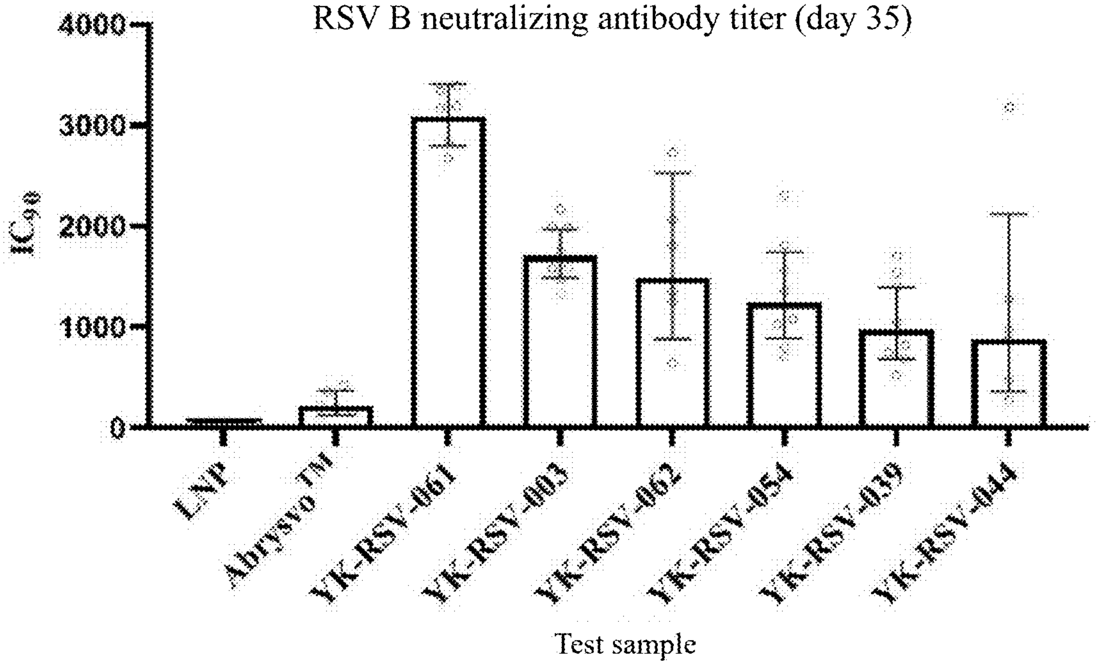
FIGS. 7A and 7B show RSV B neutralizing antibody titer $IC_{90}$ in the serum of mice on day 35, respectively.
Figure 7B:
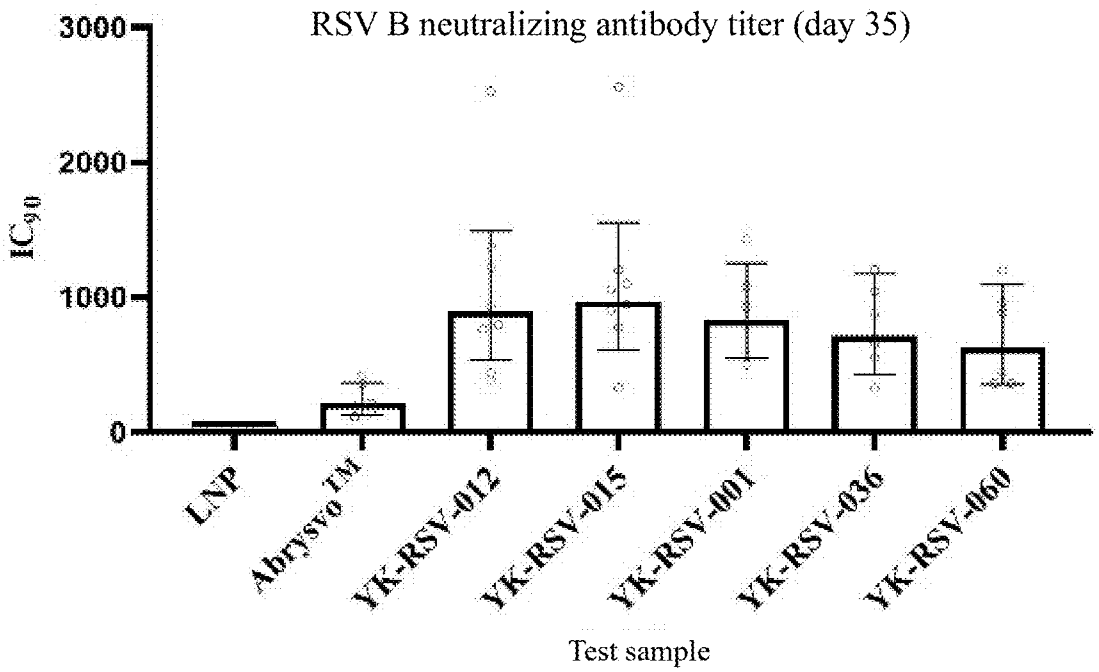
Figure 8A:
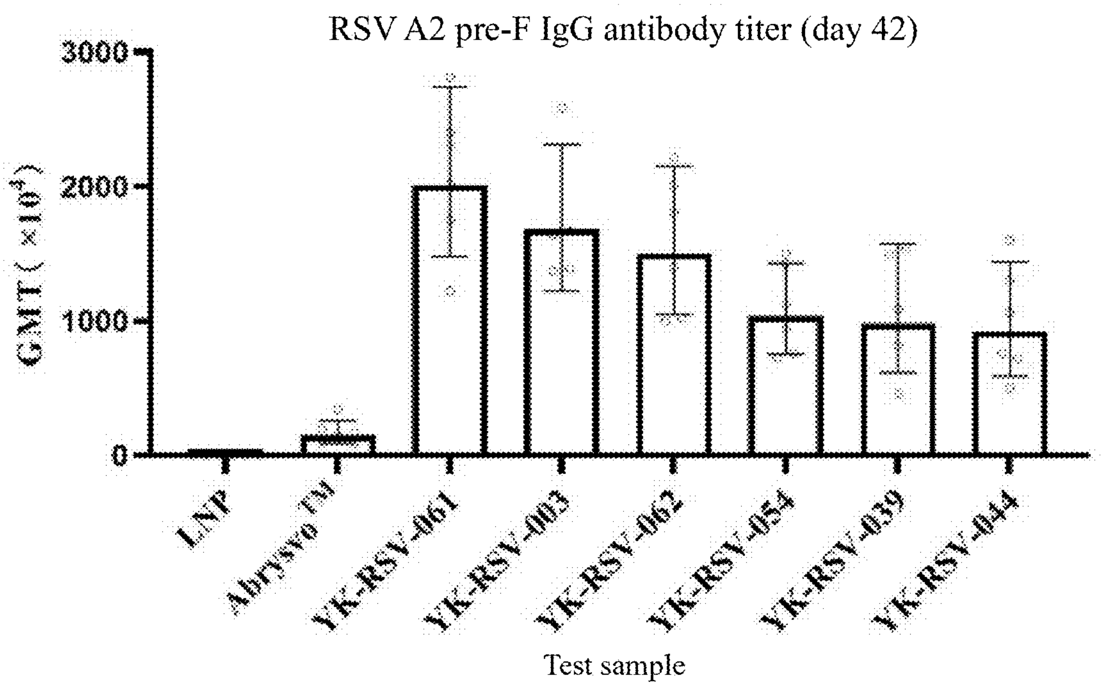
FIGS. 8A and 8B show RSV A2 pre-F binding antibody titers in the serum of cotton rats on day 42, respectively.
Figure 8B:
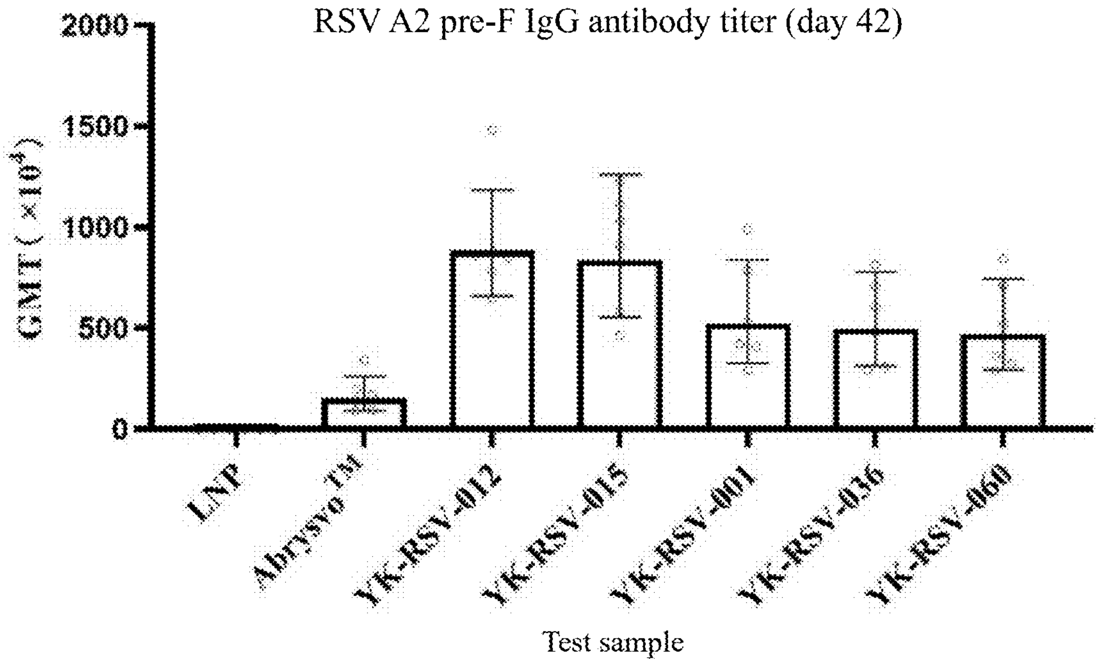
Figure 9A:
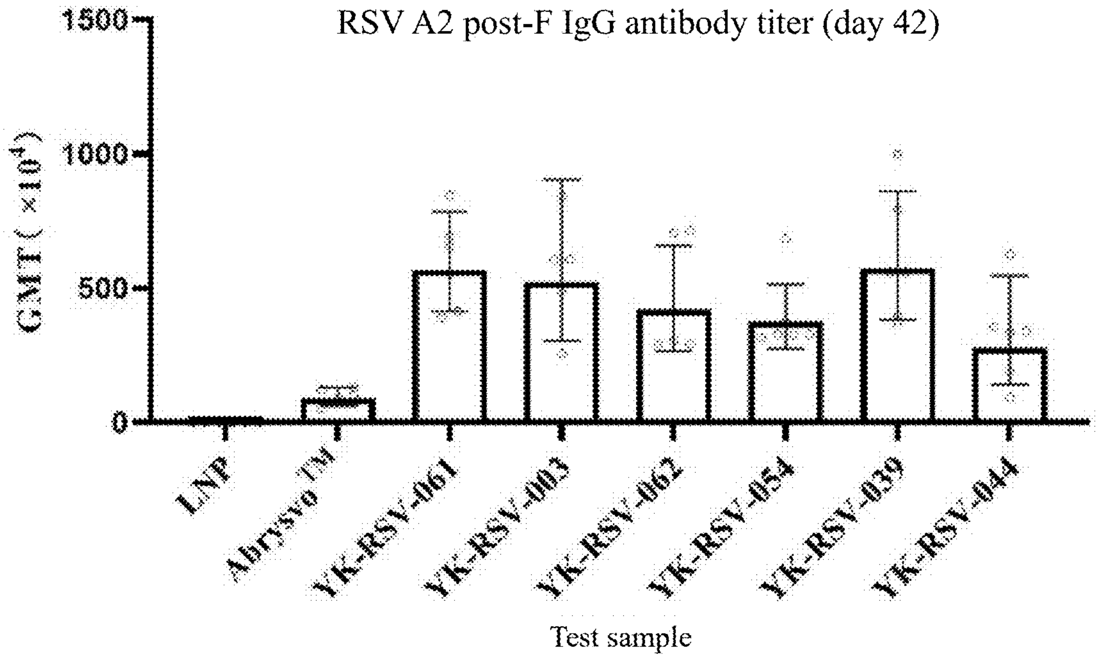
FIGS. 9A and 9B show RSV A2 post-F binding antibody titers in the serum of cotton rats on day 42, respectively.
Figure 9B:
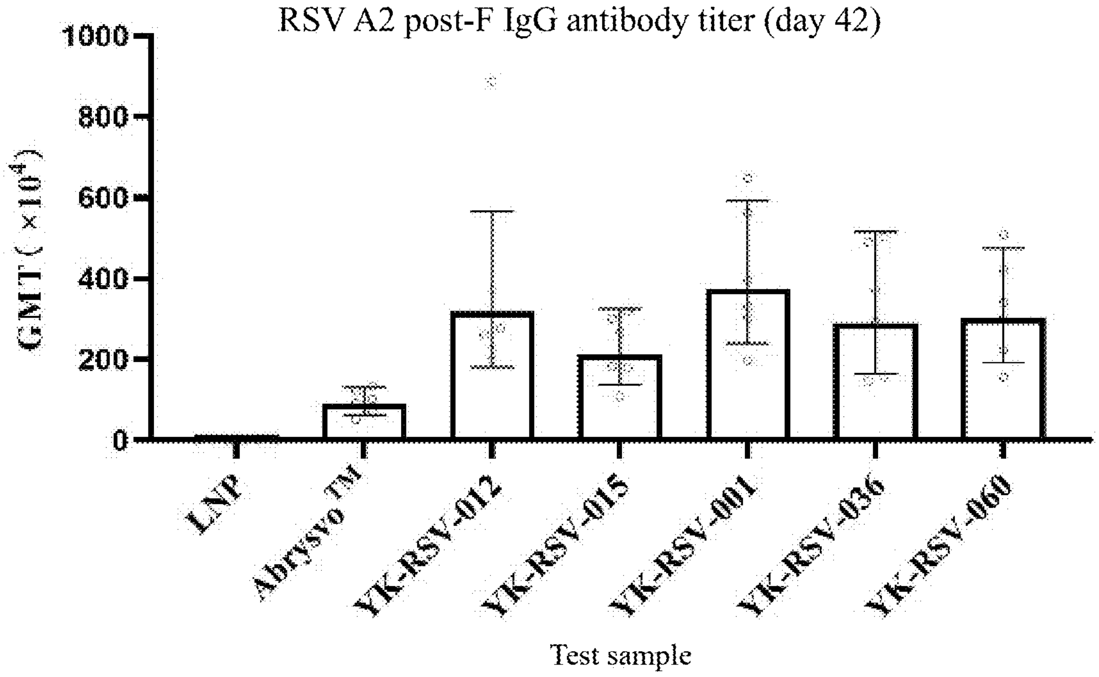
Figure 10A:
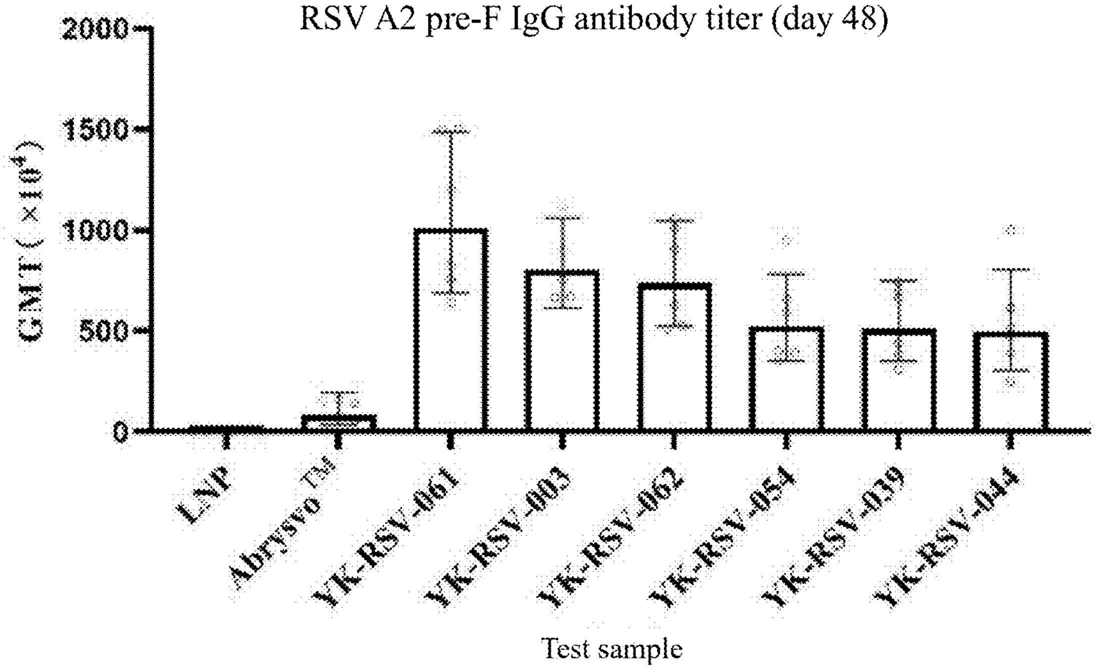
FIGS. 10A and 10B show RSV A2 pre-F binding antibody titers in the serum of cotton rats on day 48, respectively.
Figure 10B:
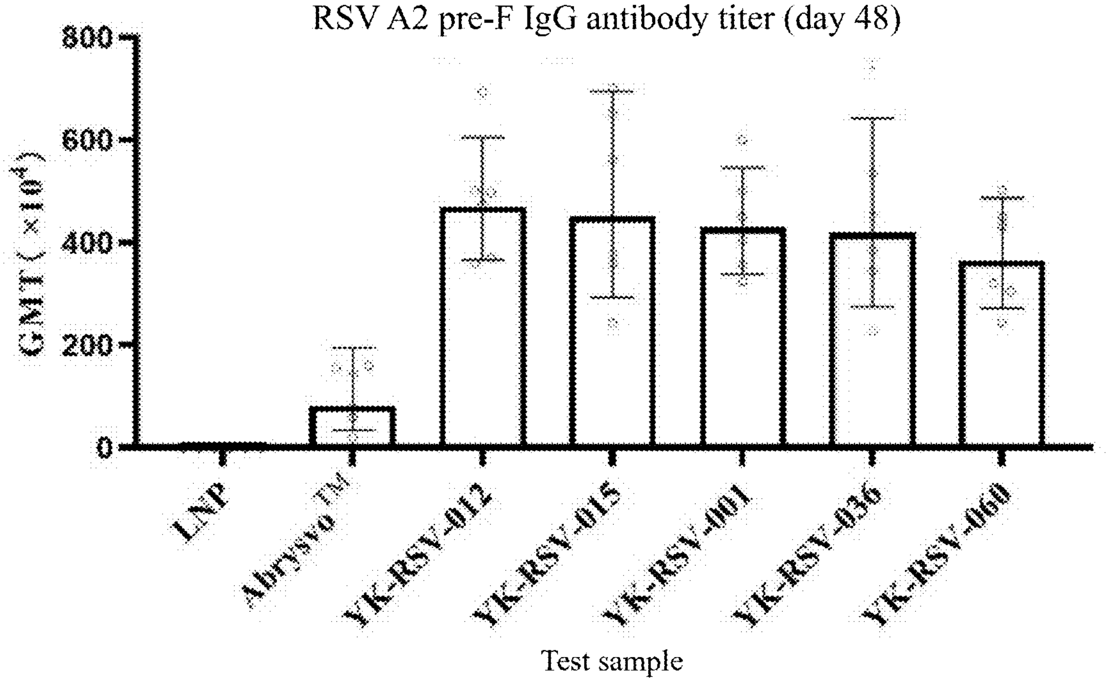
Figure 11A:
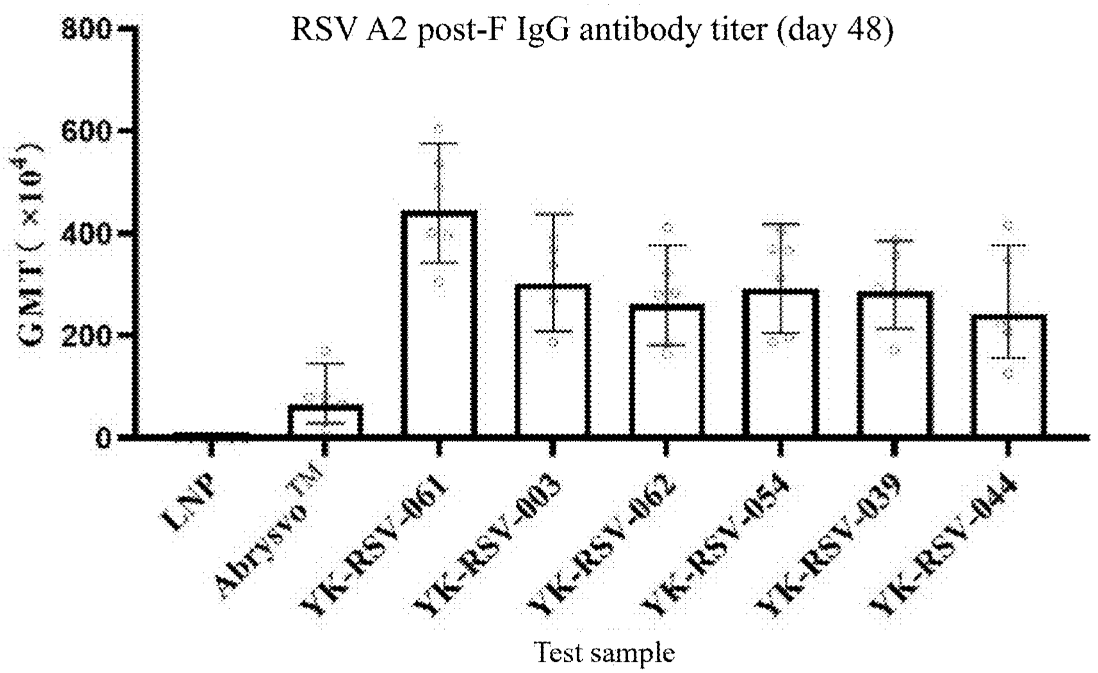
FIGS. 11A and 11B show RSV A2 post-F binding antibody titers in the serum of cotton rats on day 48, respectively.
Figure 11B:
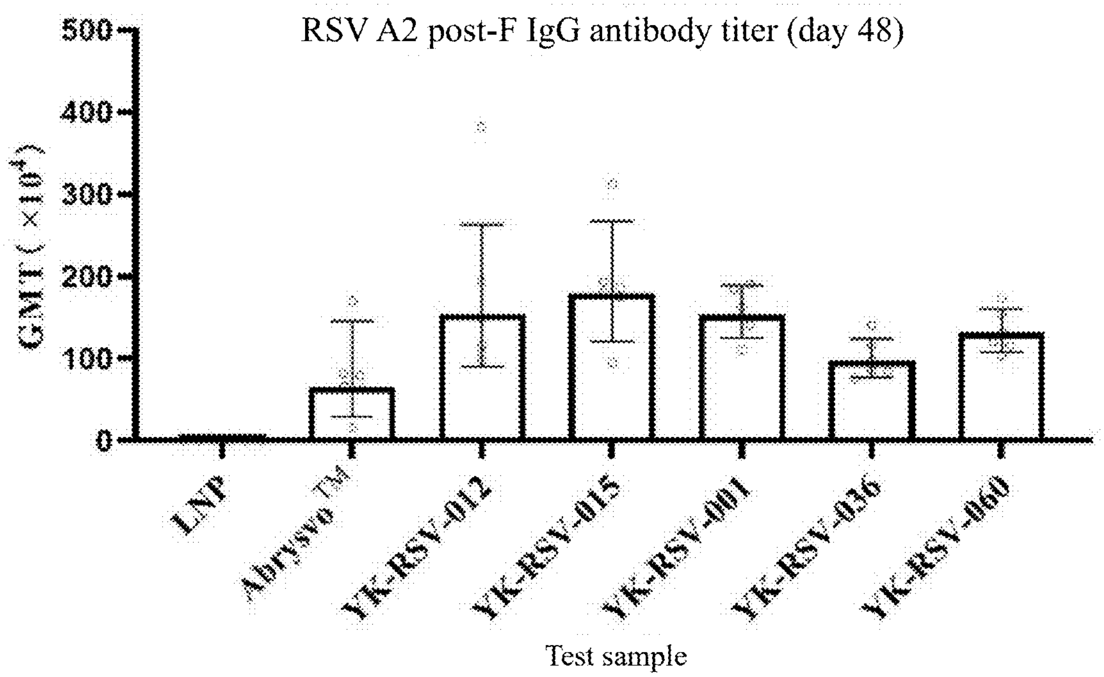

The present disclosure is further illustrated by the following examples. It should be understood that the embodiments of the present disclosure are given for illustration only and not for limitation, and the simple modifications of the present disclosure in the light of the technical solutions of the present disclosure are within the scope of the present disclosure.

As used herein, amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The following terms used herein have the meanings indicated below.

Vaccine

Vaccine refers to a substance comprising immunogen capable of eliciting a prophylactic or therapeutic immune response in an individual, which may be in the form of a pharmaceutical composition. Generally, vaccines elicit antigen-specific immune responses against antigens of pathogens, e.g., viral pathogens.

Nucleic Acid

Nucleic acid is a polymer comprising nucleotides (nucleotide monomers). Thus, the nucleic acid is also referred to as polynucleotides. The nucleic acid may be or may comprise, for example, deoxyribonucleic acid (DNA), ribonucleic acid (RNA), threose nucleic acid (TNA), glycol nucleic acid (GNA), peptide nucleic acid (PNA), locked nucleic acid (LNA, including LNA having a β-D-ribose configuration, α-LNA having an α-L-ribose configuration (diastereomer of LNA), 2'-amino-LNA having 2'-amino functionalization, and 2'-amino-α-LNA having 2'-amino functionalization), ethylene nucleic acid (ENA), cyclohexenyl nucleic acid (CeNA), and/or chimeras thereof and/or combinations thereof.

Messenger RNA (mRNA) is any RNA that encodes (at least one) protein (a naturally occurring, non-naturally occurring, or modified polymer of amino acids) and that can be translated in vitro, in vivo, in situ, or ex vivo to produce the encoded protein. Those skilled in the art will understand that unless otherwise stated, nucleic acid sequences set forth herein may be enumerated with "T" in a representative DNA sequence, but in the case where the sequence represents RNA (e.g., mRNA), "T" will be replaced by "U". Thus, for any DNA disclosed and identified herein by a particular sequence identification number, a corresponding RNA (e.g., mRNA) sequence complementary to the DNA is also disclosed, wherein each "T" of the DNA sequence is replaced by "U".

An open reading frame (ORF) is a contiguous stretch of DNA or RNA, beginning with an initiation codon (e.g., methionine (ATG or AUG)) and ending with a termination codon (e.g., TAA, TAG or TGA, or UAA, UAG or UGA). The ORF generally encodes a protein. It should be understood that the sequence disclosed herein may also comprise additional elements, e.g., 5' and 3' UTRs, but unlike ORF, these elements are not necessarily present in the RNA polynucleotide of the disclosure.

The composition of the present disclosure comprises RNA having an open reading frame (ORF) encoding a respiratory syncytial virus antigen. In some embodiments, the RNA is messenger RNA (mRNA). In some embodiments, the RNA (e.g., mRNA) further comprises a 5' UTR, a 3' UTR, a poly(A) tail, and/or a 5' cap analog (or 5' cap structure).

It should also be understood that the mRNA vaccine of the present disclosure may comprise any 5' untranslated region (UTR) and/or any 3' UTR. Exemplary UTR sequences are provided in the sequence listing; however, other UTR sequences may be used or substituted by any UTR sequence described herein. UTRs may also be omitted from the RNA polynucleotide provided herein.

Antigen

An antigen is a protein that is capable of inducing an immune response (e.g., causing an immune system to produce an antibody against an antigen). Herein, the use of the term “antigen” encompasses immunogenic proteins and immunogenic fragments (which induce (or are capable of inducing) an immune response to (at least one) respiratory syncytial virus, e.g., RSV A2 (138251)), unless otherwise stated. It should be understood that the term “protein” encompasses peptides and the term “antigen” encompasses fragments of antigens.

Exemplary sequences of a respiratory syncytial virus antigen and RNA encoding the respiratory syncytial virus antigen of the composition of the present disclosure are provided in the sequence listing.

Epitope

Epitope, also referred to as an antigenic determinant, refers to a particular region of an antigen molecule that can be recognized by a specific antibody, where one or more epitopes may be present on an antigenic molecule. The antigenic epitope can be recognized by a B-cell receptor (BCR), triggering subsequent antibody synthesis and secretion and mediating a humoral immune response. The pre-fusion pre-F conformation has six major antigenic sites/epitopes (including epitopes Φ, I, II, III, IV, and V), and by crystal structure analysis of the RSV F protein, it is found that the AM14 antibody specifically recognizes an epitope Quaternary spanning two protomers, including a region that undergoes extensive conformational changes in the transition of pre-fusion to post-fusion F proteins. These epitopes are highly antigenic, but relatively unstable. The post-fusion post-F conformation has only four antigenic sites/epitopes (including epitopes I, II, III, and IV), which are relatively stable but less antigenic. Compared with the epitopes I, II, III, and IV that are present in both pre-fusion and post-fusion conformations, the epitopes Φ and V are present only in the pre-F conformation, and studies have demonstrated that they are sites sensitive to neutralizing antibodies and can induce higher neutralizing antibody responses. The antibodies in the present disclosure recognize epitopes as follows:

(1) The RSV pre-F antibody (3C12) recognizing the epitope Φ specifically binds only to the F protein in the pre-fusion conformation.

(2) The RSV pre-F antibody (7H11) recognizes the epitope Quaternary (spanning both epitopes IV and V) and specifically binds to the F protein in the pre-fusion conformation.

(3) The RSV F antibody (11A9) recognizing the epitope II can recognize both pre-fusion and post-fusion conformations of the F protein.

(4) The RSV F antibody (4B9) recognizing the epitope III preferentially recognizes the pre-fusion conformation while having weaker binding activity for the post-fusion conformation.

(5) The RSV pre-F antibody (7E11) recognizes the epitope V and specifically binds to the F protein in the pre-fusion conformation.

Studies have shown that whether to be able to bind specifically to the epitope Φ of the pre-fusion antigen and the ability to bind are closely related to the effect of the novel vaccine in preventing the RSV infection. The epitopes Φ and II account for 35% and <10% of the neutralizing activity, respectively, and the neutralizing activity of RSV in human serum is mainly derived from the pre-fusion specific antibodies. Therefore, the use of pre-fusion antigens retaining the epitope Φ will help to induce or enhance neutralizing activity by vaccination.

The antigenic epitopes of the pre-fusion and post-fusion conformations of the RSV F protein are changed, with the epitope Φ retained only in the pre-fusion conformation and the epitope II retained in both the pre-fusion and post-fusion conformations. An antibody specific for the antigenic epitope Φ differs from neutralizing antibodies for other known epitopes on the RSV F protein in that it specifically recognizes only the pre-F structure. Studies have shown that whether to be able to bind specifically to the epitope Φ of the pre-fusion antigen and the ability to bind are closely related to the effect of the novel vaccine in preventing the RSV infection, and therefore, they are used as primary indicators for investigation. The epitope Φ is located at the top end of the pre-F trimer structure, has a small steric hindrance, and is beneficial to antibody binding. Thus, the higher the ability of the antibody to bind to the epitope Φ, the better the prophylactic effect on RSV.

Epitope binding assays are performed using monoclonal antibodies (mAbs), and the results show that the ability to bind to the epitope Φ-specific antibodies (e.g., number, binding rate, binding capacity, degree of binding, etc.) is related to the neutralizing activity, while the degree of binding to the epitope II is poorly related to the neutralizing activity. Moreover, the neutralizing activity of RSV in human serum is mainly derived from pre-F specific antibodies, and therefore, the neutralizing activity is improved by vaccination using the epitope Φ in the pre-fusion conformation.

Pre-Fusion Conformation of RSV F Protein

The pre-fusion conformation of the RSV F protein is a structural conformation adopted by an RSV F protein prior to triggering a fusogenic event that results in the transition of RSV F to a post-fusion conformation and enables RSV F to become a mature RSV F protein in the secretory system after processing. In some embodiments, whether the antigen encoded by the mutant nucleic acid is stable in the pre-fusion conformation can be determined by binding to a particular epitope. The stable pre-fusion RSV F mutants of the present disclosure are in the pre-fusion conformation, i.e., they comprise (display) at least one epitope which is specific for the F protein in the pre-fusion conformation. Epitopes specific for the F protein in the pre-fusion conformation are epitopes that are not present in the post-fusion conformation. The pre-fusion conformation of the RSV F protein may contain the same epitopes as those on the RSV F proteins expressed on natural RSV virions, and thus may provide advantages for eliciting protective neutralizing antibodies.

In some embodiments, stable pre-fusion RSV F mutants can specifically bind to the RSV pre-F antibody (3C12) recognizing the epitope Φ and to the RSV pre-F antibody (7H11) recognizing the epitope Quaternary.

Post-Fusion Conformation of RSV F Protein

The post-fusion conformation of the RSV F protein is a structural conformation adopted by an RSV F protein that is not in the pre-fusion conformation, in which the N-terminus and C-terminus of the RSV F protein are proximal in a stable helix-helix. The post-fusion conformation of the RSV F protein has been described at the atomic level (see, e.g., McLellan et al., *J. Virol.,* 85, 7788, 2011; Swanson et al., *Proc. Nat. Acad. Sci. U.S.A.,* 108, 9619, 2011; and structural coordinates deposited under PDB accession No. 3RRR; each of which is incorporated herein by reference). In the post-fusion conformation, the RSV F protein cannot be bound by certain antibodies, e.g., antibodies recognizing the epitope Φ.

Variant

In some embodiments, the composition of the present disclosure comprises RNA encoding a respiratory syncytial virus antigen variant. An antigen variant or other polypeptide variant refers to a molecule whose amino acid sequence differs from that of the wild-type, natural, or reference sequence. An antigen/polypeptide variant may have substitutions, deletions, and/or insertions at certain positions within the amino acid sequence compared with the natural or reference sequence. Generally, the variant has at least 50% identity to the wild-type, natural, or reference sequence. In some embodiments, the variant has at least 80% or at least 90% identity, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% or 100% identity compared with the wild-type, native, or reference sequence. Herein, "mutant" and "variant" are used interchangeably.

Mutation

The term "mutation" refers to a change in the amino acid sequence compared with the wild-type protein sequence. In the present disclosure, the antigen mutant has one or more base mutations compared with the wild-type RSV F protein. After mutation, a truncation, a deletion of an amino acid residue, or a substitution of an amino acid residue occurs in the amino acid sequence of the protein or polypeptide compared with an amino acid sequence of a reference protein or polypeptide. Herein, an amino acid substitution at a particular position in a protein sequence is indicated using the annotation "(amino acid residue in a wild-type protein) (amino acid position) (amino acid residue in an engineered protein)". For example, Y44C refers to the substitution of a tyrosine (Y) residue at position 44 of an amino acid sequence of a reference protein with a cysteine (C) residue (in a variant of the reference protein). In the case of variations in amino acid residues at the same position between different wild-type sequences, the amino acid code preceding the position number may be omitted from the annotation, such as "44C".

Sequence Truncation

Sequence truncation refers to a truncation of a contiguous portion of an amino acid sequence at the C terminus based on the wild-type RSV F protein. For example, in the present disclosure, the sequence truncation is to truncate amino acids at positions 550 to 574 of the C-terminus of the RSV F protein.

Sequence Deletion

Sequence deletion refers to a deletion of a part of bases at amino acid sites based on the wild-type RSV F protein. For example, in the present disclosure, the sequence deletion is selected from one or more of the following: amino acid deletions at positions 104 to 136 and amino acid deletions at positions 104 to 144.

Site Mutation

Site mutation refers to an alteration in one or more amino acid sites in the wild-type RSV F protein to stabilize the RSV F protein in the pre-fusion conformation. For example, in the present disclosure, the site mutation is selected from the following: P102A, I379V and M447V, S46G, S215P, L373R, S213P and N216P, Q26C, N27C, T29C, E31C, F32C, Q34C, T36C, S41C, Y44C, Y53C, T54C, S55C, T100C, T103C, L138C, G139C, F140C, L141C, L142C, G145C, S146C, A147C, I148C, A149C, S150C, V152C, A153C, V154C, S155C, N183GC, S186C, L188C, S287C, I288C, S290C, I291C, I292C, V300C, L305C, Y306C, S319C, N325C, S330C, T337C, R339C, Q354C, T369C, M370C, N371C, S377C, N428C, Y458C, K461C, Q462C, K465C, L467C, Y468C, K470C, G471C; T54H, T58L, S190I, S190F, V207L, T219I, V296I; E92D, K465Q, D486S; V152I, $C_{69}$Y, D73E, A74V, N88S. In the above optional site mutations, one of the site mutations may occur at the amino acid at the same position, for example, the above mutations include T54C or T54H, which means that T at position 54 may be mutated to C or H, but not both.

Lack of Cytoplasmic Domain

The cytoplasmic domain consists of residues 550 to 574 of a polypeptide chain of a mature RSV F protein. For example, in the present disclosure, the lack of a cytoplasmic domain means that an amino acid sequence of 550 to 574 at the C-terminus of an antigen mutant is truncated.

"One or More"/"Selected From"

Herein, "one or more" means one, two or more selected from the listed objects or elements. Similarly, "selected from" means that one, two or more are selected from the list of listed objects or elements, including any combination of the listed objects or elements, such as a combination of any two of the listed objects or elements, a combination of any three of the listed objects or elements, . . . , a combination of any multiple of the listed objects or elements, including a combination of all the objects. In this sense, "more" may include two or three or more.

Variant antigens/polypeptides encoded by the nucleic acid of the present disclosure may contain amino acid changes that confer any one of a variety of desirable properties, e.g., improving their stability or enhancing immunogenicity in animals. Variant antigens/polypeptides may be prepared using conventional mutagenesis techniques and assayed as appropriate to determine whether they have the desired properties. Assays to determine expression levels and immunogenicity are well known in the art, and examples of such assays are set forth in the Example section.

In some embodiments, the composition comprises an RNA or RNA ORF comprising a nucleotide sequence of any one of the sequences provided herein (see sequence listing), or a nucleotide sequence having at least 80%, at least 85%, at least 90%, at least 95%, at least 96%, at least 97%, at least 98% or at least 99% or 100% identity to the nucleotide sequence of any one of the sequences provided herein.

The term "identity" refers to a relationship between the sequences of two or more polypeptides (e.g., antigens) or polynucleotides (nucleic acids), as determined by comparing the sequences. The identity also refers to the degree of sequence correlation between or among sequences, as determined by the number of matches between two or more strings of amino acid residues or nucleic acid residues. An identity measure refers to the percentage of identity matches between the smaller of two or more sequences having gap alignments (if any) that are processed by a particular mathematical model or computer program (e.g., an "algorithm"). The identity of the relevant antigen or nucleic acid can be readily calculated by known methods. "Percent identity (%)", when applied to a polypeptide or polynucleotide sequence, is defined as the percentage of residues in a candidate amino acid or nucleic acid sequence that are identical to residues (amino acid residues or nucleic acid residues) in an amino acid sequence or nucleic acid sequence of the second sequence, after aligning the sequences and introducing gaps, if necessary, to achieve the maximum percent identity. Methods and computer programs for alignment are well known in the art. It should be understood that the identity depends on the calculation of percent identity, but the value of identity may differ due to gaps and penalties introduced in the calculation. Generally, a variant of a particular polynucleotide or polypeptide (e.g., antigen) has at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% but less than 100% sequence identity to a particular reference polynucleotide or polypeptide, as determined by sequence alignment programs and parameters described herein and known to those of skill in the art. Such tools for alignment include those of the BLAST kit (Stephen F. Altschul et al. (1997), "Gapped BLAST and PSI-BLAST: a new generation of protein database search programs", *Nucleic Acids Res.* 25: 3389-3402). Another common local alignment technique is based on the Smith-Waterman algorithm (Smith, T. F. and Waterman, M. S. (1981) "Identification of common molecular subsequences." *J. Mol. Biol.* 147: 195-197). A general global alignment technique based on dynamic programming is the Needleman-Wunsch algorithm (Needleman, S. B. and Wunsch, C. D. (1970) "A general method applicable to the search for similarities in the amino acid sequences of two proteins." *J. Mol Biol.* 48: 443-453). Recently, a fast optimal global sequence alignment algorithm (FOGSAA) has been developed, which is said to produce global alignments of nucleotide and protein sequences more quickly than other optimal global alignment methods, including the Needleman-Wunsch algorithm.

Thus, polynucleotides encoding a peptide or a polypeptide containing substitutions, insertions and/or additions, deletions, and covalent modifications relative to a reference sequence, particularly the polypeptide (e.g., antigen) sequence disclosed herein, are included within the scope of the present disclosure. In some embodiments, sequences of (or encoding) a signal sequence, a termination sequence, a transmembrane domain, a linker, etc., may be replaced by alternative sequences that perform the same or similar functions. In some embodiments, the stability may be improved, for example, by introducing larger amino acids into the cavity in the protein core. In other embodiments, the stability may be improved by replacing the embedded hydrogen bonding network by hydrophobic residue. Such sequences can be readily identified by those skilled in the art.

The RSV F mutant provided by the present disclosure comprises an F1 polypeptide and an F2 polypeptide, wherein both the F1 polypeptide and the F2 polypeptide comprise a plurality of introduced amino acid mutations relative to an amino acid sequence of a corresponding natural F protein. The introduction of such amino acid mutations into the RSV F mutant confers beneficial properties to the mutant, such as enhanced immunogenicity, improved stability, or formation of a particular desired physical form or conformation of the mutant, or improved stability.

Mutant (Variant) Structure of RSV F Protein

The F glycoprotein of human RSV is first translated from mRNA into a single polypeptide precursor (F0) of 574 amino acids that contains a signal peptide sequence at the N-terminus. After translation, the signal peptide is removed by a signal peptidase in the endoplasmic reticulum. F0 is cleaved at two sites (between amino acid residues 109/110 and 136/137) by a cellular protease (particularly furin) in the trans-Golgi, a short glycosylated intervening sequence (also referred to as the pep27 region; amino acid residues 110 to 136), and two domains or subunits called F1 (C-terminal portion; amino acids 137 to 574) and F2 (N-terminal portion; amino acids 26 to 109). F2 is linked to F1, and the F1-F2 heterodimer assembles into a homotrimer in the virion.

Signal Peptide

"Signal peptide" is a short amino acid sequence (e.g., about 18 to 25 amino acids in length) that is generally required for transmembrane translocation over the secretory pathway to control the entry of most proteins into the secretory pathway in eukaryotes and prokaryotes. The signal peptide is often, but not universally, located at the N-terminus of the polypeptide and is often cleaved off by a signal peptidase after the protein has crossed the membrane.

To enhance production, the F2 domain may be preceded by a secretion signal peptide, such as a natural F protein signal peptide or a heterologous signal peptide, for enhancing the production and secretion in a host cell in which the recombinant pre-F antigen is to be expressed.

F1 Polypeptide

The term "F1 polypeptide" (F1) refers to a polypeptide chain of a mature RSV F protein. Natural F1 consists of approximate residues 137 to 574 of the RSV F0 precursor. As used herein, the term encompasses both the natural F1 polypeptide and the F1 polypeptide derived from the natural sequence that comprises modifications (e.g., amino acid substitutions, insertions, or deletions), e.g., modifications designed to stabilize the F mutant or enhance the immunogenicity of the F mutant.

F1 comprises a hydrophobic fusion peptide (FP) and a heptad repeat region A (HRA) at the N-terminus of 137 to 216 and comprises a heptad repeat region B (HRB), a transmembrane (TM, amino acid residues 530 to 550), and a cytoplasmic region (amino acid residues 551 to 574) at the C-terminus. In the structure of the RSV F protein mutant, it is not strictly necessary to include the entire F1 domain. Typically, at least a subsequence (or fragment) of the F1 domain is selected and designed to maintain a stable conformation that includes immunodominant epitopes of the F protein. F1 contains many subsequences of epitopes recognized by neutralizing antibodies, for example, amino acid residues 262 to 275 are a subsequence of an epitope recognized by palivizumab; amino acid residues 423 to 436 are a subsequence of an epitope recognized by the ch101F monoclonal antibody of Centocor; amino acid residues 328 to 355 comprise a T cell epitope. Thus, the polypeptide of the F1 domain comprises at least about amino acids 262 to 436 of the polypeptide of the RSV F protein.

Linker

One or two furin recognition sites may be eliminated by deleting or substituting one or more amino acids of the furin recognition sites. By virtue of this design, the fusion peptide is not cleaved from F2, which prevents release from the globular head of the pre-fusion conformer and accessibility to adjacent membranes. It is predicted that the interaction between the fusion peptide and the membrane interface is a major problem of the instability of the pre-fusion state. In the fusion process, the interaction between the fusion peptide and the target membrane results in the exposure of the fusion peptide from the globular head structure, which enhances instability of the pre-fusion state and allows folding into a post-fusion conformer. This conformational change realizes the membrane fusion process. It is predicted that removal of one or both of the two furin cleavage sites prevents accessibility of the membrane to the N-terminal portion of the fusion peptide, which stabilizes the pre-fusion state. Optionally, an intervening pep27 peptide may also be removed or replaced by, for example, a linker peptide. Additionally, or optionally, a non-furin cleavage site (e.g., a metalloprotease site at positions 112 to 113) proximal to the fusion peptide may be removed or replaced.

In the present application, a linker peptide is used to replace the intervening pep27 peptide. The analysis of a structural model of the RSV F protein in the pre to fusion state suggests that pep27 produces a large unconstrained loop between F1 and F2, which does not contribute to the stabilization of the pre-fusion state and is removed after cleavage of the natural protein by furin. Commonly used protein linkers include flexible linkers, rigid linkers, and cleavable linkers. The linker used in the present application is a flexible linker.

The linker used in the present application can be used in this context without disrupting the conformation of the pre-F antigen.

F2 Polypeptide

The term "F2 polypeptide" (F2) refers to a polypeptide chain of a mature RSV F protein. Natural F2 includes approximate residues 26 to 109 of the RSV F0 precursor. As used herein, the term encompasses both the natural F2 polypeptide and the F2 polypeptide derived from the natural sequence that comprises modifications (e.g., amino acid substitutions, insertions, or deletions), e.g., modifications designed to stabilize the F mutant or enhance the immunogenicity of the F mutant.

Those skilled in the art will recognize that it is not strictly necessary to include the entire F2 domain. Typically, consideration of conformation is important in selecting a subsequence (or a fragment) of the F2 domain. As such, the F2 domain generally comprises a portion of the F2 domain that facilitates assembly and stability of the polypeptide.

Stabilization Element

A naturally occurring eukaryotic mRNA molecule may contain stabilization elements, including, but not limited to, an untranslated region (UTR) at its 5' end (5' UTR) and/or at its 3' end (3' UTR), in addition to other structural features such as a 5'-cap structure or a 3'-poly(A) tail. Both the 5' UTR and the 3' UTR are elements that are generally transcribed from genomic DNA and are pre-mature mRNAs. Characteristic structural features of mature mRNA (e.g., the 5'-cap and the 3'-poly(A) tail) are generally added to transcribed (pre-mature) mRNA during mRNA processing.

In some embodiments, the composition comprises an RNA polynucleotide having an open reading frame encoding at least one antigenic polypeptide having at least one modification, and at least one 5' cap, and is formulated within a lipid nanoparticle. 5'-capping of a polynucleotide can be accomplished simultaneously during the in vitro transcription reaction according to the manufacturer's protocol using the following chemical RNA cap analogs to produce a 5'-guanosine cap structure.

3'-poly(A) tail, i.e., poly(A) tail, is generally a stretch of adenine nucleotides added to the 3' end of transcribed mRNA, which is located in a region downstream, e.g., directly downstream (i.e., 3'), of the 3' UTR containing multiple consecutive adenosines monophosphates. In some cases, it may comprise about 10 to 400 adenine nucleotides. In some embodiments, the length of the 3'-poly(A) tail may be an essential element for the stability of individual mRNAs. In the relevant biological environment (e.g., in a cell, in vivo), the poly(A) tail serves to protect the mRNA from enzymatic degradation, e.g., in the cytoplasm, and to aid in transcription termination, and/or the export of mRNA from the nucleus and translation.

Untranslated Region (UTR)

The mRNA of the present disclosure may comprise one or more regions or portions that serve or function as untranslated regions. When the mRNA is designed to encode at least one target antigen, the nucleic acid may comprise one or more of these untranslated regions (UTRs). The wild-type untranslated region of the nucleic acid is transcribed, but not translated. In the mRNA, 5' UTR starts at the transcription start site and continues to the initiation codon, but does not include the initiation codon; while the 3' UTR starts immediately after the termination codon and continues to the transcription termination signal. There is increasing evidence for a regulatory role played by UTRs in the stability and translation of nucleic acid molecules. Regulatory features of the UTRs can be incorporated into the polynucleotide of the present disclosure to particularly enhance the stability of the molecule. Particular features may also be incorporated to ensure controlled down-regulation of transcripts in the event that they are misdirected to undesired organ sites.

5' UTR refers to a region of the mRNA that does not encode a polypeptide and is immediately upstream (5') of the initiation codon (the first codon of a mRNA transcript translated by a ribosome). 5' UTR does not encode the protein (is non-coding). Natural 5' UTRs have a feature of playing a role in translation initiation. They bear imprints such as the Kozak sequence, which is generally known to be involved in the process of initiating translation of many genes at the ribosome. The Kozak sequence has a consensus CCR(A/G)CCAUGG, where R is a purine (adenine or guanine) three bases upstream of the initiation codon (AUG), and the initiation codon (AUG) is followed by another 'G'. 5' UTR is also known to form a secondary structure involved in the binding of elongation factors.

3' UTR refers to a region of the mRNA that does not encode a polypeptide and is directly downstream (3') of the termination codon (a codon of a mRNA transcript that signals translation termination). 3' UTR does not encode the protein (is non-coding). Natural or wild-type 3' UTRs are known to have segments of adenosine and uridine embedded therein.

Those of ordinary skill in the art will understand that heterologous or synthetic 5' UTRs may be used with any desired 3' UTR sequence. For example, a heterologous 5' UTR may be used with a synthetic 3' UTR or a heterologous 3' UTR.

In Vitro Transcription of RNA cDNA encoding the polynucleotide described herein can be transcribed using an in vitro transcription (IVT) system. In vitro transcription of RNA is known in the art and is described in international publication WO/2014/152027, which is incorporated herein by reference in its entirety.

In some embodiments, the RNA transcript is produced in an in vitro transcription reaction using a linearized DNA template to produce the RNA transcript.

In some embodiments, the in vitro transcription template encodes a 5' untranslated region (UTR), contains an open reading frame, and encodes a 3' UTR and a poly(A) tail. The particular nucleic acid sequence composition and length of the in vitro transcription template will depend on the mRNA encoded by the template.

The in vitro transcription system generally comprises a transcription buffer, nucleotide triphosphates (NTPs), an RNase inhibitor, and a polymerase.

The NTPs may be manufactured internally or from a supplier. The NTPs may be selected from, but are not limited to, those described herein, including natural and non-natural (modified) NTPs.

In some embodiments, the RNA transcript is capped by enzymatic capping. In some embodiments, the RNA comprises a 5' cap.

Lipid Nanoparticle (LNP)

In some embodiments, the RNA (e.g., mRNA) of the present disclosure is formulated in a lipid nanoparticle (LNP). The lipid nanoparticle generally comprises an ionizable cationic lipid, a non-cationic lipid, sterol and PEG lipid components, and a target nucleic acid. The lipid nanoparticle of the present disclosure can be produced using components, compositions, and methods generally known in the art.

RSV F Protein Mutant Stability

In some embodiments, the mutant antigen encoded by the nucleic acid of the present disclosure has superior properties, such as enhanced stability of the pre-fusion conformation, compared with the wild-type. In this example, assay methods used to determine the stability of the pre-fusion conformation have been specifically described.

In some embodiments, the stability of an antigen encoded by a mutant nucleic acid can be measured by determining the thermostability and the low temperature stability. "Thermostability", in this example, means that after being subjected to an increased temperature (i.e., 50° C.) for 60 min, the mutant still exhibits the binding to at least one pre-fusion specific epitope, e.g., the epitope Φ as determined in the present application. "Low temperature stability", in this example, means that after one week of low temperature storage at 4° C., the mutant still displays the binding to at least one pre-fusion specific epitope, e.g., the epitope Φ as determined in the present application. Some pre-fusion RSV F mutants according to the present disclosure have increased stability when stored at a low temperature or when exposed to heat compared with RSV F polypeptides that do not have one or more of the mutations described above.

In some embodiments, the stability of an antigen encoded by a mutant nucleic acid can be measured by determining the stability under conditions of low and high osmotic pressure.

"High osmotic pressure stability", in this example, means that after incubation for 60 min under a low osmotic pressure condition of 10 mM NaCl, the mutant still displays the binding to at least one pre-fusion specific epitope, e.g., the epitope Φ as determined in the present application. Some pre-fusion RSV F mutants according to the present disclosure have increased stability under a low osmotic pressure condition compared with RSV F polypeptides that do not have one or more of the mutations described above.

"High osmotic pressure stability", in this example, means that after incubation for 60 min under a high osmotic pressure condition of 3.0 M $MgCl_2$, the mutant still displays the binding to at least one pre-fusion specific epitope, e.g., the epitope Φ as determined in the present application. Some pre-fusion RSV F mutants according to the present disclosure also have increased stability under a high osmotic pressure condition compared with RSV F polypeptides that do not have one or more of the mutations described above.

In some embodiments, the stability of an antigen encoded by a mutant nucleic acid can be measured by determining the stability under acid and base conditions.

"Acid and base stability", in this example, means that after the RSV F mutant is incubated at pH 3.5 and pH 10 for 60 min at room temperature and subsequently neutralized to pH 7.4, the mutant still exhibits the binding to at least one pre-fusion specific epitope, e.g., the epitope Φ as determined in the present application. Some pre-fusion RSV F mutants according to the present disclosure have increased stability under acid and base conditions compared with RSV F polypeptides that do not have one or more of the mutations described above.

Bio-Layer Interferometry

Bio-Layer interferometry (referred to as BLI) is a label-free real-time monitoring optical detection technique, mainly used for comprehensive quantitative analysis of the interaction between biomolecules and protein concentration determination. BLI can monitor the entire intermolecular binding process in real time and calculate important data such as affinity constant ($K_D$), association rate constant ($K_a$), dissociation rate constant ($K_D$), etc., between molecules.

In some embodiments, the affinity of the RSV F protein mutants for antibodies recognizing different epitope is determined by BLI. In this example, the affinity for the RSV pre-F antibody (3C12) and the RSV pre-F antibody (7H11) was mainly detected.

Immunogenicity of Vaccine

The term "immunogenicity" refers to the ability of a substance to cause, elicit, stimulate, or induce an immune response against a particular antigen in an animal in the presence or absence of an adjuvant. In the sense of the present disclosure, an immunogen is a translation product of the provided artificial nucleic acid, preferably RNA, which comprises at least one coding sequence encoding at least one antigenic peptide or protein derived from the RSV as defined herein.

The term "neutralizing antibody" refers to an antibody that can prevent a pathogen from binding to a receptor on the surface of a host cell during infection by the pathogen, such that the pathogen cannot adhere to and invade the target cell for replication and reproduction. The effect of the vaccine is generally reflected visually by the level of "neutralizing antibody".

In some embodiments, the ability of an immune composition (e.g., an RNA vaccine) to be effective is measured in a murine model. For example, the immune composition can be administered to a murine model and the induction of neutralizing antibody titers in the murine model is determined. In some embodiments, the antigen-specific immune response is measured as the geometric mean titer (GMT) of neutralizing antibody titers in the serum of mice or cotton rats. Geometric mean titer (GMT) is the mean antibody titer for a group of subjects calculated by multiplying all values and taking the n-th root of the number, where n is the number of subjects with available data.

Virus challenge studies can also be used to evaluate the efficacy of the vaccine of the present disclosure. For example, the immune composition may be administered to a murine model, the murine model is challenged with a virus, and the survival and/or immune response (e.g., neutralizing antibody response) of the murine model is determined.

"Heterocyclic ring" and "heterocyclyl" are used interchangeably herein and both refer to non-aromatic heterocyclyl in which one or more ring-forming atoms are heteroatoms such as oxygen, nitrogen, sulfur, etc., including monocyclic, fused, bridged, and spiro rings. Preferably, it has a 5- to 7-membered monocyclic ring or a 7- to 10-membered bicyclic or tricyclic ring, which may contain 1, 2, or 3 atoms selected from nitrogen, oxygen, and/or sulfur. Examples of "heterocyclyl" include, but are not limited to, morpholinyl, oxetanyl, thiomorpholinyl, tetrahydropyranyl, morpholinyl, piperidinyl, 2-oxo-piperidinyl, pyrrolidinyl, 2-oxo-pyrrolidinyl, piperazin-2-one, and piperazinyl. The heterocyclyl may be substituted or unsubstituted.

1.1 Example 1: Design of RSV F Antigen Mutants

The present disclosure mainly referred to an RSV A2 (138251) protein sequence, on the basis of which P102A, I379V, and M447V mutations (52 antigen sequences of candidate mutants (Nos. 1 to 52) and 6 control sequences (Nos. 53 to 58) all contained the above 3 mutations, with other mutation forms shown in the table below) were performed.

52 antigen sequences of candidate mutants (Nos. 1 to 52) and 6 control sequences (Nos. 53 to 58), 1 wild sequence (No. 59), and 1 positive control (No. 60) were designed in total using various mutation combinations, with specific mutation combinations of the mutants shown in the table below.

The positive control is derived from the marketed vaccine of Pfizer, Abrysvo™ (NDC 0069-0344-05), and different from the mRNA vaccines designed by the present disclosure, it is a protein vaccine.

Design thought of control sequences: on the basis of the mutants designed by the present application, different control sequences were designed to investigate the effect of different site mutations. For example, (1) To investigate the influence of mutations in groups 2 and 3 of site mutations, PC—RSV-063 was designed based on a YK-RSV-003 mutation combination.

(2) To investigate the influence of mutations in group 1 of site mutations, PC—RSV-067 and PC—RSV-068 were designed by changing mutation types in group 1 based on a YK-RSV-061 mutation combination.

(3) To investigate the influence of mutations in groups 2 and 3 of site mutations, PC—RSV-064, PC—RSV-065, and PC—RSV-066 were designed based on a YK-RSV-061 mutation combination.

1. By referring to "in design cycle 4, RSV F variant: sc9-10 DS-Cav1 A149C Y458C S46G K465Q S215P E92D; Mutations: A149C, S155C, S190F, V207L, S290C, L373R, Y458C, S46G, K465Q, S215P, E92D; F1-F2 Linker residues: 103 to 145; Linker sequence: GS; End residue: 513" in "M Gordon Joyce et al., Iterative structure-based improvement of a fusion-glycoprotein vaccine against RSV, *Nature Structural & Molecular Biology, volume* 23, 811-820 (2016), doi: 10.1038/nsmb.3267", a mutant PC—RSV-063 was designed.

2. By referring to "SEQ ID NO: 6" in the patent application publication "WO2023/166079 A1", a mutant PC—RSV-064 was designed.

TABLE 1

Amino acid mutation sites of RSV F proteins

| No. | Antigen No. | Sequence truncation | Sequence deletion | Site mutation Group 1 | Group 2 | Group 3 | Group 4 | Group 5 |
|---|---|---|---|---|---|---|---|---|
| 1 | YK-RSV-001 | 550 to 574 aa were truncated based on the wild-type RSV F protein, that is, 1 to 549 aa were retained | 104 to 144 aa were deleted and replaced by a GS linker | A149C, S155C, S290C, Y458C | S190I | E92D, D486S, K465Q | S46G, S215P, L373R | / |
| 2 | YK-RSV-002 | | | A149C, S155C, S290C, Y458C | T54H, S190F | E92D, K465Q, D486S | S46G, S215P, L373R | / |
| 3 | YK-RSV-003 | | | A149C, S155C, S290C, Y458C | S190F, V296I | E92D, K465Q, D486S | S46G, S215P, L373R | / |
| 4 | YK-RSV-004 | | | A149C, S155C, S290C, Y458C | S190I | E92D, K465Q, D486S | S46G, S213P, L373R | / |
| 5 | YK-RSV-005 | | | A149C, S155C, S290C, Y458C | S190I | E92D, K465Q, D486S | S46G, N216P, L373R | / |
| 6 | YK-RSV-008 | | | S55C, L188C, | S190I | E92D, K465Q, D486S | S46G, S215P, L373R | / |
| 7 | YK-RSV-009 | | | Q34C, G471C | T58L, S190F | E92D, K465Q, D486S | S46G, S215P, L373R | / |
| 8 | YK-RSV-010 | | | S55C, L188C | T58L, S190F | E92D, K465Q, D486S | S46G, S215P, L373R | / |
| 9 | YK-RSV-011 | | | Q34C, G471C | S190F, T219I | E92D, K465Q, D486S | S46G, S215P, L373R | / |
| 10 | YK-RSV-012 | | | S55C, L188C | S190F, T219I | E92D, K465Q, D486S | S46G, S215P, L373R | / |
| 11 | YK-RSV- | | | T103C, I148C, | S190F | E92D, | S46G, S215P, | / |

TABLE 1-continued

Amino acid mutation sites of RSV F proteins

| No. | Antigen No. | Sequence truncation | Sequence deletion | Site mutation Group 1 | Group 2 | Group 3 | Group 4 | Group 5 |
|---|---|---|---|---|---|---|---|---|
| | 013 | | | Y458C | | K465Q, D486S | L373R | |
| 12 | YK-RSV-014 | | | Q34C, A149C, Y458C, G471C | S190I | E92D, K465Q, D486S | S46G, S215P, L373R | / |
| 13 | YK-RSV-015 | | | S55C, A149C, L188C, Y458C | S190I | E92D, K465Q, D486S | S46G, S215P, L373R | / |
| 14 | YK-RSV-016 | | | Q34C, A149C, Y458C, G471C | T58L, S190F | E92D, K465Q, D486S | S46G, S215P, L373R | / |
| 15 | YK-RSV-017 | | | S55C, A149C, L188C, Y458C | T58L, S190F | E92D, K465Q, D486S | S46G, S215P, L373R | / |
| 16 | YK-RSV-018 | | | Q34C, A149C, Y458C, G471C | S190F, T219I | E92D, K465Q, D486S | S46G, S215P, L373R | / |
| 17 | YK-RSV-019 | | | S55C, A149C, L188C, Y458C | S190F, T219I | E92D, K465Q, D486S | S46G, S215P, L373R | / |
| 18 | YK-RSV-022 | | | T103C, I148C, N183GC, N428C | S190F | E92D, K465Q, D486S | S46G, S215P, L373R | / |
| 19 | YK-RSV-029 | | | T29C, K465C | S190F, V207L | E92D | S46G, S215P, L373R | / |
| 20 | YK-RSV-030 | | | E31C, L467C | S190F, V207L | E92D, K465Q | S46G, S215P, L373R | / |
| 21 | YK-RSV-031 | | | F32C, Y468C | S190F, V207L | E92D, K465Q | S46G, S215P, L373R | / |
| 22 | YK-RSV-032 | | | Q34C, K470C | S190F, V207L | E92D, K465Q | S46G, S215P, L373R | / |
| 23 | YK-RSV-033 | | | T36C, G471C | S190F, V207L | E92D, K465Q | S46G, S215P, L373R | / |
| 24 | YK-RSV-034 | | | Q26C, K461C | S190F, V207L | E92D. K465Q | S46G, S215P, L373R | / |
| 25 | YK-RSV-035 | | | N27C, Q462C | S190F, V207L | E92D, K465Q | S46G, S215P, L373R | / |
| 26 | YK-RSV-036 | | | S55C, V154C | S190F, V207L | E92D, K465Q | S46G, S215P, L373R | / |
| 27 | YK-RSV-037 | | | Y53C, A153C | S190F, V207L | E92D. K465Q | S46G, S215P, L373R | / |
| 28 | YK-RSV-038 | | | S55C, S186C | S190F, V207L | E92D, K465Q | S46G, S215P, L373R | / |
| 29 | YK-RSV-039 | | | T54C, V152C | S190F, V207L | E92D K465Q | S46G, S215P, L373R | / |
| 30 | YK-RSV-040 | | | T54C, A153C | S190F, V207L | E92D, K465Q | S46G, S215P, L373R | / |
| 31 | YK-RSV-041 | | | S41C, S319C | S190F, V207L | E92D, K465Q | S46G, S215P, L373R | / |
| 32 | YK-RSV-042 | | | Y44C, S319C | S190F, V207L | E92D, K465Q | S46G, S215P, L373R | / |
| 33 | YK-RSV-043 | | | T100C, S150C | S190F, V207L | E92D, K465Q | S46G, S215P, L373R | / |
| 34 | YK-RSV-044 | | | T100C, A149C | S190F, V207L | E92D, K465Q | S46G, S215P, L373R | / |
| 35 | YK-RSV-045 | | | T100C, V300C | S190F, V207L | E92D. K465Q | S46G, S215P, L373R | / |
| 36 | YK-RSV-046 | | 104-136 aa, | L138C, T337C | S190F, V207L | E92D K465Q | S46G, S215P, L373R | / |
| 37 | YK-RSV-047 | | amino acids | G139C, Q354C | S190F, V207L | E92D, K465Q | S46G, S215P, L373R | / |
| 38 | YK-RSV-048 | | deleted from the | L142C, N371C | S190F, V207L | E92D, K465Q | S46G, S215P, L373R | / |
| 39 | YK-RSV-049 | | sequence were | G145C, M370C | S190F, V207L | E92D, K465Q | S46G, S215P, L373R | / |
| 40 | YK-RSV-050 | | replaced by a | L141C, N371C | S190F, V207L | E92D, K465Q | S46G, S215P, L373R | / |
| 41 | YK-RSV-051 | | GSGS linker | F140C, T369C | S190F, V207L | E92D, K465Q | S46G, S215P, L373R | / |
| 42 | YK-RSV-052 | | 104-144 aa, | S146C, L305C | S190F, V207L | E92D, K465Q | S46G, S215P, L373R | / |
| 43 | YK-RSV-053 | | amino acids | A149C, Y306C | S190F, V207L | E92D, K465Q | S46G, S215P, L373R | / |

TABLE 1-continued

Amino acid mutation sites of RSV F proteins

| No. | Antigen No. | Sequence truncation | Sequence deletion | Site mutation Group 1 | Group 2 | Group 3 | Group 4 | Group 5 |
|---|---|---|---|---|---|---|---|---|
| 44 | YK-RSV-054 | | deleted from the sequence were replaced by a GS linker | I148C, I288C | S190F, V207L | E92D, K465Q | S46G, S215P, L373R | / |
| 45 | YK-RSV-055 | | | A147C, I292C | S190F, V207L | E92D, K465Q | S46G, S215P, L373R | / |
| 46 | YK-RSV-056 | | | A147C, S287C | S190F, V207L | E92D. K465Q | S46G, S215P, L373R | / |
| 47 | YK-RSV-057 | | | A147C, I291C | S190F, V207L | E92D, K465Q | S46G, S215P, L373R | / |
| 48 | YK-RSV-058 | | | S330C, G471C | S190F, V207L | E92D, K465Q | S46G, S215P, L373R | / |
| 49 | YK-RSV-059 | | | N325C, G471C | S190F, V207L | E92D. K465Q | S46G, S215P, L373R | / |
| 50 | YK-RSV-060 | | | R339C, S377C | S190F, V207L | E92D, K465Q | S46G, S215P, L373R | |
| 51 | YK-RSV-061 | | | A149C, S155C, S290C, Y458C | S190F, V296I | E92D, K465Q, D486S | S46G, S215P, L373R | V152I |
| 52 | YK-RSV-062 | | | A149C, S155C, S290C, Y458C | S190F, V296I | E92D, K465Q, D486S | S46G, S215P, L373R | C69Y, D73E, A74V, N88S, V152I |
| 53 | PC-RSV-063 | | | A149C, S155C, S290C,Y458C | S190F, V207L | E92D, K465Q | S46G, S215P, L373R | / |
| 54 | PC-RSV-064 | | | A149C, S155C, S290C, Y458C | S190F | E92D, K465Q | S46G, S215P, L373R | V152I |
| 55 | PC-RSV-065 | | | A149C, S155C, S290C, Y458C | S190F, V296I | E92D, K465Q | S46G, S215P, L373R | V152I |
| 56 | PC-RSV-066 | | | A149C, S155C, S290C, Y458C | S190F | E92D, K465Q, D486S | S46G, S215P, L373R | V152I |
| 57 | PC-RSV-067 | | | T103C, I148C | S190F, V296I | E92D, K465Q, D486S | S46G, S215P, L373R | V152I |
| 58 | PC-RSV-068 | | | S55C, L188C | S190F, V296I | E92D. K465Q, D486S | S46G, S215P, L373R | V152I |
| 59 | RSV A2 (138251)-wt | Full length (1 to 574 aa) | / | / | / | / | / | / |
| 60 | Abrysvo ™ | Retention (1 to 513 aa) | / | T103C, I148C | S190I | D486S | / | / |

1.2 Example 2: Preparation of RSV F Antigen mRNA Vaccines

The antigen sequences, after being designed, were each synthesized on a vector pVaX1 with optimized 5'-UTR, 3'-UTR, and polyA tail. All plasmids were synthesized by Azenta Life Sciences. The synthesized plasmid was subjected to linearized enzymatic cleavage, an mRNA stock solution was prepared by in vitro transcription, and LNP encapsulation was performed to obtain an mRNA formulation sample.

mRNA transcribed with pVaX1 as a basic backbone was used for subsequent analysis of the binding of antigenic epitopes by Western Blot or flow cytometry, detection of the binding of antigenic epitopes by ELISA, and detection of affinity of antigens for antibodies by BLI. An HIS-tag and a T4 fibritin folder were added to the vector backbone for detecting the stability of a trimer formed by secreted proteins.

The specific preparation process of an mRNA sample was as follows.

1.2.1 Preparation of mRNA Stock Solution

1) Experimental Materials

NEB® Golden Gate assembly kit (BsaI-HFv2) (NEB, Cat. No.: R3733);
DNA product purification kit (purchased from Tiangen Biotech (Beijing) Co., Ltd. (referred to as Tiangen), Cat. No.: DP205);
ATP (purchased from Hongene Biotech Corporation (referred to as Hongene), Cat. No.: R1-051);
CTP (Hongene, Cat. No.: R3-056);
GTP (Hongene, Cat. No.: R2-057);
N1-Me-pUTP (Hongene, Cat. No.: R5-064);
Cap1-GAG m7G(5')ppp(5')(2'OMeA)pG (Hongene, Cat. No.: ON-134);
T7 RNA polymerase (Hongene, Cat. No.: ON-004);
RNase inhibitor (Hongene, Cat. No.: ON-039);
Pyrophosphatase (Hongene, Cat. No.: ON-025);
10×IVT reaction buffer (Hongene, Cat. No.: ON-062);
DNase I (Hongene, Cat. No.: ON-109).

2) Experimental Procedures (1) Linearized Enzymatic Cleavage for Plasmid

Plasmid DNA was linearized using a BsaI-HFv2 endonuclease, and the enzymatic cleavage system comprised plasmid DNA inserted with a target gene, a 10× rCutSmart buffer, BsaI-HFv2, and RNase-free $ddH_2O$. The temperature of the enzymatic cleavage reaction was 37° C. and the time for the enzymatic cleavage reaction was 15 to 30 min. The enzymatic cleavage system is shown in the table below.

TABLE 2

Enzymatic cleavage reaction system

| Component | 50 μL of reaction system |
|---|---|
| DNA | 1 μg |
| 10 × rCutSmart buffer | 5 μl(1×) |
| BsaI-HFv2 | 1 μl |
| RNase-free $ddH_2O$ | Making up to 50 μL |

After the enzymatic cleavage reaction was completed, the linearized product was extracted using a DNA product purification kit, the concentration of the product was determined using an ultra-micro UV spectrophotometer (Denovix), and the length and state of a linearized plasmid template was detected by agarose gel.

(2) Co-Transcriptional Capping mRNA was synthesized by transcription with T7 RNA polymerase using the linearized plasmid prepared in the above step as a template and NTP solutions (NTPs) and a cap1 cap analog as starting materials. The above cap1 cap analog was Cap1-GAG, having a structure of m7G(5')ppp (5')(2'-OMeA)pG, and with a molecular formula of $C_{32}H_{43}N_5O_{24}P_4$.

The specific reaction system is shown in the table below. The formulated reaction system was placed in a constant temperature incubator at 37° C. for shaking culture for 3 h.

TABLE 3

Transcription reaction system

| Reaction component | Final concentration/volume of addition | |
|---|---|---|
| T7 transcription buffer solution (10×) | T7 transcription buffer: 1/10 total volume | |
| NTPs | ATP | 10 mM |
| | CTP | 10 mM |
| | GTP | 10 mM |
| | N1-Me-Pseudo UTP | 10 mM |
| Cap1 | 10 mM | |
| Linearized plasmid | 50 μg/ml | |
| RNase inhibitors | 1 KU/ml | |
| Inorganic pyrophosphatase | Adding 10 to 40 U per 1 mg of linearized plasmid | |
| T7 RNA polymerase | Adding 150 to 300 KU per 1 mg of linearized plasmid | |
| RNase-free $ddH_2O$ | Making up to a target volume of 20 μL | |

1 μL of DNase I was added to the above 20 μL of co-transcriptional capping reaction system after the reaction was completed, and the mixture was uniformly mixed and then placed at 37° C. for digestion for 30 min to obtain a co-transcriptional capped product.

(3) Purification by LiCl Precipitation Method

The co-transcriptional capped product obtained above was purified by a lithium chloride precipitation method as follows:

Adding LiCl: LiCl was added to the co-transcriptional capped product to make a final concentration of 2.8 M, and low temperature precipitation was performed for 2 h.

Precipitation: The mixture was centrifuged at a high speed of 12,000 rpm for 15 min, and the precipitate was retained.

Washing: The precipitate was washed with 75% ethanol 2 times, and dissolved with RNase-free $ddH_2O$ to obtain an mRNA stock solution.

Detection: the purified transcript was determined for concentration by ultra-micro UV spectrophotometer (Denovix) and integrity by capillary electrophoresis.

1.2.2 Preparation of mRNA-LNP (mRNA Vaccine)

A cationic lipid, DSPC, cholesterol, and DMG-PEG2000 were separately weighed accurately and dissolved with anhydrous ethanol, and a excipient mixed solution was formulated according to a molar ratio (controlling the molar ratio of the cationic lipid, the neutral lipid, the structural lipid, and the polymer-conjugated lipid to be 49:10:39.5:1.5) as an organic phase for later use.

mRNA was dissolved with a citric acid buffer and diluted to formulate a solution as an aqueous phase for later use. The organic phase and the aqueous phase were separately extracted with a BD™ Syringe. An LNP intermediate solution was prepared in a microfluidic device with the organic phase placed in the left pump, and the aqueous phase placed in the right pump.

The above LNP intermediate solution was diluted with a PBS solution and subjected to concentration by ultrafiltration on an ultrafiltration device. The solution, after being concentrated to a certain volume, was diluted with a PBS solution and concentrated on the ultrafiltration device, and the ultrafiltration was stopped when the final concentration volume was less than 5 mL.

1.3 Example 3: Detection of Expression of RSV F Antigen Mutants by Western Blot

To verify whether the designed antigen mRNAs can be expressed in the cells, the mRNAs were transfected into the cells, and the expression of the antigen mRNAs in the cells was detected using Western Blot.

1) Experimental Materials

- 293T cells (purchased from ATCC cell bank);
- primary antibody: HRSV—F (purchased from AbMax Biotechnology Co., Ltd., hereinafter referred to as AbMax, Cat. No.: 11049-R302);
- secondary antibody: goat anti-mouse IgG (H+L) secondary antibody, HRP (purchased from Shanghai Beyotime Biotechnology Co., Ltd., hereinafter referred to as Beyotime, Cat. No.: A0286);
- experimental group: a protein sample mixed solution obtained by lysis treatment after cells were transfected by a series of mRNA vaccines prepared in Example 2;
- internal reference protein: glyceraldehyde-3-phosphate dehydrogenase GAPDH;

2) Experimental Procedures

Cell culture and transfection: 293T cells were seeded at $1.3\times10^5$ cells/well in a 24-well plate. The next day, mRNA-LNP samples (containing 300 ng of mRNA) were added directly to the cells, and the mixture was uniformly mixed.

Preparation of protein samples: (1) the cells were taken out from the incubator after 16 h of transfection, pipetted repeatedly using a pipettor to allow the cells to be completely separated from the bottom of the dish, then transferred into a 1.5 mL centrifuge tube, and centrifuged at 1500 rpm for 3 min at 25° C. (2) The supernatant was discarded, and the cells were resuspended in 1 mL of PBS by pipetting and centrifuged at 1500 rpm for 3 min. (3) The previous step was repeated 2 times. (4) 50 μL of RIPA lysis buffer (0.5 μL of 100× protein inhibitor was added to the RIPA lysis buffer before use) was added to each tube of cells, and the mixture was incubated on ice for 30 min, during which the samples were vortexed for 30 s every 5 min. (5) The centrifuge was pre-cooled, and after the cells were fully lysed, the samples were centrifuged at 12,000 rpm for 10 min at 4° C., and the supernatant was transferred into a new 1.5 mL centrifuge tube by pipetting to obtain test protein samples.

Development and analysis: the concentrations of the protein samples were detected using a BCA quantification kit. The samples were pipetted for spotting, 4 μL of marker was spotted, and 200 V electrophoresis was performed for 30 min. The membrane transfer was performed using a dry membrane transfer apparatus. The gel was taken out, a membrane transfer "sandwich" was made and covered with a negative plate, and the membrane transfer was performed at 21 V, 23 V, and 25 V for 1 min, 4 min, and 2 min, respectively; then blocking was performed at room temperature for 1 h. Primary antibody incubation: incubation was performed at room temperature for 1 h. Membrane washing: with a 1×TBST buffer solution as a washing buffer, washing was performed for 5 min/time for 3 times. Secondary antibody incubation: incubation was performed at room temperature for 1 h. Membrane washing: washing was performed using a 1×TBST buffer solution for 5 min/time for 3 times. Color development: 1 mL of developing solution and 1 mL of fixing solution were mixed at 1:1, and the mixture was added dropwise to the membrane for color development and photographing.

1.4 Example 4: Detection of Binding of Epitopes (D and II of RSV F Antigen Mutants by Flow Cytometry To investigate whether the RSV F antigen mutants have pre-fusion epitopes, an RSV pre-F antibody (3C12) (specifically binding to the RSV pre-F epitope (I)) and an RSV F antibody (11A9) (binding to pre-F and post-F epitopes II) were detected by flow cytometry in this example, and RSV F protein mutants in the pre-F conformation were expected to bind to the antibodies tested.

1) Experimental Materials

- 293T cells (purchased from ATCC cell bank); RSV pre-F antibody (3C12), epitope q (Novoprotein, Cat. No.: DA101); RSV F antibody (11A9), epitope II (Novoprotein, Cat. No.: DA091);
- experimental groups: mRNA vaccines corresponding to the expressed antigens in Example 3;

2) Experimental Procedures (1) Cell transfection: 293T cells were seeded at $1.3\times10^5$ cells/well in a 24-well plate. The next day, mRNA-LNP samples (containing 300 ng of mRNA) were added directly to the cells, and the mixture was uniformly mixed.

(2) Cell collection: The cells were taken out of the incubator after 16 h of transfection, the medium was pipetted off, 500 μL of 0.1% BSA solution was pipetted to wash the medium remaining in the well plate, taking care not to resuspend the cells, and the 0.1% BSA solution was pipetted off. 500 μL of 0.1% BSA solution was added to each well, and the cells were pipetted and transferred to a 1.5 mL centrifuge tube.

(3) Centrifugation: The cells were harvested by centrifugation at 400 g for 5 min at 4° C. in the dark, and the supernatant was discarded.

(4) Straining: 50.6 μL of RSV fluorescent antibody diluent was added to each of the control sample and the test samples to resuspend the cells, and the samples were incubated at 4° C. for 2 h in the dark.

(5) Cleaning: After the incubation was completed, 500 μL of 0.1% BSA solution was added to each tube, the cells were harvested by centrifugation at 400 g for 5 min at 4° C. in the dark, and the supernatant was discarded. This operation was repeated three times.

(6) Resuspension of cells: 200 μL of 0.1% BSA solution was added to each sample, and the cells were carefully pipetted to prepare a cell suspension.

(7) Detection on flow cytometer: The binding kinetics of RSV F mutants to antibodies were measured using flow cytometry, with $1\times10^4$ cells detected in each measurement.

1.5 Example 5: Detection of Stability of RSV F Antigen Mutants by ELISA

To investigate the stability of the RSV F antigen mutants under different pH, temperature, osmotic pressure and other conditions, the mutants were subjected to stress tests under different treatment conditions in this example.

1) Experimental Materials

- 293T cells (purchased from ATCC cell bank);
- Primary antibody: RSV pre-F antibody (3C12), epitope Φ (purchased from Suzhou Novoprotein Scientific Co., Ltd. (hereinafter referred to as Novoprotein), Cat. No.: DA101);
- Standard: RSV pre-F trimer protein (Novoprotein, Cat. No.: DRA230);
- Secondary antibody: peroxidase AffiniPure goat anti-human IgG (H+L) (purchased from Yeasen Biotechnology (Shanghai) Co., Ltd. (hereinafter referred to as Yeasen), Cat. No.: N/A);
- Experimental group: mRNA vaccines after screening in Example 4;

2) Experimental Procedures (1) Cell transfection and collection: The transfection procedure was the same as in Example 3, and the cell supernatant was collected.

(2) Different pH conditions: The RSV F protein solution was adjusted to pH 3.5 and pH 10 with 10% NaOH and a 1 M HCl solution, respectively, and incubated at room temperature for 60 min, followed by neutralization to pH 7.4.

(3) High-temperature treatment: The RSV F protein solution was incubated at 50° C. for 60 min.

(4) Low-temperature treatment: The RSV F protein solution was stored at low temperature of 4° C. for one week.

(5) Low osmotic pressure treatment: The cell supernatant containing 110 mM NaCl was diluted to 10 mM NaCl with a 2.5 mM Tris buffer (pH 7.5) and incubated at room temperature for 60 min.

(6) High osmotic pressure treatment: The cell supernatant was adjusted to 3.0 M $MgCl_2$ with 4.5 M $MgCl_2$ and incubated at room temperature for 60 min.

(7) Detection of antigen expression by ELISA:

Coating: A 96-well microplate was coated with a working solution and incubated at 2 to 8° C. for 16 to 20 h.

Plate washing: Phosphate buffered saline PBST was added to each well, and the plate was washed 5 times using a plate washer and patted dry on absorbent paper.

Blocking: After a blocking solution was added, the cells were placed on a constant temperature microplate shaker and incubated at 400 rpm for 1.5 h at 37° C.

Plate washing: PBST was added to each well, and the plate was washed 5 times using a plate washer and patted dry on absorbent paper.

Primary antibody incubation: A primary antibody dilution was added to each well, and the plate was sealed with a sealing film, and then incubated at 400 rpm for 1.5 h at 37° C.

Plate washing: PBST was added to each well, and the plate was washed 5 times using a plate washer and patted dry on absorbent paper.

Secondary antibody incubation: A secondary antibody dilution was added to each well, and the plate was sealed with a sealing film, and then incubated at 400 rpm for 45 min at 37° C.

Plate washing: PBST was added to each well, and the plate was washed 5 times using a plate washer and patted dry on absorbent paper.

Color development: A chromogenic solution was added, and the plate was sealed with a sealing film, and then placed on a constant temperature microplate shaker and incubated at 400 rpm for 25 min at 37° C.

Reaction stopping: After the color development was completed, a stop buffer was added at 50 Lt/well to the microplate to stop the reaction.

Plate reading: Absorbance values (OD values) were read within 5 min using a multimode microplate reader, with dual wavelengths of 450 nm and 630 nm set.

1.6 Example 6: Detection of Binding of RSV F Antigen Mutants to Different Epitopes by ELISA To investigate the binding of the RSV F antigen mutants to antibodies recognizing different epitopes, the binding amount was determined by an ELISA method in this example.

1) Experimental Materials 293T cells (purchased from ATCC cell bank);
Primary antibody: RSV pre-F antibody (3C12), epitope (D (Novoprotein, Cat. No.: DA101);
RSV pre-F antibody (7H11), epitope Quaternary (Novoprotein, Cat. No.: DA109);
RSV F antibody (11A9), epitope II (Novoprotein, Cat. No.: DA091);
RSV F antibody (4B9), epitope III (Novoprotein, Cat. No.: DA110);
RSV pre-F antibody (7E11), epitope V (Cat. No.: DA119);
Standard: RSV-pre-F trimer protein (Novoprotein, Cat. No.: DRA230);
Secondary antibody: peroxidase AffiniPure goat anti-human IgG (H+L) (Yeasen, Cat. No.: N/A);
Experimental group: mRNA vaccines after screening in Example 5;

2) Experimental Procedures

Cell culture and transfection, and protein sample preparation: the experimental procedures were the same as in Example 3.

Detection of antigen expression by ELISA: the experimental procedures were the same as in Example 5.

1.7 Example 7: Detection of Affinity of RSV F Antigen Mutants for Different Antibodies by BLI To investigate the affinity of the RSV F antigen mutants for antibodies specifically recognizing epitopes in a prefusion conformation, the affinity was determined by a biolayer interferometry (BLI) method in this example.

1) Experimental Materials 293T cells (purchased from ATCC cell bank);
RSV pre-F antibody (3C12), epitope Φ (Novoprotein, Cat. No.: DA101);
RSV pre-F antibody (7H11), epitope Quaternary (Novoprotein, Cat. No.: DA109);
Experimental group: mRNA vaccines after screening in Example 6;

2) Experimental Procedures

Protein sample preparation: the experimental procedure was the same as in Example 3.

The antibodies were each diluted to 10 g/mL with a 1×PBST solution.

Antibodies RSV pre-F antibody (3C12) and RSV pre-F antibody (7H11) were each captured with a ProA probe in a 1×PBST solution, with a capture level limited to 4.0 nm; then, they were sequentially reacted with the diluted target protein, and the solid phase conjugates were subjected to dissociation analysis in a 1×PBST buffer after complete reaction.

The detection was performed using a protein interaction analyzer, and the results were analyzed using Data Analysis 12.0 software to obtain the binding rate, dissociation rate, and affinity constants.

1.8 Example 8: Study of Immunogenicity of RSV F Antigen Mutants in Mice

To investigate antibody titers of the RSV F antigens produced in mice, the mice were subjected to in vivo immunization in this example.

1.8.1 Immunization of Balb/c Mice

1) Experimental Materials

Animals: Balb/c mice, female, 6 to 8 weeks;
negative control: LNP sample;
positive control: Abrysvo™;
test samples: YK-RSV-001, YK-RSV-011, YK-RSV-030, YK-RSV-036, YK-RSV-044, YK-RSV-060, YK-RSV-062, YK-RSV-061, YK-RSV-003, YK-RSV-012, YK-RSV-015, YK-RSV-039, and YK-RSV-054;

2) Immunization Regimen for Mice

TABLE 4

| Immunization regimen for mice | | | | | | | | |
|---|---|---|---|---|---|---|---|---|
| | | Immunization | | | | | | |
| Group | Number of animals | Test vaccine | Administration dose (μg/animal) | Administration volume (μL/animal) | Route | Frequency | Blood sampling time point | Time of sacrifice |
| 1 | 6 | LNP | 0 | 100 | Intramuscular injection | Days 0 and 21 | Day 35 | Day 49 |
| 2 | 6 | Abrysvo ™ | 1 | 100 | | | | |
| 3 | 6 | YK-RSV-001 | 5 | 100 | | | | |
| 4 | 6 | YK-RSV-011 | 5 | 100 | | | | |
| 5 | 6 | YK-RSV-030 | 5 | 100 | | | | |
| 6 | 6 | YK-RSV-036 | 5 | 100 | | | | |
| 7 | 6 | YK-RSV-044 | 5 | 100 | | | | |
| 8 | 6 | YK-RSV-060 | 5 | 100 | | | | |
| 9 | 6 | YK-RSV-062 | 5 | 100 | | | | |
| 10 | 6 | YK-RSV-061 | 5 | 100 | | | | |
| 11 | 8 | YK-RSV-003 | 5 | 100 | | | | |
| 12 | 8 | YK-RSV-012 | 5 | 100 | | | | |
| 13 | 8 | YK-RSV-015 | 5 | 100 | | | | |
| 14 | 8 | YK-RSV-039 | 5 | 100 | | | | |
| 15 | 8 | YK-RSV-054 | 5 | 100 | | | | |

Note:
The administration volume is calculated according to the actual concentration of the administration dose 3) Sample Collection and Pretreatment 0.2 mL of blood was taken from the orbital venous plexus of each animal, and the serum was separated (centrifugation at 4000 rpm/min for 10 min at 4° C.) and stored in a refrigerator at 4° C. for further treatment.

4) Health Detection

Once daily, including but not limited to death, illness, respiration, secretions, faeces, and food and water consumption.

5) Humane Endpoint

Any mice that lost more than 20% of their body weight during the experiment (with body weight on day 0 as baseline weight before infection, and body weight on the day of inoculation as baseline weight after infection) or/and exhibited symptoms of dying, would be euthanized and scored as dead animals in the results, as specified by the IACUC protocol.

1.8.2 Detection of Neutralizing Antibody Titers of RSVs in Serum of Mice

1) Objective

The neutralizing antibody titers of respiratory syncytial viruses RSV A2 and RSV B18357 in the serum were detected by a spot reduction-based micro-neutralization test method.

2) Key Reagents

Primary antibody: research grade palivizumab (purchased from Wuhan Chemstan Biotechnology Co., Ltd., hereinafter referred to as Wuhan Chemstan, Cat. No.: CSD00024);

secondary antibody: rabbit anti-human IgG H & L (HRP) (Abcam, Cat. No.: ab6759);

3) Calculation Formula for Data (1) Sample inhibition rate: calculated by Excel (single-well calculation), sample inhibition rate=(1−(number of sample spots/number of virus control spots))×100%.

(2) The sample dilution factor as an X axis and the inhibition rate as a Y axis were input into GraphPad software, and $IC_{50}$ value and the linear correlation coefficient R2 of the sample were calculated by four-parameter fitting, wherein the $IC_{50}$ value was the neutralizing antibody titer of the sample. The titer was retained as an integer and the linear correlation coefficient R2 was retained to the second decimal place.

(3) Mean value:

$$\frac{\sum_{i=1}^{n} X_i}{n},$$

$X_i$ represents the $i^{th}$ measurement, and n represents the number of measurements; calculated by Excel, and retained to the second decimal place. Note: If the calculation result is the titer value, it is retained as an integer.

4) Experimental Procedures

After the test serum sample was subjected to gradient dilution, a certain amount of RSV virus was added. After a neutralization reaction, the mixture was added to a cell plate for culture for 22 to 26 h, and finally, the neutralizing antibody titer level of the serum sample was calculated according to the formation of spots. The operation process was as follows:

Cell preparation and plating: HEp-2 cells were purchased from Yuchi (Shanghai) Biotechnology Co., Ltd. The cells were thawed and cultured before the experiment, and the cells used in the detection were 3 to 20 generations after the thawing. The cells were digested in advance and seeded into a 96-well plate at $2.5\times10^5$ cells/mL and 0.1 mL/well, and the plate was placed in an incubator at 37° C. with 5% $CO_2$ for culture for 17 to 23 h. When no abnormality was observed in the cells, the serum sample was taken and diluted in a gradient.

Control setting: Controls were set in a 96-well plate (neutralization plate), and the dilutions were added to cell controls (CCs) and virus controls (VCs), with duplicate wells set.

Virus addition: viruses diluted with the diluent were taken and added to the sample wells and the VC wells of the 96-well plate, the 96-well plate was gently patted to uniformly mix the samples and the viruses, and then placed in an incubator at 37° C. with 5% $CO_2$ for incubation for neutralization reactions.

Cell preparation, infection, and culture: a 96-well plate seeded with the cells in advance was taken, the original culture medium was discarded by pipetting, a mixed solution from the neutralization plate was pipetted and added to the 96-well plate placed with the cells, which was then placed in an incubator at 37° C. with 5% $CO_2$ for culture.

Fixing and staining: after the culture, the original culture medium was discarded by pipetting, and a certain volume of fixative was added to each well. After fixation, the fixative was discarded, and the plate was repeatedly washed with 1×PBS 2 times. After a blocking buffer was added for blocking, the blocking buffer was discarded, and the plate was repeatedly washed with 1×PBS 2 times; after a primary antibody working solution was added for incubation, the antibody was discarded, and the plate was repeatedly washed with 1×PBS 2 times; after an HRP secondary antibody working solution was added for incubation, the antibody was discarded, and the plate was repeatedly washed with 1×PBS 2 times; a chromogenic solution was added, and the plate was incubated at room temperature for 5 to 20 min; the chromogenic solution was discarded, the plate was patted dry, and spots were counted by an enzyme-linked immunospot reader.

Calculation for results: neutralizing antibody titers: the inhibition rates of gradients of the sample were calculated, the dilution factor-inhibition rate of the sample was input into GraphPad software for fitting, and the $IC_{50}$ and $IC_{90}$ values of the sample were calculated, wherein the $IC_{50}$ and $IC_{90}$ values were the neutralizing antibody titers of the sample.

1.8.3 Detection of Binding Antibody Titers of RSVs in Serum of Mice

1) Objective

Serum samples in an immunogenicity test of RSV mRNA vaccines were detected by a qualified self-constructed indirect ELISA method, with detection indexes including RSV pre-F protein- and post-F protein-specific antibody titers, which provide data support for analysis of immunogenicity and protection against challenge of vaccines.

2) Key Reagents

- Coating working solution: RSV-pre-F-11 protein (Vazyme, Cat. No.: RM2187); RSV-post-F-11 protein (Vazyme, Cat. No.: RM2188);
- positive quality control: monoclonal anti-RSV-pre-F0 specific antibody* (Acro, Cat. No.: RSO—Y132); monoclonal anti-RSV-post-F0 specific antibody* (Acro, Cat. No.: RSV—Y180);
- secondary antibody: rabbit anti-mouse IgG HL (HRP) (Abcam, Ab6728);

3) Calculation formula for data

- Mean: Mean=Average (OD value X1:OD value Xn);
- signal-to-noise ratio (SNR): SNR=mean OD value of sample/mean OD value of NC;
- coefficient of variation (CV %): CV %=STDEV (OD value X1:OD value Xn)/mean OD value×100;
- calculation of binding antibody titers: the titer values in each analysis batch were calculated using the FORECAST (x, known_y's, known x's) function, where x represents the Cut off value, known_y's represents two dilution factors across the Cut off value, and known x's represents two OD values across the Cut off value, and the corresponding dilution factor obtained was the titer value for each sample.

4) Experimental Procedures

The procedures were the same as in the ELISA method in Example 5. In the primary antibody incubation step, the diluted test serum sample was added, and after being sealed with a sealing film, the plate was placed on a constant temperature microplate shaker and incubated at 400 rpm for 1.5 h at 37° C.

1.9 Example 9: Study of Immunogenicity of RSV F Antigen Mutants in Cotton Rats

To investigate antibody titers of the RSV F antigens in cotton rats and the immunoprotective effect after challenge, cotton rats were subjected to in vivo immunization in this example.

1.9.1 Immunization of Cotton Rats

1) Experimental Materials

- Animals: cotton rats, female, 6-8 weeks;
- negative control: LNP sample;
- positive control: Abrysvo™;
- test samples: YK-RSV-001, YK-RSV-061, YK-RSV-062, YK-RSV-003, YK-RSV-012, YK-RSV-015, YK-RSV-036, YK-RSV-039, YK-RSV-044, YK-RSV-054, and YK-RSV-060;

2) Immunization Regimen for Cotton Rats

TABLE 5

Immunization regimen for cotton rats

| Group | Number of animals | Test vaccine | Immunization: Administration dose (μg/animal) | Administration volume (μL/animal) | Route | Frequency | Blood sampling time point | Time of sacrifice |
|---|---|---|---|---|---|---|---|---|
| 1 | 6 | LNP | 0 | 100 | Intramuscular injection | Days 0 and 28 | Days 42 and 48 | Day 54 |
| 2 | 6 | Abrysvo ™ | 50 | 208 | | | | |
| 3 | 6 | YK-RSV-001 | 5 | 100 | | | | |
| 4 | 6 | YK-RSV-061 | 5 | 100 | | | | |
| 5 | 6 | YK-RSV-062 | 5 | 100 | | | | |
| 6 | 6 | YK-RSV-003 | 5 | 100 | | | | |
| 7 | 6 | YK-RSV-012 | 5 | 100 | | | | |
| 8 | 6 | YK-RSV-015 | 5 | 100 | | | | |
| 9 | 6 | YK-RSV-036 | 5 | 100 | | | | |
| 10 | 6 | YK-RSV-039 | 5 | 100 | | | | |
| 11 | 6 | YK-RSV-044 | 5 | 100 | | | | |
| 12 | 6 | YK-RSV-054 | 5 | 100 | | | | |
| 13 | 6 | YK-RSV-060 | 5 | 100 | | | | |

Note:
The administration volume is calculated according to the actual concentration of the administration dose. The injection dose of Abrysvo ™ includes 25 μg of each of type A and type B.

3) Tissue Sample Collection

The lungs and turbinates were aseptically taken on Day 54.

4) Information of Challenge

On day 49, the challenge was performed by nasal drip, the virus strain was RSV A2 virus, and the challenge volume was 50 μL (5×$10^5$ PFU).

1.9.2 Determination of Binding Antibody and Neutralizing Antibody Titers of RSVs in Serum of Cotton Rats The detection methods for the binding antibody and neutralizing antibody titers were the same as in Examples 4.8.2 and 4.8.3.

1.9.3 Detection of Respiratory Syncytial Virus (RSV) Titers in Tissue Samples of Cotton Rats by a Plaque Assay 1) Objective The respiratory syncytial virus (RSV) titers in the left lung and turbinate tissue samples of cotton rats were determined by a plaque assay, which was completed for all biological samples.

2) Key Reagents

Primary antibody: research grade palivizumab (Wuhan Chemstan, Cat. No.: CSD00024);

secondary antibody: rabbit anti-human IgG H & L (HRP) (Abcam, Cat. No.: ab6759);

quality control virus RSV A2;

(3) Experimental Procedures

After the test samples were subjected to gradient dilution, the cells were infected. After the infection solution was removed, a covering layer solution was added, and the cells were continued to be cultured until plaques were formed. The results for the virus titers in the tissue samples were finally calculated according to the appearance of plaques or lesions. The operation process was as follows:

Cell preparation and plating: HEp-2 cells were purchased from Yuchi (Shanghai) Biotechnology Co., Ltd. The cells were thawed and cultured before the experiment, and the cells used in the detection were 3 to 20 generations after the thawing. The cells were digested in advance and seeded into a 24-well plate at 2×$10^5$ cells/mL and 1 mL/well, and the plate was placed in an incubator at 37° C. with 5% $CO_2$ for culture for 17 to 23 h.

Treatment of tissue samples: after the left lung and the turbinate tissue samples were obtained, a virus preservation solution was added, the tissues were ground, and the samples were centrifuged to obtain supernatants, which were subjected to gradient dilution.

Cell treatment: a cell plate seeded in advance was taken from an incubator at 37° C. with carbon dioxide, the culture supernatant was discarded by pipetting, then the plate was repeatedly washed with 1× PBS 2 times, and the residual liquid was discarded by pipetting.

Virus infection and adsorption: the supernatant of the diluted tissue homogenate was taken and added to corresponding wells of the cell plate, and the 24-well plate was placed in an incubator at 37° C. with 5% $CO_2$ to enable the viruses to be fully adsorbed on the cells.

Addition of covering layer: after the adsorption was completed, the virus solution was discarded by pipetting, a covering layer was added to each well, the cell plate was placed in an incubator at 37° C. with 5% $CO_2$ for culture, and the formation of lesions and plaques were observed daily.

Fixing: after typical plaque appeared in the virus wells, the covering layer was discarded by pipetting, and 4% paraformaldehyde was added to each well for fixing.

Straining: after the cell plate was fixed, the fixative was discarded, and the cell plate was repeatedly washed with 1×PBS 3 times and blocked with a blocking buffer; the blocking buffer was discarded, the plate was repeatedly washed with 1×PBS 3 times, and a primary antibody working solution was added for incubation; the antibody was discarded, the plate was repeatedly washed with 1×PBS 3 times, and an HRP secondary antibody working solution was added for incubation; the antibody was discarded, the plate was washed with 1×PBS 3 times, a chromogenic solution was added, and the plate was incubated at room temperature for 10 to 20 min; the chromogenic solution was discarded, and spots were observed and counted by a film camera.

Calculation for Results

Virus titer [PFU/mL]=(mean plaque number×sample dilution factor)/inoculum size (mL);

Tissue virus titer [PFU/g][1]*=[(mean plaque number×tissue sample dilution factor)/inoculum size (mL)×volume of tissue grinding fluid (mL)]/tissue weight (g).

The tissue virus Lg titer [Lg PFU/g] is the logarithm of the tissue virus titer [PFU/g] at a base of 10.

1*: plaques of all dilutions which can be accurately counted are selected for statistical calculation, and the arithmetic mean is used during the calculation.

1.9.4 Detection of Lung Tissue Inflammation Indexes by HE Staining

1) Objective

The lung tissue inflammation indexes were detected by HE staining.

2) Key Reagents

Xylene solution (Shanghai Zhanyun Chemical Co., Ltd., Cat. No. 1330-20-7); hematoxylin solution (Mayer) (Baso, Cat. No.: BASO-BA-4021); eosin solution (alcohol soluble) (Baso, Cat. No.: BASO-BA-4022);

3) Experimental Procedures

Lung tissues were perfused, fixed in 4% paraformaldehyde for more than 24 h, dehydrated, and sliced at the maximum parenchyma area with a section thickness of 4 m. A staining rack loaded with the slices was placed in an oven at 60 to 65° C. for baking the slices for 1 h. After paraffin was melted to be in a transparent liquid state, the staining rack was placed in a room temperature environment for 10 min for cooling. After the cooling was completed, HE staining was performed, and finally the slices were sealed.

4) Results

Manual semi-quantitative scoring was performed with the scoring criteria shown in the table below. Data were analyzed by Mean+SEM and analyzed by one-way ANOVA.

TABLE 6

Semi-quantitative histopathological scoring criteria

| Histological characterization | Score | Criteria |
|---|---|---|
| Alveolar region | 0 | No visible lesion |
| Inflammatory infiltrations of | 1 | Mild |
| macrophages, lymphocytes, | 2 | Moderate |
| neutrophils, etc., are observed | 3 | Severe |
| in the alveolar tissue | 4 | Serious |
| Perivascular region | 0 | No visible lesion |
| Inflammatory infiltrations of | 1 | Mild |
| macrophages, lymphocytes, | 2 | Moderate |
| neutrophils, etc., are observed in | 3 | Severe |
| the perivascular region | 4 | Serious |
| Peribronchiolar region | 0 | No visible lesion |
| Inflammatory infiltrations of | 1 | Mild |
| macrophages, lymphocytes, | 2 | Moderate |
| neutrophils, etc., are observed | 3 | Severe |
| in the peribronchiolar region | 4 | Serious |
| Interstitium | 0 | No visible lesion |
| Inflammatory infiltrations of | 1 | Mild |
| macrophages, lymphocytes, | 2 | Moderate |
| neutrophils, etc., are | 3 | Severe |
| observed in the interstitium | 4 | Serious |

2 Analysis of Results 2.1 Results for Expression of RSV F Antigen Mutants

YK-RSV-001, YK-RSV-002, YK-RSV-003, YK-RSV-004, YK-RSV-005, YK-RSV-008, YK-RSV-009, YK-RSV-010, YK-RSV-011, YK-RSV-012, YK-RSV-013, YK-RSV-014, YK-RSV-015, YK-RSV-016, YK-RSV-017, YK-RSV-018, YK-RSV-019, YK-RSV-022, YK-RSV-029, YK-RSV-030, YK-RSV-031, YK-RSV-032, YK-RSV-033, YK-RSV-034, YK-RSV-035, YK-RSV-036, YK-RSV-037, YK-RSV-038, YK-RSV-039, YK-RSV-040, YK-RSV-041, YK-RSV-042, YK-RSV-043, YK-RSV-044, YK-RSV-045, YK-RSV-046, YK-RSV-048, YK-RSV-050, YK-RSV-051, YK-RSV-052, YK-RSV-053, YK-RSV-054, YK-RSV-055, YK-RSV-056, YK-RSV-057, YK-RSV-058, YK-RSV-059, YK-RSV-060, YK-RSV-061, and YK-RSV-062 mutants all showed significant protein expression at a size of about 75 kDa, which was consistent with the theoretical size of the antigen, and could be used as effective candidate antigens for next immunogenicity screening and evaluation. Thus, the above 50 mutants would be further determined for antigenic epitope binding by flow cytometry for further screening. As shown in FIG. 1.

2.2 Results for Determination of Epitope Binding of RSV F Antigen Mutants

Among major neutralizing active antigenic epitopes of the RSV F protein, the epitope Φ is located only in the pre-fusion conformation, and the epitope II is retained in both the pre-fusion and post-fusion conformations.

The ability of the antibodies to specifically bind to the epitope Φ correlates with neutralizing activity, and the low binding rates to the epitope Φ affect neutralizing activity, resulting in poor neutralizing activity.

The RSV pre-F antibody (3C12) used in this example specifically binds to the RSV pre-F epitope Φ, and the RSV F antibody (11A9) binds to the pre-F and post-F epitopes II. Whether the pre-fusion conformations of the RSV F mutants are stable can be further determined by detecting the binding of the epitope Φ and the epitope II on the mutants to corresponding epitopes of antibodies 3C12 and 11A9, respectively, by flow cytometry. Data for epitope binding are shown in the table below.

TABLE 7

Results for epitope binding of RSV F mutants-general table

| No. | RSV pre-F antibody (3C12) Epitope Φ (%) | RSV F antibody (11A9) Epitope II (%) | Φ/II (%) |
|---|---|---|---|
| YK-RSV-001 | 91.7 | 97.6 | 94.0 |
| YK-RSV-002 | 88.0 | 93.5 | 94.1 |
| YK-RSV-003 | 94.5 | 96.9 | 97.5 |
| YK-RSV-004 | 82.1 | 90.1 | 91.1 |
| YK-RSV-005 | 91.6 | 95.2 | 96.2 |
| YK-RSV-008 | 83.9 | 92.5 | 90.7 |
| YK-RSV-009 | 87.4 | 93.1 | 93.9 |
| YK-RSV-010 | 90.3 | 92.8 | 97.3 |
| YK-RSV-011 | 78.9 | 86.6 | 91.1 |
| YK-RSV-012 | 93.3 | 97.2 | 96.0 |
| YK-RSV-013 | 89.3 | 94.3 | 94.7 |
| YK-RSV-014 | 0.0 | 0.1 | 0.0 |
| YK-RSV-015 | 94.9 | 98.5 | 96.3 |
| YK-RSV-016 | 79.8 | 83.4 | 95.7 |
| YK-RSV-017 | 91.3 | 94.6 | 96.5 |
| YK-RSV-018 | 68.4 | 76.3 | 89.6 |
| YK-RSV-019 | 84.5 | 90.4 | 93.5 |
| YK-RSV-022 | 0.2 | 2.1 | 9.5 |
| YK-RSV-029 | 79.6 | 86.7 | 91.8 |
| YK-RSV-030 | 91.0 | 96.8 | 94.0 |
| YK-RSV-031 | 75.5 | 83.4 | 90.5 |
| YK-RSV-032 | 86.1 | 94.8 | 90.8 |
| YK-RSV-033 | 72.0 | 82.4 | 87.4 |
| YK-RSV-034 | 82.5 | 91.0 | 90.7 |
| YK-RSV-035 | 79.6 | 87.1 | 91.4 |
| YK-RSV-036 | 93.3 | 96.7 | 96.5 |
| YK-RSV-037 | 79.0 | 86.9 | 90.9 |
| YK-RSV-038 | 90.7 | 95.7 | 94.8 |
| YK-RSV-039 | 93.0 | 97.1 | 95.8 |
| YK-RSV-040 | 84.3 | 92.0 | 91.6 |
| YK-RSV-041 | 73.7 | 81.5 | 90.4 |
| YK-RSV-042 | 49.8 | 61.1 | 81.5 |
| YK-RSV-043 | 90.7 | 95.2 | 95.3 |
| YK-RSV-044 | 92.9 | 96.9 | 95.9 |
| YK-RSV-045 | 78.3 | 86.0 | 91.0 |
| YK-RSV-046 | 84.0 | 89.8 | 93.5 |
| YK-RSV-048 | 89.6 | 95.1 | 94.2 |
| YK-RSV-050 | 86.5 | 93.0 | 93.0 |
| YK-RSV-051 | 76.8 | 87.1 | 88.2 |
| YK-RSV-052 | 89.4 | 93.7 | 95.4 |
| YK-RSV-053 | 40.0 | 67.0 | 59.7 |
| YK-RSV-054 | 94.4 | 97.5 | 96.8 |
| YK-RSV-055 | 93.3 | 96.2 | 97.0 |
| YK-RSV-056 | 94.6 | 97.1 | 97.4 |
| YK-RSV-057 | 94.4 | 97.2 | 97.1 |
| YK-RSV-058 | 81.2 | 88.7 | 91.5 |
| YK-RSV-059 | 83.1 | 89.8 | 92.5 |
| YK-RSV-060 | 91.6 | 95.2 | 96.2 |
| YK-RSV-061 | 93.8 | 95.7 | 98.0 |
| YK-RSV-062 | 92.5 | 94.5 | 97.9 |
| PC-RSV-064 | 88.0 | 91.2 | 96.5 |
| PC-RSV-065 | 84.0 | 92.6 | 90.7 |
| PC-RSV-066 | 85.1 | 90.8 | 93.7 |
| PC-RSV-067 | 84.9 | 89.8 | 94.5 |
| PC-RSV-068 | 87.7 | 90.5 | 96.9 |
| RSVA2 (138251)-wt | 1.0 | 23.1 | 4.3 |

There was a total of 20 mutants with a binding rate of the epitope Φ on the RSV F mutant to the antibody 3C12 of greater than 90%. The binding rates of the epitope on these RSV F mutants to the antibody 3C12 were all superior to those of controls PC—RSV-064, PC—RSV-065, PC—RSV-066, PC—RSV-067, PC—RSV-068, and wild-type RSVA2 (138251)-wt.

1) the Binding Rates of the Epitope (D on the Following 11 RSV F Mutants to the Antibody 3C12 were Higher than 90%, Ranging from 91.6% to 94.9%, which was Significantly Superior to Those of Controls The mutants within this range are shown in the table below, including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, and YK-RSV-060.

TABLE 8

Results for epitope binding of RSV F mutants-1

| No. | RSV pre-F antibody (3C12) Epitope Φ (%) | RSV F antibody (11A9) Epitope II (%) | Φ/II (%) |
|---|---|---|---|
| YK-RSV-061 | 93.8 | 95.7 | 98.0 |
| YK-RSV-003 | 94.5 | 96.9 | 97.5 |
| YK-RSV-062 | 92.5 | 94.5 | 97.9 |
| YK-RSV-054 | 94.4 | 97.5 | 96.8 |
| YK-RSV-039 | 93.0 | 97.1 | 95.8 |
| YK-RSV-044 | 92.9 | 96.9 | 95.9 |
| YK-RSV-012 | 93.3 | 97.2 | 96.0 |
| YK-RSV-015 | 94.9 | 98.5 | 96.3 |
| YK-RSV-001 | 91.7 | 97.6 | 94.0 |
| YK-RSV-036 | 93.3 | 96.7 | 96.5 |
| YK-RSV-060 | 91.6 | 95.2 | 96.2 |
| PC-RSV-064 | 88.0 | 91.2 | 96.5 |
| PC-RSV-065 | 84.0 | 92.6 | 90.7 |
| PC-RSV-066 | 85.1 | 90.8 | 93.7 |
| PC-RSV-067 | 84.9 | 89.8 | 94.5 |
| PC-RSV-068 | 87.7 | 90.5 | 96.9 |
| RSV A2 (138251)-wt | 1.0 | 23.1 | 4.3 |

2) the Binding Rates of the Epitope (D on the Following 9 RSV F Mutants to the Antibody 3C12 were Also all Higher than 90%, which was Significantly Superior to Those of Controls The binding rates of the epitope Φ on 9 mutants to the antibody 3C12 in the table below were 90.300 to 94.6%. The mutants within this range are shown in the table below.

TABLE 9

Results for epitope binding of RSV F mutants-2

| No. | RSV pre-F antibody (3C12) Epitope Φ (%) | RSV F antibody (11A9) Epitope II (%) | Φ/II (%) |
|---|---|---|---|
| YK-RSV-056 | 94.6 | 97.1 | 97.4 |
| YK-RSV-057 | 94.4 | 97.2 | 97.1 |
| YK-RSV-055 | 93.3 | 96.2 | 97.0 |
| YK-RSV-005 | 91.6 | 95.2 | 96.2 |
| YK-RSV-017 | 91.3 | 94.6 | 96.5 |
| YK-RSV-030 | 91.0 | 96.8 | 94.0 |
| YK-RSV-038 | 90.7 | 95.7 | 94.8 |
| YK-RSV-043 | 90.7 | 95.2 | 95.3 |
| YK-RSV-010 | 90.3 | 92.8 | 97.3 |
| PC-RSV-064 | 88.0 | 91.2 | 96.5 |
| PC-RSV-065 | 84.0 | 92.6 | 90.7 |
| PC-RSV-066 | 85.1 | 90.8 | 93.7 |
| PC-RSV-067 | 84.9 | 89.8 | 94.5 |
| PC-RSV-068 | 87.7 | 90.5 | 96.9 |
| RSVA2 (138251)-wt | 1.0 | 23.1 | 4.3 |

The mutants within this range are shown in the table below. The binding rates of the epitope Φ on these mutants to the antibody 3C12 were 81.2% to 89.6%, the binding rates of the epitope Φ on these mutants to the antibody I11I9 were 88.7% to 95.1%, and the ratio of 0/JJ was 90.7% to 95.4%.

TABLE 10

| Results for epitope binding of RSV F mutants-3 | | | |
|---|---|---|---|
| No. | RSV pre-F antibody (3C12) Epitope Φ (%) | RSV F antibody (11A9) Epitope II (%) | Φ/II (%) |
| YK-RSV-048 | 89.6 | 95.1 | 94.2 |
| YK-RSV-052 | 89.4 | 93.7 | 95.4 |
| YK-RSV-013 | 89.3 | 94.3 | 94.7 |
| YK-RSV-002 | 88.0 | 93.5 | 94.1 |
| YK-RSV-009 | 87.4 | 93.1 | 93.9 |
| YK-RSV-050 | 86.5 | 93.0 | 93.0 |
| YK-RSV-032 | 86.1 | 94.8 | 90.8 |
| YK-RSV-019 | 84.5 | 90.4 | 93.5 |
| YK-RSV-040 | 84.3 | 92.0 | 91.6 |
| YK-RSV-046 | 84.0 | 89.8 | 93.5 |
| YK-RSV-008 | 83.9 | 92.5 | 90.7 |
| YK-RSV-059 | 83.1 | 89.8 | 92.5 |
| YK-RSV-034 | 82.5 | 91.0 | 90.7 |
| YK-RSV-004 | 82.1 | 90.1 | 91.1 |
| YK-RSV-058 | 81.2 | 88.7 | 91.5 |
| PC-RSV-064 | 88.0 | 91.2 | 96.5 |
| PC-RSV-065 | 84.0 | 92.6 | 90.7 |
| PC-RSV-066 | 85.1 | 90.8 | 93.7 |
| PC-RSV-067 | 84.9 | 89.8 | 94.5 |
| PC-RSV-068 | 87.7 | 90.5 | 96.9 |
| RSV A2 (138251)-wt | 1.0 | 23.1 | 4.3 |

There were a total of 15 mutants with a binding rate of the epitope Φ on the RSV F mutant to the antibody 3C12 of a less than 80%.

4) the Binding Rates of the Epitope Φ on 7 RSV F Mutants to the Antibody 3C12 were Less than 80%

The binding rates of the epitope Φ on the following 7 mutants to the antibody 3C12 were 76.8% to 79.800, the binding rates of the epitope II to antibody 11A9 were 83.4% to 87.100, and the ratio of Φ/II was 88.2% to 95.7%. The mutants within this range are shown in the table below.

TABLE 11

| Results for epitope binding of RSV F mutants-4 | | | |
|---|---|---|---|
| No. | RSV pre-F antibody (3C12) Epitope Φ (%) | RSV F antibody (11A9) Epitope II (%) | Φ/II (%) |
| YK-RSV-016 | 79.8 | 83.4 | 95.7 |
| YK-RSV-029 | 79.6 | 86.7 | 91.8 |
| YK-RSV-035 | 79.6 | 87.1 | 91.4 |
| YK-RSV-037 | 79.0 | 86.9 | 90.9 |
| YK-RSV-011 | 78.9 | 86.6 | 91.1 |
| YK-RSV-045 | 78.3 | 86.0 | 91.0 |
| YK-RSV-051 | 76.8 | 87.1 | 88.2 |
| PC-RSV-064 | 88.0 | 91.2 | 96.5 |
| PC-RSV-065 | 84.0 | 92.6 | 90.7 |
| PC-RSV-066 | 85.1 | 90.8 | 93.7 |
| PC-RSV-067 | 84.9 | 89.8 | 94.5 |
| PC-RSV-068 | 87.7 | 90.5 | 96.9 |
| RSV A2 (138251)-wt | 1.0 | 23.1 | 4.3 |

In summary, the binding rates of the epitope (1 on the 42 mutants selected above (see Tables 8, 9, 10, and 11) to the corresponding antibodies were relatively high.

2.3 Results for Stability Screening of RSV F Antigen Mutants

The RSV F pre-fusion conformation is in a metastable state and can spontaneously rearrange to a highly stable post-fusion conformation. The trigger for the transition from the pre-fusion conformation to the post-fusion conformation during cellular entry is not clear. However, when the F protein is extracted from the membrane with surfactants such as Triton X-100, Triton X-114, NP-40, Brij-35, Brij-58, Tween 20, Tween 80, octylglucoside, octylthioglucoside, SDS, CHAPS, and CHAPSO, or expressed as an extracellular domain, the F glycoprotein is readily transferred to the post-fusion conformation after physical or chemical stress or storage (J. S. McLellan et al., 2013; J. O. Ngwuta et al., 2015). RSV F in the pre-fusion conformation helps the vaccine to induce or enhance neutralizing activity, and the physical stability directly affects the protein conformation. Therefore, antigens with superior stability were selected through different treatment conditions in this example.

In this example, stability screening of the mutants through different treatment conditions was defined as a stress test, including storage at 4° C. for one week; incubation at 50° C. for 60 min; treatment at room temperature under low osmotic pressure and high osmotic pressure conditions for 60 min; treatment at room temperature under acid and base conditions for 60 min. The binding of the mutants to the RSV pre-F antibody (3C12) recognizing the epitope Φ was detected by ELISA. The stress resistance parameter in this example was calculated as follows:

Stress resistance parameter=the binding amount of stressed sample to antibody+the binding amount of unstressed sample to antibody;

More stable mutants were expected to have relatively high stress resistance. The results for stability screening were as follows:

1) the Mutants all Retained the Binding Capacity to the Antibody Under Different Stress Tests From the results for the ELISA, it could be seen that the mutants still retained affinity for the RSV pre-F antibody (3C12) after different stress tests, as the RSV pre-F antibody (3C12) specifically bound to the epitope Φ of the pre-fusion conformation of the RSV F protein, indicating that the mutants could still be stabilized in the pre-fusion conformation after different stress tests.

2) Some Mutants were Still Very Stable after Stress Tests

Through an inter-group analysis of the stability results of all mutants, it was found that the mutants with a stress resistance parameter of less than 0.4 after storage for one week at 4° C., a stress resistance parameter of less than 0.5 after incubation at 50° C. for 60 min, a stress resistance parameter of less than 0.5 after high osmotic pressure treatment for 60 min, and a stress resistance parameter of less than 0.5 after low osmotic pressure treatment for 60 min showed relatively significant differences among groups, and thus are used as criteria for antigen screening.

TABLE 12

| Results for stability screening of RSV F mutants - general table | | | | | | |
|---|---|---|---|---|---|---|
| | Determination of physical stability, RSV pre-F antibody (3C12) | | | | | |
| | Temperature (° C.) | | Osmotic pressure (mM) | | pH | |
| No. | 4 | 50 | 3000 | 10 | 3.5 | 10 |
| YK-RSV-001 | 0.67 ± 0.10 | 0.70 ± 0.06 | 0.86 ± 0.22 | 0.97 ± 0.26 | 0.75 ± 0.03 | 1.00 ± 0.10 |
| YK-RSV-002 | 0.61 ± 0.11 | 0.46 ± 0.06 | 0.44 ± 0.13 | 0.84 ± 0.14 | 0.65 ± 0.08 | 0.97 ± 0.14 |
| YK-RSV-003 | 0.65 ± 0.01 | 0.81 ± 0.03 | 0.83 ± 0.06 | 0.89 ± 0.17 | 1.04 ± 0.32 | 1.02 ± 0.17 |
| YK-RSV-004 | 0.72 ± 0.06 | 0.48 ± 0.05 | 0.46 ± 0.13 | 0.91 ± 0.23 | 0.97 ± 0.21 | 1.00 ± 0.27 |
| YK-RSV-005 | 0.55 ± 0.09 | 0.44 ± 0.06 | 0.47 ± 0.08 | 0.57 ± 0.00 | 0.64 ± 0.20 | 0.88 ± 0.14 |
| YK-RSV-008 | 0.65 ± 0.06 | 0.45 ± 0.08 | 0.33 ± 0.02 | 0.81 ± 0.09 | 0.76 ± 0.21 | 0.99 ± 0.19 |
| YK-RSV-009 | 0.71 ± 0.11 | 0.84 ± 0.04 | 0.69 ± 0.15 | 0.78 ± 0.15 | 0.60 ± 0.14 | 0.91 ± 0.04 |
| YK-RSV-010 | 0.86 ± 0.08 | 1.04 ± 0.09 | 0.84 ± 0.11 | 0.97 ± 0.07 | 0.82 ± 0.05 | 0.93 ± 0.05 |
| YK-RSV-011 | 0.85 ± 0.08 | 0.76 ± 0.01 | 0.80 ± 0.11 | 0.97 ± 0.23 | 0.63 ± 0.18 | 0.86 ± 0.01 |
| YK-RSV-012 | 0.69 ± 0.11 | 1.22 ± 0.24 | 0.73 ± 0.08 | 0.76 ± 0.17 | 0.67 ± 0.07 | 1.22 ± 0.00 |
| YK-RSV-013 | 0.69 ± 0.11 | 0.91 ± 0.23 | 0.43 ± 0.04 | 0.59 ± 0.08 | 0.84 ± 0.19 | 0.92 ± 0.04 |
| YK-RSV-015 | 0.57 ± 0.08 | 0.70 ± 0.06 | 0.72 ± 0.03 | 0.73 ± 0.18 | 0.80 ± 0.12 | 0.87 ± 0.12 |
| YK-RSV-016 | 0.28 ± 0.05 | 0.80 ± 0.01 | 0.53 ± 0.07 | 0.77 ± 0.08 | 0.91 ± 0.06 | 0.98 ± 0.14 |
| YK-RSV-017 | 0.35 ± 0.07 | 0.60 ± 0.04 | 0.46 ± 0.06 | 0.59 ± 0.03 | 0.76 ± 0.11 | 0.93 ± 0.06 |
| YK-RSV-019 | 0.37 ± 0.08 | 0.58 ± 0.05 | 0.63 ± 0.04 | 0.81 ± 0.04 | 0.77 ± 0.05 | 0.88 ± 0.09 |
| YK-RSV-029 | 0.32 ± 0.06 | 0.57 ± 0.08 | 0.40 ± 0.01 | 0.61 ± 0.05 | 0.63 ± 0.03 | 0.82 ± 0.01 |
| YK-RSV-030 | 0.44 ± 0.08 | 1.05 ± 0.00 | 0.83 ± 0.06 | 0.89 ± 0.15 | 0.89 ± 0.06 | 1.00 ± 0.11 |
| YK-RSV-032 | 0.34 ± 0.08 | 0.78 ± 0.02 | 0.37 ± 0.02 | 0.66 ± 0.14 | 1.01 ± 0.35 | 0.98 ± 0.06 |
| YK-RSV-034 | 0.37 ± 0.07 | 0.68 ± 0.07 | 0.34 ± 0.15 | 0.84 ± 0.14 | 0.81 ± 0.09 | 0.91 ± 0.04 |
| YK-RSV-035 | 0.31 ± 0.07 | 0.39 ± 0.02 | 0.21 ± 0.06 | 0.39 ± 0.05 | 0.57 ± 0.03 | 0.82 ± 0.01 |
| YK-RSV-036 | 0.69 ± 0.08 | 0.75 ± 0.08 | 0.72 ± 0.02 | 0.80 ± 0.06 | 0.98 ± 0.03 | 1.16 ± 0.23 |
| YK-RSV-037 | 0.27 ± 0.07 | 0.50 ± 0.06 | 0.21 ± 0.03 | 0.54 ± 0.11 | 0.68 ± 0.10 | 1.24 ± 0.11 |
| YK-RSV-038 | 0.32 ± 0.08 | 0.70 ± 0.10 | 0.55 ± 0.13 | 0.74 ± 0.08 | 0.88 ± 0.17 | 0.82 ± 0.26 |
| YK-RSV-039 | 0.62 ± 0.08 | 0.82 ± 0.21 | 0.80 ± 0.05 | 0.92 ± 0.06 | 0.74 ± 0.04 | 0.73 ± 0.07 |
| YK-RSV-040 | 0.38 ± 0.08 | 0.91 ± 0.14 | 0.61 ± 0.09 | 0.75 ± 0.13 | 0.93 ± 0.09 | 1.00 ± 0.23 |
| YK-RSV-043 | 0.70 ± 0.13 | 0.66 ± 0.06 | 0.72 ± 0.09 | 0.84 ± 0.18 | 0.90 ± 0.13 | 0.75 ± 0.28 |
| YK-RSV-044 | 0.56 ± 0.08 | 0.75 ± 0.13 | 0.73 ± 0.00 | 0.86 ± 0.20 | 0.87 ± 0.00 | 0.97 ± 0.04 |
| YK-RSV-045 | 0.29 ± 0.02 | 0.41 ± 0.03 | 0.46 ± 0.05 | 0.57 ± 0.09 | 0.47 ± 0.09 | 0.97 ± 0.07 |
| YK-RSV-046 | 0.24 ± 0.07 | 0.63 ± 0.03 | 0.41 ± 0.02 | 0.46 ± 0.14 | 0.83 ± 0.04 | 1.03 ± 0.03 |
| YK-RSV-048 | 0.46 ± 0.08 | 0.70 ± 0.07 | 0.61 ± 0.17 | 0.75 ± 0.00 | 0.61 ± 0.07 | 1.13 ± 0.19 |
| YK-RSV-050 | 0.46 ± 0.07 | 0.69 ± 0.15 | 0.66 ± 0.15 | 0.87 ± 0.19 | 1.23 ± 0.27 | 1.16 ± 0.37 |
| YK-RSV-051 | 0.33 ± 0.05 | 0.60 ± 0.08 | 0.44 ± 0.00 | 0.51 ± 0.13 | 0.69 ± 0.14 | 1.00 ± 0.17 |
| YK-RSV-052 | 0.42 ± 0.10 | 0.69 ± 0.09 | 0.30 ± 0.06 | 0.88 ± 0.21 | 0.80 ± 0.04 | 1.22 ± 0.14 |
| YK-RSV-054 | 0.71 ± 0.08 | 0.75 ± 0.18 | 0.83 ± 0.20 | 0.96 ± 0.23 | 0.91 ± 0.13 | 0.97 ± 0.04 |
| YK-RSV-055 | 0.48 ± 0.11 | 0.78 ± 0.19 | 0.71 ± 0.23 | 0.72 ± 0.20 | 0.69 ± 0.08 | 0.79 ± 0.26 |
| YK-RSV-056 | 0.69 ± 0.10 | 0.91 ± 0.09 | 0.44 ± 0.08 | 0.82 ± 0.07 | 0.64 ± 0.12 | 0.72 ± 0.14 |
| YK-RSV-057 | 0.61 ± 0.10 | 0.64 ± 0.17 | 0.64 ± 0.15 | 0.70 ± 0.07 | 0.56 ± 0.08 | 0.56 ± 0.09 |
| YK-RSV-058 | 0.36 ± 0.07 | 0.73 ± 0.09 | 0.50 ± 0.05 | 0.60 ± 0.04 | 0.72 ± 0.03 | 0.81 ± 0.05 |
| YK-RSV-059 | 0.52 ± 0.10 | 0.74 ± 0.07 | 0.44 ± 0.03 | 0.49 ± 0.02 | 0.73 ± 0.03 | 0.82 ± 0.09 |
| YK-RSV-060 | 0.56 ± 0.08 | 0.82 ± 0.13 | 0.61 ± 0.07 | 0.80 ± 0.13 | 0.73 ± 0.11 | 0.76 ± 0.24 |
| YK-RSV-061 | 0.68 ± 0.08 | 0.87 ± 0.05 | 0.85 ± 0.24 | 0.88 ± 0.17 | 1.02 ± 0.24 | 0.98 ± 0.28 |
| YK-RSV-062 | 0.65 ± 0.04 | 0.84 ± 0.04 | 0.87 ± 0.16 | 0.89 ± 0.05 | 0.97 ± 0.04 | 0.95 ± 0.09 |
| PC-RSV-063 | 0.45 ± 0.08 | 0.66 ± 0.11 | 0.52 ± 0.04 | 0.71 ± 0.05 | 0.73 ± 0.02 | 0.91 ± 0.02 |
| PC-RSV-064 | 0.34 ± 0.04 | 0.62 ± 0.05 | 0.57 ± 0.05 | 0.74 ± 0.05 | 0.65 ± 0.06 | 0.80 ± 0.08 |
| PC-RSV-065 | 0.45 ± 0.07 | 0.71 ± 0.10 | 0.62 ± 0.06 | 0.76 ± 0.12 | 0.72 ± 0.05 | 0.81 ± 0.11 |
| PC-RSV-066 | 0.49 ± 0.09 | 0.46 ± 0.07 | 0.67 ± 0.11 | 0.70 ± 0.03 | 0.68 ± 0.10 | 0.77 ± 0.11 |
| PC-RSV-067 | 0.58 ± 0.08 | 0.68 ± 0.08 | 0.42 ± 0.07 | 0.68 ± 0.12 | 0.70 ± 0.07 | 0.83 ± 0.08 |
| PC-RSV-068 | 0.55 ± 0.06 | 0.73 ± 0.12 | 0.47 ± 0.09 | 0.69 ± 0.19 | 0.63 ± 0.09 | 0.86 ± 0.10 |

The following mutants had a stress resistance parameter of above 0.44, up to 0.86, after storage at 4° C. for one week; a stress resistance parameter of above 0.64 after incubation at 50° C. for 60 min; a stress resistance parameter of above 0.61 after treatment under a high osmotic pressure condition for 60 m; a stress resistance parameter of above 0.70 after treatment under a low osmotic pressure condition for 60 min; stress resistance parameters both above 0.56 after treatment under conditions of pH=3.5 and pH=10 for 60 m. The stress resistance parameters after treatment under different conditions were all superior to or comparable to those of the controls.

TABLE 13

| Results for stability screening of RSV F mutants - 1 | | | | | | |
|---|---|---|---|---|---|---|
| | Determination of physical stability, RSV pre-F antibody (3C12) | | | | | |
| | Temperature (° C.) | | Osmotic pressure (mM) | | pH | |
| No. | 4 | 50 | 3000 | 10 | 3.5 | 10 |
| YK-RSV-061 | 0.68 ± 0.08 | 0.87 ± 0.05 | 0.85 ± 0.24 | 0.88 ± 0.17 | 1.02 ± 0.24 | 0.98 ± 0.28 |
| YK-RSV-003 | 0.65 ± 0.01 | 0.81 ± 0.03 | 0.83 ± 0.06 | 0.89 ± 0.17 | 1.04 ± 0.32 | 1.02 ± 0.17 |
| YK-RSV-062 | 0.65 ± 0.04 | 0.84 ± 0.04 | 0.87 ± 0.16 | 0.89 ± 0.05 | 0.97 ± 0.04 | 0.95 ± 0.09 |
| YK-RSV-054 | 0.71 ± 0.08 | 0.75 ± 0.18 | 0.83 ± 0.20 | 0.96 ± 0.23 | 0.91 ± 0.13 | 0.97 ± 0.04 |
| YK-RSV-039 | 0.62 ± 0.08 | 0.82 ± 0.21 | 0.80 ± 0.05 | 0.92 ± 0.06 | 0.74 ± 0.04 | 0.73 ± 0.07 |
| YK-RSV-044 | 0.56 ± 0.08 | 0.75 ± 0.13 | 0.73 ± 0.00 | 0.86 ± 0.20 | 0.87 ± 0.00 | 0.97 ± 0.04 |
| YK-RSV-012 | 0.69 ± 0.11 | 1.22 ± 0.24 | 0.73 ± 0.08 | 0.76 ± 0.17 | 0.67 ± 0.07 | 1.22 ± 0.00 |
| YK-RSV-015 | 0.57 ± 0.08 | 0.70 ± 0.06 | 0.72 ± 0.03 | 0.73 ± 0.18 | 0.80 ± 0.12 | 0.87 ± 0.12 |
| YK-RSV-001 | 0.67 ± 0.10 | 0.70 ± 0.06 | 0.86 ± 0.22 | 0.97 ± 0.26 | 0.75 ± 0.03 | 1.00 ± 0.10 |
| YK-RSV-036 | 0.69 ± 0.08 | 0.75 ± 0.08 | 0.72 ± 0.02 | 0.80 ± 0.06 | 0.98 ± 0.03 | 1.16 ± 0.23 |
| YK-RSV-060 | 0.56 ± 0.08 | 0.82 ± 0.13 | 0.61 ± 0.07 | 0.80 ± 0.13 | 0.73 ± 0.11 | 0.76 ± 0.24 |
| PC-RSV-063 | 0.45 ± 0.08 | 0.66 ± 0.11 | 0.52 ± 0.04 | 0.71 ± 0.05 | 0.73 ± 0.02 | 0.91 ± 0.02 |
| PC-RSV-064 | 0.34 ± 0.04 | 0.62 ± 0.05 | 0.57 ± 0.05 | 0.74 ± 0.05 | 0.65 ± 0.06 | 0.80 ± 0.08 |
| PC-RSV-065 | 0.45 ± 0.07 | 0.71 ± 0.10 | 0.62 ± 0.06 | 0.76 ± 0.12 | 0.72 ± 0.05 | 0.81 ± 0.11 |
| PC-RSV-066 | 0.49 ± 0.09 | 0.46 ± 0.07 | 0.67 ± 0.11 | 0.70 ± 0.03 | 0.68 ± 0.10 | 0.77 ± 0.11 |
| PC-RSV-067 | 0.58 ± 0.08 | 0.68 ± 0.08 | 0.42 ± 0.07 | 0.68 ± 0.12 | 0.70 ± 0.07 | 0.83 ± 0.08 |
| PC-RSV-068 | 0.55 ± 0.06 | 0.73 ± 0.12 | 0.47 ± 0.09 | 0.69 ± 0.19 | 0.63 ± 0.09 | 0.86 ± 0.10 |

TABLE 14

| Results for stability screening of RSV F mutants - 2 | | | | | | |
|---|---|---|---|---|---|---|
| | Determination of physical stability, RSV pre-F antibody (3C12) | | | | | |
| | Temperature (° C.) | | Osmotic pressure (mM) | | pH | |
| No. | 4 | 50 | 3000 | 10 | 3.5 | 10 |
| YK-RSV-009 | 0.71 ± 0.11 | 0.84 ± 0.04 | 0.69 ± 0.15 | 0.78 ± 0.15 | 0.60 ± 0.14 | 0.91 ± 0.04 |
| YK-RSV-010 | 0.86 ± 0.08 | 1.04 ± 0.09 | 0.84 ± 0.11 | 0.97 ± 0.07 | 0.82 ± 0.05 | 0.93 ± 0.05 |
| YK-RSV-011 | 0.85 ± 0.08 | 0.76 ± 0.01 | 0.80 ± 0.11 | 0.97 ± 0.23 | 0.63 ± 0.18 | 0.86 ± 0.01 |
| YK-RSV-030 | 0.44 ± 0.08 | 1.05 ± 0.00 | 0.83 ± 0.06 | 0.89 ± 0.15 | 0.89 ± 0.06 | 1.00 ± 0.11 |
| YK-RSV-043 | 0.70 ± 0.13 | 0.66 ± 0.06 | 0.72 ± 0.09 | 0.84 ± 0.18 | 0.90 ± 0.13 | 0.75 ± 0.28 |
| YK-RSV-048 | 0.46 ± 0.08 | 0.70 ± 0.07 | 0.61 ± 0.17 | 0.75 ± 0.00 | 0.61 ± 0.07 | 1.13 ± 0.19 |
| YK-RSV-050 | 0.46 ± 0.07 | 0.69 ± 0.15 | 0.66 ± 0.15 | 0.87 ± 0.19 | 1.23 ± 0.27 | 1.16 ± 0.37 |
| YK-RSV-055 | 0.48 ± 0.11 | 0.78 ± 0.19 | 0.71 ± 0.23 | 0.72 ± 0.20 | 0.69 ± 0.08 | 0.79 ± 0.26 |
| YK-RSV-057 | 0.61 ± 0.10 | 0.64 ± 0.17 | 0.64 ± 0.15 | 0.70 ± 0.07 | 0.56 ± 0.08 | 0.56 ± 0.09 |
| PC-RSV-063 | 0.45 ± 0.08 | 0.66 ± 0.11 | 0.52 ± 0.04 | 0.71 ± 0.05 | 0.73 ± 0.02 | 0.91 ± 0.02 |
| PC-RSV-064 | 0.34 ± 0.04 | 0.62 ± 0.05 | 0.57 ± 0.05 | 0.74 ± 0.05 | 0.65 ± 0.06 | 0.80 ± 0.08 |
| PC-RSV-065 | 0.45 ± 0.07 | 0.71 ± 0.10 | 0.62 ± 0.06 | 0.76 ± 0.12 | 0.72 ± 0.05 | 0.81 ± 0.11 |
| PC-RSV-066 | 0.49 ± 0.09 | 0.46 ± 0.07 | 0.67 ± 0.11 | 0.70 ± 0.03 | 0.68 ± 0.10 | 0.77 ± 0.11 |
| PC-RSV-067 | 0.58 ± 0.08 | 0.68 ± 0.08 | 0.42 ± 0.07 | 0.68 ± 0.12 | 0.70 ± 0.07 | 0.83 ± 0.08 |
| PC-RSV-068 | 0.55 ± 0.06 | 0.73 ± 0.12 | 0.47 ± 0.09 | 0.69 ± 0.19 | 0.63 ± 0.09 | 0.86 ± 0.10 |

3) Summary (1) From the results for physical stability screening, it could be seen that the stability was significantly improved under certain stress tests as compared to that of the controls, and 20 mutants (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, YK-RSV-060, YK-RSV-009, YK-RSV-010, YK-RSV-011, YK-RSV-030, YK-RSV-043, YK-RSV-048, YK-RSV-050, YK-RSV-055, and YK-RSV-057) had superior stability under each stress test as compared with the other mutant groups, showing stronger overall stability. The binding capacity of the mutants to different epitope antibodies was further detected by ELISA as follows.

2.4 ELISA Results of the Binding of RSV F Antigen Mutants to Antibodies Recognizing Different Epitopes Among the epitopes Φ, Quaternary, V, II, and III to which the present application relates, antibodies recognizing the epitopes Φ, Quaternary, and V specifically bound only to the pre-fusion conformation compared with the epitopes II and III that are present in both the pre-fusion and post-fusion conformations. Studies have demonstrated that specific epitopes present only in the pre-fusion conformation are sites to which neutralizing antibodies are sensitive and can induce a higher neutralizing antibody response.

In the present application, the binding of different mutant antigens to antibodies recognizing different epitopes was detected by ELISA, and the strength of the binding of the antigens to the antibodies was measured by the binding amount. (1) The RSV pre-F antibody (3C12) recognizing the epitope Φ binds only to the F protein in the pre-fusion conformation; (2) the RSV pre-F antibody (7H11) recognizes the epitope Quaternary (spanning both epitopes IV and V) and specifically binds to the F protein in the pre-fusion conformation; (3) the RSV F antibody (11A9) recognizing the epitope II can recognize both the pre-fusion and post-fusion conformations of the F protein; (4) the RSV F antibody (4B39) recognizing the epitope III preferentially recognizes the pre-fusion conformation and has relatively weak binding activity for the post-fusion conformation; (5) the RSV pre-F antibody (7E11) recognizing the epitope V binds only to the F protein in the pre-fusion conformation. The results for the ELISA were as follows.

TABLE 15

ELISA results of RSV F mutants-general table

| | ELISA results (ng/ml) | | | | | | | | | |
|---|---|---|---|---|---|---|---|---|---|---|
| | Epitope Φ | | Epitope Quaternary | | Epitope V | | Epitope II | | Epitope III | |
| No. | RSV pre-F antibody (3C12) | Binding amount to antibody/binding amount of PC-RSV-064 to antibody | RSV pre-F antibody (7H11) | Binding amount to antibody/binding amount of PC-RSV-064 to antibody | RSV F antibody (7E11) | Binding amount to antibody/binding amount of PC-RSV-064 to antibody | RSV F antibody (11A9) | Binding amount to antibody/binding amount of PC-RSV-064 to antibody | RSV F antibody (4B9) | Binding amount to antibody/binding amount of PC-RSV-064 to antibody |
| YK-RSV-001 | 5136 | 1.86 | 7401 | 2.05 | 431 | 1.34 | 1593 | 0.76 | 2133 | 0.74 |
| YK-RSV-003 | 5541 | 2.00 | 7249 | 2.01 | 452 | 1.41 | 1994 | 0.95 | 3171 | 1.11 |
| YK-RSV-009 | 521 | 0.19 | 29 | 0.01 | 43 | 0.13 | 203 | 0.10 | 358 | 0.12 |
| YK-RSV-010 | 838 | 0.30 | 39 | 0.01 | 139 | 0.43 | 336 | 0.16 | 534 | 0.19 |
| YK-RSV-011 | 8036 | 2.90 | 6549 | 1.81 | 866 | 2.70 | 4388 | 2.09 | 7072 | 2.47 |
| YK-RSV-012 | 6709 | 2.42 | 4919 | 1.36 | 459 | 1.43 | 3219 | 1.53 | 4689 | 1.63 |
| YK-RSV-015 | 5932 | 2.14 | 8943 | 2.48 | 420 | 1.31 | 1886 | 0.90 | 2933 | 1.02 |
| YK-RSV-030 | 5376 | 1.94 | 2485 | 0.69 | 441 | 1.37 | 1822 | 0.87 | 3688 | 1.29 |
| YK-RSV-036 | 7027 | 2.54 | 7769 | 2.15 | 1069 | 3.33 | 3384 | 1.61 | 7424 | 2.59 |
| YK-RSV-039 | 9467 | 3.42 | 5583 | 1.55 | 584 | 1.82 | 4097 | 1.95 | 7659 | 2.67 |
| YK-RSV-043 | 9445 | 3.41 | 922 | 0.26 | 223 | 0.69 | 4610 | 2.20 | 6529 | 2.28 |
| YK-RSV-044 | 6909 | 2.50 | 2031 | 0.56 | 442 | 1.38 | 4039 | 1.92 | 7078 | 2.47 |
| YK-RSV-048 | 3306 | 1.19 | 2873 | 0.80 | 217 | 0.68 | 2255 | 1.07 | 4655 | 1.62 |
| YK-RSV-050 | 3068 | 1.11 | 3722 | 1.03 | 923 | 2.88 | 2474 | 1.18 | 3494 | 1.22 |
| YK-RSV-054 | 6979 | 2.52 | 6589 | 1.82 | 1060 | 3.30 | 3754 | 1.79 | 6502 | 2.27 |
| YK-RSV-055 | 8589 | 3.10 | 4317 | 1.20 | 91 | 0.28 | 3856 | 1.84 | 7298 | 2.54 |
| YK-RSV-057 | 5210 | 1.88 | 6346 | 1.76 | 129 | 0.40 | 2823 | 1.34 | 4779 | 1.67 |
| YK-RSV-060 | 5993 | 2.17 | 2203 | 0.61 | 409 | 1.27 | 2657 | 1.27 | 5613 | 1.96 |
| YK-RSV-061 | 5261 | 1.90 | 7661 | 2.12 | 595 | 1.85 | 2505 | 1.19 | 3683 | 1.28 |
| YK-RSV-062 | 5059 | 1.83 | 7350 | 2.03 | 487 | 1.52 | 2063 | 0.98 | 3260 | 1.14 |
| PC-RSV-063 | 2727 | 0.99 | 3557 | 0.98 | 461 | 1.44 | 2053 | 0.98 | 2993 | 1.04 |
| PC-RSV-064 | 2768 | 1.00 | 3612 | 1.00 | 321 | 1.00 | 2100 | 1.00 | 2868 | 1.00 |
| PC-RSV-065 | 3378 | 1.22 | 3705 | 1.03 | 436 | 1.36 | 1864 | 0.89 | 3102 | 1.08 |
| PC-RSV-066 | 2169 | 0.78 | 3213 | 0.89 | 374 | 1.17 | 1682 | 0.80 | 2058 | 0.72 |
| PC-RSV-067 | 2828 | 1.02 | 2869 | 0.79 | 298 | 0.93 | 2509 | 1.19 | 3608 | 1.26 |
| PC-RSV-068 | 3168 | 1.14 | 3667 | 1.02 | 312 | 0.97 | 3191 | 1.52 | 4321 | 1.51 |

1) The epitopes Φ, Quaternary, and V on the following 11 mutants were all able to well bind to corresponding antibodies with relatively strong binding capacity, and the binding capacity of the epitopes II and/or III to the corresponding antibodies was superior to or comparable to that on the controls.

For example, the binding levels of the epitope Φ on YK-RSV-061, YK-RSV-003, and YK-RSV-062 to the RSV pre-F antibody (3C12) were 1.83 to 2.00 times that on the control PC—RSV-064; the binding levels of the epitope Quaternary to the RSV pre-F antibody (71111) were 2.01 to 2.12 times that on the control PC—RSV-064.

The binding level of the epitope Φ on YK-RSV-054 to the RSV pre-F antibody (312) was 2.52 times that on the control PC—RSV-064; the binding level of the epitope Quaternary to the RSV pre-F antibody (711) was 1.82 times that on the control PC—RSV-064; the binding level of the epitope V to the RSV F antibody (7E11) was 3.30 times that on the control PC—RSV-064; the binding level of the epitope II to the RSV F antibody (11A9) was 1.79 times that on the control PC—RSV-064; the binding level of the epitope III to the RSV F antibody (4B9) was 2.27 times that on the control PC—RSV-064.

TABLE 16

ELISA results of RSV F mutants - 1

| No. | ELISA results (ng/ml) | | | | | | | | | |
|---|---|---|---|---|---|---|---|---|---|---|
| | Epitope Φ | | Epitope Quaternary | | Epitope V | | Epitope II | | Epitope III | |
| | RSV pre-F antibody (3C12) | Binding amount to antibody/ binding amount of PC-RSV-064 to antibody | RSV pre-F antibody (7H11) | Binding amount to antibody/ binding amount of PC-RSV-064 to antibody | RSV F antibody (7E11) | Binding amount to antibody/ binding amount of PC-RSV-064 to antibody | RSV F antibody (11A9) | Binding amount to antibody/ binding amount of PC-RSV-064 to antibody | RSV F antibody (4B9) | Binding amount to antibody/ binding amount of PC-RSV-064 to antibody |
| YK-RSV-061 | 5261 | 1.90 | 7661 | 2.12 | 595 | 1.85 | 2505 | 1.19 | 3683 | 1.28 |
| YK-RSV-003 | 5541 | 2.00 | 7249 | 2.01 | 452 | 1.41 | 1994 | 0.95 | 3171 | 1.11 |
| YK-RSV-062 | 5059 | 1.83 | 7350 | 2.03 | 487 | 1.52 | 2063 | 0.98 | 3260 | 1.14 |
| YK-RSV-054 | 6979 | 2.52 | 6589 | 1.82 | 1060 | 3.30 | 3754 | 1.79 | 6502 | 2.27 |
| YK-RSV-039 | 9467 | 3.42 | 5583 | 1.55 | 584 | 1.82 | 4097 | 1.95 | 7659 | 2.67 |
| YK-RSV-044 | 6909 | 2.50 | 2031 | 0.56 | 442 | 1.38 | 4039 | 1.92 | 7078 | 2.47 |
| YK-RSV-012 | 6709 | 2.42 | 4919 | 1.36 | 459 | 1.43 | 3219 | 1.53 | 4689 | 1.63 |
| YK-RSV-015 | 5932 | 2.14 | 8943 | 2.48 | 420 | 1.31 | 1886 | 0.90 | 2933 | 1.02 |
| YK-RSV-001 | 5136 | 1.86 | 7401 | 2.05 | 431 | 1.34 | 1593 | 0.76 | 2133 | 0.74 |
| YK-RSV-036 | 7027 | 2.54 | 7769 | 2.15 | 1069 | 3.33 | 3384 | 1.61 | 7424 | 2.59 |
| YK-RSV-060 | 5993 | 2.17 | 2203 | 0.61 | 409 | 1.27 | 2657 | 1.27 | 5613 | 1.96 |
| PC-RSV-063 | 2727 | 0.99 | 3557 | 0.98 | 461 | 1.44 | 2053 | 0.98 | 2993 | 1.04 |
| PC-RSV-064 | 2768 | 1.00 | 3612 | 1.00 | 321 | 1.00 | 2100 | 1.00 | 2868 | 1.00 |
| PC-RSV-065 | 3378 | 1.22 | 3705 | 1.03 | 436 | 1.36 | 1864 | 0.89 | 3102 | 1.08 |
| PC-RSV-066 | 2169 | 0.78 | 3213 | 0.89 | 374 | 1.17 | 1682 | 0.80 | 2058 | 0.72 |
| PC-RSV-067 | 2828 | 1.02 | 2869 | 0.79 | 298 | 0.93 | 2509 | 1.19 | 3608 | 1.26 |
| PC-RSV-068 | 3168 | 1.14 | 3667 | 1.02 | 312 | 0.97 | 3191 | 1.52 | 4321 | 1.51 |

2) The epitopes Φ, Quaternary, and V on the following 4 mutants were also able to well bind to corresponding antibodies with relatively strong binding capacity.

For example, the binding level of the epitope Φ on YK-RSV-011 to the RSV pre-F antibody (3C12) was 2.90 times that on the control PC—RSV-064; the binding level of the epitope Quaternary to the RSV pre-F antibody (7H11) was 1.81 times that on the control PC—RSV-064; the binding level of the epitope V to the RSV F antibody (7E11) was 2.70 times that on the control PC—RSV-064; the binding level of the epitope II to the RSV F antibody (11A9) was 2.09 times that on the control PC—RSV-064; the binding level of the epitope III to the RSV F antibody (4B9) was 2.47 times that on the control PC—RSV-064.

In summary, the above contents showed the detection of the binding levels of 5 different epitopes on the mutants, and the mutants with better binding level (see Tables 16 and 17) were further screened for candidate antigens.

2.5 Results for Detection of Affinity of the RSV F Antigen Mutants for Antibodies Recognizing Different Epitopes Bio-Layer interferometry (referred to as BLI) is a label-free real-time monitoring optical detection technique,

TABLE 17

Results for ELISA results of RSV F mutants - 2

| No. | ELISA results (ng/ml) | | | | | | | | | |
|---|---|---|---|---|---|---|---|---|---|---|
| | Epitope Φ | | Epitope Quaternary | | Epitope V | | Epitope II | | Epitope III | |
| | RSV pre-F antibody (3C12) | Binding amount to antibody/ binding amount of PC-RSV-064 to antibody | RSV pre-F antibody (7H11) | Binding amount to antibody/ binding amount of PC-RSV-064 to antibody | RSV F antibody (7E11) | Binding amount to antibody/ binding amount of PC-RSV-064 to antibody | RSV F antibody (11A9) | Binding amount to antibody/ binding amount of PC-RSV-064 to antibody | RSV F antibody (4B9) | Binding amount to antibody/ binding amount of PC-RSV-064 to antibody |
| YK-RSV-011 | 8036 | 2.90 | 6549 | 1.81 | 866 | 2.70 | 4388 | 2.09 | 7072 | 2.47 |
| YK-RSV-030 | 5376 | 1.94 | 2485 | 0.69 | 441 | 1.37 | 1822 | 0.87 | 3688 | 1.29 |
| YK-RSV-048 | 3306 | 1.19 | 2873 | 0.80 | 217 | 0.68 | 2255 | 1.07 | 4655 | 1.62 |
| YK-RSV-050 | 3068 | 1.11 | 3722 | 1.03 | 923 | 2.88 | 2474 | 1.18 | 3494 | 1.22 |
| PC-RSV-063 | 2727 | 0.99 | 3557 | 0.98 | 461 | 1.44 | 2053 | 0.98 | 2993 | 1.04 |
| PC-RSV-064 | 2768 | 1.00 | 3612 | 1.00 | 321 | 1.00 | 2100 | 1.00 | 2868 | 1.00 |
| PC-RSV-065 | 3378 | 1.22 | 3705 | 1.03 | 436 | 1.36 | 1864 | 0.89 | 3102 | 1.08 |
| PC-RSV-066 | 2169 | 0.78 | 3213 | 0.89 | 374 | 1.17 | 1682 | 0.80 | 2058 | 0.72 |
| PC-RSV-067 | 2828 | 1.02 | 2869 | 0.79 | 298 | 0.93 | 2509 | 1.19 | 3608 | 1.26 |
| PC-RSV-068 | 3168 | 1.14 | 3667 | 1.02 | 312 | 0.97 | 3191 | 1.52 | 4321 | 1.51 |

mainly used for comprehensive quantitative analysis of the interaction between biomolecules and protein concentration determination. The BLI can monitor the binding process between molecules in real time and calculate important data such as affinity constant ($K_D$), association rate constant ($K_{on}$ or $k_a$), dissociation rate constant ($K_{off}$, $K_{dis}$, or $k_d$), etc., between molecules.

$K_D=K_{off}+K_{on}$;

$K_D$: the affinity constant, representing the strength of the binding of two molecules, wherein the greater the $K_D$, the weaker the binding, and otherwise, the stronger the binding;

$K_{on}$: the association rate constant;

$K_{dis}$ ($k_{off}$): the dissociation rate constant;

$K_{on}$ and $K_{off}$ mainly represent the mode of molecular interaction, whether it is fast binding and fast dissociation, slow binding and slow dissociation, or the like.

In the present application, the affinity of target proteins for 2 antibodies was analyzed by a BLI method, wherein the RSV pre-F antibody (3C12) recognizes the epitope D, and the RSV pre-F antibody (7H11) recognizes the epitope Quaternary. The detection results were as follows:

TABLE 18

Results for affinity of different epitopes on RSV F mutants for corresponding antibodies-general table

| No. | $K_D$ value (M)<br>RSV pre-F antibody (3C12) Epitope Φ | RSV pre-F antibody (7H11) Epitope Quaternary |
|---|---|---|
| YK-RSV-039 | 3.26E−12 | 2.83E−11 |
| YK-RSV-036 | 2.10E−11 | 8.09E−12 |
| YK-RSV-044 | 4.66E−11 | 4.05E−10 |
| YK-RSV-001 | 4.73E−11 | 9.38E−12 |
| YK-RSV-054 | 5.16E−11 | 1.25E−11 |
| YK-RSV-060 | 5.18E−11 | 6.13E−10 |
| YK-RSV-061 | 6.21E−11 | 3.05E−12 |
| YK-RSV-062 | 6.26E−11 | 3.62E−12 |
| YK-RSV-003 | 6.35E−11 | 3.47E−12 |
| YK-RSV-012 | 6.87E−11 | 3.82E−11 |
| YK-RSV-011 | 6.93E−11 | 3.27E−11 |
| YK-RSV-015 | 7.41E−11 | 5.09E−12 |
| YK-RSV-030 | 7.79E−11 | 2.88E−10 |
| YK-RSV-048 | 1.83E−10 | 2.27E−10 |
| YK-RSV-050 | 5.52E−10 | 1.15E−10 |
| PC-RSV-063 | 1.36E−10 | 1.07E−10 |
| PC-RSV-064 | 1.24E−10 | 1.56E−10 |
| PC-RSV-065 | 1.62E−10 | 1.22E−10 |
| PC-RSV-066 | 2.63E−10 | 1.33E−10 |
| PC-RSV-067 | 5.29E−10 | 3.06E−10 |
| PC-RSV-068 | 6.61E−10 | 2.25E−10 |

The affinity constant $K_D$ values for the binding of the epitope Φ on the following mutants to the RSV pre-F antibody (3C12) were 3.26E-12 M to 7.79E-11 M, which were significantly lower than the $K_D$ values ($K_D$ of E-1K M, with a difference of 1 to 2 orders of magnitude) of the controls, indicating that the affinity of the antigens for the antibody was stronger.

The affinity constant $K_D$ values for the binding of the epitope Quaternary on the mutants to the RSV pre-F antibody (711) were 3.05E-12 M to 6.13E-12 M, and except that the $K_D$ values for YK-RSV-044, YK-RSV-060, and YK-RSV-030 were comparable to those of the controls, the $K_D$ values for the other mutants were significantly lower than those of the controls (with a difference of 1 to 2 orders of magnitude), indicating that the affinity of the antigens for the antibody was stronger.

The following mutants will be subjected to animal experiments for further screening.

TABLE 19

Results for affinity of different epitopes on RSV F mutants for corresponding antibodies

| No. | $K_D$ value (M)<br>RSV pre-F antibody (3C12) Epitope Φ | RSV pre-F antibody (7H11) Epitope Quaternary |
|---|---|---|
| YK-RSV-039 | 3.26E−12 | 2.83E−11 |
| YK-RSV-036 | 2.10E−11 | 8.09E−12 |
| YK-RSV-044 | 4.66E−11 | 4.05E−10 |
| YK-RSV-001 | 4.73E−11 | 9.38E−12 |
| YK-RSV-054 | 5.16E−11 | 1.25E−11 |
| YK-RSV-060 | 5.18E−11 | 6.13E−10 |
| YK-RSV-061 | 6.21E−11 | 3.05E−12 |
| YK-RSV-062 | 6.26E−11 | 3.62E−12 |
| YK-RSV-003 | 6.35E−11 | 3.47E−12 |
| YK-RSV-012 | 6.87E−11 | 3.82E−11 |
| YK-RSV-011 | 6.93E−11 | 3.27E−11 |
| YK-RSV-015 | 7.41E−11 | 5.09E−12 |
| YK-RSV-030 | 7.79E−11 | 2.88E−10 |
| PC-RSV-063 | 1.36E−10 | 1.07E−10 |
| PC-RSV-064 | 1.24E−10 | 1.56E−10 |
| PC-RSV-065 | 1.62E−10 | 1.22E−10 |
| PC-RSV-066 | 2.63E−10 | 1.33E−10 |
| PC-RSV-067 | 5.29E−10 | 3.06E−10 |
| PC-RSV-068 | 6.61E−10 | 2.25E−10 |

2.6 Results for Immunogenicity of RSV F Antigen Mutants in Balb/c Mice

Mice are small in size, fast in growth, low in feeding cost, and applicable to many commercially available detection reagents. For the above reasons, mice are currently the most widely used in animal models of RSV infection. Prince reported mice as animal models of hRSV infection for the first time in 1979. Balb/c mice are used more frequently, and after infection by transluminal drip, the RSV titer is 105 to 107 PFU, and significant inflammatory changes in the lower respiratory tract and a significant increase in part of cytokines and CC/CXC chemokines such as TNF-α, IL-6, and IFN-γ in tracheal perfusate can be observed in animals, and the infiltration of peribronchiolar and perivascular mononuclear cells (lymphocytes and macrophages) or interstitial pneumonia can be observed by histopathology. Mice infected with different RSV subtypes (such as Along, A2, and clinical isolates) have different symptoms. Mice infected with RSV show an increased respiratory rate with airway obstruction and airway hyperresponsiveness, and the airway hyperreactivity lasts for a long time, which is very similar to the RSV infection in children. Moreover, mice are one of the most common model animals for pharmacological and toxicological studies, with a clear genetic background, a large number of strains, and the ability to meet particular experimental needs through gene-targeted transfection or knockout techniques. Therefore, mice were used as animal models for detection in the following experiments.

2.6.1 Results for Detection of Binding Antibody Titers

The IgG titers specific for the pre-fusion and post-fusion F proteins in the serum of mice on day 35 after the immunization were detected by an ELISA method. The detection results are shown in the table below and in FIGS. 2A to 3B:

1. The pre-F IgG antibody titers of the following 11 test samples were 2.52 to 5.31 times that of the Abrysvo™ positive control, and the post-F IgG antibody titers were 1.13 to 5.21 times that of the Abrysvo™ positive control.

The pre-F IgG antibody titers of YK-RSV-061, YK-RSV-003, and YK-RSV-062 were 4.29 to 5.31 times that of the Abrysvo™ positive control, and the post-F ngG antibody titers were 4.32 to 5.21 times that of the Abrysvo™ positive control.

Among them, the pre-F IgG antibody titers of the YK-RSV-061 mutant were the highest, with the pre-F IgG antibody titer being 5.31 times that of the Abrysvo™ positive control, and the post-F IgG antibody titers being 5.21 times that of the Abrysvo™ positive control.

In all of the test samples being detected, the pre-F/post-F ratios were all higher than 1, indicating that the IgG titers produced by the pre-fusion F proteins of the test samples were higher than those produced by the post-fusion F proteins.

TABLE 20

RSV F protein-specific IgG antibody titers in serum of mice (day 35)-1

| | pre-F IgG | | post-F IgG | | |
|---|---|---|---|---|---|
| Test sample | Antibody GMT (×10$^4$) | Test sample GMT/ Abrysvo ™ GMT (times) | Antibody GMT (×10$^4$) | Test sample GMT/ Abrysvo ™ GMT (times) | pre-F/ post-F |
| YK-RSV-061 | 669 | 5.31 | 542 | 5.21 | 1.23 |
| YK-RSV-003 | 618 | 4.90 | 510 | 4.90 | 1.21 |
| YK-RSV-062 | 541 | 4.29 | 449 | 4.32 | 1.20 |
| YK-RSV-054 | 495 | 3.93 | 405 | 3.89 | 1.22 |
| YK-RSV-039 | 493 | 3.91 | 386 | 3.71 | 1.28 |
| YK-RSV-044 | 452 | 3.59 | 257 | 2.47 | 1.76 |
| YK-RSV-012 | 462 | 3.67 | 310 | 2.98 | 1.49 |
| YK-RSV-015 | 474 | 3.76 | 411 | 3.95 | 1.15 |
| YK-RSV-001 | 449 | 3.56 | 332 | 3.19 | 1.35 |
| YK-RSV-036 | 386 | 3.06 | 375 | 3.61 | 1.03 |
| YK-RSV-060 | 318 | 2.52 | 118 | 1.13 | 2.69 |
| LNP | 0.01 | 0.00 | 0.01 | 0.00 | 1.00 |
| Abrysvo ™ | 126 | 1.00 | 104 | 1.00 | 1.21 |

2. The pre-F IgG antibody titers of YK-RSV-011 and YK-RSV-030 were 2.38 to 2.50 times that of the Abrysvo™ positive control, and the post-F IgG antibody titers were 1.30 to 2.81 times that of the Abrysvo™ positive control.

TABLE 21

RSV F protein-specific IgG antibody titers in serum of mice (day 35) - 2

| | pre-F IgG | | post-F IgG | | |
|---|---|---|---|---|---|
| Test sample | Antibody GMT (×10$^4$) | Test sample GMT/ Abrysvo ™ GMT (times) | Antibody GMT (×10$^4$) | Test sample GMT/ Abrysvo ™ GMT (times) | pre-F/ post-F |
| YK-RSV-011 | 300 | 2.38 | 135 | 1.30 | 2.22 |
| YK-RSV-030 | 315 | 2.50 | 292 | 2.81 | 1.08 |
| LNP | 0.01 | 0.00 | 0.01 | 0.00 | 1.00 |
| Abrysvo ™ | 126 | 1.00 | 104 | 1.00 | 1.21 |

The above test samples would be further evaluated for immunogenicity by determining the level of neutralizing antibodies produced.

2.6.2 Results for Detection of Neutralizing Antibody Titers

The neutralizing antibody titers in the serum of mice on day 35 after the immunization were detected by a spot reduction-based micro-neutralization assay. The results are shown in the table below and in FIGS. 4A to 7B:

1. Results for RSV Type a Virus-Neutralizing Antibody Titers

The neutralizing antibody titer $IC_{50}$ values of the following 11 test samples were 3.72 to 12.67 times that of the Abrysvo™ positive control, and $IC_{90}$ values were 2.34 to 14.41 times that of the Abrysvo™ positive control, all of which were higher than those of the positive control.

The neutralizing antibody titer $IC_{50}$ values of YK-RSV-061, YK-RSV-003, and YK-RSV-062 were 6.34 to 12.67 times that of the Abrysvo™ positive control, and $IC_{90}$ values were 9.56 to 14.41 times that of the Abrysvo™ positive control, indicating significantly higher neutralizing antibody titers.

Among them, YK-RSV-061 had the highest neutralizing antibody titers, with $IC_{50}$ being 12.67 times that of the Abrysvo™ positive control, and $IC_{90}$ being 14.41 times that of the positive control.

TABLE 22

Neutralizing antibody titers of RSV A2 in serum of mice (day 35)

| | $IC_{50}$ | | $IC_{90}$ | |
|---|---|---|---|---|
| Test sample | Titer | Test sample $IC_{50}$/Abrysvo ™ $IC_{50}$ (times) | Titer | Test sample $IC_{90}$/Abrysvo ™ $IC_{90}$ (times) |
| YK-RSV-061 | 51997 | 12.67 | 3472 | 14.41 |
| YK-RSV-003 | 30330 | 7.39 | 2311 | 9.59 |
| YK-RSV-062 | 26022 | 6.34 | 2305 | 9.56 |
| YK-RSV-054 | 24748 | 6.03 | 1705 | 7.07 |
| YK-RSV-039 | 20758 | 5.06 | 1586 | 6.58 |
| YK-RSV-044 | 19263 | 4.69 | 1283 | 5.32 |
| YK-RSV-012 | 19706 | 4.80 | 1362 | 5.65 |
| YK-RSV-015 | 20496 | 5.00 | 1458 | 6.05 |
| YK-RSV-001 | 18693 | 4.56 | 1097 | 4.55 |
| YK-RSV-036 | 17880 | 4.36 | 722 | 3.00 |
| YK-RSV-060 | 15272 | 3.72 | 563 | 2.34 |
| LNP | 40 | 0.01 | 40 | 0.17 |
| Abrysvo ™ | 4103 | 1.00 | 241 | 1.00 |

2. Results for RSV Type B Virus-Neutralizing Antibody Titers

The above 11 test samples obtained by screening were further detected for the levels of neutralizing antibodies produced for RSV B18357 virus. The detection results are shown in the table below:

The neutralizing antibody titer $IC_{50}$ values of the following 11 mutants were 2.85 to 10.63 times that of the Abrysvo™ positive control, and $IC_{90}$ values were 2.88 to 14.23 times that of the Abrysvo™ positive control, indicating that the neutralizing antibody titers were all significantly higher than those of the positive control.

The neutralizing antibody titer $IC_{50}$ values of YK-RSV-061, YK-RSV-003, and YK-RSV-062 were 5.68 to 10.63 times that of the Abrysvo™ positive control, and $IC_{90}$ values were 6.87-14.23 times that of the Abrysvo™ positive control, indicating very high neutralizing antibody titers.

Among them, YK-RSV-061 had the highest neutralizing antibody titers, with $IC_{50}$ being 10.63 times that of the Abrysvo™ positive control, and $IC_{90}$ being 14.23 times that of the positive control.

TABLE 23

Neutralizing antibody titers of RSV B18357 in serum of mice (day 35)

| Test sample | $IC_{50}$ Titer | $IC_{50}$ Test sample $IC_{50}$/Abrysvo ™ $IC_{50}$ (times) | $IC_{90}$ Titer | $IC_{90}$ Test sample $IC_{90}$/Abrysvo ™ $IC_{90}$ (times) |
|---|---|---|---|---|
| YK-RSV-061 | 34877 | 10.63 | 3088 | 14.23 |
| YK-RSV-003 | 23943 | 7.30 | 1712 | 7.89 |
| YK-RSV-062 | 18615 | 5.68 | 1490 | 6.87 |
| YK-RSV-054 | 16175 | 4.93 | 1243 | 5.73 |
| YK-RSV-039 | 12814 | 3.91 | 976 | 4.50 |
| YK-RSV-044 | 10303 | 3.14 | 877 | 4.04 |
| YK-RSV-012 | 11641 | 3.55 | 895 | 4.12 |
| YK-RSV-015 | 12359 | 3.77 | 970 | 4.47 |
| YK-RSV-001 | 9661 | 2.95 | 829 | 3.82 |
| YK-RSV-036 | 9420 | 2.87 | 713 | 3.29 |
| YK-RSV-060 | 9337 | 2.85 | 625 | 2.88 |
| LNP | 40 | 0.01 | 40 | 0.18 |
| Abrysvo ™ | 3280 | 1.00 | 217 | 1.00 |

In summary, the above 11 test samples (including YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, and YK-RSV-060) were all able to produce relatively high neutralizing antibody titers for different subtypes of RSV A2 and RSV B18357.

2.7 Results for Immunogenicity of RSV F Antigen Mutants in Cotton Rats

Dreizin reported cotton rats as animal models of hRSV infection for the first time in 1971. After the cotton rats are infected by hRSV, the virus is mainly replicated and amplified in the lungs and lower respiratory tract. Mild to moderate bronchiolitis or pneumonia, airway epithelial cell shedding, and pulmonary atelectasis can be observed by pathological examination, the symptoms of the upper respiratory tract infection are significant, and changes in the related cytokines are not significant. Cotton rats are standard animal models for the evaluation of the efficacy of vaccines, antiviral drugs, and monoclonal antibodies (such as palivizumab). Therefore, cotton rats were used as animal models for detection in the following experiments.

2.7.1 Results for Detection of Binding Antibody Titers

The IgG titers specific for the pre-fusion and post-fusion F proteins in the serum of cotton rats on days 42 and 48 after the immunization were detected by an ELISA method (see FIGS. 8A to 11B). The detection results of IgG titers on day 42 are shown in the table below:

(1) On day 42, the pre-F IgG antibody titers of the following 11 test samples were 3.05 to 13.10 times that of the Abrysvo™ positive control, and the post-F IgG antibody titers were 2.36 to 6.38 times that of the Abrysvo™ positive control, all of which were significantly higher than those of the positive control.

The pre-F IgG antibody titers of YK-RSV-061, YK-RSV-003, and YK-RSV-062 were 9.76 to 13.10 times that of the Abrysvo™ positive control, and the post-F IgG antibody titers were 4.66 to 6.33 times that of the Abrysvo™ positive control.

Among them, the IgG antibody titers of the test sample YK-RSV-061 were the highest, with the pre-F IgG antibody titer being 13.10 times that of the Abrysvo™ positive control, and the post-F IgG antibody titers being 6.33 times that of the Abrysvo™ positive control.

The pre-F/post-F ratios of all the test samples range from 1.39 to 3.95, indicating that the IgG antibody titers produced by the pre-fusion F proteins are significantly higher than those of the post-fusion F proteins.

TABLE 24

RSV F protein-specific IgG antibody titers in serum of cotton rats (day 42)

| Test sample | pre-F IgG Antibody GMT ($\times 10^4$) | pre-F IgG Test sample GMT/Abrysvo ™ GMT (times) | post-F IgG Antibody GMT ($\times 10^4$) | post-F IgG Test sample GMT/Abrysvo ™ GMT (times) | pre-F/post-F |
|---|---|---|---|---|---|
| YK-RSV-061 | 2017 | 13.10 | 570 | 6.33 | 3.54 |
| YK-RSV-003 | 1681 | 10.92 | 523 | 5.81 | 3.21 |
| YK-RSV-062 | 1503 | 9.76 | 419 | 4.66 | 3.59 |
| YK-RSV-054 | 1037 | 6.73 | 376 | 4.18 | 2.76 |
| YK-RSV-039 | 982 | 6.38 | 574 | 6.38 | 1.71 |
| YK-RSV-044 | 921 | 5.98 | 277 | 3.08 | 3.32 |
| YK-RSV-012 | 885 | 5.75 | 319 | 3.54 | 2.77 |
| YK-RSV-015 | 837 | 5.44 | 212 | 2.36 | 3.95 |
| YK-RSV-001 | 524 | 3.40 | 376 | 4.18 | 1.39 |
| YK-RSV-036 | 495 | 3.21 | 291 | 3.23 | 1.70 |
| YK-RSV-060 | 469 | 3.05 | 302 | 3.36 | 1.55 |
| LNP | 0.01 | 0.00 | 0.01 | 0.00 | 1.00 |
| Abrysvo ™ | 154 | 1.00 | 90 | 1.00 | 1.71 |

Meanwhile, the IgG titers in the serum of cotton rats on day 48 were detected. The detection results are shown in the table below:

(2) On day 48, the pre-F IgG antibody titers of the 11 test samples were 4.44 to 12.35 times that of the Abrysvo™ positive control, and the post-F IgG antibody titers were 1.51 to 6.83 times that of the Abrysvo™ positive control, all of which were significantly higher than those of the positive control.

The pre-F IgG antibody titers of YK-RSV-061, YK-RSV-003, and YK-RSV-062 were 9.02 to 12.35 times that of the Abrysvo™ positive control, and the post-F IgG antibody titers were 4.03 to 6.83 times that of the Abrysvo™ positive control.

Among them, the IgG antibody titers of the test sample YK-RSV-061 were the highest, with the pre-F IgG antibody titer being 12.35 times that of the Abrysvo™ positive control, and the post-F IgG antibody titers being 6.83 times that of the Abrysvo™ positive control.

The pre-F/post-F ratios of all the test samples range from 1.78 to 4.29, indicating that the IgG antibody titers produced by the pre-fusion F proteins are still significantly higher than those produced by the post-fusion F proteins on day 48 after the immunization.

TABLE 25

| RSV F protein-specific IgG antibody titers in serum of cotton rats (day 48) | | | | | |
|---|---|---|---|---|---|
| | pre-F IgG | | post-F IgG | | |
| Test sample | Antibody GMT ($\times 10^4$) | Test sample GMT/ Abrysvo ™ GMT (times) | Antibody GMT ($\times 10^4$) | Test sample GMT/ Abrysvo ™ GMT (times) | pre-F/ post-F |
| YK-RSV-061 | 1013 | 12.35 | 444 | 6.83 | 2.28 |
| YK-RSV-003 | 806 | 9.83 | 302 | 4.65 | 2.67 |
| YK-RSV-062 | 740 | 9.02 | 262 | 4.03 | 2.82 |
| YK-RSV-054 | 524 | 6.39 | 293 | 4.51 | 1.79 |
| YK-RSV-039 | 511 | 6.23 | 287 | 4.42 | 1.78 |
| YK-RSV-044 | 495 | 6.04 | 242 | 3.72 | 2.05 |
| YK-RSV-012 | 471 | 5.74 | 154 | 2.37 | 3.06 |
| YK-RSV-015 | 451 | 5.50 | 180 | 2.77 | 2.51 |
| YK-RSV-001 | 430 | 5.24 | 154 | 2.37 | 2.79 |
| YK-RSV-036 | 420 | 5.12 | 98 | 1.51 | 4.29 |
| YK-RSV-060 | 364 | 4.44 | 131 | 2.02 | 2.78 |
| LNP | 0.01 | 0.00 | 0.01 | 0.00 | 1.00 |
| Abrysvo ™ | 82 | 1.00 | 65 | 1.00 | 1.26 |

2.7.2 Results for Detection of Neutralizing Antibody Titers

Figure 12A:
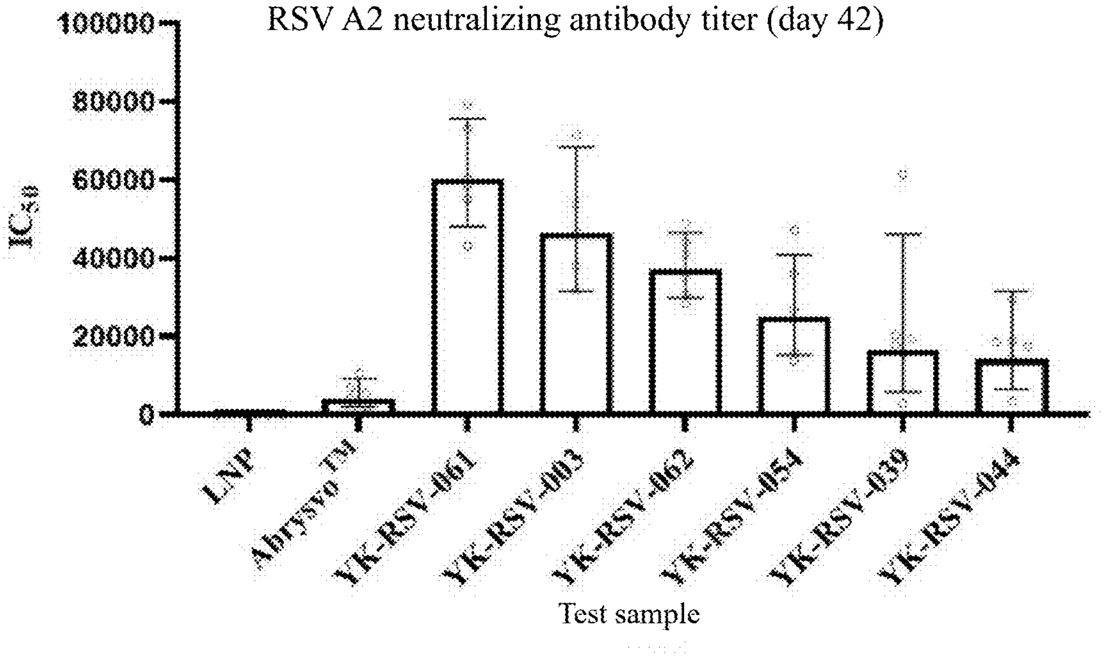
FIGS. 12A and 12B show RSV A2 neutralizing antibody titer $IC_{50}$ in the serum of cotton rats on day 42, respectively.
Figure 12B:
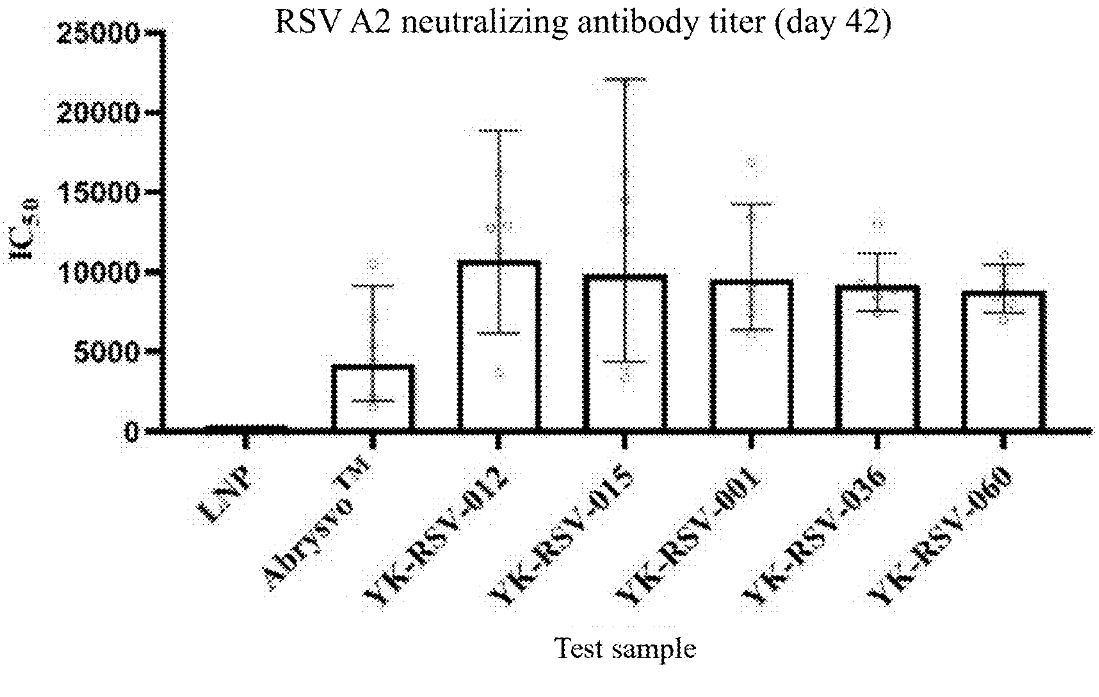
Figure 13A:
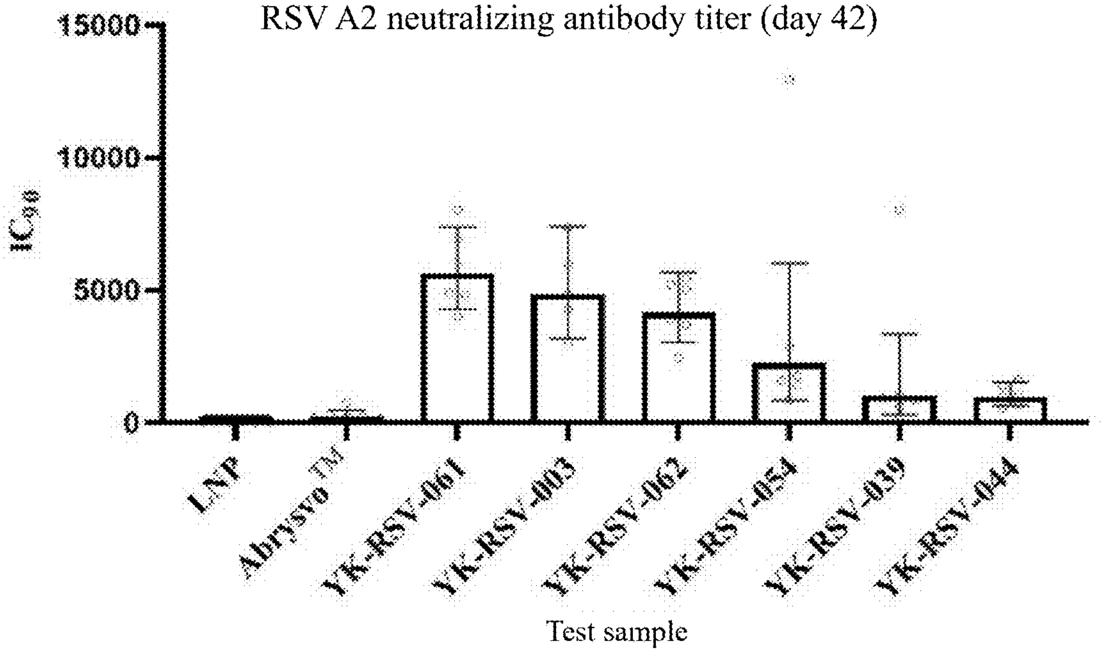
FIGS. 13A and 13B show RSV A2 neutralizing antibody titer $IC_{90}$ in the serum of cotton rats on day 42, respectively.
Figure 13B:
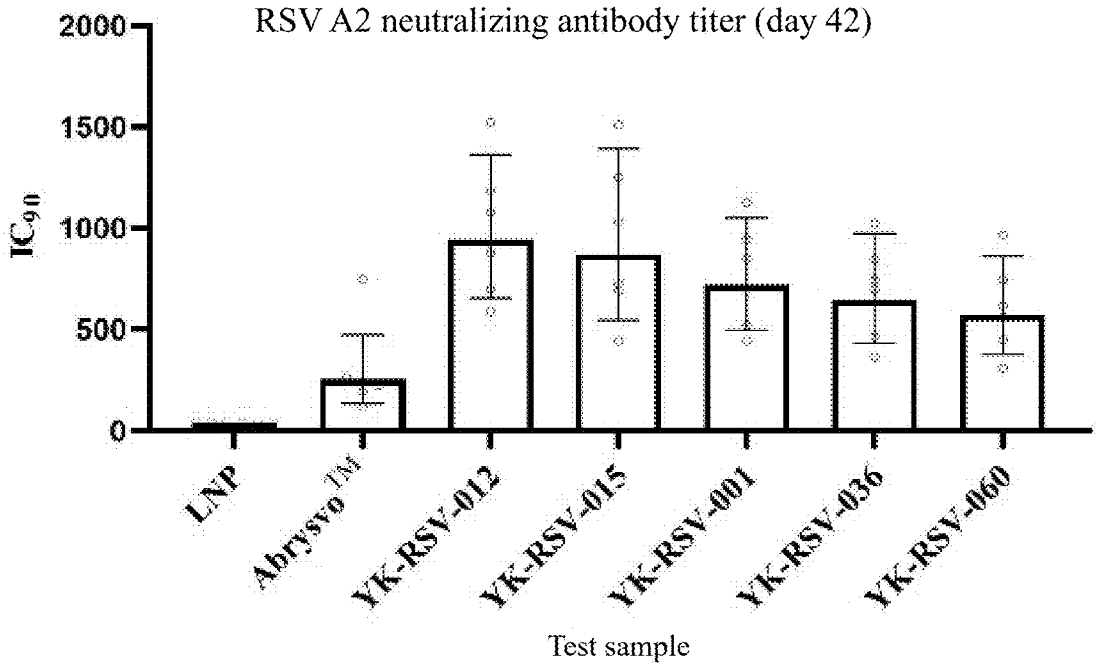
Figure 16A:
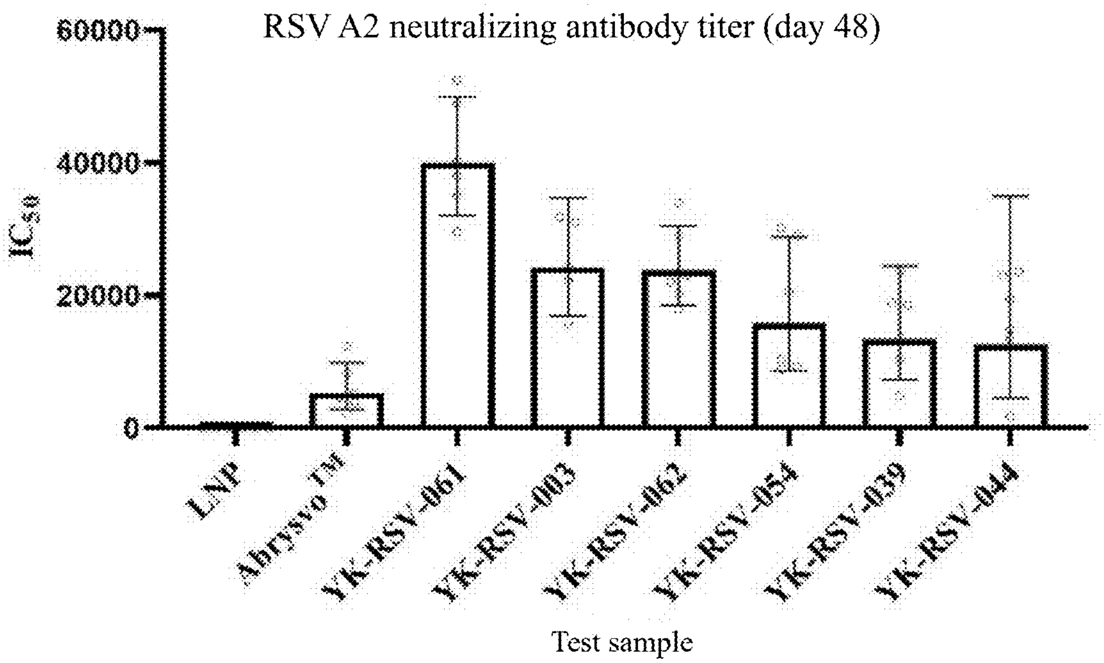
FIGS. 16A and 16B show RSV A2 neutralizing antibody titer $IC_{50}$ in the serum of cotton rats on day 48, respectively.
Figure 16B:
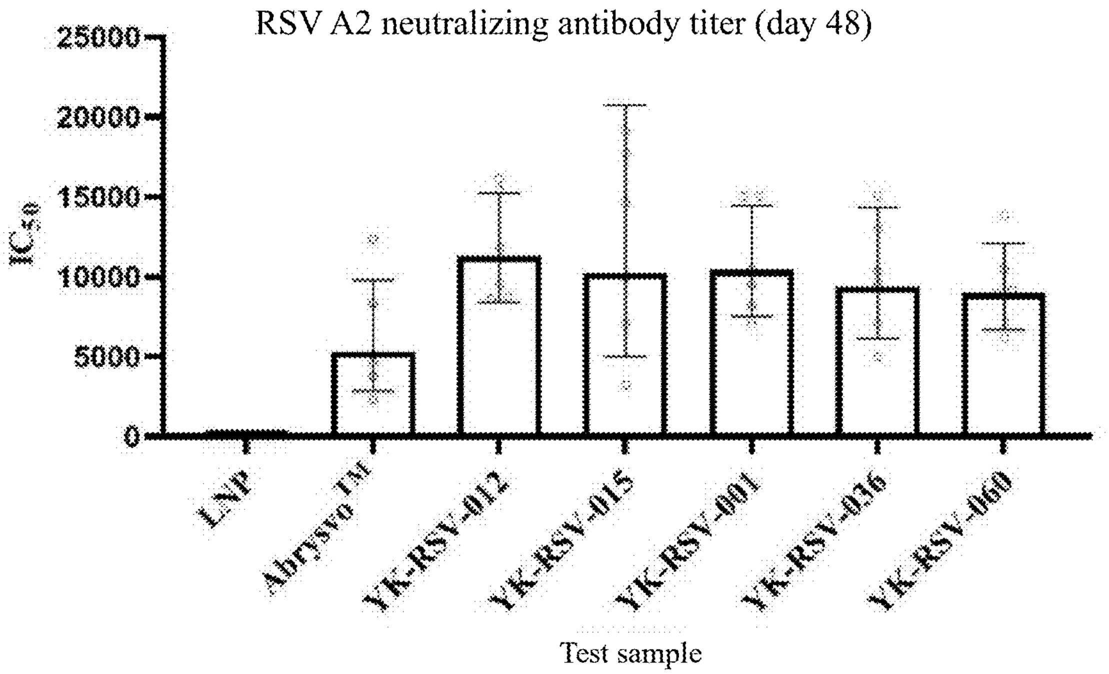
Figure 17A:
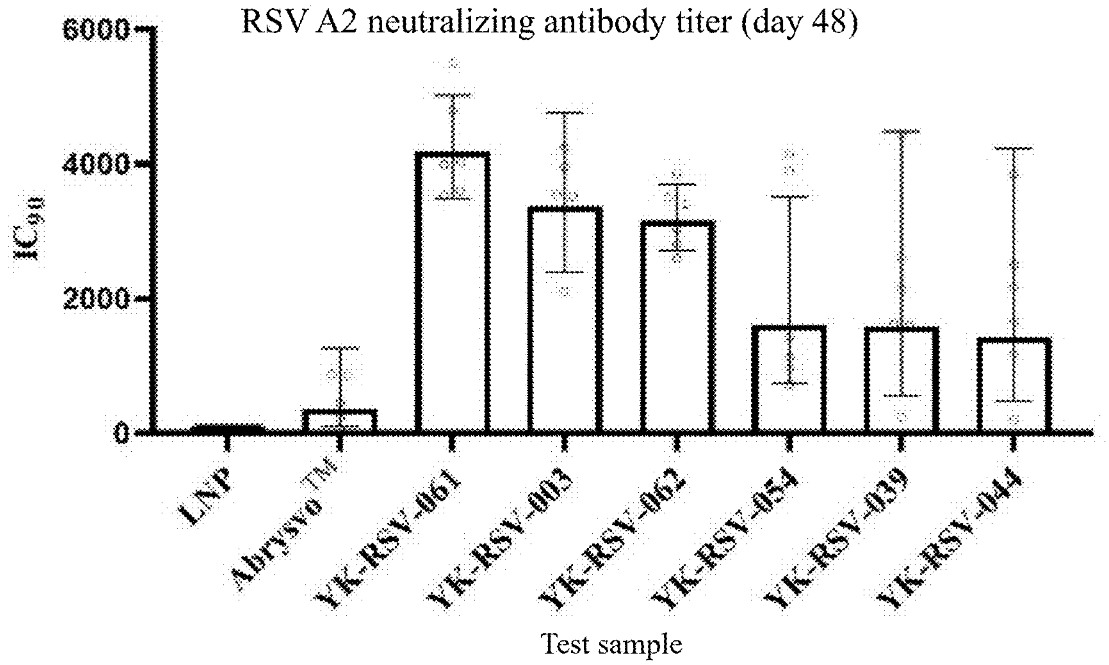
FIGS. 17A and 17B show RSV A2 neutralizing antibody titer $IC_{90}$ in the serum of cotton rats on day 48, respectively.
Figure 17B:
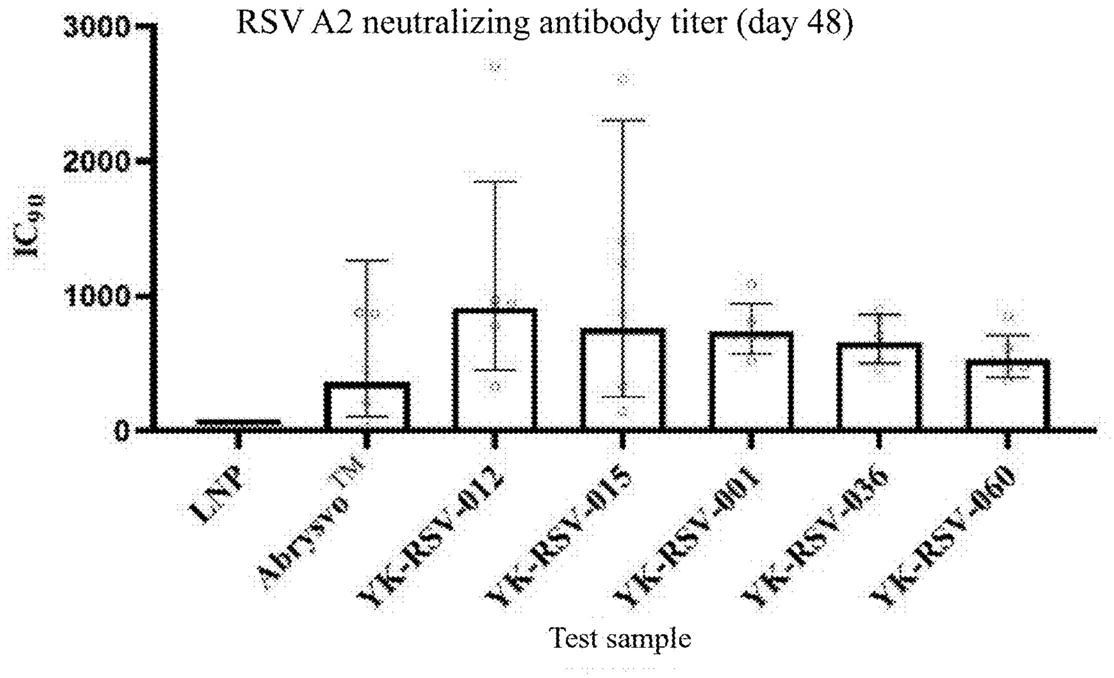

The neutralizing antibody titers produced for RSV A2 virus in the serum of cotton rats were detected on days 42 and 48 (see FIGS. 12 A and 12 B, FIGS. 13 A and 13 B, FIGS. 16 A and 16 B, and FIGS. 17 A and 17 B). The detection results for the neutralizing antibody titers on day 42 are shown in the table below:

(1) On day 42 after the immunization, the neutralizing antibody titer $IC_{50}$ values of the following 11 test samples detected in the serum of cotton rats were 2.10 to 14.30 limes that of the Abrysvo™ positive control, and $IC_{90}$ values were 2.26 to 22.33 times that of the Abrysvo™ positive control, all of which were significantly higher than those of the positive control.

The neutralizing antibody titer $IC_{50}$ values of YK-RSV-061, YK-RSV-003, and YK-RSV-062 were 8.84 to 14.30 times that of the Abrysvo™ positive control, and $IC_{90}$ values were 16.46 to 22.33 times that of the Abrysvo™ positive control.

Among them, $IC_{50}$ of YK-RSV-061 was 14.30 times that of the Abrysvo™ positive control, and $IC_{90}$ was 22.33 times that of the positive control, indicating the highest neutralizing antibody titers.

TABLE 26

| Neutralizing antibody titers of RSV A2 in serum of cotton rats (day 42) | | | | |
|---|---|---|---|---|
| | $IC_{50}$ | | $IC_{90}$ | |
| Test sample | Titer | Test sample $IC_{50}$/Abrysvo ™ $IC_{50}$ (times) | Titer | Test sample $IC_{90}$/Abrysvo ™ $IC_{90}$ (times) |
| YK-RSV-061 | 60321 | 14.30 | 5628 | 22.33 |
| YK-RSV-003 | 46401 | 11.00 | 4852 | 19.25 |
| YK-RSV-062 | 37265 | 8.84 | 4147 | 16.46 |
| YK-RSV-054 | 24933 | 5.91 | 2238 | 8.88 |
| YK-RSV-039 | 16421 | 3.89 | 1017 | 4.04 |
| YK-RSV-044 | 14249 | 3.38 | 984 | 3.90 |
| YK-RSV-012 | 10774 | 2.55 | 944 | 3.75 |
| YK-RSV-015 | 9842 | 2.33 | 870 | 3.45 |
| YK-RSV-001 | 9547 | 2.26 | 723 | 2.87 |
| YK-RSV-036 | 9206 | 2.18 | 650 | 2.58 |

TABLE 26-continued

| Neutralizing antibody titers of RSV A2 in serum of cotton rats (day 42) | | | | |
|---|---|---|---|---|
| | $IC_{50}$ | | $IC_{90}$ | |
| Test sample | Titer | Test sample $IC_{50}$/Abrysvo ™ $IC_{50}$ (times) | Titer | Test sample $IC_{90}$/Abrysvo ™ $IC_{90}$ (times) |
| YK-RSV-060 | 8839 | 2.10 | 570 | 2.26 |
| LNP | 40 | 0.01 | 40 | 0.16 |
| Abrysvo ™ | 4217 | 1.00 | 252 | 1.00 |

Figure 14A:
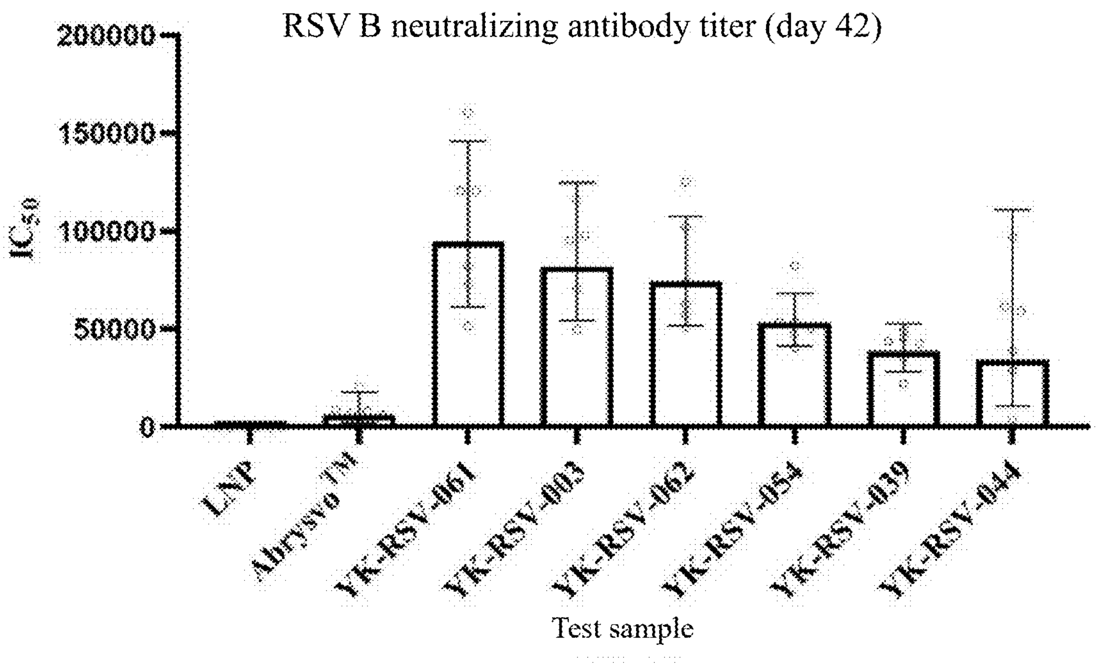
FIGS. 14A and 14B show RSV B neutralizing antibody titer $IC_{50}$ in the serum of cotton rats on day 42, respectively.
Figure 14B:
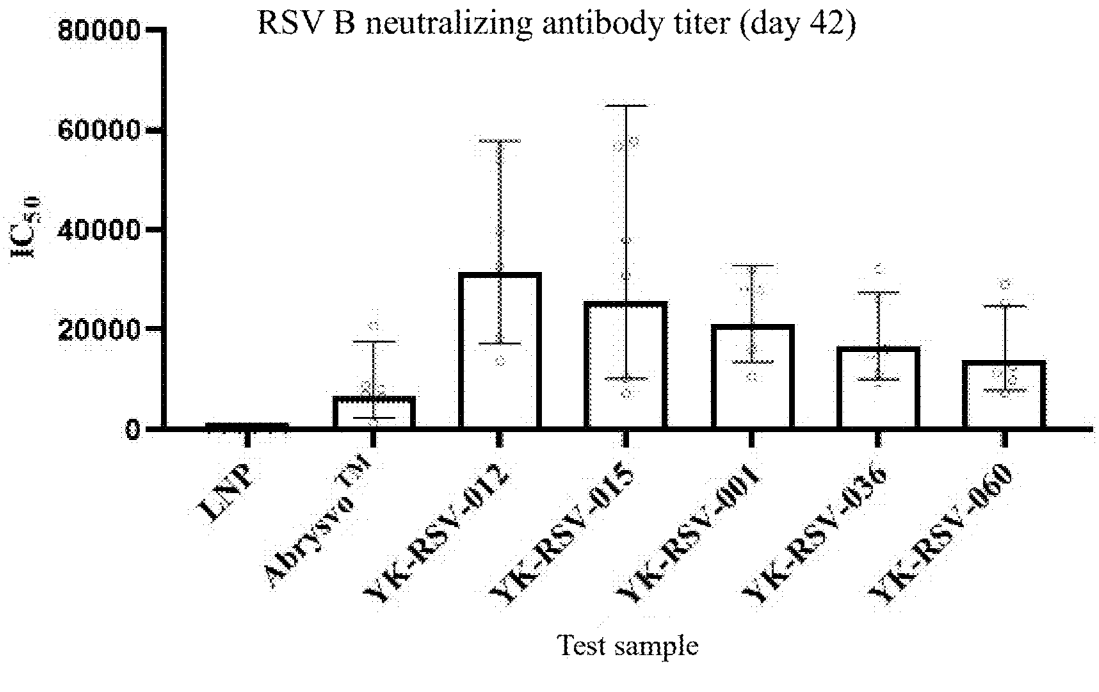
Figure 15A:
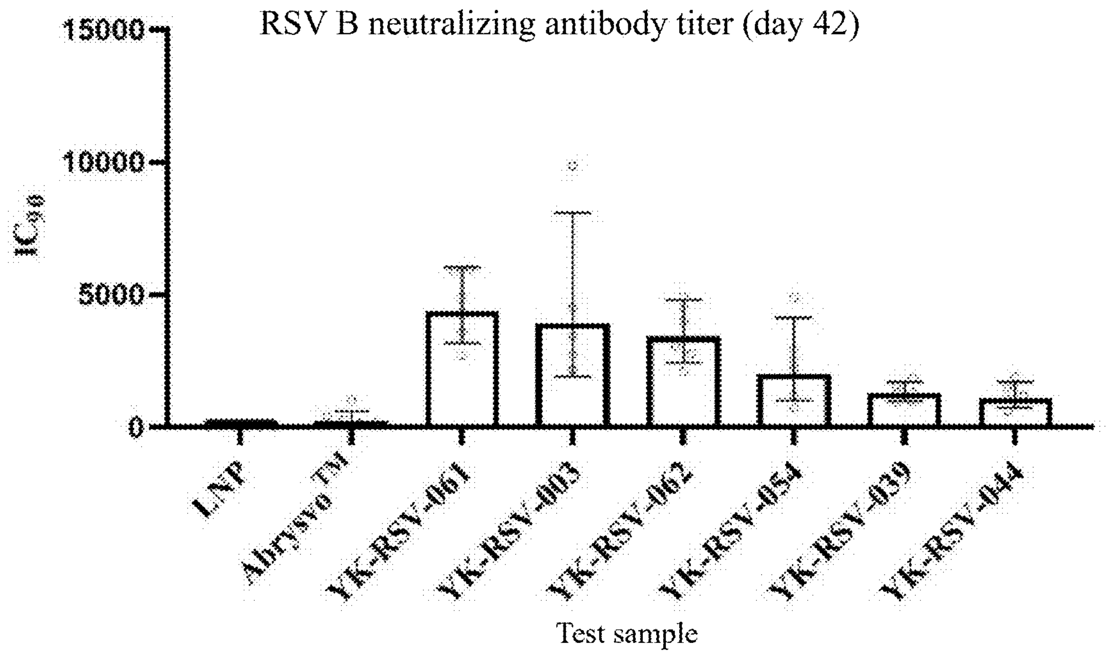
FIGS. 15A and 15B show RSV B neutralizing antibody titer $IC_{90}$ in the serum of cotton rats on day 42, respectively.
Figure 15B:
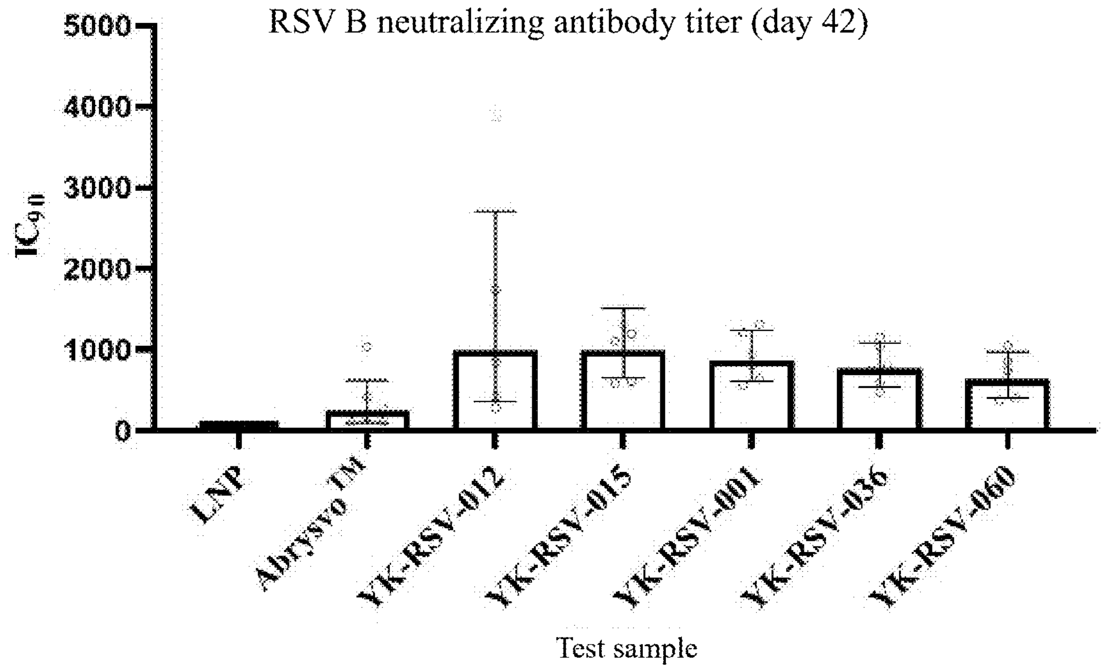

(2) The neutralizing antibody titers produced for RSV B virus in the serum of cotton rats on day 42 were also detected. The results are shown in the table below and in FIGS. 14 A and 14 B and FIGS. 15 A and 15 B:

The neutralizing antibody titer $IC_{50}$ values of the following 11 test samples were 2.16 to 14.63 times that of the Abrysvo™ positive control, and $C_{90}$ values were 2.49 to 17.26 times that of the Abrysvo™ positive control, all of which were significantly higher than those of the positive control.

The neutralizing antibody titer $IC_{50}$ values of YK-RSV-061, YK-RSV-003, and YK-RSV-062 were 11.52 to 14.63 times that of the Abrysvo™ positive control, and $C_{90}$ values were 13.44 to 17.26 times that of the Abrysvo™ positive control.

Among them, $IC_{50}$ of YK-RSV-061 was 14.63 times that of the Abrysvo™ positive control, and $IC_{90}$ was 17.26 times that of the positive control, indicating the highest neutralizing antibody titers.

TABLE 27

| Neutralizing antibody titers of RSV B in serum of cotton rats (day 42) | | | | |
|---|---|---|---|---|
| | $IC_{50}$ | | $IC_{90}$ | |
| Test sample | Titer | Test sample $IC_{50}$/Abrysvo ™ $IC_{50}$ (times) | Titer | Test sample $IC_{90}$/Abrysvo ™ $IC_{90}$ (times) |
| YK-RSV-061 | 94685 | 14.63 | 4384 | 17.26 |
| YK-RSV-003 | 82331 | 12.72 | 3913 | 15.41 |
| YK-RSV-062 | 74557 | 11.52 | 3414 | 13.44 |
| YK-RSV-054 | 53282 | 8.23 | 2035 | 8.01 |
| YK-RSV-039 | 38643 | 5.97 | 1289 | 5.07 |
| YK-RSV-044 | 34308 | 5.30 | 1111 | 4.37 |
| YK-RSV-012 | 31475 | 4.86 | 994 | 3.91 |
| YK-RSV-015 | 25684 | 3.97 | 992 | 3.91 |
| YK-RSV-001 | 21034 | 3.25 | 871 | 3.43 |
| YK-RSV-036 | 16633 | 2.57 | 767 | 3.02 |
| YK-RSV-060 | 13980 | 2.16 | 632 | 2.49 |
| LNP | 40 | 0.01 | 40 | 0.16 |
| Abrysvo ™ | 6472 | 1.00 | 254 | 1.00 |

(3) On day 48 after the immunization, the neutralizing antibody titers produced for RSV A2 virus in the serum of cotton rats were detected. The detection results are shown in the table below:

The neutralizing antibody titer $IC_{50}$ values of the following 11 test samples were 1.70 to 7.57 times that of the Abrysvo™ positive control, and $IC_{90}$ values were 1.46 to 11.56 times that of the Abrysvo™ positive control, all of which were higher than those of the positive control.

The neutralizing antibody titer $IC_{50}$ values of YK-RSV-061, YK-RSV-003, and YK-RSV-062 were 4.51 to 7.57 times that of the Abrysvo™ positive control, and $IC_{90}$ values were 8.75 to 11.56 times that of the Abrysvo™ positive control.

Among them, $IC_{50}$ of YK-RSV-061 was 7.57 times that of the Abrysvo™ positive control, and $IC_{90}$ was 11.56 times that of the positive control, indicating the highest neutralizing antibody titers.

TABLE 28

Neutralizing antibody titers of RSV A2 in serum of cotton rats (day 48)

| Test sample | $IC_{50}$ Titer | $IC_{50}$ Test sample $IC_{50}$/Abrysvo ™ $IC_{50}$ (times) | $IC_{90}$ Titer | $IC_{90}$ Test sample $IC_{90}$/Abrysvo ™ $IC_{90}$ (times) |
|---|---|---|---|---|
| YK-RSV-061 | 40016 | 7.57 | 4185 | 11.56 |
| YK-RSV-003 | 24244 | 4.59 | 3377 | 9.33 |
| YK-RSV-062 | 23814 | 4.51 | 3168 | 8.75 |
| YK-RSV-054 | 15798 | 2.99 | 1612 | 4.45 |
| YK-RSV-039 | 13376 | 2.53 | 1581 | 4.37 |
| YK-RSV-044 | 12567 | 2.38 | 1418 | 3.92 |
| YK-RSV-012 | 11331 | 2.14 | 913 | 2.52 |
| YK-RSV-015 | 10210 | 1.93 | 759 | 2.10 |
| YK-RSV-001 | 10436 | 1.98 | 735 | 2.03 |
| YK-RSV-036 | 9399 | 1.78 | 655 | 1.81 |
| YK-RSV-060 | 8995 | 1.70 | 529 | 1.46 |
| LNP | 40 | 0.01 | 40 | 0.11 |
| Abrysvo ™ | 5284 | 1.00 | 362 | 1.00 |

In summary, on days 42 and 48 after the immunization of cotton rats, the binding antibody and neutralizing antibody titer levels produced by all the test samples were significantly higher than those of the control Abrysvo™, and the humoral immunity effect was significantly improved. Among them, the test sample YK-RSV-061 had the best immune effect. All the test samples also had a good immune effect on different subtypes of virus, including RSV types A and B.

2.7.3 Results for Pathological Sections of the Lungs of Cotton Rats

Figure 18:
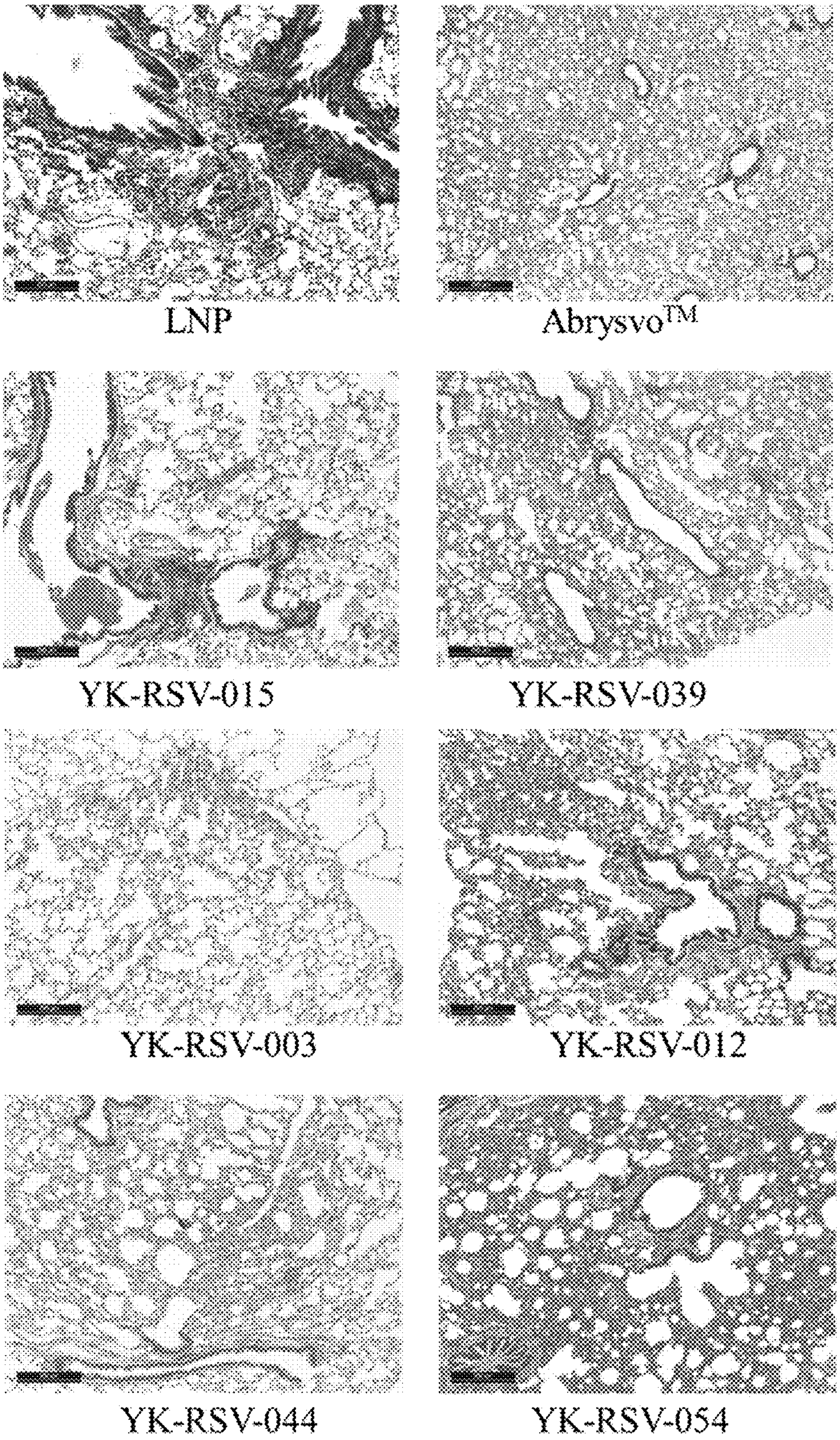
FIG. 18 shows the results for pathological sections of the lungs of cotton rats after treatment with the test samples of the present disclosure.

Pathological sections of the lungs of cotton rats are shown in FIG. 18, and the scoring results are shown in the table below:

TABLE 29

Scoring results for pathological sections of the lungs of cotton rats

| Test sample | Perivascular infiltration | Peribronchiolar infiltration | Alveolar infiltration | Interstitial infiltration | Total score |
|---|---|---|---|---|---|
| YK-RSV-061 | 0.00 | 0.33 | 0.00 | 0.67 | 1.00 |
| YK-RSV-003 | 0.00 | 0.50 | 0.00 | 0.83 | 1.33 |
| YK-RSV-062 | 0.00 | 0.50 | 0.00 | 1.00 | 1.50 |
| YK-RSV-054 | 0.00 | 0.50 | 0.00 | 1.00 | 1.50 |
| YK-RSV-039 | 0.00 | 0.67 | 0.00 | 1.00 | 1.67 |
| YK-RSV-044 | 0.00 | 0.67 | 0.00 | 1.17 | 1.84 |
| YK-RSV-012 | 0.00 | 0.67 | 0.00 | 1.00 | 1.67 |
| YK-RSV-015 | 0.00 | 0.33 | 0.00 | 1.00 | 1.33 |
| YK-RSV-001 | 0.00 | 0.83 | 0.00 | 1.00 | 1.83 |
| YK-RSV-036 | 0.00 | 0.83 | 0.00 | 1.17 | 2.00 |
| YK-RSV-060 | 0.00 | 0.67 | 0.00 | 0.83 | 1.50 |
| LNP | 0.00 | 2.33 | 0.00 | 1.50 | 3.83 |
| Abrysvo ™ | 0.00 | 0.67 | 0.00 | 1.33 | 2.00 |

From the above results, it could be seen that the peribronchiolar infiltration scores of the test samples were all 0.33 to 0.83, indicating mild inflammatory infiltration.

All the test samples had interstitial infiltration scores superior to those of the positive control Abrysvo™, and the scores were 0.67 to 1.17, indicating mild inflammatory infiltration.

All the test samples had low overall inflammatory response scores, and the total pathological scores were 1.00 to 2.00, all of which were lower than that of the control LNP. The scores of two indicators of perivascular infiltration and alveolar infiltration of the control and the test samples were all 0, indicating that there were no visible lesions in the tissue.

2.7.4 Results for Viral Loads in the Lungs and Turbinates of Cotton Rats

After the cotton rats were sacrificed on day 54, the lung and turbinate tissues were aseptically taken for the determination of viral titers. The results are shown in the table below.

TABLE 30

Viral loads in the lungs and turbinates of cotton rats (day 54)

| Test sample | Viral load in the lungs GMT | Viral load in the lungs Test sample viral load/Abrysvo ™ viral load (times) | Viral load in the turbinate GMT | Viral load in the turbinate Test sample viral load/Abrysvo ™ viral load (times) |
|---|---|---|---|---|
| YK-RSV-061 | 1.61 | 0.75 | 0.62 | 0.19 |
| YK-RSV-003 | 1.69 | 0.79 | 0.80 | 0.24 |
| YK-RSV-062 | 1.85 | 0.86 | 0.94 | 0.28 |
| YK-RSV-054 | 1.94 | 0.91 | 1.10 | 0.33 |
| YK-RSV-039 | 1.82 | 0.85 | 1.08 | 0.32 |
| YK-RSV-044 | 1.91 | 0.89 | 1.44 | 0.43 |
| YK-RSV-012 | 1.84 | 0.86 | 1.40 | 0.42 |
| YK-RSV-015 | 2.06 | 0.96 | 1.44 | 0.43 |
| YK-RSV-001 | 1.85 | 0.86 | 1.27 | 0.38 |
| YK-RSV-036 | 1.89 | 0.88 | 1.40 | 0.42 |
| YK-RSV-060 | 2.08 | 0.97 | 1.51 | 0.45 |
| LNP | 4.52 | 2.11 | 4.12 | 1.23 |
| Abrysvo ™ | 2.14 | 1.00 | 3.35 | 1.00 |

The viral loads in the lungs of cotton rats were determined, and the results showed that the tissue viral load of the negative control LNP after the immunization was 4.52, which was significantly higher than those of the positive control Abrysvo™ and the other test samples. The tissue viral load of the control Abrysvo™ after the immunization was 2.14, and the tissue viral loads of the other test samples after the immunization were 1.61 to 2.08, which were lower than that of the positive control Abrysvo™

The viral loads in the turbinates of cotton rats were determined, and the results showed that the tissue viral load of the negative control LNP after the immunization was 4.12, which was significantly higher than those of the other test samples. The tissue viral load of the control Abrysvo™ after the immunization was 3.35, the tissue viral load of the other test samples after the immunization was 0.62 to 1.51, which was only 0.19 to 0.45 times that of the control Abrysvo™, with a significant reduction in the viral load, indicating that the test samples had a better antiviral effect.

2.8 Analysis of Mutant Differences

In summary, in the present disclosure, by designing 52 antigen sequences encoding the RSV F protein mutants, a total of at least 11 (YK-RSV-061, YK-RSV-003, YK-RSV-062, YK-RSV-054, YK-RSV-039, YK-RSV-044, YK-RSV-012, YK-RSV-015, YK-RSV-001, YK-RSV-036, and YK-RSV-060), particularly at least 5 (YK-RSV-061, YK-RSV-003, YK-RSV-062, YK-RSV-054, and YK-RSV-039) of these sequences were selected, which had superior effects to those of the positive control Abrysvo™ and the designed controls PC—RSV-063, PC—RSV-064, PC—RSV-065, PC—RSV-066, PC—RSV-067, and PC—RSV-068.

(1)

TABLE 31

Comparison of mutant differences

| No. | Sequence truncation | Sequence deletion | Site mutation Group 1 | Group 2 | Group 3 | Group 4 | Group 5 |
|---|---|---|---|---|---|---|---|
| YK-RSV-003 | 550 to 574 aa were truncated based on the wild-type RSV F protein, that is, (1 to 549 aa) were retained | 104 to 144 aa were deleted, with amino acids replaced by a GS linker | A149C, S155C, S290C, Y458C | S190F, V296I | E92D, K465Q, D486S | S46G, S215P, L373R | / |
| YK-RSV-061 | | | A149C, S155C, S290C, Y458C | S190F, V296I | E92D, K465Q, D486S | S46G, S215P, L373R | V152I |
| YK-RSV-062 | | | A149C, S155C, S290C, Y458C | S190F, V296I | E92D, K465Q, D486S | S46G, S215P, L373R | C69Y, D73E, A74V, N88S, V152I |

TABLE 32

ELISA results of RSV F mutants

| No. | ELISA results (ng/ml) Epitope Φ RSV pre-F antibody (3C12) | Epitope Φ Binding amount to antibody/binding amount of PC-RSV-064 to antibody | Epitope Quaternary RSV pre-F antibody (7H11) | Epitope Quaternary Binding amount to antibody/binding amount of PC-RSV-064 to antibody | Epitope V RSV F antibody (7E11) | Epitope V Binding amount to antibody/binding amount of PC-RSV-064 to antibody | Epitope II RSV F antibody (11A9) | Epitope II Binding amount to antibody/binding amount of PC-RSV-064 to antibody | Epitope III RSV F antibody (4B9) | Epitope III Binding amount to antibody/binding amount of PC-RSV-064 to antibody |
|---|---|---|---|---|---|---|---|---|---|---|
| YK-RSV-003 | 5541 | 2.00 | 7249 | 2.01 | 452 | 1.41 | 1994 | 0.95 | 3171 | 1.11 |
| YK-RSV-061 | 5261 | 1.90 | 7661 | 2.12 | 595 | 1.85 | 2505 | 1.19 | 3683 | 1.28 |
| YK-RSV-062 | 5059 | 1.83 | 7350 | 2.03 | 487 | 1.52 | 2063 | 0.98 | 3260 | 1.14 |
| PC-RSV-064 | 2768 | 1.00 | 3612 | 1.00 | 321 | 1.00 | 2100 | 1.00 | 2868 | 1.00 |

TABLE 33

Neutralizing antibody titers of RSV A2 in serum of mice (day 35)

| Test sample | $IC_{50}$ Titer | $IC_{50}$ Test sample $IC_{50}$/Abrysvo ™ $IC_{50}$ (times) | $IC_{90}$ Titer | $IC_{90}$ Test sample $IC_{90}$/Abrysvo ™ $IC_{90}$ (times) |
|---|---|---|---|---|
| YK-RSV-061 | 51997 | 12.67 | 3472 | 14.41 |
| YK-RSV-003 | 30330 | 7.39 | 2311 | 9.59 |
| YK-RSV-062 | 26022 | 6.34 | 2305 | 9.56 |
| LNP | 40 | 0.01 | 40 | 0.17 |
| Abrysvo ™ | 4103 | 1.00 | 241 | 1.00 |

TABLE 34

Neutralizing antibody titers of RSV B18357 in serum of mice (day 35)

| Test sample | $IC_{50}$ Titer | $IC_{50}$ Test sample $IC_{50}$/Abrysvo ™ $IC_{50}$ (times) | $IC_{90}$ Titer | $IC_{90}$ Test sample $IC_{90}$/Abrysvo ™ $IC_{90}$ (times) |
|---|---|---|---|---|
| YK-RSV-061 | 34877 | 10.63 | 3088 | 14.23 |
| YK-RSV-003 | 23943 | 7.30 | 1712 | 7.89 |
| YK-RSV-062 | 18615 | 5.68 | 1490 | 6.87 |
| LNP | 40 | 0.01 | 40 | 0.18 |
| Abrysvo ™ | 3280 | 1.00 | 217 | 1.00 |

Compared with the YK-RSV-003 mutant, YK-RSV-061 had 1 additional site mutation V152I on its basis; YK-RSV-062 had 5 additional site mutations C69Y, D73E, A745, N88S, and V152 on its basis; epitopes on three mutants of YK-RSV-003, YK-RSV-061, and YK-RSV-062 all had good binding levels to the corresponding antibodies. For example, the binding levels of the epitope Quaternary on YK-RSV-061, YK-RSV-003, and YK-RSV-062 to the RSV pre-F antibody (7H11) were 2.01 to 2.12 times that on the control PC—RSV-064.

However, the neutralizing antibody titers $IC_{50}$ and $IC_{90}$ of YK-RSV-061 for RSV type A virus were 12.67 and 14.41 times those of the Abrysvo™ positive control, respectively, while the neutralizing antibody titers $IC_{50}$ and $IC_{90}$ of YK-RSV-003 were 7.39 and 9.59 times those of the Abrysvo™ positive control. Although the two differed by only 1 site mutation V152I, the neutralizing antibody titers of YK-RSV-061 were significantly increased, which was an unexpected result. The neutralizing antibody titers of YK-RSV-062 were comparable to those of YK-RSV-003. Similarly, the neutralizing antibody titers of YK-RSV-061 for RSV type B virus were also significantly superior.

(2)

TABLE 37

Results for affinity of RSV F mutants for different epitope antibodies

| No. | $K_D$ value (M) RSV pre-F antibody (3C12) Epitope Φ | RSV pre-F antibody (7H11) Epitope Quaternary |
|---|---|---|
| YK-RSV-061 | 6.21E−11 | 3.05E−12 |
| YK-RSV-003 | 6.35E−11 | 3.47E−12 |
| YK-RSV-062 | 6.26E−11 | 3.62E−12 |
| PC-RSV-063 | 1.36E−10 | 1.07E−10 |
| PC-RSV-064 | 1.24E−10 | 1.56E−10 |

TABLE 35

Comparison of mutant differences

| No. | Sequence truncation | Sequence deletion | Site mutation Group 1 | Group 2 | Group 3 | Group 4 | Group 5 |
|---|---|---|---|---|---|---|---|
| YK-RSV-003 | 550 to 574 aa were | 104 to 144 aa, amino acids | A149C, S155C, S290C, Y458C | S190F, V296I | E92D, K465Q, D486S | S46G, S215P, L373R | / |
| YK-RSV-061 | truncated based on the | deleted from the sequence | A149C, S155C, S290C, Y458C | S190F, V296I | E92D, K465Q, D486S | S46G, S215P, L373R | V152I |
| YK-RSV-062 | wild-type RSV F protein, that | were replaced by a GS linker | A149C, S155C, S290C, Y458C | S190F, V296I | E92D, K465Q, D486S | S46G, S215P, L373R | C69Y, D73E, A74V, N88S, V152I |
| PC-RSV-063 | is, (1 to 549 aa) were | | A149C, S155C, S290C Y458C, | S190F, V207L | E92D, K465Q | S46G, S215P, L373R | / |
| PC-RSV-064 | retained | | A149C, S155C, S290C, Y458C | S190F | E92D, K465Q | S46G, S215P, L373R | V152I |
| PC-RSV-065 | | | A149C, S155C, S290C, Y458C | S190F, V296I | E92D, K465Q | S46G, S215P, L373R | V152I |
| PC-RSV-066 | | | A149C, S155C, S290C, Y458C | S190F | E92D, K465Q, D486S | S46G, S215P, L373R | V152I |
| PC-RSV-067 | | | T103C, I148C | S190F, V296I | E92D, K465Q, D486S | S46G, S215P, L373R | V152I |
| PC-RSV-068 | | | S55C, L188C | S190F, V296I | E92D, K465Q, D486S | S46G, S215P, L373R | V152I |

TABLE 36

ELISA results n of RSV F mutants

| No. | ELISA results (ng/ml) Epitope Φ RSV pre-F antibody (3C12) | Binding amount to antibody/binding amount of PC-RSV-064 to antibody | Epitope Quaternary RSV pre-F antibody (7H11) | Binding amount to antibody/binding amount of PC-RSV-064 to antibody | Epitope V RSV F antibody (7E11) | Binding amount to antibody/binding amount of PC-RSV-064 to antibody | Epitope II RSV F antibody (11A9) | Binding amount to antibody/binding amount of PC-RSV-064 to antibody | Epitope III RSV F antibody (4B9) | Binding amount to antibody/binding amount of PC-RSV-064 to antibody |
|---|---|---|---|---|---|---|---|---|---|---|
| YK-RSV-061 | 5261 | 1.90 | 7661 | 2.12 | 595 | 1.85 | 2505 | 1.19 | 3683 | 1.28 |
| YK-RSV-003 | 5541 | 2.00 | 7249 | 2.01 | 452 | 1.41 | 1994 | 0.95 | 3171 | 1.11 |
| YK-RSV-062 | 5059 | 1.83 | 7350 | 2.03 | 487 | 1.52 | 2063 | 0.98 | 3260 | 1.14 |
| PC-RSV-063 | 2727 | 0.99 | 3557 | 0.98 | 461 | 1.44 | 2053 | 0.98 | 2993 | 1.04 |
| PC-RSV-064 | 2768 | 1.00 | 3612 | 1.00 | 321 | 1.00 | 2100 | 1.00 | 2868 | 1.00 |
| PC-RSV-065 | 3378 | 1.22 | 3705 | 1.03 | 436 | 1.36 | 1864 | 0.89 | 3102 | 1.08 |
| PC-RSV-066 | 2169 | 0.78 | 3213 | 0.89 | 374 | 1.17 | 1682 | 0.80 | 2058 | 0.72 |
| PC-RSV-067 | 2828 | 1.02 | 2869 | 0.79 | 298 | 0.93 | 2509 | 1.19 | 3608 | 1.26 |
| PC-RSV-068 | 3168 | 1.14 | 3667 | 1.02 | 312 | 0.97 | 3191 | 1.52 | 4321 | 1.51 |

TABLE 37-continued

Results for affinity of RSV F mutants for different epitope antibodies

| No. | $K_D$ value (M) RSV pre-F antibody (3C12) Epitope Φ | RSV pre-F antibody (7H11) Epitope Quaternary |
|---|---|---|
| PC-RSV-065 | 1.62E−10 | 1.22E−10 |
| PC-RSV-066 | 2.63E−10 | 1.33E−10 |
| PC-RSV-067 | 5.29E−10 | 3.06E−10 |
| PC-RSV-068 | 6.61E−10 | 2.25E−10 |

Compared with the YK-RSV-003 mutant, the control PC—RSV-063 had 1 mutation type in group 2 of site mutations changed, from V296I to V207L; and a D486S site mutation in group 3 of site mutations deleted. However, the binding level of the epitope Quaternary on YK-RSV-003 to the RSV pre-F antibody (7H11) was 2.04 times that of the control PC—RSV-063, with a significant difference in binding levels.

Compared with the YK-RSV-061 mutant, the controls PC—RSV-065 and PC—RSV-066 each had 1 site mutation (D486S or V296I) reduced, the control PC—RSV-064 had 2 site mutations (D486S and V296I) reduced, and the controls PC—RSV-067 and PC—RSV-068 had the mutation type in group 1 of site mutations changed. The results showed that: the affinity constant $K_D$ for the binding of the epitope Φ on the YK-RSV-061 mutant to the RSV pre-F antibody (3C12) was 6.21E-11 M; the affinity constant $K_D$ for the binding of the epitope Quaternary to the RSV pre-F antibody (7H11) was 3.05E-12 M, and the $K_D$ values for the other controls were all E-10 M, with a difference of 1 to 2 orders of magnitude, indicating that the affinity of the antigen YK-RSV-061 for the antibodies was higher than that of the other controls.

From the above comparison, it could be seen that the binding level and the binding force of the epitope on the YK-RSV-003 mutant to a corresponding antibody were both significantly higher than those of the controls PC—RSV-063 to PC—RSV-068; meanwhile, in conjunction with the comparison results in section (1). the YK-RSV-061 mutant had a significantly superior effect to the YK-RSV-003 mutant, and the YK-RSV-062 had a comparable effect to the YK-RSV-003, so that YK-RSV-061, YK-RSV-003, and YK-RSV-062 were all superior to the controls PC—RSV-063 to PC—RSV-068.

The table below shows the complete sequence information and the serial numbers thereof in the present application. Taking the antigen sequence of YK-RSV-001 as an example, SEQ ID NOs: 3 and 4 are the DNA sequence and amino acid sequence of the open reading frame of the antigen YK-RSV-001, respectively; SEQ ID NOs: 2 and 5 are the DNA sequence and mRNA sequence of the antigen YK-RSV-001, respectively.

TABLE 38

Sequence numbers, names, and types thereof in the present application

| SEQ ID NO: | Name | Sequence type |
|---|---|---|
| 1 | RSV A2 (138251)-wt | AA |
| 2 | YK-RSV-001-DNA | DNA |
| 3 | YK-RSV-001- ORF-NT | ORF-NT |
| 4 | YK-RSV-001- ORF-AA | ORF-AA |
| 5 | YK-RSV-001- mRNA | mRNA |
| 6 | YK-RSV-002- DNA | DNA |
| 7 | YK-RSV-002- ORF-NT | ORF-NT |
| 8 | YK-RSV-002- ORF-AA | ORF-AA |
| 9 | YK-RSV-002-mRNA | mRNA |
| 10 | YK-RSV-003-DNA | DNA |
| 11 | YK-RSV-003-ORF-NT | ORF-NT |
| 12 | YK-RSV-003-ORF-AA | ORF-AA |
| 13 | YK-RSV-003-mRNA | mRNA |
| 14 | YK-RSV-004-DNA | DNA |
| 15 | YK-RSV-004- ORF-NT | ORF-NT |
| 16 | YK-RSV-004- ORF-AA | ORF-AA |
| 17 | YK-RSV-004- mRNA | mRNA |
| 18 | YK-RSV-005-DNA | DNA |
| 19 | YK-RSV-005- ORF-NT | ORF-NT |
| 20 | YK-RSV-005- ORF-AA | ORF-AA |
| 21 | YK-RSV-005- mRNA | mRNA |
| 22 | YK-RSV-008-DNA | DNA |
| 23 | YK-RSV-008-ORF-NT | ORF-NT |
| 24 | YK-RSV-008-ORF-AA | ORF-AA |
| 25 | YK-RSV-008-mRNA | mRNA |
| 26 | YK-RSV-009-DNA | DNA |
| 27 | YK-RSV-009-ORF-NT | ORF-NT |
| 28 | YK-RSV-009-ORF-AA | ORF-AA |
| 29 | YK-RSV-009-mRNA | mRNA |
| 30 | YK-RSV-010-DNA | DNA |
| 31 | YK-RSV-010-ORF-NT | ORF-NT |
| 32 | YK-RSV-010-ORF-AA | ORF-AA |
| 33 | YK-RSV-010-mRNA | mRNA |
| 34 | YK-RSV-011-DNA | DNA |
| 35 | YK-RSV-011-ORF-NT | ORF-NT |
| 36 | YK-RSV-011-ORF-AA | ORF-AA |
| 37 | YK-RSV-011-mRNA | mRNA |
| 38 | YK-RSV-012-DNA | DNA |
| 39 | YK-RSV-012-ORF-NT | ORF-NT |
| 40 | YK-RSV-012-ORF-AA | ORF-AA |
| 41 | YK-RSV-012-mRNA | mRNA |
| 42 | YK-RSV-013-DNA | DNA |
| 43 | YK-RSV-013-ORF-NT | ORF-NT |
| 44 | YK-RSV-013-ORF-AA | ORF-AA |
| 45 | YK-RSV-013-mRNA | mRNA |
| 46 | YK-RSV-014-DNA | DNA |
| 47 | YK-RSV-014-ORF-NT | ORF-NT |
| 48 | YK-RSV-014-ORF-AA | ORF-AA |
| 49 | YK-RSV-014-mRNA | mRNA |
| 50 | YK-RSV-015-DNA | DNA |
| 51 | YK-RSV-015-ORF-NT | ORF-NT |
| 52 | YK-RSV-015-ORF-AA | ORF-AA |
| 53 | YK-RSV-015-mRNA | mRNA |
| 54 | YK-RSV-016-DNA | DNA |
| 55 | YK-RSV-016-ORF-NT | ORF-NT |
| 56 | YK-RSV-016-ORF-AA | ORF-AA |
| 57 | YK-RSV-016-mRNA | mRNA |
| 58 | YK-RSV-017-DNA | DNA |
| 59 | YK-RSV-017-ORF-NT | ORF-NT |
| 60 | YK-RSV-017-ORF-AA | ORF-AA |
| 61 | YK-RSV-017-mRNA | mRNA |
| 62 | YK-RSV-018-DNA | DNA |
| 63 | YK-RSV-018-ORF-NT | ORF-NT |
| 64 | YK-RSV-018-ORF-AA | ORF-AA |
| 65 | YK-RSV-018-mRNA | mRNA |
| 66 | YK-RSV-019-DNA | DNA |
| 67 | YK-RSV-019-ORF-NT | ORF-NT |
| 68 | YK-RSV-019-ORF-AA | ORF-AA |
| 69 | YK-RSV-019-mRNA | mRNA |
| 70 | YK-RSV-022-DNA | DNA |
| 71 | YK-RSV-022-ORF-NT | ORF-NT |
| 72 | YK-RSV-022-ORF-AA | ORF-AA |
| 73 | YK-RSV-022-mRNA | mRNA |
| 74 | YK-RSV-029-DNA | DNA |
| 75 | YK-RSV-029-ORF-NT | ORF-NT |
| 76 | YK-RSV-029-ORF-AA | ORF-AA |
| 77 | YK-RSV-029-mRNA | mRNA |
| 78 | YK-RSV-030-DNA | DNA |
| 79 | YK-RSV-030-ORF-NT | ORF-NT |
| 80 | YK-RSV-030-ORF-AA | ORF-AA |
| 81 | YK-RSV-030-mRNA | mRNA |

TABLE 38-continued

Sequence numbers, names, and types thereof in the present application

| SEQ ID NO: | Name | Sequence type |
|---|---|---|
| 82 | YK-RSV-031-DNA | DNA |
| 83 | YK-RSV-031-ORF-NT | ORF-NT |
| 84 | YK-RSV-031-ORF-AA | ORF-AA |
| 85 | YK-RSV-031-mRNA | mRNA |
| 86 | YK-RSV-032-DNA | DNA |
| 87 | YK-RSV-032-ORF-NT | ORF-NT |
| 88 | YK-RSV-032-ORF-AA | ORF-AA |
| 89 | YK-RSV-032-mRNA | mRNA |
| 90 | YK-RSV-033-DNA | DNA |
| 91 | YK-RSV-033-ORF-NT | ORF-NT |
| 92 | YK-RSV-033-ORF-AA | ORF-AA |
| 93 | YK-RSV-033-mRNA | mRNA |
| 94 | YK-RSV-034-DNA | DNA |
| 95 | YK-RSV-034-ORF-NT | ORF-NT |
| 96 | YK-RSV-034-ORF-AA | ORF-AA |
| 97 | YK-RSV-034-mRNA | mRNA |
| 98 | YK-RSV-035-DNA | DNA |
| 99 | YK-RSV-035-ORF-NT | ORF-NT |
| 100 | YK-RSV-035-ORF-AA | ORF-AA |
| 101 | YK-RSV-035-mRNA | mRNA |
| 102 | YK-RSV-036-DNA | DNA |
| 103 | YK-RSV-036-ORF-NT | ORF-NT |
| 104 | YK-RSV-036-ORF-AA | ORF-AA |
| 105 | YK-RSV-036-mRNA | mRNA |
| 106 | YK-RSV-037-DNA | DNA |
| 107 | YK-RSV-037-ORF-NT | ORF-NT |
| 108 | YK-RSV-037-ORF-AA | ORF-AA |
| 109 | YK-RSV-037-mRNA | mRNA |
| 110 | YK-RSV-038-DNA | DNA |
| 111 | YK-RSV-038-ORF-NT | ORF-NT |
| 112 | YK-RSV-038-ORF-AA | ORF-AA |
| 113 | YK-RSV-038-mRNA | mRNA |
| 114 | YK-RSV-039-DNA | DNA |
| 115 | YK-RSV-039-ORF-NT | ORF-NT |
| 116 | YK-RSV-039-ORF-AA | ORF-AA |
| 117 | YK-RSV-039-mRNA | mRNA |
| 118 | YK-RSV-040-DNA | DNA |
| 119 | YK-RSV-040-ORF-NT | ORF-NT |
| 120 | YK-RSV-040-ORF-AA | ORF-AA |
| 121 | YK-RSV-040-mRNA | mRNA |
| 122 | YK-RSV-041-DNA | DNA |
| 123 | YK-RSV-041-ORF-NT | ORF-NT |
| 124 | YK-RSV-041-ORF-AA | ORF-AA |
| 125 | YK-RSV-041-mRNA | mRNA |
| 126 | YK-RSV-042-DNA | DNA |
| 127 | YK-RSV-042-ORF-NT | ORF-NT |
| 128 | YK-RSV-042-ORF-AA | ORF-AA |
| 129 | YK-RSV-042-mRNA | mRNA |
| 130 | YK-RSV-043-DNA | DNA |
| 131 | YK-RSV-043-ORF-NT | ORF-NT |
| 132 | YK-RSV-043-ORF-AA | ORF-AA |
| 133 | YK-RSV-043-mRNA | mRNA |
| 134 | YK-RSV-044-DNA | DNA |
| 135 | YK-RSV-044-ORF-NT | ORF-NT |
| 136 | YK-RSV-044-ORF-AA | ORF-AA |
| 137 | YK-RSV-044-mRNA | mRNA |
| 138 | YK-RSV-045-DNA | DNA |
| 139 | YK-RSV-045-ORF-NT | ORF-NT |
| 140 | YK-RSV-045-ORF-AA | ORF-AA |
| 141 | YK-RSV-045-mRNA | mRNA |
| 142 | YK-RSV-046-DNA | DNA |
| 143 | YK-RSV-046-ORF-NT | ORF-NT |
| 144 | YK-RSV-046-ORF-AA | ORF-AA |
| 145 | YK-RSV-046-mRNA | mRNA |
| 146 | YK-RSV-047-DNA | DNA |
| 147 | YK-RSV-047-ORF-NT | ORF-NT |
| 148 | YK-RSV-047-ORF-AA | ORF-AA |
| 149 | YK-RSV-047-mRNA | mRNA |
| 150 | YK-RSV-048-DNA | DNA |
| 151 | YK-RSV-048-ORF-NT | ORF-NT |
| 152 | YK-RSV-048-ORF-AA | ORF-AA |
| 153 | YK-RSV-048-mRNA | mRNA |
| 154 | YK-RSV-049-DNA | DNA |
| 155 | YK-RSV-049-ORF-NT | ORF-NT |
| 156 | YK-RSV-049-ORF-AA | ORF-AA |
| 157 | YK-RSV-049-mRNA | mRNA |
| 158 | YK-RSV-050-DNA | DNA |
| 159 | YK-RSV-050-ORF-NT | ORF-NT |
| 160 | YK-RSV-050-ORF-AA | ORF-AA |
| 161 | YK-RSV-050-mRNA | mRNA |
| 162 | YK-RSV-051-DNA | DNA |
| 163 | YK-RSV-051-ORF-NT | ORF-NT |
| 164 | YK-RSV-051-ORF-AA | ORF-AA |
| 165 | YK-RSV-051-mRNA | mRNA |
| 166 | YK-RSV-052-DNA | DNA |
| 167 | YK-RSV-052-ORF-NT | ORF-NT |
| 168 | YK-RSV-052-ORF-AA | ORF-AA |
| 169 | YK-RSV-052-mRNA | mRNA |
| 170 | YK-RSV-053-DNA | DNA |
| 171 | YK-RSV-053-ORF-NT | ORF-NT |
| 172 | YK-RSV-053-ORF-AA | ORF-AA |
| 173 | YK-RSV-053-mRNA | mRNA |
| 174 | YK-RSV-054-DNA | DNA |
| 175 | YK-RSV-054-ORF-NT | ORF-NT |
| 176 | YK-RSV-054-ORF-AA | ORF-AA |
| 177 | YK-RSV-054-mRNA | mRNA |
| 178 | YK-RSV-055-DNA | DNA |
| 179 | YK-RSV-055-ORF-NT | ORF-NT |
| 180 | YK-RSV-055-ORF-AA | ORF-AA |
| 181 | YK-RSV-055-mRNA | mRNA |
| 182 | YK-RSV-056-DNA | DNA |
| 183 | YK-RSV-056-ORF-NT | ORF-NT |
| 184 | YK-RSV-056-ORF-AA | ORF-AA |
| 185 | YK-RSV-056-mRNA | mRNA |
| 186 | YK-RSV-057-DNA | DNA |
| 187 | YK-RSV-057-ORF-NT | ORF-NT |
| 188 | YK-RSV-057-ORF-AA | ORF-AA |
| 189 | YK-RSV-057-mRNA | mRNA |
| 190 | YK-RSV-058-DNA | DNA |
| 191 | YK-RSV-058-ORF-NT | ORF-NT |
| 192 | YK-RSV-058-ORF-AA | ORF-AA |
| 193 | YK-RSV-058-mRNA | mRNA |
| 194 | YK-RSV-059-DNA | DNA |
| 195 | YK-RSV-059-ORF-NT | ORF-NT |
| 196 | YK-RSV-059-ORF-AA | ORF-AA |
| 197 | YK-RSV-059-mRNA | mRNA |
| 198 | YK-RSV-060-DNA | DNA |
| 199 | YK-RSV-060-ORF-NT | ORF-NT |
| 200 | YK-RSV-060-ORF-AA | ORF-AA |
| 201 | YK-RSV-060-mRNA | mRNA |
| 202 | YK-RSV-061-DNA | DNA |
| 203 | YK-RSV-061-ORF-NT | ORF-NT |
| 204 | YK-RSV-061-ORF-AA | ORF-AA |
| 205 | YK-RSV-061-mRNA | mRNA |
| 206 | YK-RSV-062-DNA | DNA |
| 207 | YK-RSV-062-ORF-NT | ORF-NT |
| 208 | YK-RSV-062-ORF-AA | ORF-AA |
| 209 | YK-RSV-062-mRNA | mRNA |
| 210 | RSV A2 (138251)-mt | AA |
| 211 | PC-RSV-063 | AA |
| 212 | PC-RSV-064 | AA |
| 213 | PC-RSV-065 | AA |
| 214 | PC-RSV-066 | AA |
| 215 | PC-RSV-067 | AA |
| 216 | PC-RSV-068 | AA |
| 217 | 5' UTR | / |
| 218 | 5' UTR | / |
| 219 | 5' UTR | / |
| 220 | 5' UTR | / |
| 221 | 5' UTR | / |
| 222 | 3' UTR | / |
| 223 | 3' UTR | / |
| 224 | 3' UTR | / |
| 225 | 3' UTR | / |

What is claimed is:

1. An immunogenic composition, comprising a ribonucleic acid (RNA) of a respiratory syncytial virus (RSV), wherein the RNA encodes a variant of a wild-type RSV F protein;

wherein a sequence of the wild-type RSV F protein is SEQ ID NO: 1;

the variant of the RSV F protein comprises mutations P102A, I379V, and M447V, the variant of the RSV F protein is a truncated protein in which amino acids at positions 550 to 574 of SEQ ID NO: 1 are truncated, and amino acids at positions 104 to 144 are substituted by a GS linker, and the variant of the RSV F protein further comprises a combination of site mutations selected from any one of the following groups of Group 1 to Group 5, therefore obtain the variant of the RSV F protein selected from YK-RSV-061, YK-RSV-003 and/or YK-RSV-062:

| Protein variant | Site mutation | | | | |
|---|---|---|---|---|---|
| No. | Group 1 | Group 2 | Group 3 | Group 4 | Group 5 |
| YK-RSV-061 | A149C, S155C, S290C, Y458C | S190F, V296I | E92D, K465Q, D486S | S46G, S215P, L373R | V152I |
| YK-RSV-003 | A149C, S155C, S290C, Y458C | S190F, V296I | E92D, K465Q, D486S | S46G, S215P, L373R | / |
| YK-RSV-062 | A149C, S155C, S290C, Y458C | S190F, V296I | E92D, K465Q, D486S | S46G, S215P, L373R | C69Y, D73E, A74V, N88S, V152I |

2. The composition according to claim 1, wherein an amino acid sequence of the variant of the RSV F protein is: SEQ ID NO: 204, SEQ ID NO: 12 or SEQ ID NO: 208.

3. The composition according to claim 1, wherein a nucleotide sequence of an open reading frame (ORF) encoding the variant of the RSV F protein is: SEQ ID NO: 203, SEQ ID NO: 11 or SEQ ID NO: 207.

4. The composition according to claim 1, wherein the RNA of the RSV further comprises a 5' untranslated region (UTR).

5. The composition according to claim 4, wherein a sequence of the 5' untranslated region is: SEQ ID NO: 217, SEQ ID NO: 218, SEQ ID NO: 219, SEQ ID NO: 220, or SEQ ID NO: 221.

6. The composition according to claim 1, wherein the RNA of the RSV further comprises a 3' untranslated region (UTR).

7. The composition according to claim 6, wherein a sequence of the 3' untranslated region is: SEQ ID NO: 222, SEQ ID NO: 223, SEQ ID NO: 224, or SEQ ID NO: 225.

8. The composition according to claim 1, wherein the RNA of the RSV further comprises a poly(A) tail.

9. The composition according to claim 1, wherein the RNA of the RSV further comprises a 5' cap structure.

10. The composition according to claim 9, wherein the 5' cap structure is: 7mG(5')ppp(5')NlmpNp.

11. The composition according to claim 1, wherein a sequence of an open reading frame (ORF) encoding the RSV F protein or the variant thereof in the RSV RNA is codon-optimized.

12. The composition according to claim 11, wherein the sequence of the ORF comprises at least one base modification.

13. The composition according to claim 12, wherein the base modification comprises any one or more selected from the following: pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyluridine.

14. The composition according to claim 1, wherein a sequence of the RNA of the RSV is: SEQ ID NO: 205, SEQ ID NO: 13 or SEQ ID NO: 209.

15. The composition according to claim 1, wherein a DNA sequence encoding the variant of the RSV F protein is: SEQ ID NO: 202, SEQ ID NO: 10 or SEQ ID NO: 206.

16. The composition according to claim 1, wherein the composition is a vaccine and further comprises a pharmaceutically acceptable excipient.

17. The composition according to claim 16, wherein the pharmaceutically acceptable excipient comprises a lipid mixture, and the lipid mixture is a lipid nanoparticle (LNP).

18. The composition according to claim 16, wherein the vaccine is an mRNA vaccine.

19. The composition according to claim 17, wherein the lipid nanoparticle comprises a cationic lipid, a neutral lipid, a structural lipid, and a polymer-conjugated lipid.

20. The composition according to claim 19, wherein the cationic lipid is a compound with a structure of formula I, or a N-oxide, a solvate, a pharmaceutically acceptable salt or a stereoisomer thereof, wherein $G_1$ is $C_{1-6}$ alkylene; $G_2$ is $C_{2-8}$ alkylene; $G_3$ is $C_{1-3}$ alkylene; L1 is $C_{6-15}$ linear alkyl; L2 is $C_{12-25}$ branched alkyl

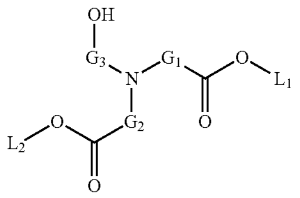

formula I; or the cationic lipid is a compound with a structure of formula II, or a N-oxide, a solvate, a pharmaceutically acceptable salt or a stereoisomer thereof, wherein $G_1$ is $C_{2-8}$ alkylene; $G_2$ is $C_{2-8}$ alkylene; $L_1$ is —C(O)O— or —OC(O)—; $L_2$ is —C(O)O— or —OC(O)—; R1 is $C_{6-25}$ linear or branched alkyl; R2 is $C_{6-25}$ linear or branched alkyl; $G_3$ is $HO(CH_2)_2$— or $HO(CH_2)_3$—; $G_4$ is $HO(CH_2)_2$— or $HO(CH_2)_3$—; L is $—(CH_2)_2—$ or $—(CH_2)_3—$ or $—(CH_2)_4—$

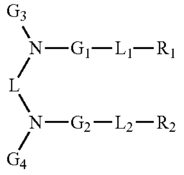

formula II; or the cationic lipid is a compound with structure of formula III, or a N-oxide, a solvate, a pharmaceutically acceptable salt or a stereoisomer thereof, wherein $G_1$ is $C_{1-6}$ alkylene; $G_2$ is $C_{2-8}$ alkylene; $R_1$ is $C_{6-20}$ linear or branched alkyl; $R_2$ is $C_{12-25}$ branched alkyl; $G_3$ is: $HO(CH_2)_2N(CH_3)(CH_2)_2$—, $HO(CH_2)_2N(CH_2CH_3)(CH_2)_2$—, $(HO(CH_2)_2)_2N(CH_2)_2$—, $CH_3O(CH_2)_2N(CH_3)(CH_2)_2$—, $(CH_3)_2N(CH_2)_3SC(O)O(CH_2)_2$—, $(CH_3)_2N(CH_2)_3SC(O)$—, $CH_3NH(CH_2)_2N(CH_3)(CH_2)_2$—, or $CH_3CH_2NH(CH_2)_2$—

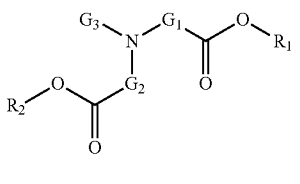

formula III; or the cationic lipid is a compound with a structure of formula IV, or a N-oxide, a solvate, a pharmaceutically acceptable salt or a stereoisomer thereof, wherein $G_1$ is $C_{1-8}$ alkylene; $G_2$ is $C_{2-8}$ alkylene; $R_1$ is $C_{6-25}$ linear or branched alkyl; $R_2$ is $C_{12-25}$ linear or branched alkyl; $G_3$ is $HO(CH_2)_2N(R_3)CH_2CH(OH)CH_2$—, wherein $R_3$ is $—CH_3$ or $—CH_2CH_3$ or $—CH_2CH_2OH$

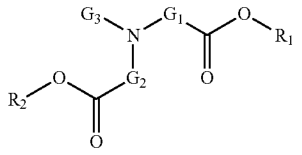

formula IV; or the cationic lipid is a compound with a structure of formula V, or a N-oxide, a solvate, a pharmaceutically acceptable salt or a stereoisomer thereof, wherein $G_1$ and $G_2$ are each independently unsubstituted $C_6$-$C_{10}$ alkylene; $G_3$ is unsubstituted $C_1$-$C_{12}$ alkylene; $R_1$ and $R_2$ are each independently $C_6$-$C_{24}$ alkyl or $C_6$-$C_{24}$ alkenyl; $R_3$ is $OR_5$, N, —C(═O)$OR_4$, —OC(═O)$R_4$, or —$NR_5$C(═O)$R_4$; $R_4$ is $C_1$-$C_{12}$ alkyl; and $R_5$ is H or $C_1$-$C_6$ alkyl

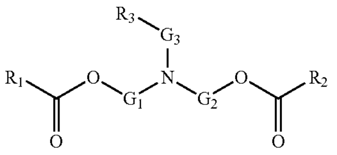

formula V; or the cationic lipid is a compound with a structure of formula VI, or a N-oxide, a solvate, a pharmaceutically acceptable salt or a stereoisomer thereof, wherein $R_4$ is selected from $—(CH_2)_nQ$ and $—(CH_2)_nCHQR$; Q is selected from the group consisting of: —OR, —OH, $—O(CH_2)_nN(R)_2$, —OC(O)R, $—CX_3$, —CN, —N(R)C(O)R, —N(H)C(O)R, $—N(R)S(O)_2R$, $—N(H)S(O)_2R$, $—N(R)C(O)N(R)_2$, $—N(H)C(O)N(R)_2$, —N(H)C(O)N(H)(R), $—N(R)C(S)N(R)_2$, $—N(H)C(S)N(R)_2$, —N(H)C(S)N(H)(R), $—N(R)S(O)_2R_8$, and a heterocyclic ring; n is 1, 2, or 3; wherein R is hydrogen, $C_{1-3}$ alkyl, $C_{2-3}$ alkenyl, or $(CH_2)_qOR^*$, wherein q is 1, 2, or 3, R* is $C_{1-12}$ alkyl or $C_{2-12}$ alkenyl; X is fluoro, chloro, bromo, or iodo; $R_8$ is $C_{3-6}$ cycloalkyl or a heterocyclic ring formula VI

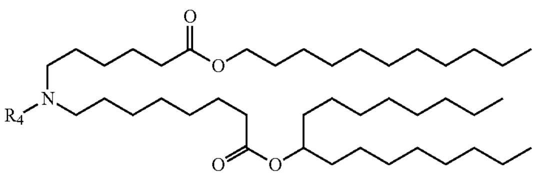

; or formula VI; or the cationic lipid is a compound with a structure of formula VII, or a N-oxide, a solvate, a pharmaceutically acceptable salt, or a stereoisomer thereof:

formula VII

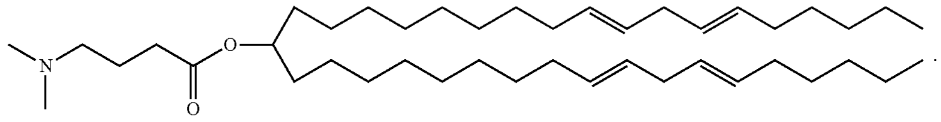

21. The composition according to the preceding claim 19 wherein the cationic lipid is selected from the following compounds: YK-009 YK-401 YK-305 ALC0315 SM102 DLIN-MC3

YK-009

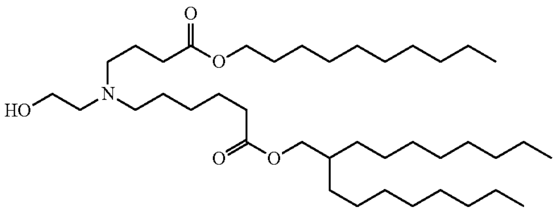

-continued

YK-401

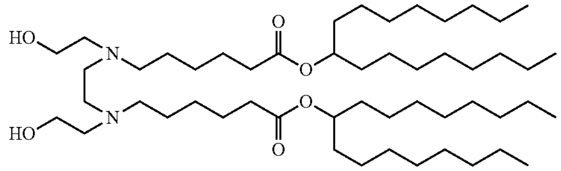

YK-305

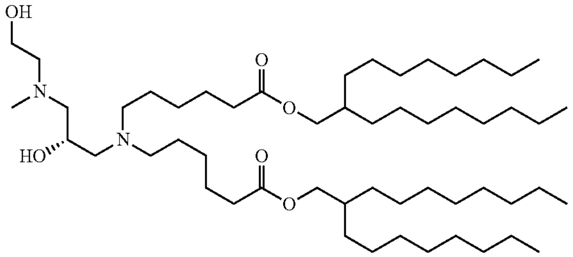

ALC0315

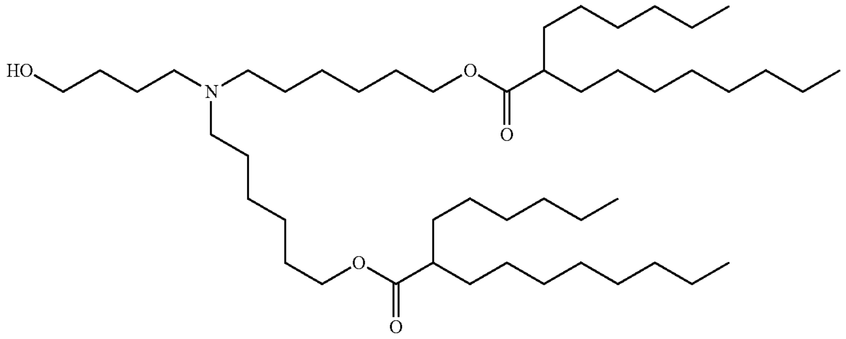

SM102

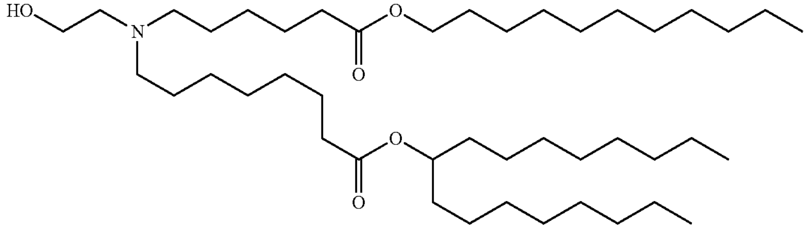

DLIN-MC3

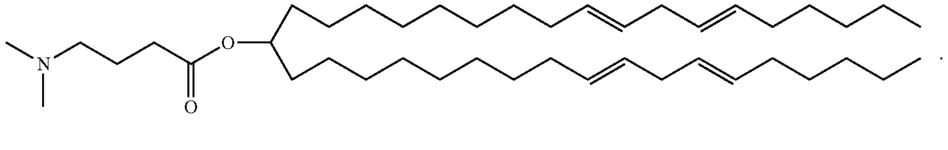

22. The composition according to claim 19, wherein the cationic lipid and the neutral lipid are at a molar ratio of (1-10):1; or, the cationic lipid and the structural lipid are at a molar ratio of (1-5):1; or, the cationic lipid, the neutral lipid, the structural lipid, and the polymer-conjugated lipid are at a molar ratio of (25-75):(5-25):(15-65):(0.5-10).

23. The composition according to claim 19, wherein the neutral lipid is selected from one or more of phosphatidylcholine, phosphatidylethanolamine, sphingomyelin, ceramide, sterol, and derivatives thereof.

24. The composition according to claim 19, wherein the neutral lipid is selected from one or more of the following: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphorylcholine (DUPC), 1-palmitoyl-2-oleoyl-sn-glycero-3-phosphocholine (POPC), 1,2-di-O-octadecadienyl-sn-glycero-3-phosphocholine (18:0 Diether PC), 1-oleoyl-2-cholesterolhemisuccinyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonyl-sn-glycero-3-phosphorylcholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16OPE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphatidylethanolamine (DMPE), 1-stearyl-2-oleoyl-stearoylethanolamine (SOPE), 1-stearoyl-2-oleoyl-phosphatidyicholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, and lysophosphatidylethanolamine (LPE).

25. The composition according to claim 19, wherein the structural lipid is selected from one or more of the following: cholesterol, nonsterol, sitosterol, ergosterol, campesterol, stigmasterol, brassicasterol, tomatidine, ursolic acid, α-tocopherol and corticosteroid.

26. The composition according to claim 19, wherein the polymer-conjugated lipid is selected from one or more of the following: PEG-modified phosphatidylethanolamine, PEG-modified phosphatidic acid, PEG-modified ceramide, PEG-modified dialkylamine, PEG-modified diacylglycerol, PEG-modified dialkylglycerol.

27. The composition according to the preceding claim 26, wherein the polymer-conjugated lipid is selected from one or more of the following: distearoyl phosphatidylethanolamine polyethylene glycol 2000 (DSPE-PEG2000), dimyristoylglycerol-3-methoxy polyethylene glycol 2000 (DMG-PEG2000), and methoxypoly(ethylene glycol) ditetradecylacetamide (ALC-0159).

28. The composition according to claim 16, wherein an effective dose of the RSV RNA is 25 to 200 g.

29. The composition according to claim 16, wherein the vaccine is in a form of an injection.

30. The composition according to claim 1, wherein the composition induces a protective immune response to RSV in a subject.

* * * * *